(12) United States Patent
Hyde et al.

(10) Patent No.: US 10,679,309 B2
(45) Date of Patent: Jun. 9, 2020

(54) EVIDENCE-BASED HEALTHCARE INFORMATION MANAGEMENT PROTOCOLS

(71) Applicant: Elwha LLC, Bellevue, WA (US)

(72) Inventors: Roderick A. Hyde, Redmond, WA (US); Edward K.Y. Jung, Bellevue, WA (US); Jordin T. Kare, Seattle, WA (US); Eric C. Leuthardt, St Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Dennis J. Rivet, Chesapeake, VA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/705,413

(22) Filed: Dec. 5, 2012

(65) Prior Publication Data

US 2013/0173304 A1 Jul. 4, 2013

Related U.S. Application Data

(63) Continuation-in-part of application No. 13/374,519, filed on Dec. 30, 2011, and a continuation-in-part of
(Continued)

(51) Int. Cl.
*G06Q 40/00* (2012.01)
*G06Q 50/24* (2012.01)
(Continued)

(52) U.S. Cl.
CPC ............. *G06Q 50/24* (2013.01); *G16H 10/20* (2018.01); *G16H 10/60* (2018.01); *G16H 40/20* (2018.01)

(58) Field of Classification Search
CPC .................... G06Q 50/22; G06Q 50/24; G06F 19/322–327; G06F 19/363
See application file for complete search history.

(56) References Cited

U.S. PATENT DOCUMENTS

| 3,843,841 A | 10/1974 | Rubinstein |
| 5,537,314 A | 7/1996 | Kanter |

(Continued)

FOREIGN PATENT DOCUMENTS

WO    WO 00/75748    12/2000

OTHER PUBLICATIONS

U.S. Appl. No. 13/199,053, Hyde et al.
(Continued)

*Primary Examiner* — Rajesh Khattar

(57) ABSTRACT

Structures and protocols are presented for signaling a status or decision (processing or transmitting a medical record or other resource, e.g.) conditionally. Such signaling may be partly based on one or more symptoms, regimen attributes, performance indicia (compliance indications, e.g.), privacy considerations (patient consent, e.g.), contextual considerations (being in or admitted by a care facility, e.g.), sensor data, or other such determinants. In some contexts this may trigger an incentive being manifested (as a dispensation of an item, e.g.), an intercommunication (telephone call, e.g.) beginning, a device being configured (enabled or customized, e.g.), data distillations being presented or tracked, or other such results.

38 Claims, 46 Drawing Sheets

Related U.S. Application Data application No. 13/374,747, filed on Jan. 9, 2012, and a continuation-in-part of application No. 13/374,750, filed on Jan. 9, 2012, and a continuation-in-part of application No. 13/374,745, filed on Jan. 9, 2012, and a continuation-in-part of application No. 13/374,744, filed on Jan. 9, 2012, and a continuation-in-part of application No. 13/374,748, filed on Jan. 9, 2012.

(51) Int. Cl.
*G16H 10/60* (2018.01)
*G16H 10/20* (2018.01)
*G16H 40/20* (2018.01)

(56) References Cited

U.S. PATENT DOCUMENTS

| | | |
|---|---|---|
| 5,612,869 A | 3/1997 | Letzt et al. |
| 5,724,025 A | 3/1998 | Tavori |
| 5,902,234 A | 5/1999 | Webb |
| 5,945,651 A | 8/1999 | Chorosinski et al. |
| 5,954,641 A | 9/1999 | Kehr et al. |
| 5,991,429 A | 11/1999 | Coffin et al. |
| 6,000,828 A | 12/1999 | Leet |
| 6,014,626 A | 1/2000 | Cohen |
| 6,038,333 A | 3/2000 | Wang |
| 6,094,573 A | 7/2000 | Heinonen et al. |
| 6,108,709 A | 8/2000 | Shinomura et al. |
| 6,111,946 A | 8/2000 | O'Brien |
| 6,112,074 A | 8/2000 | Pinder |
| 6,122,485 A | 9/2000 | Archer |
| 6,124,136 A | 9/2000 | Kell |
| 6,134,014 A | 10/2000 | Tzu et al. |
| 6,137,914 A | 10/2000 | Ligtenberg et al. |
| 6,161,095 A | 12/2000 | Brown |
| 6,167,398 A | 12/2000 | Wyard et al. |
| 6,185,573 B1 | 2/2001 | Angelucci et al. |
| 6,198,383 B1 | 3/2001 | Sekura et al. |
| 6,198,695 B1 | 3/2001 | Kirton et al. |
| 6,205,326 B1 | 3/2001 | Tell et al. |
| 6,211,791 B1 | 4/2001 | Ponce de Leon et al. |
| 6,266,645 B1 | 7/2001 | Simpson |
| 6,307,937 B1 | 10/2001 | Dillon et al. |
| 6,310,554 B1 | 10/2001 | Carrell |
| 6,310,556 B1 | 10/2001 | Green et al. |
| 6,336,048 B1 | 1/2002 | Bonnet |
| 6,338,039 B1 | 1/2002 | Lonski et al. |
| 6,366,809 B1 | 4/2002 | Olson et al. |
| 6,371,931 B1 | 4/2002 | Guillen |
| 6,373,392 B1 | 4/2002 | Au |
| 6,375,038 B1 | 4/2002 | Daansen et al. |
| 6,380,858 B1 | 4/2002 | Yarin et al. |
| 6,392,747 B1 | 5/2002 | Allen et al. |
| 6,397,181 B1 | 5/2002 | Li et al. |
| 6,400,304 B1 | 6/2002 | Chubbs, III |
| 6,405,165 B1 | 6/2002 | Blum et al. |
| 6,421,726 B1 | 7/2002 | Kenner et al. |
| 6,424,729 B1 | 7/2002 | Soon |
| 6,437,707 B1 | 8/2002 | Johnson |
| 6,442,485 B2 | 8/2002 | Evans |
| 6,452,487 B1 | 9/2002 | Krupinski |
| 6,473,824 B1 | 10/2002 | Kreissig et al. |
| 6,513,014 B1 | 1/2003 | Walker et al. |
| 6,514,200 B1 | 2/2003 | Khouri |
| 6,519,327 B1 | 2/2003 | Cannon et al. |
| 6,536,189 B1 | 3/2003 | Murray |
| 6,553,341 B1 | 4/2003 | Mullaly et al. |
| 6,561,811 B2 | 5/2003 | Rapoza et al. |
| 6,575,901 B2 | 6/2003 | Stoycos et al. |
| 6,594,519 B2 | 7/2003 | Stoycos et al. |
| 6,636,592 B2 | 10/2003 | Marchand et al. |
| 6,650,751 B1 | 11/2003 | Becker |
| 6,655,545 B1 | 12/2003 | Sonneborn |
| 6,655,583 B2 | 12/2003 | Walsh et al. |
| 6,656,122 B2 | 12/2003 | Davidson et al. |
| 6,665,558 B2 | 12/2003 | Kalgren et al. |
| 6,671,548 B1 | 12/2003 | Mouchawar et al. |
| 6,693,512 B1 | 2/2004 | Frecska et al. |
| 6,697,456 B2 | 2/2004 | Chan et al. |
| 6,699,124 B2 | 3/2004 | Suchocki |
| 6,700,604 B1 | 3/2004 | Murata et al. |
| 6,704,595 B2 | 3/2004 | Bardy |
| 6,721,921 B1 | 4/2004 | Altman |
| 6,726,634 B2 | 4/2004 | Freeman |
| 6,738,613 B1 | 5/2004 | Ogawa et al. |
| 6,739,508 B2 | 5/2004 | Ushioda et al. |
| 6,748,687 B2 | 6/2004 | Riley |
| 6,768,420 B2 | 7/2004 | McCarthy et al. |
| 6,790,668 B1 | 9/2004 | Ferreira et al. |
| 6,791,477 B2 | 9/2004 | Sari et al. |
| 6,799,165 B1 | 9/2004 | Boesjes |
| 6,807,532 B1 | 10/2004 | Kolls |
| 6,831,993 B2 | 12/2004 | Lemelson et al. |
| 6,832,245 B1 | 12/2004 | Isaacs et al. |
| 6,839,403 B1 | 1/2005 | Kotowski et al. |
| 6,882,278 B2 | 4/2005 | Winings et al. |
| 6,893,396 B2 | 5/2005 | Schulze et al. |
| 6,901,347 B1 | 5/2005 | Murray et al. |
| 6,920,699 B2 | 7/2005 | Reusing et al. |
| 6,926,667 B2 | 8/2005 | Khouri |
| 6,944,599 B1 | 9/2005 | Vogel et al. |
| 6,952,678 B2 | 10/2005 | Williams et al. |
| 6,957,076 B2 | 10/2005 | Hunzinger |
| 6,973,371 B1 | 12/2005 | Benouali |
| 6,978,177 B1 | 12/2005 | Chen et al. |
| 6,980,958 B1 | 12/2005 | Surwit et al. |
| 6,981,080 B2 | 12/2005 | Thompson et al. |
| 6,985,206 B2 | 1/2006 | Anderson et al. |
| 6,988,132 B2 | 1/2006 | Horvitz |
| 6,988,498 B2 | 1/2006 | Berthon-Jones et al. |
| 7,002,454 B1 | 2/2006 | Gustafson |
| 7,016,854 B2 | 3/2006 | Himes |
| 7,020,458 B2 | 3/2006 | Bossemeyer, Jr. et al. |
| 7,031,734 B2 | 4/2006 | Kim |
| 7,034,934 B2 | 4/2006 | Manning |
| 7,042,338 B1 | 5/2006 | Weber |
| 7,046,162 B2 | 5/2006 | Dunstan |
| 7,047,083 B2 | 5/2006 | Gunderson et al. |
| 7,054,688 B1 | 5/2006 | Uhrenius et al. |
| 7,062,073 B1 | 6/2006 | Tumey et al. |
| 7,068,992 B1 | 6/2006 | Massie et al. |
| 7,069,085 B2 | 6/2006 | Cao et al. |
| 7,076,235 B2 | 7/2006 | Esque et al. |
| 7,087,036 B2 | 8/2006 | Busby et al. |
| 7,092,566 B2 | 8/2006 | Krumm |
| 7,100,210 B2 | 8/2006 | Kuo et al. |
| 7,107,095 B2 | 9/2006 | Manolas |
| 7,114,954 B2 | 10/2006 | Eggert et al. |
| 7,119,814 B2 | 10/2006 | Meron et al. |
| 7,127,493 B1 | 10/2006 | Gautier |
| 7,132,238 B2 | 11/2006 | Danenberg |
| 7,163,151 B2 | 1/2007 | Kiiskinen |
| 7,170,823 B2 | 1/2007 | Fabricius et al. |
| 7,172,124 B2 | 2/2007 | Wang et al. |
| 7,177,684 B1 | 2/2007 | Kroll et al. |
| 7,181,192 B2 | 2/2007 | Panasik et al. |
| 7,181,375 B2 | 2/2007 | Rao et al. |
| 7,203,633 B2 | 4/2007 | Gabele et al. |
| 7,204,805 B2 | 4/2007 | Dean |
| 7,223,246 B2 | 5/2007 | Don |
| 7,233,745 B2 | 6/2007 | Loechner |
| 7,239,275 B2 | 7/2007 | Dybdal et al. |
| 7,242,462 B2 | 7/2007 | Huang |
| 7,246,619 B2 | 7/2007 | Truschel et al. |
| 7,257,158 B1 | 8/2007 | Figueredo et al. |
| 7,260,205 B1 | 8/2007 | Murphy et al. |
| 7,263,493 B1 | 8/2007 | Provost et al. |
| 7,269,787 B2 | 9/2007 | Amitay et al. |
| 7,271,728 B2 | 9/2007 | Taylor et al. |
| 7,272,571 B2 | 9/2007 | Tuttrup et al. |
| 7,283,566 B2 | 10/2007 | Siemens et al. |
| 7,283,807 B2 | 10/2007 | Bossemeyer, Jr. et al. |
| 7,286,894 B1 | 10/2007 | Grant et al. |
| 7,287,031 B1 | 10/2007 | Karpf et al. |

(56) References Cited

U.S. PATENT DOCUMENTS

| | | |
|---|---|---|
| 7,289,651 B2 | 10/2007 | Vining et al. |
| 7,293,645 B2 | 11/2007 | Harper et al. |
| 7,295,120 B2 | 11/2007 | Waldner et al. |
| 7,313,515 B2 | 12/2007 | Crouch et al. |
| 7,319,378 B1 | 1/2008 | Thompson et al. |
| 7,319,876 B2 | 1/2008 | Jha et al. |
| 7,330,101 B2 | 2/2008 | Sekura |
| 7,335,106 B2 | 2/2008 | Johnson |
| 7,345,574 B2 | 3/2008 | Fitzgibbon |
| 7,346,523 B1 | 3/2008 | Provost et al. |
| 7,346,555 B2 | 3/2008 | Rippingale et al. |
| 7,346,642 B1 | 3/2008 | Briggs et al. |
| 7,366,571 B2 | 4/2008 | Armstrong |
| 7,369,476 B2 | 5/2008 | Kravtchenko et al. |
| 7,370,069 B2 | 5/2008 | Chambers et al. |
| 7,373,318 B2 | 5/2008 | Kutsumi et al. |
| 7,373,342 B2 | 5/2008 | Cragun et al. |
| 7,376,700 B1 | 5/2008 | Clark et al. |
| 7,385,516 B2 | 6/2008 | Contractor |
| 7,386,101 B2 | 6/2008 | Pugliese |
| 7,389,245 B1 | 6/2008 | Ashford et al. |
| 7,394,011 B2 | 7/2008 | Huffman |
| 7,395,214 B2 | 7/2008 | Shillingburg |
| 7,395,216 B2 | 7/2008 | Rosenfeld et al. |
| 7,403,656 B2 | 7/2008 | Koga |
| 7,415,414 B2 | 8/2008 | Azara et al. |
| 7,417,205 B2 | 8/2008 | Faries, Jr. et al. |
| 7,433,827 B2 | 10/2008 | Rosenfeld et al. |
| 7,433,834 B2 | 10/2008 | Joao |
| 7,438,072 B2 | 10/2008 | Izuchukwu |
| 7,443,787 B2 | 10/2008 | Karino et al. |
| 7,444,291 B1 | 10/2008 | Prasad et al. |
| 7,454,067 B1 | 11/2008 | Pati |
| 7,454,299 B2 | 11/2008 | Bolz |
| 7,460,052 B2 | 12/2008 | Zemany et al. |
| 7,461,000 B2 | 12/2008 | Davis et al. |
| 7,464,043 B1 | 12/2008 | Dussia |
| 7,465,551 B2 | 12/2008 | Blumenthal et al. |
| 7,469,155 B2 | 12/2008 | Chu |
| 7,481,370 B2 | 1/2009 | Davis et al. |
| 7,483,721 B1 | 1/2009 | Vesikivi |
| 7,484,048 B2 | 1/2009 | Whitehouse |
| 7,485,095 B2 | 2/2009 | Shusterman |
| 7,487,114 B2 | 2/2009 | Florance et al. |
| 7,487,774 B2 | 2/2009 | Acker |
| 7,488,291 B2 | 2/2009 | Cho et al. |
| 7,490,048 B2 | 2/2009 | Joao |
| 7,493,281 B2 | 2/2009 | Vogel et al. |
| 7,508,298 B2 | 3/2009 | Pisz et al. |
| 7,511,260 B2 | 3/2009 | Sannomiya et al. |
| 7,525,425 B2 | 4/2009 | Diem |
| 7,526,123 B2 | 4/2009 | Moon et al. |
| 7,529,214 B2 | 5/2009 | Omae et al. |
| 7,533,353 B2 | 5/2009 | Dvorak et al. |
| 7,536,301 B2 | 5/2009 | Jaklitsch et al. |
| 7,536,360 B2 | 5/2009 | Stolfo et al. |
| 7,539,500 B2 | 5/2009 | Chiang |
| 7,539,656 B2 | 5/2009 | Fratkina et al. |
| 7,545,257 B2 | 6/2009 | Brue |
| 7,546,524 B1 | 6/2009 | Bryar et al. |
| 7,548,158 B2 | 6/2009 | Titus et al. |
| 7,552,039 B2 | 6/2009 | Dodds |
| 7,555,159 B2 | 6/2009 | Pishva |
| 7,555,444 B1 | 6/2009 | Wilson et al. |
| 7,557,728 B1 | 7/2009 | Bicheno et al. |
| 7,558,961 B2 | 7/2009 | Sharma et al. |
| 7,573,369 B2 | 8/2009 | Hayles, Jr. et al. |
| 7,580,832 B2 | 8/2009 | Allamanche et al. |
| 7,580,952 B2 | 8/2009 | Logan et al. |
| 7,587,369 B2 | 9/2009 | Ginter et al. |
| 7,590,275 B2 | 9/2009 | Clarke et al. |
| 7,590,547 B2 | 9/2009 | Lagadec et al. |
| 7,592,859 B2 | 9/2009 | Hastings |
| 7,599,892 B1 | 10/2009 | Berger et al. |
| 7,605,688 B1 | 10/2009 | Seah |
| 7,610,556 B2 | 10/2009 | Guo et al. |
| 7,613,620 B2 | 11/2009 | Salwan |
| 7,616,594 B2 | 11/2009 | Roberts et al. |
| 7,617,162 B2 | 11/2009 | Saini |
| 7,624,027 B1 | 11/2009 | Stern et al. |
| 7,624,051 B2 | 11/2009 | Gellman |
| 7,624,447 B1 | 11/2009 | Horowitz et al. |
| 7,627,334 B2 | 12/2009 | Cohen et al. |
| 7,627,577 B1 | 12/2009 | Lee et al. |
| 7,630,544 B1 | 12/2009 | Zhou |
| 7,630,762 B2 | 12/2009 | Sullivan et al. |
| 7,630,913 B2 | 12/2009 | Kay |
| 7,635,846 B2 | 12/2009 | Chi et al. |
| 7,639,396 B2 | 12/2009 | Bezryadin |
| 7,640,175 B1 | 12/2009 | Prasad et al. |
| 7,643,465 B2 | 1/2010 | Lorek et al. |
| 7,643,828 B2 | 1/2010 | Malladi et al. |
| 7,644,055 B2 | 1/2010 | Furst et al. |
| 7,647,049 B2 | 1/2010 | Engdahl et al. |
| 7,650,321 B2 | 1/2010 | Krishnan et al. |
| 7,650,811 B2 | 1/2010 | Matsui et al. |
| 7,653,457 B2 | 1/2010 | Bloom |
| 7,653,594 B2 | 1/2010 | Davis |
| 7,664,339 B2 | 2/2010 | Turski |
| 7,664,659 B2 | 2/2010 | Lancaster et al. |
| 7,668,647 B2 | 2/2010 | Barber et al. |
| 7,668,747 B2 | 2/2010 | Murphy et al. |
| 7,668,843 B2 | 2/2010 | Ertoz et al. |
| 7,671,795 B2 | 3/2010 | Rofougaran |
| 7,680,260 B2 | 3/2010 | Abramson et al. |
| 7,681,231 B2 | 3/2010 | Combs et al. |
| 7,682,025 B2 | 3/2010 | Sur et al. |
| 7,689,705 B1 | 3/2010 | Lester et al. |
| 7,693,653 B2 | 4/2010 | Hussain et al. |
| 7,696,751 B2 | 4/2010 | Molyneaux et al. |
| 7,698,154 B2 | 4/2010 | Marchosky |
| 7,703,691 B2 | 4/2010 | Patel et al. |
| 7,706,034 B2 | 4/2010 | Monga et al. |
| 7,706,068 B2 | 4/2010 | Takaaki |
| 7,707,044 B2 | 4/2010 | Graves et al. |
| 7,707,047 B2 | 4/2010 | Hasan et al. |
| 7,707,624 B2 | 4/2010 | Tomkow |
| 7,715,659 B2 | 5/2010 | Zhao et al. |
| 7,716,072 B1 | 5/2010 | Green, Jr. et al. |
| 7,716,378 B2 | 5/2010 | Chen et al. |
| 7,725,253 B2 | 5/2010 | Foxlin |
| 7,730,005 B2 | 6/2010 | Gilliam et al. |
| 7,739,115 B1 | 6/2010 | Pettay et al. |
| 7,739,126 B1 | 6/2010 | Cave et al. |
| 7,742,193 B2 | 6/2010 | Kaltenbach et al. |
| 7,743,099 B2 | 6/2010 | Szeto |
| 7,752,058 B2 | 7/2010 | Sasaki et al. |
| 7,753,091 B2 | 7/2010 | Ozanne et al. |
| 7,775,329 B2 | 8/2010 | Eckenstein et al. |
| 7,778,483 B2 | 8/2010 | Messina et al. |
| 7,778,752 B1 | 8/2010 | Hunt et al. |
| 7,778,792 B2 | 8/2010 | Huang et al. |
| 7,778,816 B2 | 8/2010 | Reynar |
| 7,783,023 B2 | 8/2010 | Balk et al. |
| 7,783,379 B2 | 8/2010 | Beane et al. |
| 7,787,692 B2 | 8/2010 | Noguchi et al. |
| 7,787,693 B2 | 8/2010 | Siegemund |
| 7,793,835 B1 | 9/2010 | Coggeshall et al. |
| 7,797,145 B2 | 9/2010 | Dodds |
| 7,805,318 B1 | 9/2010 | Kuhn |
| 7,809,192 B2 | 10/2010 | Gokturk et al. |
| 7,809,378 B2 | 10/2010 | Contractor |
| 7,809,559 B2 | 10/2010 | Kushner et al. |
| 7,813,481 B1 | 10/2010 | Hursey et al. |
| 7,826,310 B2 | 11/2010 | Unkrich |
| 7,826,965 B2 | 11/2010 | Sadri et al. |
| 7,827,043 B2 | 11/2010 | Tahan |
| 7,827,234 B2 | 11/2010 | Eisenberger et al. |
| 7,828,554 B2 | 11/2010 | Fustolo |
| 7,831,559 B1 | 11/2010 | Mohan et al. |
| 7,835,506 B2 | 11/2010 | Groff et al. |
| 7,836,073 B2 | 11/2010 | Ahn |
| 7,844,363 B1 | 11/2010 | Mehdizadeh |
| 7,844,470 B2 | 11/2010 | Portnoy et al. |

(56) References Cited

U.S. PATENT DOCUMENTS

| | | | |
|---|---|---|---|
| 7,844,837 | B2 | 11/2010 | Youssef |
| 7,847,970 | B1 | 12/2010 | McGrady |
| 7,847,989 | B2 | 12/2010 | Blonde et al. |
| 7,849,398 | B2 | 12/2010 | Dabet et al. |
| 7,853,586 | B1 | 12/2010 | Patel et al. |
| 7,853,626 | B2 | 12/2010 | Jung et al. |
| 7,856,137 | B2 | 12/2010 | Yonezawa et al. |
| 7,856,142 | B2 | 12/2010 | Ferman et al. |
| 7,856,289 | B2 | 12/2010 | Schanin et al. |
| 7,860,281 | B2 | 12/2010 | Pfister et al. |
| 7,860,552 | B2 | 12/2010 | Borsook et al. |
| 7,860,732 | B2 | 12/2010 | Elizabeth et al. |
| 7,860,935 | B2 | 12/2010 | Lee et al. |
| 7,865,171 | B2 | 1/2011 | Karlsson |
| 7,865,566 | B2 | 1/2011 | Ashtekar et al. |
| 7,869,807 | B2 | 1/2011 | Shimizu |
| 7,873,189 | B2 | 1/2011 | Jee et al. |
| 7,885,687 | B2 | 2/2011 | Serceki et al. |
| 7,887,493 | B2 | 2/2011 | Stahmann et al. |
| 7,890,622 | B2 | 2/2011 | Coca et al. |
| 7,894,448 | B1 | 2/2011 | Lillibridge et al. |
| 7,894,812 | B1 | 2/2011 | Durig et al. |
| 7,898,423 | B2 | 3/2011 | Cavanaugh |
| 7,898,995 | B2 | 3/2011 | Shahidi et al. |
| 7,899,677 | B2 | 3/2011 | Kuo et al. |
| 7,899,739 | B2 | 3/2011 | Allin et al. |
| 7,899,764 | B2 | 3/2011 | Martin et al. |
| 7,903,880 | B2 | 3/2011 | Wyatt et al. |
| 7,903,905 | B2 | 3/2011 | Lapstun et al. |
| 7,908,518 | B2 | 3/2011 | West, Jr. et al. |
| 7,911,482 | B1 | 3/2011 | Mariano et al. |
| 7,912,201 | B2 | 3/2011 | Martin et al. |
| 7,912,288 | B2 | 3/2011 | Winn et al. |
| 7,913,162 | B2 | 3/2011 | Hansen et al. |
| 7,916,137 | B2 | 3/2011 | Pearman et al. |
| 7,916,707 | B2 | 3/2011 | Fontaine |
| 7,917,377 | B2 | 3/2011 | Rao et al. |
| 7,921,088 | B1 | 4/2011 | Mittal |
| 7,924,149 | B2 | 4/2011 | Mendelson |
| 7,925,058 | B2 | 4/2011 | Lee et al. |
| 7,929,950 | B1 | 4/2011 | Rao et al. |
| 7,932,830 | B2 | 4/2011 | Campero et al. |
| 7,932,837 | B2 | 4/2011 | Giesa et al. |
| 7,935,055 | B2 | 5/2011 | Burckhardt |
| 7,940,602 | B1 | 5/2011 | Korolenko |
| 7,940,744 | B2 | 5/2011 | Lehotsky et al. |
| 7,940,982 | B1 | 5/2011 | Shaick |
| 7,941,009 | B2 | 5/2011 | Li et al. |
| 7,941,124 | B2 | 5/2011 | Adamczyk et al. |
| 7,941,505 | B2 | 5/2011 | Jaye |
| 7,942,817 | B2 | 5/2011 | Zhang et al. |
| 7,949,191 | B1 | 5/2011 | Ramkumar et al. |
| 7,949,643 | B2 | 5/2011 | Kawale et al. |
| 7,957,966 | B2 | 6/2011 | Takeuchi |
| 7,959,568 | B2 | 6/2011 | Stahmann et al. |
| 7,962,283 | B2 | 6/2011 | Zhang et al. |
| 7,962,350 | B1 | 6/2011 | Provost et al. |
| 7,962,359 | B2 | 6/2011 | Montoya |
| 7,966,532 | B2 | 6/2011 | Bottelli et al. |
| 7,967,141 | B2 | 6/2011 | Witczak |
| 7,969,143 | B2 | 6/2011 | Gilboa |
| 7,970,552 | B1 | 6/2011 | Stefanon et al. |
| 7,970,660 | B2 | 6/2011 | Bezos et al. |
| 7,972,274 | B2 | 7/2011 | Bardy |
| 7,973,820 | B2 | 7/2011 | Ohara et al. |
| 7,975,913 | B2 | 7/2011 | Kubota et al. |
| 7,976,171 | B2 | 7/2011 | Kameoka et al. |
| 7,978,639 | B2 | 7/2011 | Maltseff et al. |
| 7,979,086 | B1 | 7/2011 | Jones et al. |
| 7,979,286 | B2 | 7/2011 | Manning et al. |
| 7,979,289 | B2 | 7/2011 | Callas |
| 7,979,585 | B2 | 7/2011 | Chen et al. |
| 7,983,611 | B2 | 7/2011 | Rao |
| 7,983,677 | B2 | 7/2011 | Dacosta |
| 7,986,237 | B2 | 7/2011 | Jung |
| 7,986,828 | B2 | 7/2011 | Rao et al. |
| 7,986,940 | B2 | 7/2011 | Lee et al. |
| 7,988,043 | B2 | 8/2011 | Davis |
| 7,991,485 | B2 | 8/2011 | Zakim |
| 7,996,074 | B2 | 8/2011 | KenKnight et al. |
| 7,996,519 | B1 | 8/2011 | Brown et al. |
| 8,000,528 | B2 | 8/2011 | Ming et al. |
| 8,000,723 | B2 | 8/2011 | Pande et al. |
| 8,000,892 | B2 | 8/2011 | Banerjee |
| 8,000,979 | B2 | 8/2011 | Blom |
| 8,002,144 | B2 | 8/2011 | Percy |
| 8,005,263 | B2 | 8/2011 | Fujimura et al. |
| 8,005,488 | B2 | 8/2011 | Staffaroni et al. |
| 8,005,672 | B2 | 8/2011 | Vierthaler et al. |
| 8,005,685 | B1 | 8/2011 | Bird |
| 8,005,687 | B1 | 8/2011 | Pederson et al. |
| 8,005,875 | B2 | 8/2011 | Hickey et al. |
| 8,008,285 | B2 | 8/2011 | Roberts et al. |
| 8,010,126 | B2 | 8/2011 | Moton, Jr. et al. |
| 8,010,664 | B2 | 8/2011 | Firminger et al. |
| 8,014,562 | B2 | 9/2011 | Rhoads et al. |
| 8,015,006 | B2 | 9/2011 | Kennewick et al. |
| 8,019,168 | B2 | 9/2011 | Hanami |
| 8,023,485 | B2 | 9/2011 | Shi et al. |
| 8,024,179 | B2 | 9/2011 | Pulz et al. |
| 8,026,850 | B2 | 9/2011 | Seong et al. |
| 8,027,784 | B2 | 9/2011 | Geelen |
| 8,032,399 | B2 | 10/2011 | Brown |
| 8,036,735 | B2 | 10/2011 | Cazares et al. |
| 8,039,093 | B2 | 10/2011 | Leenders et al. |
| 8,041,017 | B2 | 10/2011 | Goldman et al. |
| 8,041,454 | B2 | 10/2011 | Blust et al. |
| 8,041,570 | B2 | 10/2011 | Mirkovic et al. |
| 8,044,798 | B2 | 10/2011 | Icove et al. |
| 8,045,693 | B2 | 10/2011 | Yao |
| 8,045,805 | B2 | 10/2011 | Ramsay et al. |
| 8,045,929 | B2 | 10/2011 | Twitchell, Jr. |
| 8,046,371 | B2 | 10/2011 | O'Clair et al. |
| 8,049,597 | B1 | 11/2011 | Murakami et al. |
| 8,055,240 | B2 | 11/2011 | Kim |
| 8,056,118 | B2 | 11/2011 | Piliouras |
| 8,060,562 | B2 | 11/2011 | Chesley |
| 8,061,592 | B1 | 11/2011 | Clem et al. |
| 8,064,884 | B2 | 11/2011 | Wu et al. |
| 8,065,162 | B1 | 11/2011 | Curry |
| 8,065,250 | B2 | 11/2011 | Stephens |
| 8,065,347 | B1 | 11/2011 | DeMeyer et al. |
| 8,065,669 | B2 | 11/2011 | Donovan et al. |
| 8,068,008 | B2 | 11/2011 | Connell, II et al. |
| 8,068,603 | B2 | 11/2011 | Conrad et al. |
| 8,068,917 | B2 | 11/2011 | Petersen et al. |
| 8,068,933 | B2 | 11/2011 | Walker et al. |
| 8,069,080 | B2 | 11/2011 | Rastogi |
| 8,069,213 | B2 | 11/2011 | Bloch et al. |
| 8,069,236 | B2 | 11/2011 | Agraharam et al. |
| 8,070,739 | B2 | 12/2011 | Zinger et al. |
| 8,072,310 | B1 | 12/2011 | Everhart |
| 8,073,013 | B2 | 12/2011 | Coleman et al. |
| 8,073,711 | B1 | 12/2011 | McCollum et al. |
| 8,074,007 | B2 | 12/2011 | James |
| 8,078,606 | B2 | 12/2011 | Slackman |
| 8,082,122 | B2 | 12/2011 | No et al. |
| 8,083,406 | B2 | 12/2011 | Bowers et al. |
| 8,140,592 | B2 | 3/2012 | Scott et al. |
| 8,155,811 | B2 | 4/2012 | Noffsinger et al. |
| 8,188,880 | B1 | 5/2012 | Chi et al. |
| 8,203,640 | B2 | 6/2012 | Kim et al. |
| 8,255,147 | B2 | 8/2012 | Roberts et al. |
| 8,259,169 | B2 | 9/2012 | Sugio et al. |
| 8,290,701 | B2 | 10/2012 | Mason et al. |
| 8,295,556 | B2 | 10/2012 | Ohtani et al. |
| 8,392,212 | B2 | 3/2013 | Beraja et al. |
| 8,462,231 | B2 | 6/2013 | Nusbaum |
| 8,510,133 | B2 | 8/2013 | Peak et al. |
| 8,662,388 | B2 | 3/2014 | Belkin |
| 8,694,334 | B2 | 4/2014 | Ryan et al. |
| 8,700,423 | B2 | 4/2014 | Eaton, Jr. et al. |
| 8,744,876 | B2 | 6/2014 | Gross |
| 8,786,402 | B2 | 7/2014 | Barnes |

(56) References Cited

U.S. PATENT DOCUMENTS

| | | |
|---|---|---|
| 2002/0032583 A1* | 3/2002 | Joao .................. G06F 19/322 705/2 |
| 2002/0044043 A1 | 4/2002 | Chaco et al. |
| 2002/0169635 A1 | 11/2002 | Shillingburg |
| 2003/0036683 A1 | 2/2003 | Kehr et al. |
| 2003/0055685 A1* | 3/2003 | Cobb .................. A61M 5/172 705/3 |
| 2003/0212060 A1 | 11/2003 | Tollefson |
| 2003/0212314 A1 | 11/2003 | Takahashi et al. |
| 2004/0133463 A1 | 7/2004 | Benderev |
| 2004/0137539 A1 | 7/2004 | Bradford |
| 2004/0138724 A1 | 7/2004 | Sieracki et al. |
| 2005/0065815 A1 | 3/2005 | Mazar et al. |
| 2005/0102159 A1 | 5/2005 | Mondshine |
| 2006/0004606 A1 | 1/2006 | Wendl |
| 2006/0006999 A1 | 1/2006 | Walczyk et al. |
| 2006/0106646 A1* | 5/2006 | Squilla ................ G06F 19/322 705/3 |
| 2006/0122864 A1 | 6/2006 | Gottesman et al. |
| 2006/0149591 A1 | 7/2006 | Hanf et al. |
| 2006/0161457 A1 | 7/2006 | Rapaport et al. |
| 2006/0181243 A1 | 8/2006 | Graves et al. |
| 2006/0218011 A1 | 9/2006 | Walker et al. |
| 2006/0224419 A1 | 10/2006 | Servizio et al. |
| 2006/0285441 A1 | 12/2006 | Walker et al. |
| 2007/0016443 A1 | 1/2007 | Wachman et al. |
| 2007/0016447 A1 | 1/2007 | Brown |
| 2007/0046476 A1 | 3/2007 | Hinkamp |
| 2007/0179356 A1 | 8/2007 | Wessel |
| 2007/0225350 A1 | 9/2007 | Anderson et al. |
| 2007/0226012 A1 | 9/2007 | Salgado et al. |
| 2008/0045806 A1 | 2/2008 | Keppler |
| 2008/0103369 A1 | 5/2008 | Fabius et al. |
| 2008/0147953 A1 | 6/2008 | Lawandus |
| 2008/0149701 A1 | 6/2008 | Lane |
| 2008/0176655 A1 | 7/2008 | James |
| 2008/0303638 A1 | 12/2008 | Nguyen |
| 2008/0306759 A1 | 12/2008 | Ilkin et al. |
| 2009/0047645 A1 | 2/2009 | Dibenedetto et al. |
| 2009/0112770 A1 | 4/2009 | Schmidt |
| 2009/0119124 A1 | 5/2009 | Kambaloor |
| 2009/0125324 A1 | 5/2009 | Keravich et al. |
| 2009/0136094 A1 | 5/2009 | Driver et al. |
| 2009/0206992 A1 | 8/2009 | Giobbi et al. |
| 2009/0281825 A1* | 11/2009 | Larsen .................. G06Q 10/10 705/2 |
| 2010/0054601 A1 | 3/2010 | Anbalagan et al. |
| 2010/0089936 A1 | 4/2010 | Luciano et al. |
| 2010/0138232 A1 | 6/2010 | Ryan et al. |
| 2010/0145736 A1 | 6/2010 | Rohwer |
| 2010/0161353 A1 | 6/2010 | Mayaud |
| 2010/0205008 A1 | 8/2010 | Hua et al. |
| 2010/0211531 A1 | 8/2010 | Roberts et al. |
| 2010/0217623 A1* | 8/2010 | Schoenberg ...... G06F 17/30286 705/3 |
| 2010/0262430 A1 | 10/2010 | Gips et al. |
| 2010/0268303 A1 | 10/2010 | Mitchell et al. |
| 2010/0286490 A1 | 11/2010 | Koverzin |
| 2010/0306168 A1 | 12/2010 | Ostad et al. |
| 2010/0315225 A1 | 12/2010 | Teague |
| 2010/0321180 A1* | 12/2010 | Dempsey et al. ...... 340/539.12 |
| 2010/0324936 A1 | 12/2010 | Vishnubhatla et al. |
| 2011/0093296 A1* | 4/2011 | Klink .................. G16H 10/65 705/3 |
| 2011/0118555 A1 | 5/2011 | Dhumne et al. |
| 2011/0130635 A1* | 6/2011 | Ross .................. A61B 5/0816 600/301 |
| 2011/0145012 A1 | 6/2011 | Nightingale et al. |
| 2011/0166885 A1 | 7/2011 | Walker et al. |
| 2011/0213625 A1 | 9/2011 | Joao |
| 2011/0263947 A1 | 10/2011 | Utley |
| 2011/0295622 A1* | 12/2011 | Farooq et al. .................. 705/3 |
| 2011/0295631 A1 | 12/2011 | Kennedy et al. |
| 2011/0313788 A1 | 12/2011 | Amland et al. |
| 2012/0046965 A1 | 2/2012 | Ryan et al. |
| 2012/0072232 A1 | 3/2012 | Frankham et al. |
| 2012/0083715 A1 | 4/2012 | Yuen et al. |
| 2012/0095779 A1 | 4/2012 | Wengrovitz et al. |
| 2012/0129139 A1 | 5/2012 | Partovi |
| 2012/0265544 A1 | 10/2012 | Hwang et al. |
| 2012/0296671 A1 | 11/2012 | Simons-Nikolova et al. |
| 2012/0316896 A1* | 12/2012 | Rahman .............. G06F 19/3418 705/3 |
| 2012/0330684 A1 | 12/2012 | Jacobs |
| 2013/0029768 A1 | 1/2013 | Eichstaedt et al. |

OTHER PUBLICATIONS

U.S. Appl. No. 13/199,051, Hyde et al.
U.S. Appl. No. 13/066,444, Hwang et al.
U.S. Appl. No. 13/066,442, Hwang et al.
Hines, Steve; "Reducing Avoidable Hospital Readmissions"; Florida Hospital Association Meeting; Jun. 4, 2010; 34 pages; Health Research and Educational Trust.
West, Darrell; "Enabling Personalized Medicine through Health Information Technology"; Center for Technology Innovation at Brookings; Jan. 28, 2011; pp. 1-20, plus cover sheet; The Brookings Institution.
Excerpts from Google Search: "touch screen and touch input on image and recognize person in image"; Google Patents Search (as provided by Examiner) (best copy available); bearing a date of Nov. 19, 2015; pp. 1-2; located at: https://www.google.com/search?q=touch+screen+and+touch+input+on+image+and+recognize+person+in+image&biw=1851&bih=1078&source=Int&tbs=pto . . .
Google Search Excerpts: "medical devices and detect communication delay and automatic response and initiating communication"; Google Patents Search (as provided by Examiner) (best copy available); bearing a date of Oct. 13, 2016; 2 pages; located at: https://www.google.com/?tbm+pts#q=medical+devices+and+detect+communication+delay+and+automatic+response+and+initiating+communications&tbs=pt . . .
Google Search Excerpts: "building camera and capture images and person"; Google Patents Search (as provided by Examiner); bearing a date of Feb. 28, 2017; pp. 1-2; Google.
Google Search Excerpts: "selecting a person on an image and verbally validate the person on the image"; Google Patents Search (as provided by Examiner); bearing a date of Feb. 28, 2017; pp. 1-2; Google.
Portable drug dispenser and remote authorization and controlling dispensation; Google patents search; Sep. 8, 2017; pp. 1-2; (as cited by examiner).

* cited by examiner

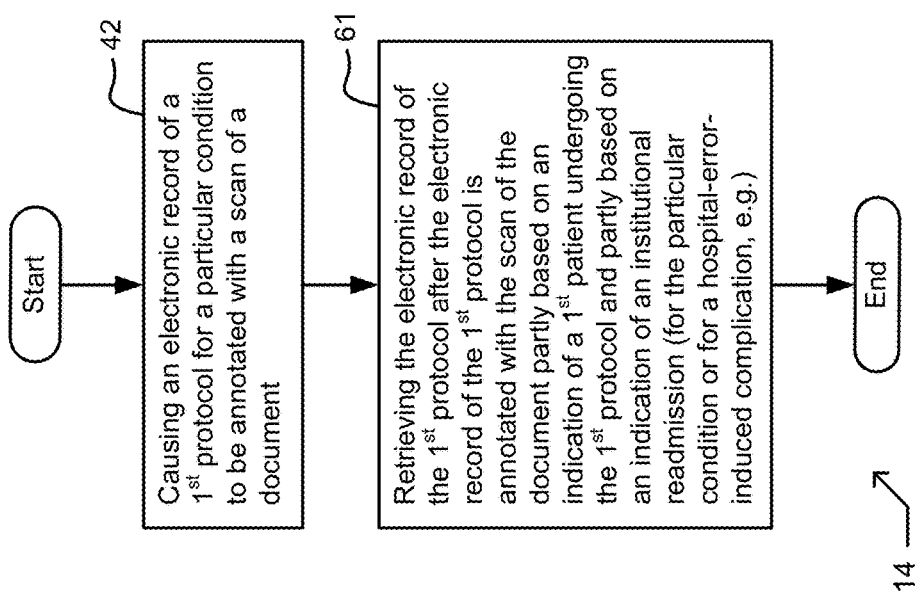
FIG. 14
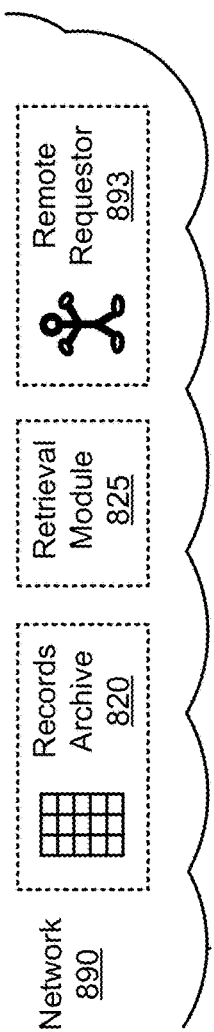
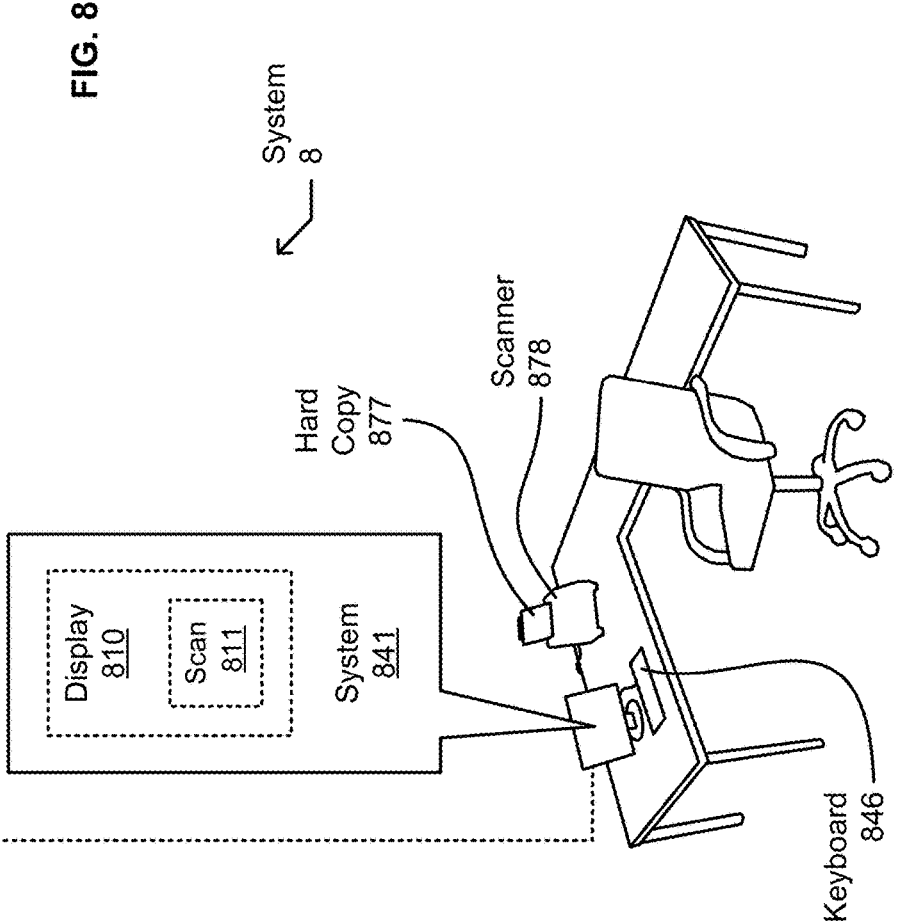
FIG. 8

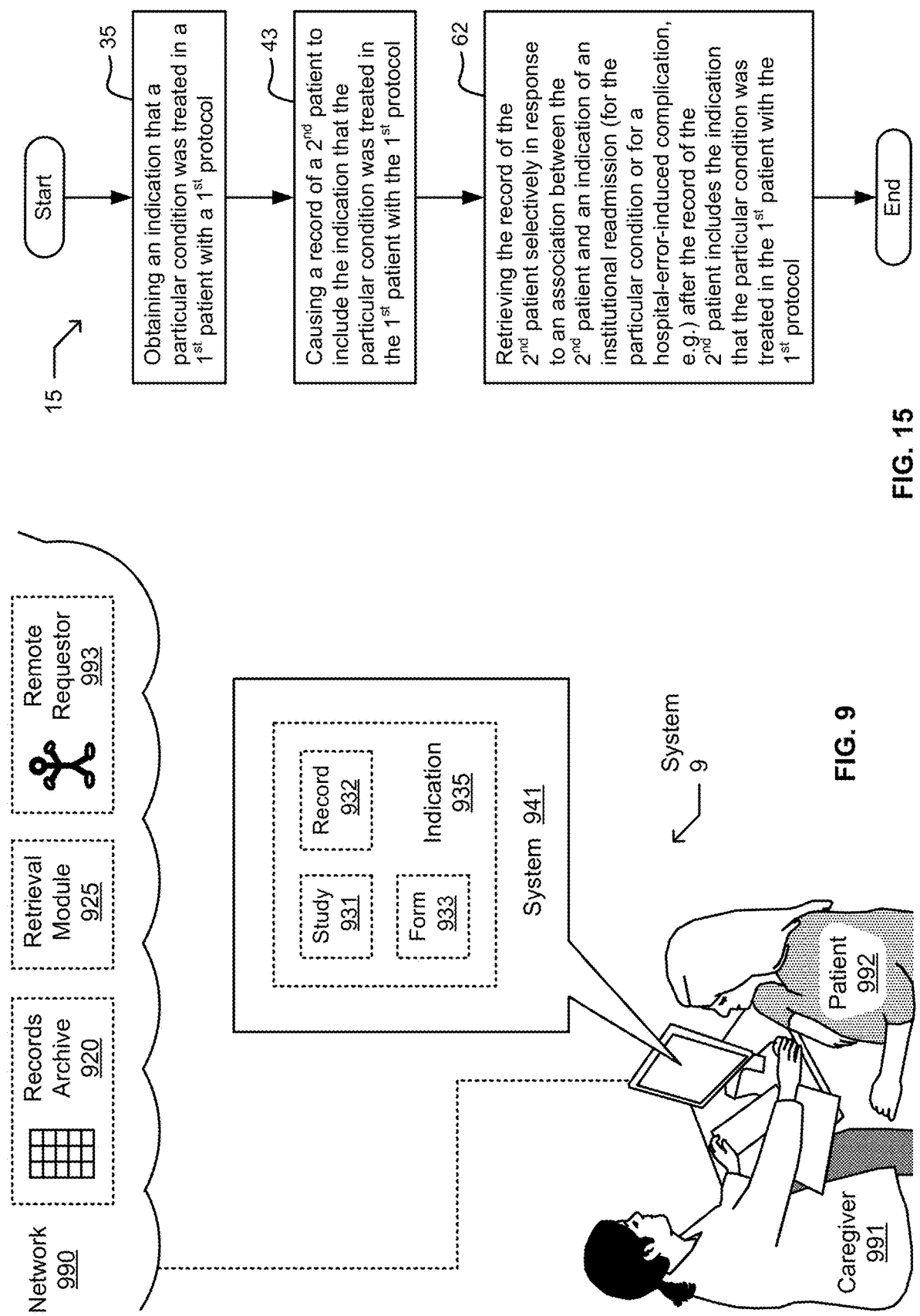

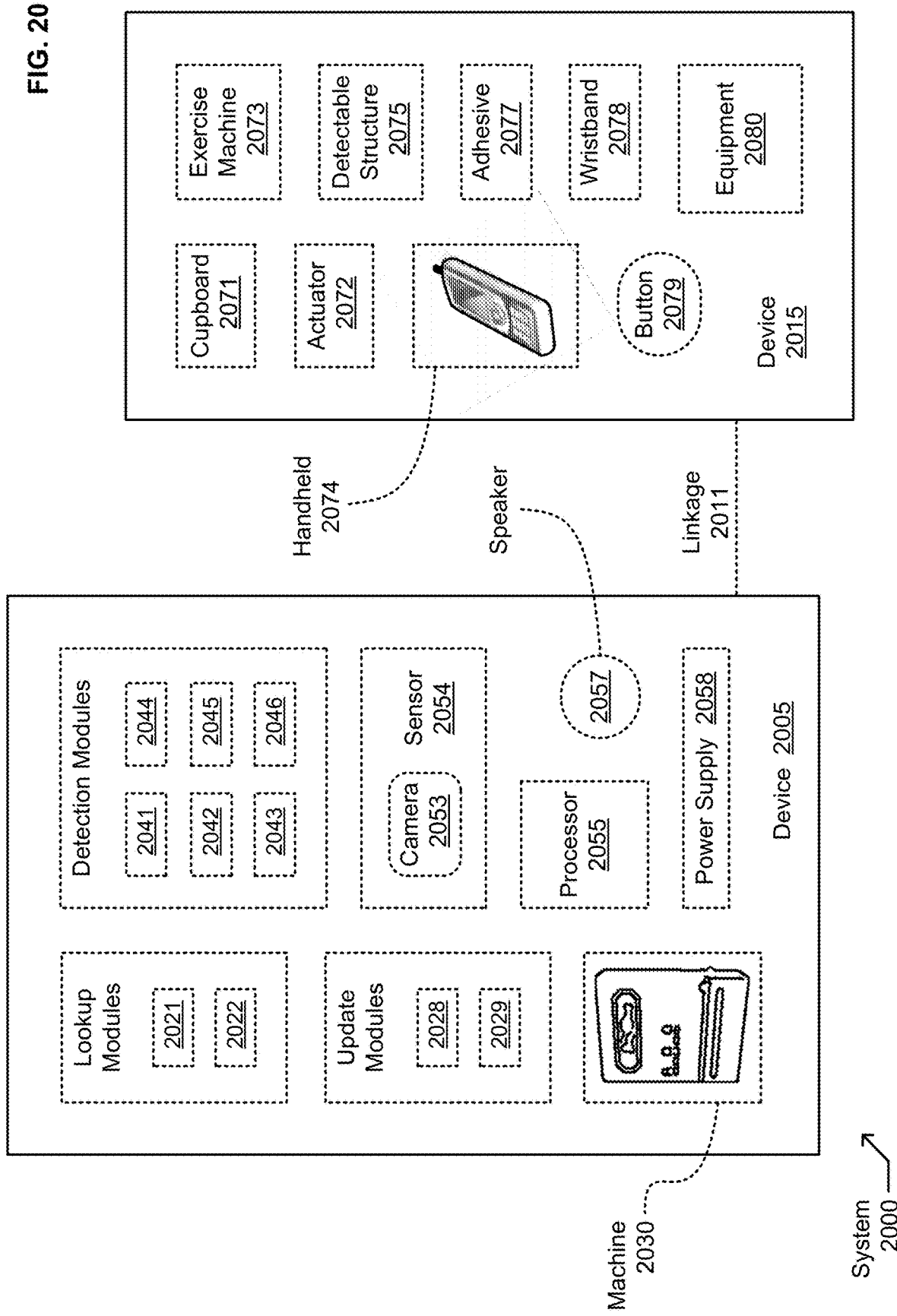

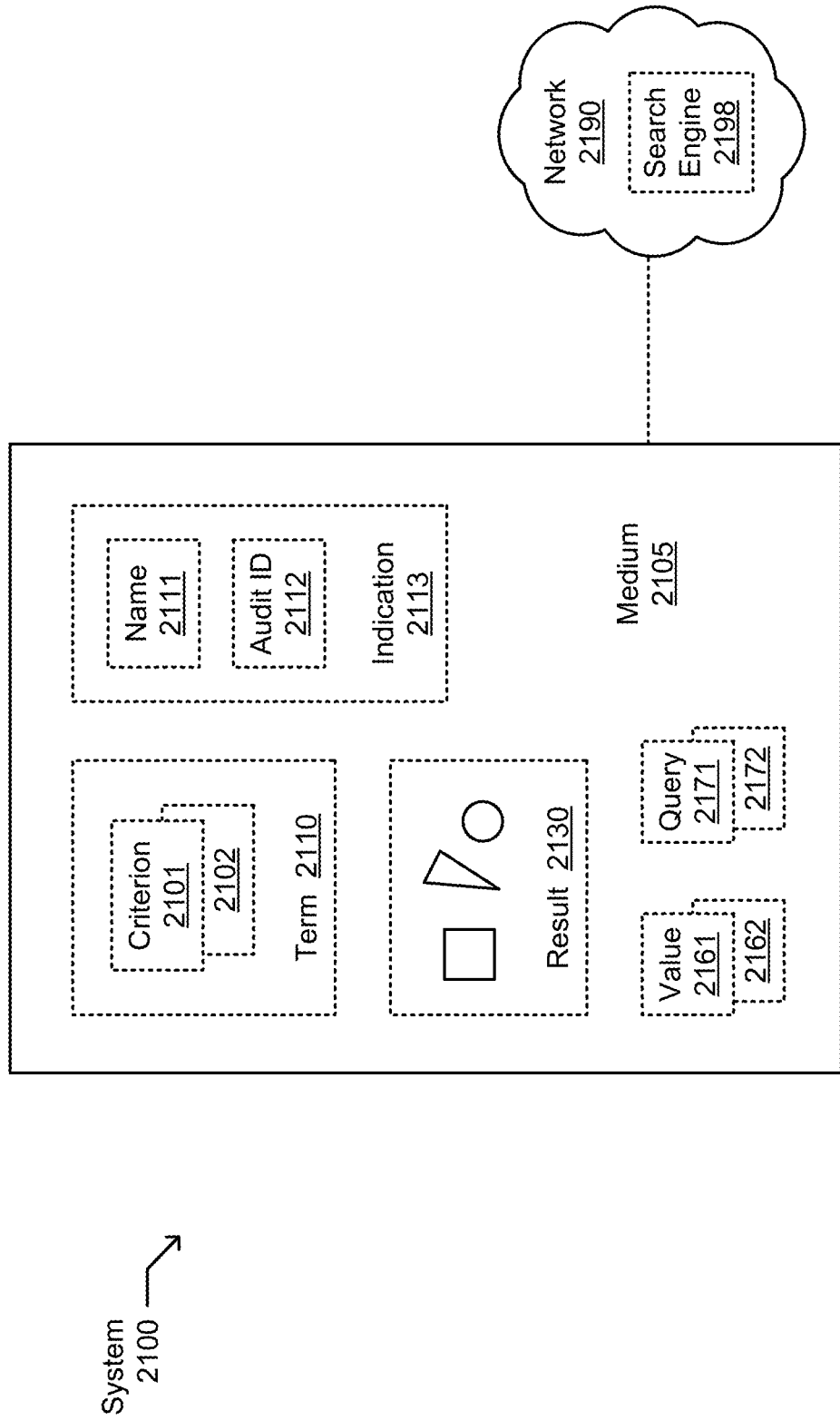

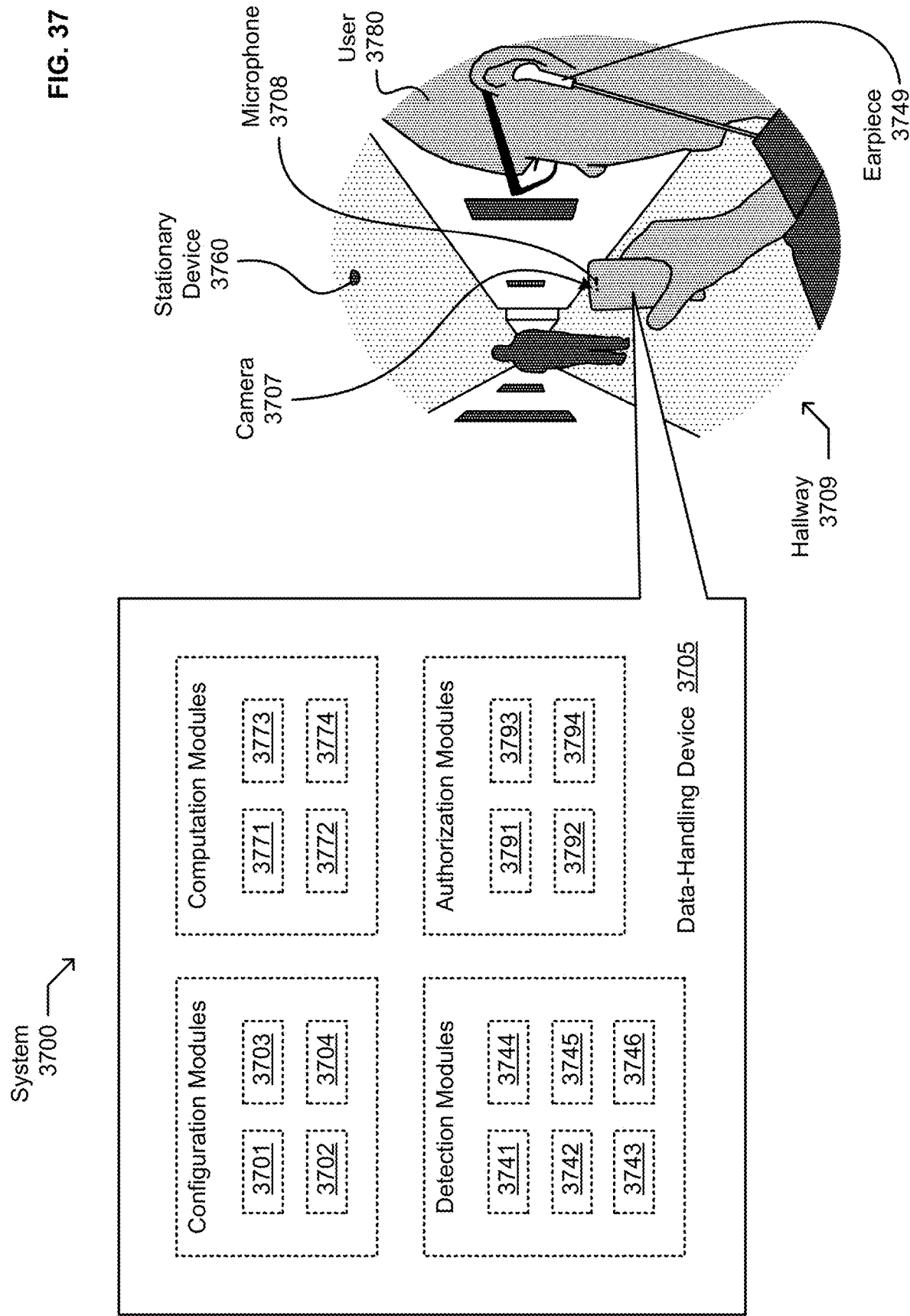

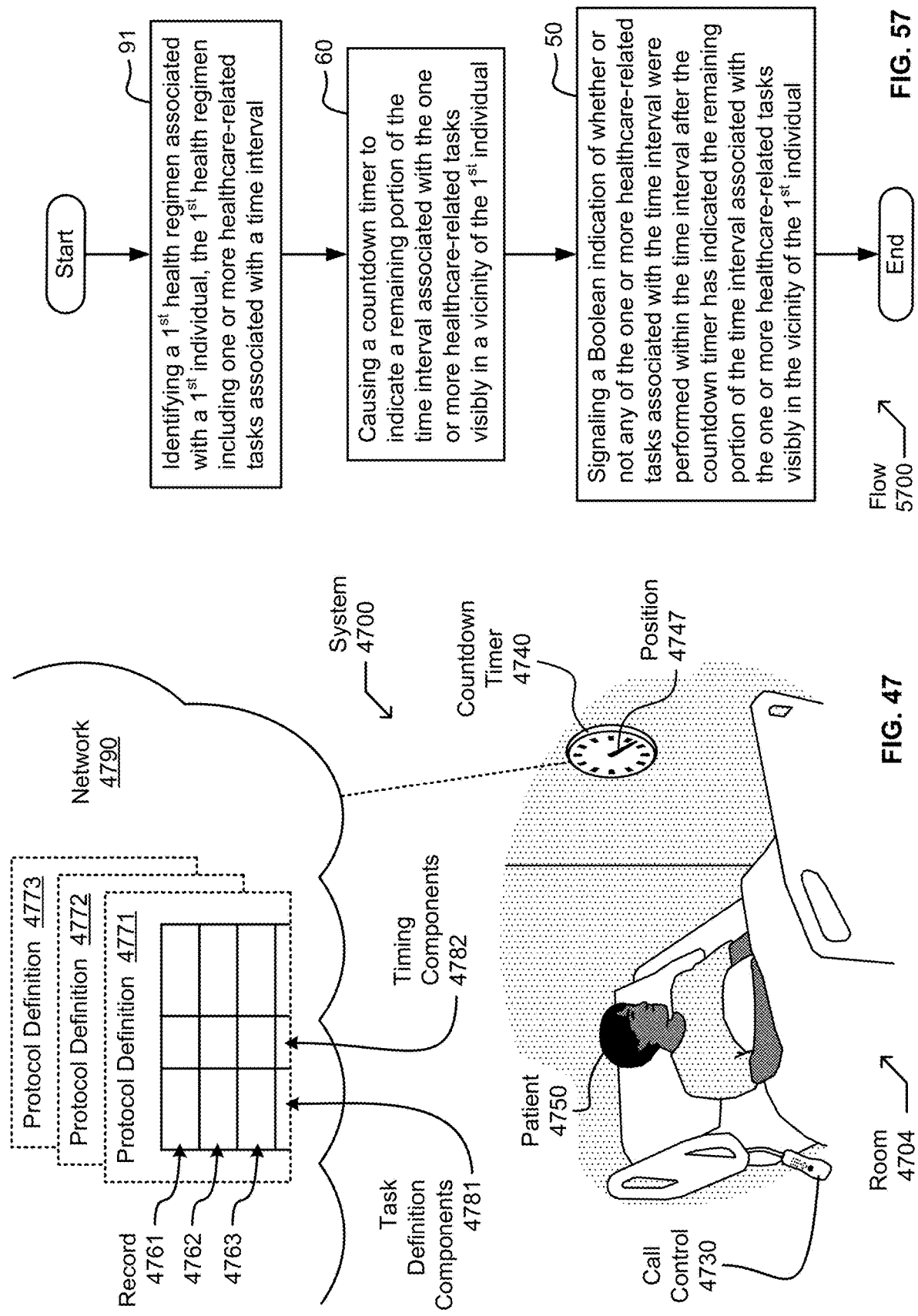

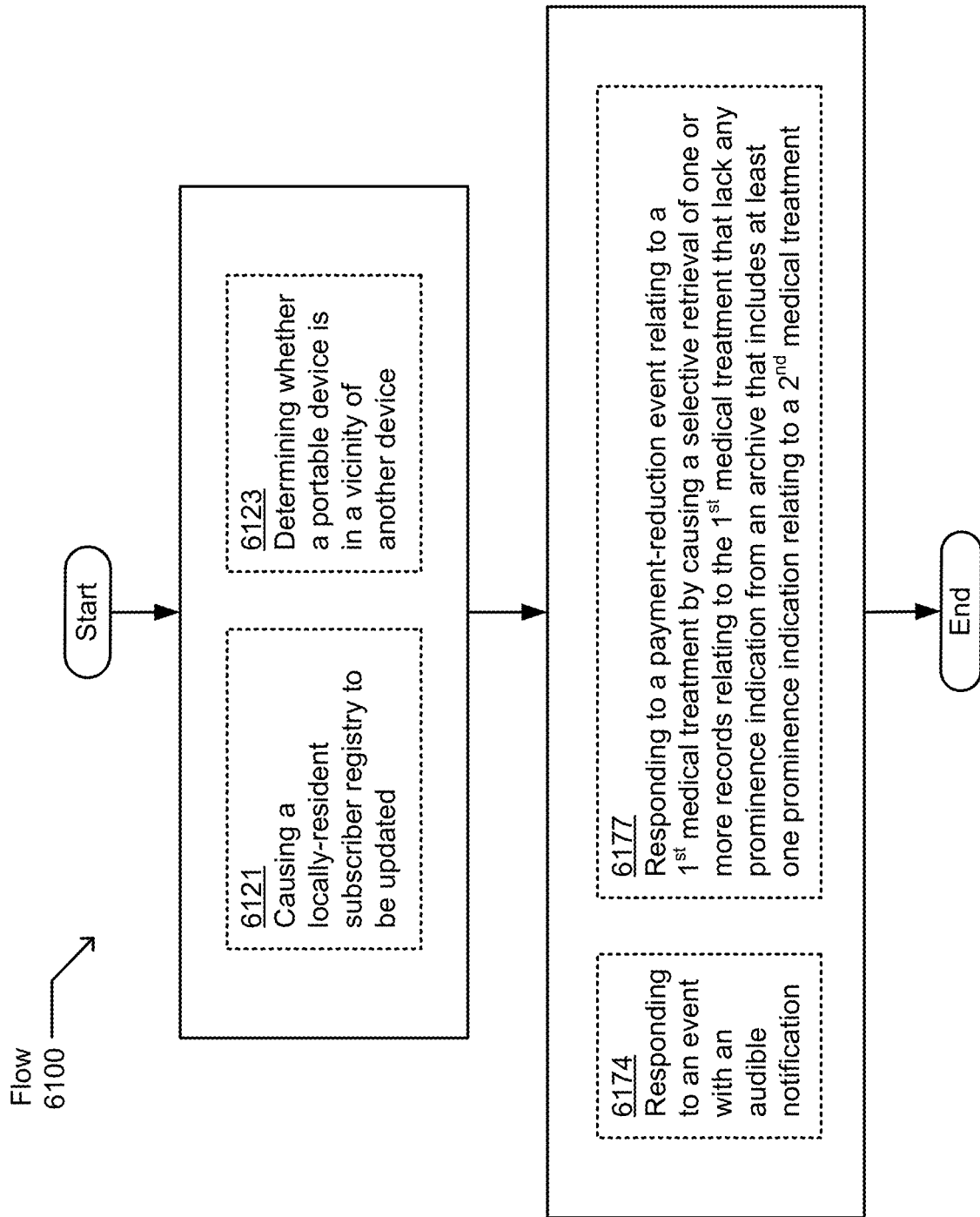

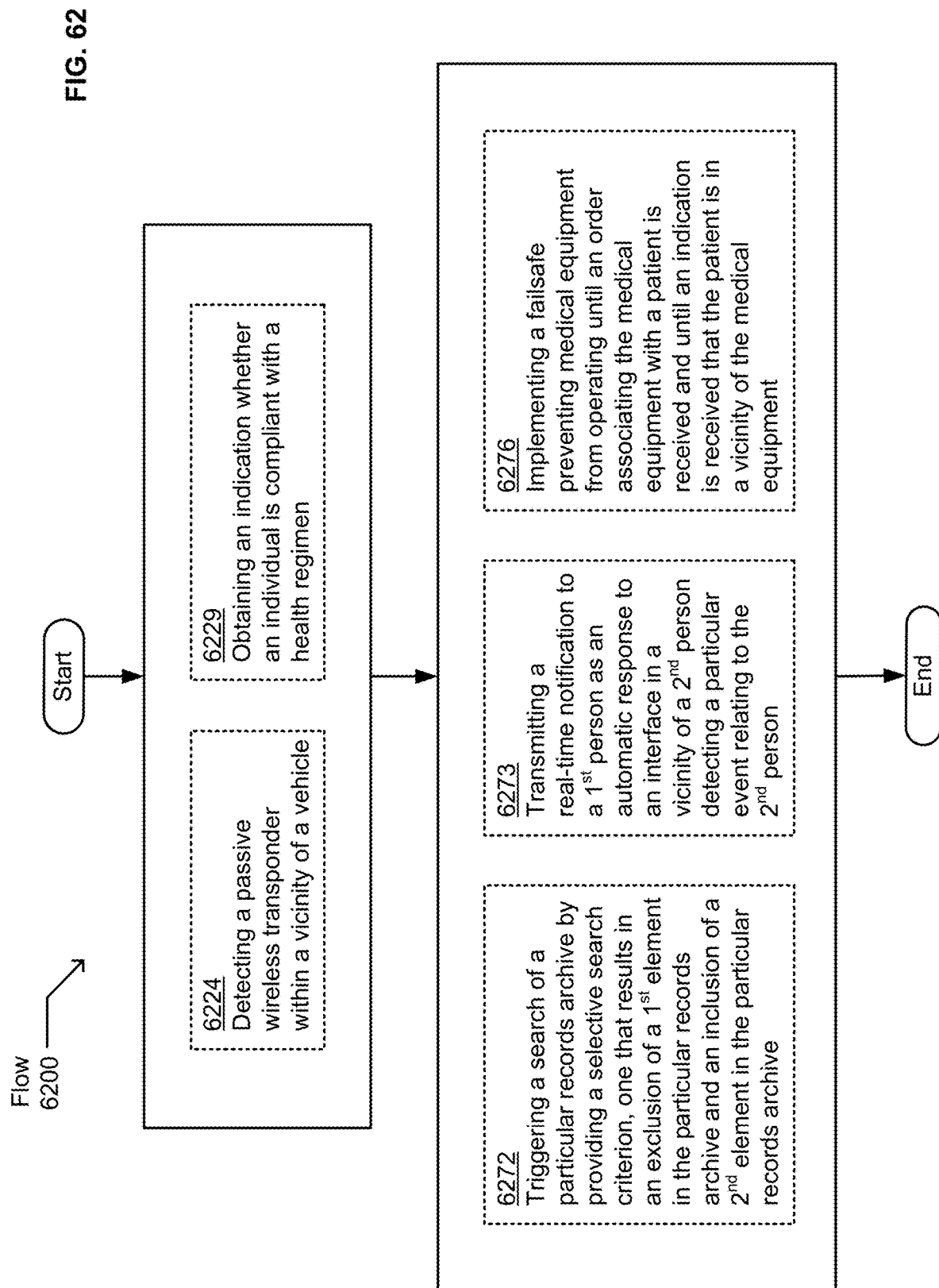

EVIDENCE-BASED HEALTHCARE INFORMATION MANAGEMENT PROTOCOLS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 13/374,519, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 30 Dec. 2011 with, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,747, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012 with, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,750, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012 with, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,745, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012 with, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,744, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012 with, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,748, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012 with, which is currently co-pending or is an application of which a currently co-pending application is entitled to the benefit of the filing date.

RELATED APPLICATIONS

U.S. patent application Ser. No. 13/705,311, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,327, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,338, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,347, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt;

Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,365, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,379, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,390 , entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,402, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

U.S. patent application Ser. No. 13/705,421, entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed on even date herewith, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

TECHNICAL FIELD

This disclosure relates to managing information in an evidence-based medical practice, particularly records of patients and treatments.

SUMMARY

An embodiment provides a method. In one implementation, the method includes but is not limited to causing an electronic record of a first protocol (comprising one or more instances of diagnostic evaluations, regimen implementations, or medical interventions, e.g.) for a particular condition (comprising one or more instances of injuries, complaints, or pathologies, e.g.) to be annotated with a scan of a document and retrieving the electronic record of the first protocol after the electronic record of the first protocol is annotated with the scan of the document partly based on an indication of a first patient undergoing the first protocol and partly based on an indication of an institutional readmission. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for causing an electronic record of a first protocol for a particular condition to be annotated with a scan of a document and circuitry for retrieving the electronic record of the first protocol after the electronic record of the first protocol is annotated with the scan of the document partly based on an indication of a first patient undergoing the first protocol and partly based on an indication of an institutional readmission. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to causing an electronic record of a first protocol for a particular condition to be annotated with a scan of a document and retrieving the electronic record of the first protocol after the electronic record of the first protocol is annotated with the scan of the document partly based on an indication of a first patient undergoing the first protocol and partly based on an indication of an institutional readmission. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for causing an electronic record of a first protocol for a particular condition to be annotated with a scan of a document and retrieving the electronic record of the first protocol after the electronic record of the first protocol is annotated with the scan of the document partly based on an indication of a first patient undergoing the first protocol and partly based on an indication of an institutional readmission. In addition to the foregoing, other system aspects are described in the claims, drawings, and text forming a part of the present disclosure.

An embodiment provides a method. In one implementation, the method includes but is not limited to obtaining an indication that a particular condition was treated in a first patient with a first protocol; causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication that a particular condition was treated in a first patient with a first protocol; circuitry for causing a record of a second patient to include the indication that the particular condition was treated in the first patient with the first protocol; and circuitry for retrieving the record of the second patient selectively in response to an association between the second patient and an indication of an institutional readmission after the record of the second patient includes the indication that the particular condition was treated in the first patient with the first protocol. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication that a particular condition was treated in a first patient with a first protocol; causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication that a particular condition was treated in a first patient with a first protocol; causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol. In addition to the foregoing, other system aspects are described in the claims, drawings, and text forming a part of the present disclosure.

An embodiment provides a method. In one implementation, the method includes but is not limited to obtaining an indication of a first protocol being employed in relation to a particular condition in a first patient; requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication of a first protocol being employed in relation to a particular condition in a first patient; circuitry for requesting an effectiveness indication of the first protocol from an entity partly based on the entity validating the first protocol and partly based on a first communication delay associated with the first protocol, the first communication delay exceeding one hour; and circuitry for signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of a first protocol being employed in relation to a particular condition in a first patient; requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication of a first protocol being employed in relation to a particular condition in a first patient; requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other system aspects are described in the claims, drawings, and text forming a part of the present disclosure.

An embodiment provides a method. In one implementation, the method includes but is not limited to obtaining an association between a particular condition and a first protocol; causing a comparison between a threshold and a prominence indication of treating the particular condition with the first protocol after the association between then particular condition and the first protocol is obtained; and signaling a decision whether to caution a caregiver partly based on the association between the particular condition and the first protocol and partly based on the comparison between the threshold and the prominence indication of treating the particular condition with the first protocol. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an association between a particular condition and a first protocol; circuitry for causing a comparison between a threshold and a prominence indication of treating the particular condition with the first protocol after the association between then particular condition and the first protocol is obtained; and circuitry for signaling a decision whether to caution a caregiver partly based on the association between the particular condition and the first protocol and partly based on the comparison between the threshold and the prominence indication of treating the particular condition with the first protocol. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an association between a particular condition and a first protocol; causing a comparison between a threshold and a prominence indication of treating the particular condition with the first protocol after the association between then particular condition and the first protocol is obtained; and signaling a decision whether to caution a caregiver partly based on the association between the particular condition and the first protocol and partly based on the comparison between the threshold and the prominence indication of treating the particular condition with the first protocol. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an association between a particular condition and a first protocol; causing a comparison between a threshold and a prominence indication of treating the particular condition with the first protocol after the association between then particular condition and the first protocol is obtained; and signaling a decision whether to caution a caregiver partly based on the association between the particular condition and the first protocol and partly based on the comparison between the threshold and the prominence indication of treating the particular condition with the first protocol. In addition to the foregoing, other system aspects are described in the claims, drawings, and text forming a part of the present disclosure.

An embodiment provides a method. In one implementation, the method includes but is not limited to obtaining an association between a care administration space and a first device; obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an association between a care administration space and a first device; circuitry for obtaining via a second device a patient consent conditionally authorizing a release of a first medical record, the second device being a mobile device; and circuitry for causing the first device to receive the first medical record partly based on the second device entering the care administration space and partly based on the patient consent authorizing the release of the first medical record. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an association between a care administration space and a first device; obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an association between a care administration space and a first device; obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record. In addition to the foregoing, other system aspects are described in the claims, drawings, and text forming a part of the present disclosure.

An embodiment provides a method. In one implementation, the method includes but is not limited to obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by a caregiver both being in a single common location; and describes causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by a caregiver both being in a single common location; and describes causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by a caregiver both being in a single common location; and describes causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by a caregiver both being in a single common location; and describes causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other system aspects are described in the claims, drawings, and text forming a part of the present disclosure.

An embodiment provides a method. In one implementation, the method includes but is not limited to obtaining an association between data indicating a current health status of a first individual and a record designator and causing a wearable article at a first care facility to include the data indicating the current health status of the first individual as an automatic and conditional response to local input at the first care facility matching the record designator. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an association between data indicating a current health status of a first individual and a record designator and circuitry for causing a wearable article at a first care facility to include the data indicating the current health status of the first individual as an automatic and conditional response to local input at the first care facility matching the record designator. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an association between data indicating a current health status of a first individual and a record designator and causing a wearable article at a first care facility to include the data indicating the current health status of the first individual as an automatic and conditional response to local input at the first care facility matching the record designator. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an association between data indicating a current health status of a first individual and a record designator and causing a wearable article at a first care facility to include the data indicating the current health status of the first individual as an automatic and conditional response to local input at the first care facility matching the record designator. In addition to the foregoing, other system aspects are described in the claims, drawings, and text forming a part of the present disclosure.

An embodiment provides a method. In one implementation, the method includes but is not limited to obtaining an indication via a first device local to a first individual that the first individual is noncompliant with a first health regimen; obtaining an indication via a second device that a second individual is available to participate in an electronic intercommunication; and signaling the electronic intercommunication as an automatic and conditional response to the indication via the first device local to the first individual that the first individual is noncompliant with the first health regimen and to the indication via the second device that the second individual is available to participate in the electronic intercommunication. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication via a first device local to a first individual that the first individual is noncompliant with a first health regimen; circuitry for obtaining an indication via a second device that a second individual is available to participate in an electronic intercommunication; and circuitry for signaling the electronic intercommunication as an automatic and conditional response to the indication via the first device local to the first individual that the first individual is noncompliant with the first health regimen and to the indication via the second device that the second individual is available to participate in the electronic intercommunication. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication via a first device local to a first individual that the first individual is noncompliant with a first health regimen; obtaining an indication via a second device that a second individual is available to participate in an electronic intercommunication; and signaling the electronic intercommunication as an automatic and conditional response to the indication via the first device local to the first individual that the first individual is noncompliant with the first health regimen and to the indication via the second device that the second individual is available to participate in the electronic intercommunication. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication via a first device local to a first individual that the first individual is noncompliant with a first health regimen; obtaining an indication via a second device that a second individual is available to participate in an electronic intercommunication; and signaling the electronic intercommunication as an automatic and conditional response to the indication via the first device local to the first individual that the first individual is noncompliant with the first health regimen and to the indication via the second device that the second individual is available to participate in the electronic intercommunication. In addition to the foregoing, other system aspects are described in the claims, drawings, and text forming a part of the present disclosure.

An embodiment provides a method. In one implementation, the method includes but is not limited to obtaining via a first device a scalar indication of how well a first health regimen has been followed by a first individual; obtaining via a second device a scalar indication of how well a second health regimen has been followed by a second individual; and characterizing a performance of a third individual with a scalar evaluation obtained by mathematically combining the scalar indication of how well the first health regimen has been followed by the first individual with the scalar indication of how well the second health regimen has been followed by the second individual. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining via a first device a scalar indication of how well a first health regimen has been followed by a first individual; circuitry for obtaining via a second device a scalar indication of how well a second health regimen has been followed by a second individual; and circuitry for characterizing a performance of a third individual with a scalar evaluation obtained by mathematically combining the scalar indication of how well the first health regimen has been followed by the first individual with the scalar indication of how well the second health regimen has been followed by the second individual. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining via a first device a scalar indication of how well a first health regimen has been followed by a first individual; obtaining via a second device a scalar indication of how well a second health regimen has been followed by a second individual; and characterizing a performance of a third individual with a scalar evaluation obtained by mathematically combining the scalar indication of how well the first health regimen has been followed by the first individual with the scalar indication of how well the second health regimen has been followed by the second individual. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining via a first device a scalar indication of how well a first health regimen has been followed by a first individual; obtaining via a second device a scalar indication of how well a second health regimen has been followed by a second individual; and characterizing a performance of a third individual with a scalar evaluation obtained by mathematically combining the scalar indication of how well the first health regimen has been followed by the first individual with the scalar indication of how well the second health regimen has been followed by the second individual. In addition to the foregoing, other system aspects are described in the claims, drawings, and text forming a part of the present disclosure.

An embodiment provides a method. In one implementation, the method includes but is not limited to obtaining a field of view within which a specific portion of the field of view includes a view of a first patient; obtaining user input selectively indicating the first patient by identifying the specific portion that depicts the first patient; and signaling medical data about the first patient as an automatic and conditional response to the user input selectively indicating the first patient by identifying the specific portion that depicts the first patient. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining a field of view within which a specific portion of the field of view includes a view of a first patient; circuitry for obtaining user input selectively indicating the first patient by identifying the specific portion that depicts the first patient; and circuitry for signaling medical data about the first patient as an automatic and conditional response to the user input selectively indicating the first patient by identifying the specific portion that depicts the first patient. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining a field of view within which a specific portion of the field of view includes a view of a first patient; obtaining user input selectively indicating the first patient by identifying the specific portion that depicts the first patient; and signaling medical data about the first patient as an automatic and conditional response to the user input selectively indicating the first patient by identifying the specific portion that depicts the first patient. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining a field of view within which a specific portion of the field of view includes a view of a first patient; obtaining user input selectively indicating the first patient by identifying the specific portion that depicts the first patient; and signaling medical data about the first patient as an automatic and conditional response to the user input selectively indicating the first patient by identifying the specific portion that depicts the first patient. In addition to the foregoing, other system aspects are described in the claims, drawings, and text forming a part of the present disclosure.

An embodiment provides a method. In one implementation, the method includes but is not limited to obtaining an indication whether or not a first individual is compliant with a first health regimen; responding to the indication whether or not the first individual is compliant with the first health regimen by causing a device associated with the first individual to receive an indication of an artificial incentive; and signaling a decision whether or not to manifest the artificial incentive after the device associated with the first individual receives the indication of the artificial incentive and responsive to an indication whether or not a dialog occurs between the first individual and a second individual. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication whether or not a first individual is compliant with a first health regimen; circuitry for responding to the indication whether or not the first individual is compliant with the first health regimen by causing a device associated with the first individual to receive an indication of an artificial incentive; and circuitry for signaling a decision whether or not to manifest the artificial incentive after the device associated with the first individual receives the indication of the artificial incentive and responsive to an indication whether or not a dialog occurs between the first individual and a second individual. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication whether or not a first individual is compliant with a first health regimen; responding to the indication whether or not the first individual is compliant with the first health regimen by causing a device associated with the first individual to receive an indication of an artificial incentive; and signaling a decision whether or not to manifest the artificial incentive after the device associated with the first individual receives the indication of the artificial incentive and responsive to an indication whether or not a dialog occurs between the first individual and a second individual. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication whether or not a first individual is compliant with a first health regimen; responding to the indication whether or not the first individual is compliant with the first health regimen by causing a device associated with the first individual to receive an indication of an artificial incentive; and signaling a decision whether or not to manifest the artificial incentive after the device associated with the first individual receives the indication of the artificial incentive and responsive to an indication whether or not a dialog occurs between the first individual and a second individual. In addition to the foregoing, other system aspects are described in the claims, drawings, and text forming a part of the present disclosure.

An embodiment provides a method. In one implementation, the method includes but is not limited to obtaining a first indication whether or not a first patient has violated a first health regimen; obtaining a second indication whether or not the first patient has violated the first health regimen; signaling a decision whether or not to initiate an electronic communication between the first patient and a provider as an automatic and conditional response to the first indication whether or not the first patient has violated the first health regimen but not to the second indication whether or not the first patient has violated the first health regimen; and signaling a decision whether or not to route the provider to the first patient as a conditional response to the first indication whether or not the first patient has violated the first health regimen and to the second indication whether or not the first patient has violated the first health regimen. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining a first indication whether or not a first patient has violated a first health regimen; circuitry for obtaining a second indication whether or not the first patient has violated the first health regimen; circuitry for signaling a decision whether or not to initiate an electronic communication between the first patient and a provider as an automatic and conditional response to the first indication whether or not the first patient has violated the first health regimen but not to the second indication whether or not the first patient has violated the first health regimen; and circuitry for signaling a decision whether or not to route the provider to the first patient as a conditional response to the first indication whether or not the first patient has violated the first health regimen and to the second indication whether or not the first patient has violated the first health regimen. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining a first indication whether or not a first patient has violated a first health regimen; obtaining a second indication whether or not the first patient has violated the first health regimen; signaling a decision whether or not to initiate an electronic communication between the first patient and a provider as an automatic and conditional response to the first indication whether or not the first patient has violated the first health regimen but not to the second indication whether or not the first patient has violated the first health regimen; and signaling a decision whether or not to route the provider to the first patient as a conditional response to the first indication whether or not the first patient has violated the first health regimen and to the second indication whether or not the first patient has violated the first health regimen. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining a first indication whether or not a first patient has violated a first health regimen; obtaining a second indication whether or not the first patient has violated the first health regimen; signaling a decision whether or not to initiate an electronic communication between the first patient and a provider as an automatic and conditional response to the first indication whether or not the first patient has violated the first health regimen but not to the second indication whether or not the first patient has violated the first health regimen; and signaling a decision whether or not to route the provider to the first patient as a conditional response to the first indication whether or not the first patient has violated the first health regimen and to the second indication whether or not the first patient has violated the first health regimen. In addition to the foregoing, other system aspects are described in the claims, drawings, and text forming a part of the present disclosure.

An embodiment provides a method. In one implementation, the method includes but is not limited to assigning a component of an artificial incentive to a first patient partly based on an indication that the first patient has been admitted to a first institution in relation to a particular condition and partly based on an indication that the first patient has not undergone an institutional readmission and transmitting to the first patient a result of assigning the component of the artificial incentive to the first patient partly based on the indication that the first patient has been admitted to the first institution in relation to the particular condition and partly based on the indication that the first patient has not undergone the institutional readmission. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for assigning a component of an artificial incentive to a first patient partly based on an indication that the first patient has been admitted to a first institution in relation to a particular condition and partly based on an indication that the first patient has not undergone an institutional readmission and circuitry for transmitting to the first patient a result of assigning the component of the artificial incentive to the first patient partly based on the indication that the first patient has been admitted to the first institution in relation to the particular condition and partly based on the indication that the first patient has not undergone the institutional readmission. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to assigning a component of an artificial incentive to a first patient partly based on an indication that the first patient has been admitted to a first institution in relation to a particular condition and partly based on an indication that the first patient has not undergone an institutional readmission and transmitting to the first patient a result of assigning the component of the artificial incentive to the first patient partly based on the indication that the first patient has been admitted to the first institution in relation to the particular condition and partly based on the indication that the first patient has not undergone the institutional readmission. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for assigning a component of an artificial incentive to a first patient partly based on an indication that the first patient has been admitted to a first institution in relation to a particular condition and partly based on an indication that the first patient has not undergone an institutional readmission and transmitting to the first patient a result of assigning the component of the artificial incentive to the first patient partly based on the indication that the first patient has been admitted to the first institution in relation to the particular condition and partly based on the indication that the first patient has not undergone the institutional readmission. In addition to the foregoing, other system aspects are described in the claims, drawings, and text forming a part of the present disclosure.

An embodiment provides a method. In one implementation, the method includes but is not limited to obtaining an indication that an order associates a first patient with a medical device; obtaining an indication that the medical device is in a vicinity of the first patient; and enabling the medical device conditionally, partly based on the indication that the order associates the first patient with the medical device and partly based on the indication that the medical device is in the vicinity of the first patient. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication that an order associates a first patient with a medical device; circuitry for obtaining an indication that the medical device is in a vicinity of the first patient; and circuitry for enabling the medical device conditionally, partly based on the indication that the order associates the first patient with the medical device and partly based on the indication that the medical device is in the vicinity of the first patient. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication that an order associates a first patient with a medical device; obtaining an indication that the medical device is in a vicinity of the first patient; and enabling the medical device conditionally, partly based on the indication that the order associates the first patient with the medical device and partly based on the indication that the medical device is in the vicinity of the first patient. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication that an order associates a first patient with a medical device; obtaining an indication that the medical device is in a vicinity of the first patient; and enabling the medical device conditionally, partly based on the indication that the order associates the first patient with the medical device and partly based on the indication that the medical device is in the vicinity of the first patient. In addition to the foregoing, other system aspects are described in the claims, drawings, and text forming a part of the present disclosure.

An embodiment provides a method. In one implementation, the method includes but is not limited to causing a first individual to receive a playable prompt that was automatically selected according to a first data component received from the first individual; receiving a second data component from the first individual after the first individual received the playable prompt that was automatically selected according to the first data component received from the first individual; and causing a wearable article at a first care facility to indicate the second data component received from the first individual after the first individual received the playable prompt that was automatically selected according to the first data component received from the first individual. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for causing a first individual to receive a playable prompt that was automatically selected according to a first data component received from the first individual; circuitry for receiving a second data component from the first individual after the first individual received the playable prompt that was automatically selected according to the first data component received from the first individual; and circuitry for causing a wearable article at a first care facility to indicate the second data component received from the first individual after the first individual received the playable prompt that was automatically selected according to the first data component received from the first individual. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to causing a first individual to receive a playable prompt that was automatically selected according to a first data component received from the first individual; receiving a second data component from the first individual after the first individual received the playable prompt that was automatically selected according to the first data component received from the first individual; and causing a wearable article at a first care facility to indicate the second data component received from the first individual after the first individual received the playable prompt that was automatically selected according to the first data component received from the first individual. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for causing a first individual to receive a playable prompt that was automatically selected according to a first data component received from the first individual; receiving a second data component from the first individual after the first individual received the playable prompt that was automatically selected according to the first data component received from the first individual; and causing a wearable article at a first care facility to indicate the second data component received from the first individual after the first individual received the playable prompt that was automatically selected according to the first data component received from the first individual. In addition to the foregoing, other system aspects are described in the claims, drawings, and text forming a part of the present disclosure.

An embodiment provides a method. In one implementation, the method includes but is not limited to identifying a first health regimen associated with a first individual, the first health regimen including one or more healthcare-related tasks associated with a time interval; causing a countdown timer to indicate a remaining portion of the time interval associated with the one or more healthcare-related tasks visibly in a vicinity of the first individual; and signaling a Boolean indication of whether or not any of the one or more healthcare-related tasks associated with the time interval were performed within the time interval after the countdown timer has indicated the remaining portion of the time interval associated with the one or more healthcare-related tasks visibly in the vicinity of the first individual. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for identifying a first health regimen associated with a first individual, the first health regimen including one or more healthcare-related tasks associated with a time interval; circuitry for causing a countdown timer to indicate a remaining portion of the time interval associated with the one or more healthcare-related tasks visibly in a vicinity of the first individual; and circuitry for signaling a Boolean indication of whether or not any of the one or more healthcare-related tasks associated with the time interval were performed within the time interval after the countdown timer has indicated the remaining portion of the time interval associated with the one or more healthcare-related tasks visibly in the vicinity of the first individual. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to identifying a first health regimen associated with a first individual, the first health regimen including one or more healthcare-related tasks associated with a time interval; causing a countdown timer to indicate a remaining portion of the time interval associated with the one or more healthcare-related tasks visibly in a vicinity of the first individual; and signaling a Boolean indication of whether or not any of the one or more healthcare-related tasks associated with the time interval were performed within the time interval after the countdown timer has indicated the remaining portion of the time interval associated with the one or more healthcare-related tasks visibly in the vicinity of the first individual. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for identifying a first health regimen associated with a first individual, the first health regimen including one or more healthcare-related tasks associated with a time interval; causing a countdown timer to indicate a remaining portion of the time interval associated with the one or more healthcare-related tasks visibly in a vicinity of the first individual; and signaling a Boolean indication of whether or not any of the one or more healthcare-related tasks associated with the time interval were performed within the time interval after the countdown timer has indicated the remaining portion of the time interval associated with the one or more healthcare-related tasks visibly in the vicinity of the first individual. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure. The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth below.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIGS. 8-13 respectively depict exemplary environments in which one or more technologies may be configured to operate between or among respective devices.

FIG. 14 depicts a high-level logic flow of an operational process (described with reference to FIG. 8, e.g.).

FIG. 15 depicts a high-level logic flow of an operational process (described with reference to FIG. 9, e.g.).

FIG. 20 depicts another exemplary environment in which one or more technologies may be configured to operate between or among respective devices.

FIGS. 21-26 each depict an exemplary environment in which one or more technologies may be implemented in one or more data-handling media.

FIG. 37 depicts another exemplary environment in which one or more technologies may be configured to implement a data-handling device (in a handheld unit, e.g.).

FIG. 47 depicts another exemplary environment in which one or more technologies may be configured to notify someone (a patient, e.g.) of a remaining portion of a time interval (associated with a task, e.g.).

FIG. 57 depicts a high-level logic flow of an operational process (described with reference to FIG. 47, e.g.).

FIG. 61 likewise depicts variants of earlier-presented flows (in any of FIG. 14-19 or 48-60).

FIG. 62 likewise depicts variants of earlier-presented flows (in any of FIG. 14-19 or 48-61).

DETAILED DESCRIPTION

Figure 1:
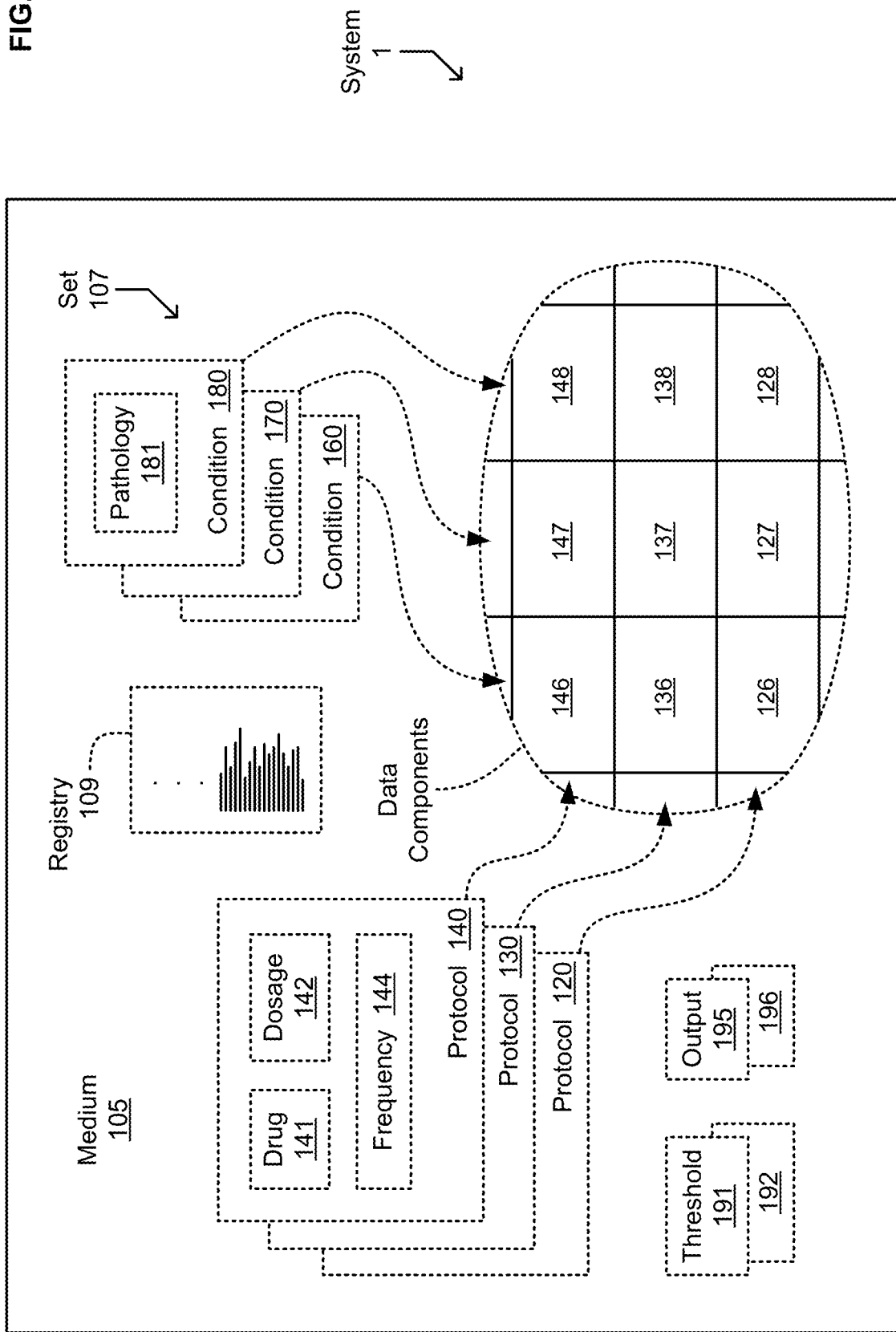
FIG. 1 depicts an exemplary environment in which one or more technologies may be implemented in one or more data-handling media.

In the following detailed description, reference is made to the accompanying drawings, which form a part hereof. In the drawings, similar symbols typically identify similar or identical components or items, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

Throughout this application, examples and lists are given, with parentheses, the abbreviation "e.g.," or both. Unless explicitly otherwise stated, these examples and lists are merely exemplary and are non-exhaustive. In most cases, it would be prohibitive to list every example and every combination. Thus, smaller, illustrative lists and examples are used, with focus on imparting understanding of the claim terms rather than limiting the scope of such terms.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to a human reader. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail herein, these logical operations/functions are not representations of abstract ideas, but rather are representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct" (e.g., that "software"—a computer program or computer programming—is somehow an ineffable mental construct, because at a high level of abstraction, it can be conceived and understood by a human reader). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of logic, such as Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011100001111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configurations, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT). Thus, programs written in machine language—which may be tens of millions of machine language instructions long—are incomprehensible to most humans. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that useful, tangible, and concrete work is done. For example, as indicated above, such machine language—the compiled version of the higher-level language—functions as a technical specification which selects out hardware logic gates, specifies voltage levels, voltage transition timings, etc., such that the useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality of logic(s), or (d) virtually any combination of the foregoing. Indeed, any physical object which has a stable, measurable, and changeable state may be used to construct a machine based on the above technical description. Charles Babbage, for example, constructed the first mechanized computational apparatus out of wood, with the apparatus powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language should not be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality.

Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

For the purposes of this application, "cloud" computing may be understood as described in the cloud computing literature. For example, cloud computing may be methods and/or systems for the delivery of computational capacity and/or storage capacity as a service. The "cloud" may refer to one or more hardware and/or software components that deliver or assist in the delivery of computational and/or storage capacity, including, but not limited to, one or more of a client, an application, a platform, an infrastructure, and/or a server The cloud may refer to any of the hardware and/or software associated with a client, an application, a platform, an infrastructure, and/or a server. For example, cloud and cloud computing may refer to one or more of a computer, a processor, a storage medium, a router, a switch, a modem, a virtual machine (e.g., a virtual server), a data center, an operating system, a middleware, a firmware, a hardware back-end, a software back-end, and/or a software application. A cloud may refer to a private cloud, a public cloud, a hybrid cloud, and/or a community cloud. A cloud may be a shared pool of configurable computing resources, which may be public, private, semi-private, distributable, scaleable, flexible, temporary, virtual, and/or physical. A cloud or cloud service may be delivered over one or more types of network, e.g., a mobile communication network, and the Internet.

As used in this application, a cloud or a cloud service may include one or more of infrastructure-as-a-service ("IaaS"), platform-as-a-service ("PaaS"), software-as-a-service ("SaaS"), and/or desktop-as-a-service ("DaaS"). As a non-exclusive example, IaaS may include, e.g., one or more virtual server instantiations that may start, stop, access, and/or configure virtual servers and/or storage centers (e.g., providing one or more processors, storage space, and/or network resources on-demand, e.g., EMC and Rackspace). PaaS may include, e.g., one or more software and/or development tools hosted on an infrastructure (e.g., a computing platform and/or a solution stack from which the client can create software interfaces and applications, e.g., Microsoft Azure). SaaS may include, e.g., software hosted by a service provider and accessible over a network (e.g., the software for the application and/or the data associated with that software application may be kept on the network, e.g., Google Apps, SalesForce). DaaS may include, e.g., providing desktop, applications, data, and/or services for the user over a network (e.g., providing a multi-application framework, the applications in the framework, the data associated with the applications, and/or services related to the applications and/or the data over the network, e.g., Citrix). The foregoing is intended to be exemplary of the types of systems and/or methods referred to in this application as "cloud" or "cloud computing" and should not be considered complete or exhaustive.

The proliferation of automation in many transactions is apparent. For example, Automated Teller Machines ("ATMs") dispense money and receive deposits. Airline ticket counter machines check passengers in, dispense tickets, and allow passengers to change or upgrade flights. Train and subway ticket counter machines allow passengers to purchase a ticket to a particular destination without invoking a human interaction at all. Many groceries and pharmacies have self-service checkout machines which allow a consumer to pay for goods purchased by interacting only with a machine. Large companies now staff telephone answering systems with machines that interact with customers, and invoke a human in the transaction only if there is a problem with the machine-facilitated transaction.

Nevertheless, as such automation increases, convenience and accessibility may decrease. Self-checkout machines at grocery stores may be difficult to operate. ATMs and ticket counter machines may be mostly inaccessible to disabled persons or persons requiring special access. Where before, the interaction with a human would allow disabled persons to complete transactions with relative ease, if a disabled person is unable to push the buttons on an ATM, there is little the machine can do to facilitate the transaction to completion. While some of these public terminals allow speech operations, they are configured to the most generic forms of speech, which may be less useful in recognizing particular speakers, thereby leading to frustration for users attempting to speak to the machine. This problem may be especially challenging for the disabled, who already may face significant challenges in completing transactions with automated machines.

In addition, smartphones and tablet devices also now are configured to receive speech commands. Speech and voice controlled automobile systems now appear regularly in motor vehicles, even in economical, mass-produced vehicles. Home entertainment devices, e.g., disc players, televisions, radios, stereos, and the like, may respond to speech commands. Additionally, home security systems may respond to speech commands. In an office setting, a worker's computer may respond to speech from that worker, allowing faster, more efficient work flows. Such systems and machines may be trained to operate with particular users, either through explicit training or through repeated interactions. Nevertheless, when that system is upgraded or replaced, e.g., a new television is purchased, that training may be lost with the device. Thus, in some embodiments described herein, adaptation data for speech recognition systems may be separated from the device which recognizes the speech, and may be more closely associated with a user, e.g., through a device carried by the user, or through a network location associated with the user.

Further, in some environments, there may be more than one device that transmits and receives data within a range of interacting with a user. For example, merely sitting on a couch watching television may involve five or more devices, e.g., a television, a cable box, an audio/visual receiver, a remote control, and a smartphone device. Some of these devices may transmit or receive speech data. Some of these devices may transmit, receive, or store adaptation data, as will be described in more detail herein. Thus, in some embodiments, which will be described in more detail herein, there may be methods, systems, and devices for determining which devices in a system should perform actions that allow a user to efficiently interact with an intended device through that user's speech.

With reference now to FIG. 1, shown is an example of a system 1 (a network subsystem, e.g.) in which one or more technologies may be implemented. One or more media 105 are configured to bear one or more instances of a registry 109 (of multiple subscribers, e.g.); organized informational data components relating to health-related protocols 120, 130, 140 relating to the treatment of various conditions 160, 170, 180 (symptoms or pathologies 181 or sets 107 thereof, e.g.); thresholds 191, 192; and outputs 195, 196. One or more such data components 126 relate specifically to the handling of condition 160 using protocol 120 prospectively or otherwise, for example, for one or more particular patients or more generally as described below. (Such sets 107 of pathologies 181 may comprise one or more of an addiction or chronic pain or major depression, for example.) One or more data components 127 likewise relate specifically to the handling of condition 170 using protocol 120 (MRI screening followed by magnetic stimulation therapy, e.g.). One or more data components 128 likewise relate specifically to the handling of condition 180 using protocol 120.

One or more data components 136 likewise relate specifically to the handling of condition 160 using protocol 130. One or more data components 137 likewise relate specifically to the handling of condition 170 (hypertension with major depression in a male of 50 years or older, e.g.) using protocol 130 (a series of ten weekly counseling sessions, e.g.). One or more data components 138 likewise relate specifically to the handling of condition 180 using protocol 130.

One or more data components 146 likewise relate specifically to the handling of condition 160 using protocol 140. One or more data components 147 likewise relate specifically to the handling of condition 170 (major depression, e.g.) using protocol 140. In some contexts, protocol 140 may comprise a particular drug 141 (sertraline, e.g.) taken at a particular dosage (50 milligrams, e.g.) with a particular frequency 144 (daily, e.g.). One or more data components 148 likewise relate specifically to the handling of condition 180 using protocol 140.

A wide variety of conditions 160, 170, 180 of interest may be identified using one or more common medical classification publications: the ICD (International Classification of Diseases); the ICSD (International Classification of Sleep Disorders); the NANDA (North American Nursing Diagnosis Association); the DSM-IV (Diagnostic and Statistical Manual of Mental Disorders); the Mendelian Inheritance in Man; and the SNOMED (Systematized Nomenclature of Human Medicine, D axis). In practical terms, records signaling such conditions may also comprise textual descriptors to locate misclassified or other data components 126, 137, 148 that signal such conditions 160, 170, 180 of interest (in a physician's remarks or other annotations relating to patients who have been readmitted to a psychiatric or other care facility, e.g.).

Likewise a wide variety of protocols 120, 130, 140 (of diagnosis or treatment, e.g.) of interest may be identified using one or more common procedure codes in various publications: the ICHI (International Classification of Health Interventions); the ICPM (International Classification of Procedures in Medicine); the ICPC-2 (International Classification of Primary Care); the HCPCS (Healthcare Common Procedure Coding System); the ICD-10-PCS and the ICD-9-CM Volume 3 (International Classification of Diseases); the NIC (Nursing Interventions Classification); the NMDS (Nursing Minimum Data Set); the NOC (Nursing Outcomes Classification); the SNOMED (Systematized Nomenclature of Human Medicine, P axis); and the CPT (Current Procedural Terminology) codes. In practical terms, records signaling such protocols may also comprise DRG (Diagnosis Related Group) codes or textual descriptors to locate misclassified or other data components 126, 137, 148 that signal such protocols 120, 130, 140 of interest.

Figure 2:
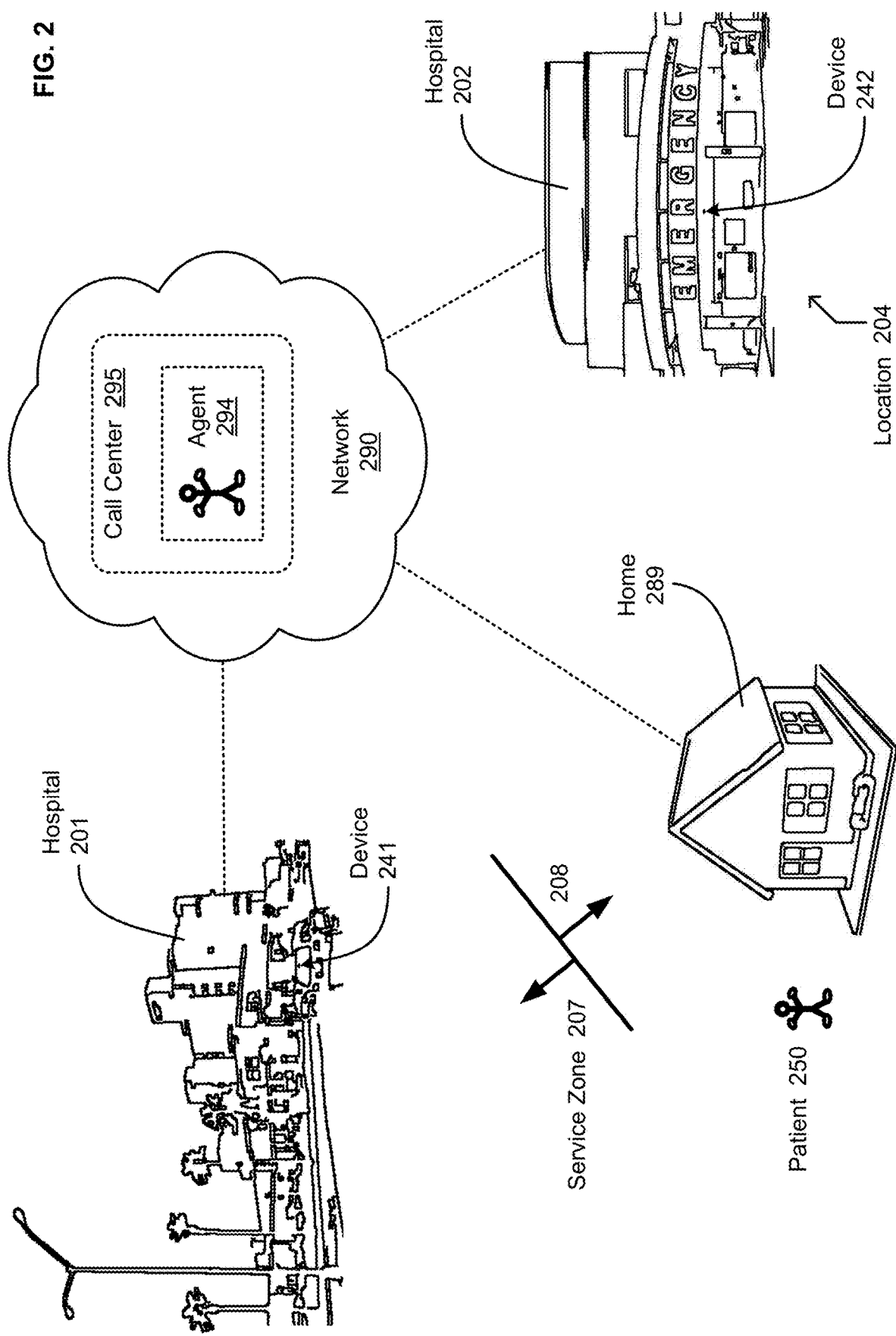
FIG. 2 depicts an exemplary environment in which one or more technologies may facilitate coordination between a hospital and one or more other facilities.

With reference now to FIG. 2, shown is an example of various institutions among which one or more technologies may be implemented. A motor vehicle bearing a mobile device 241 is shown in a vicinity of a hospital 201 on a network 290 (the Internet or a phone network, e.g.) shared with another hospital 202 and a home 289 of a patient 250. In some contexts, network 290 may include one or more call centers 295 operated by one or more agents 294 as described below. A stationary device 242 is configured to monitor a location 204 within which it resides (in or near an emergency room of hospital 202, e.g.). In the particular context as shown, hospital 201 is in one service zone 207 and hospital 202 is in a second service zone 208.

Figure 3:
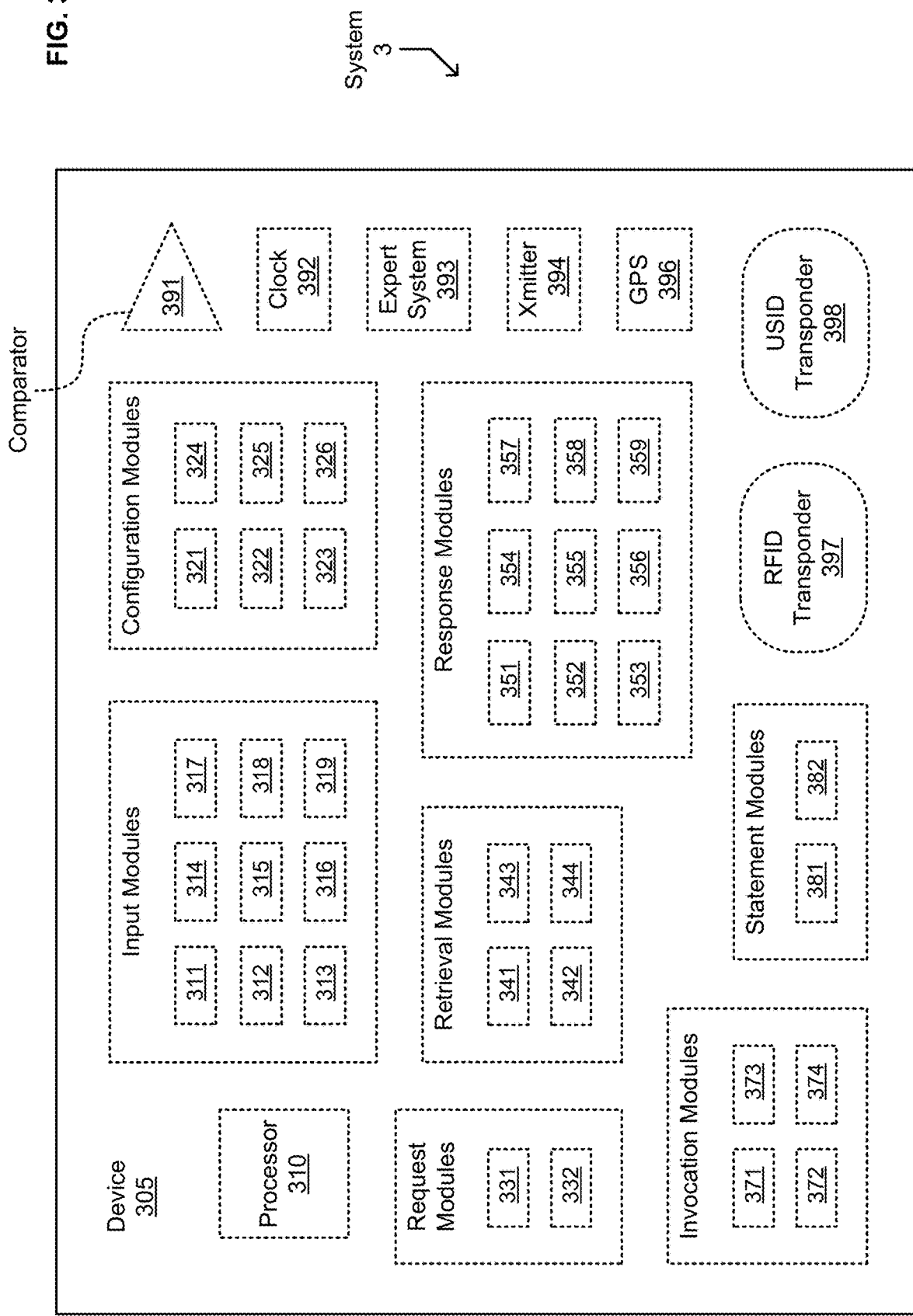
FIG. 3 depicts an exemplary environment in which one or more technologies may be implemented in a device.

With reference now to FIG. 3, shown is another example of a system 3 (a subsystem comprising network 290, e.g.) in which one or more technologies may be implemented. Device 305 may (optionally) include one or more instances of input modules 311, 312, 313, 314, 315, 316, 317, 318, 319; of configuration modules 321, 322, 323, 324, 325, 326; of request modules 331, 332; of retrieval modules 341, 342, 343, 344; of response modules 351, 352, 353, 354, 355, 356, 357, 358, 359; of invocation modules 371, 372, 373, 374; of statement modules 381, 382; of comparators 391; of clocks 392; of expert systems 393; of transmitters 394; of global positioning systems 396; of radio frequency identification (RFID) transponders 397; or of ultrasound identification (USID) transponders 398. In some contexts, moreover, a single component (an application-specific integrated circuit or device-executable software, e.g.) may implement two or more types of the modules described below. Input module 319, for example, may (optionally) be configured to implement more than one of input modules 311-318 (as an automatic response to device-detectable events as described below, e.g.). Response module 359 may likewise be configured to implement more than one of response modules 351-358 (in response to an activation signal from invocation module 374, e.g.). In many of the contexts described below, two or more instances of device 305 are configured to interact with one another or to include one or more media 105 as described below. See FIGS. 4-7, 21, and 22.

Figure 4:
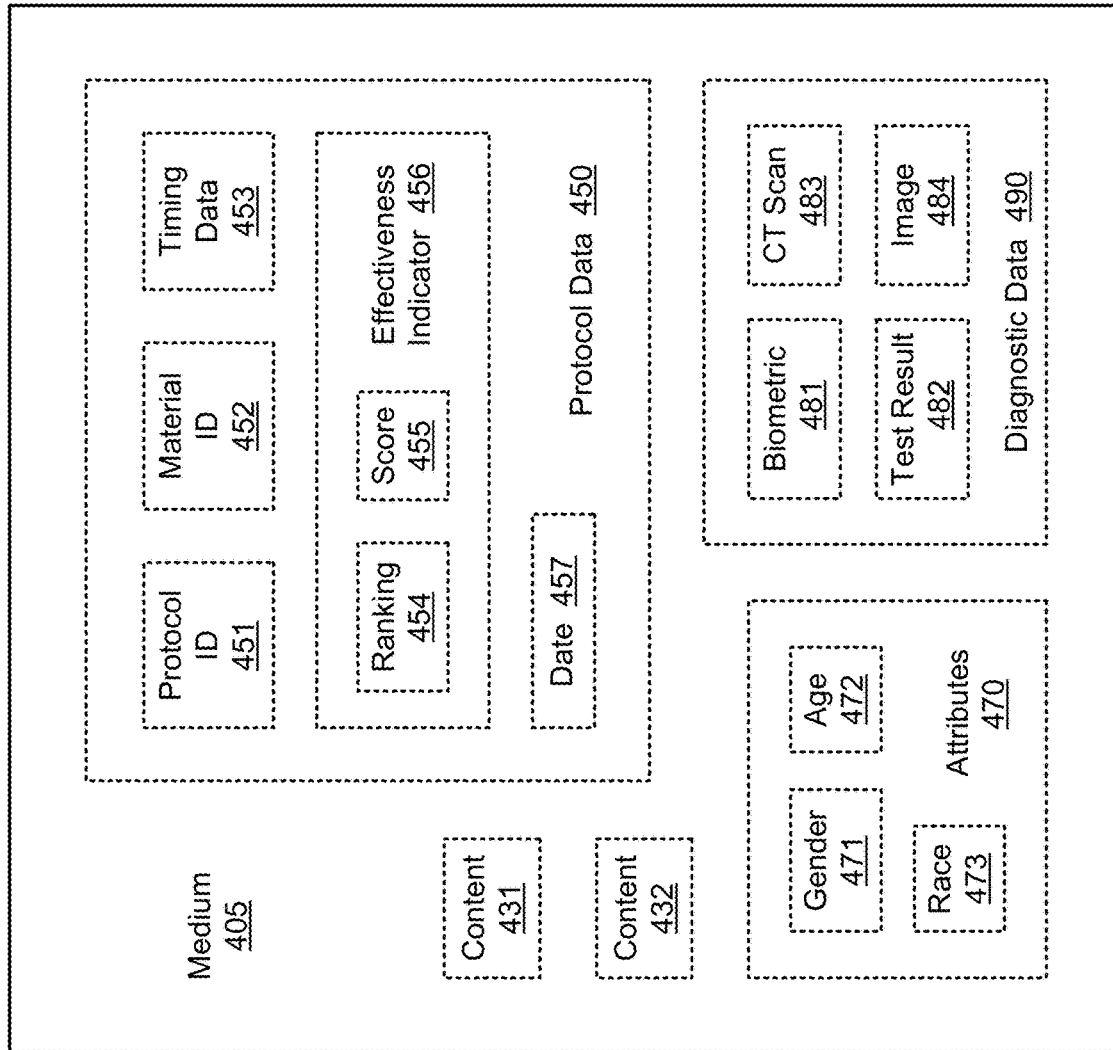
FIGS. 4-7 respectively depict other exemplary environments in which one or more technologies may be implemented in one or more data-handling media.

With reference now to FIG. 4, shown is another example of a system 4 (a network subsystem, e.g.) in which one or more technologies may be implemented. One or more media 405 are configured to bear one or more instances of content 431, 432; of protocol data 450; of patient attributes 470 (gender 471 or age 472 or race 473, e.g.); of biometrics 481, test results 482, computed tomography scans 483 or other images 484; or other such diagnostic data 490. Each of the data components 126-128, 136-138, 146-148 that pertain to a particular patient 250, for example, may (optionally) include one or more protocol identifiers 451, material identifiers 452 (of drugs, e.g.), timing data 453 (of dosages, e.g.), protocol effectiveness indicators 456 (such as rankings 454 or scores 455, e.g.), or dates 457 (of orders or enrollments or injuries or other major events, e.g.) as well as diagnostic data 490 relating to each selected protocol (documenting its rationale or apparent effect, e.g.).

Figure 5:
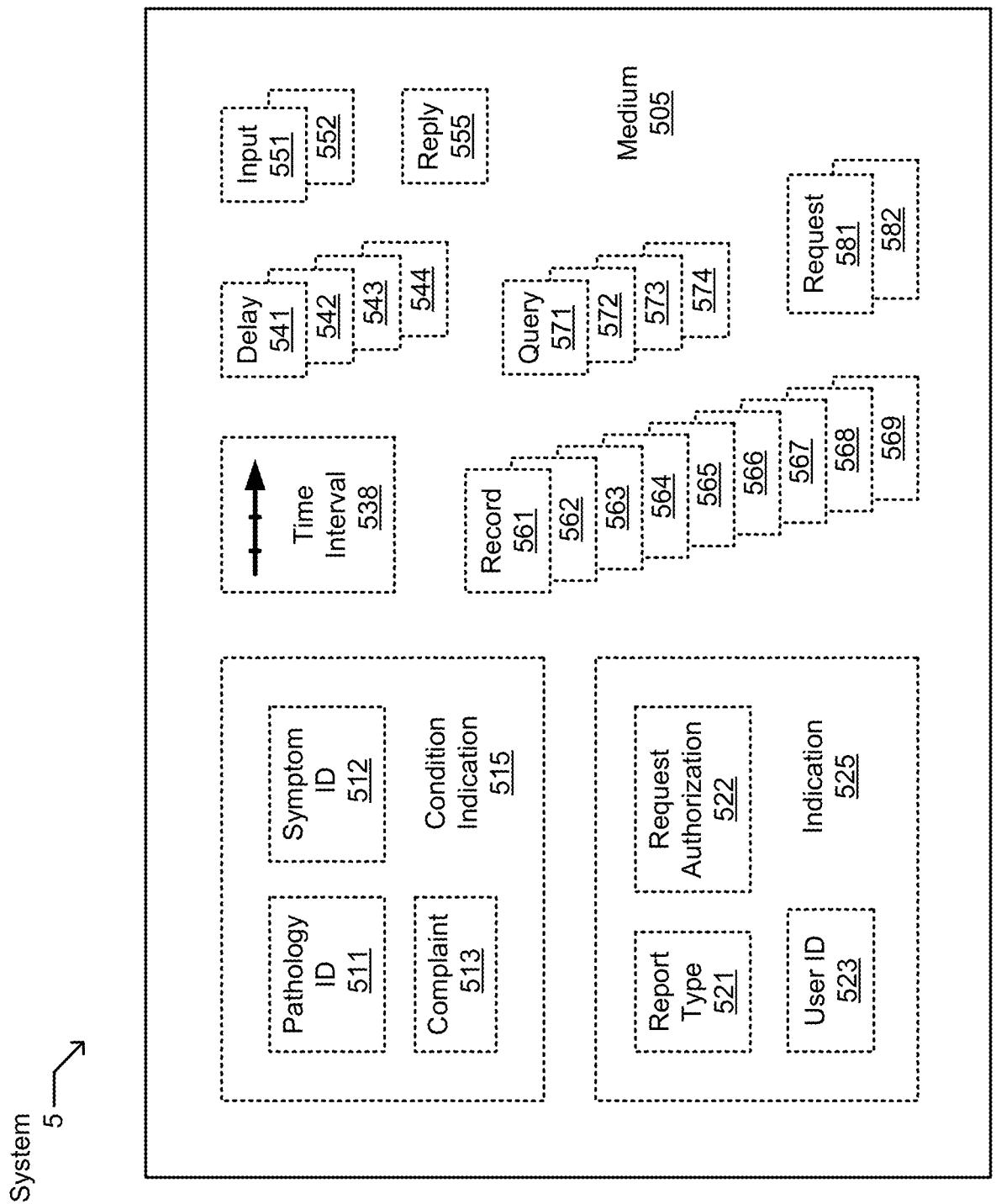

With reference now to FIG. 5, shown is another example of a system 5 (a network subsystem, e.g.) in which one or more technologies may be implemented. One or more media 505 are configured to bear one or more instances of pathology identifiers 511, symptom identifiers 512, complaints 513, or other such condition indications 515; of report types 521, request authorizations 522, user identifiers 523, or other such indications 525 (of excessive institutional readmissions or other apparently negative outcomes that warrant scrutiny, e.g.); of time intervals 538 or programmatic delays 541, 542, 543, 544; of inputs 551, 552 or replies 555; of records 561, 562, 563, 564, 565, 566, 567, 568, 569 relating to a particular patient or caregiver; of queries 571, 572, 573, 574 or requests 581, 582 as described below.

Figure 6:
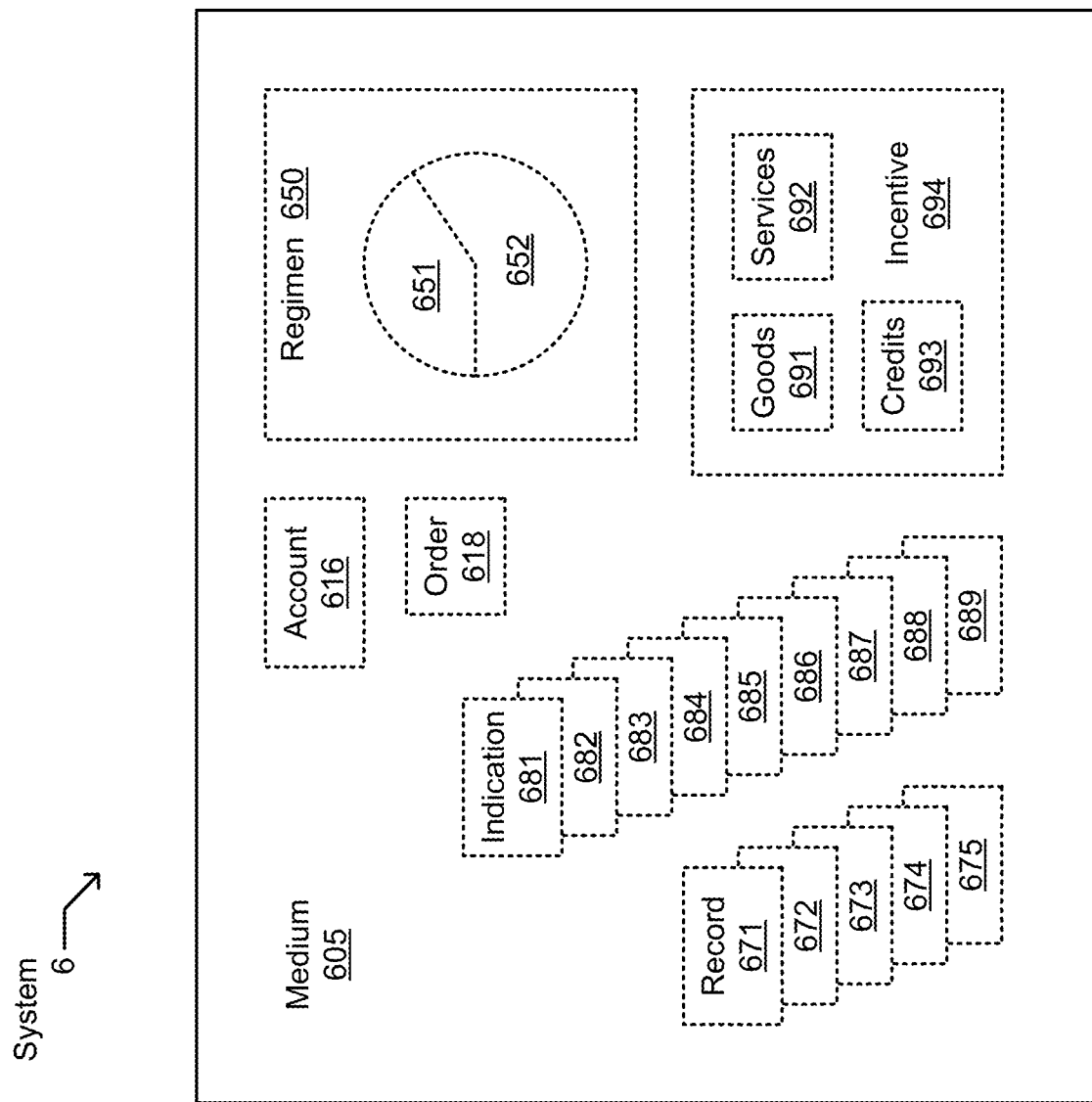

With reference now to FIG. 6, shown is another example of a system 6 (a network subsystem, e.g.) in which one or more technologies may be implemented. One or more media 605 are configured to bear one or more instances of accounts 616 (relating to funds or other inventories, e.g.); orders 618 (by a physician, e.g.); components 651, 652 of a regimen 650; records 671, 672, 673, 674, 675 relating to a particular patient or caregiver; indications 681, 682, 683, 684, 685, 686, 687, 688, 689 of various events or conditions relating to healthcare or information management; or of goods 691, services 692, credits 693, or other incentives 694 as described below.

Figure 7:
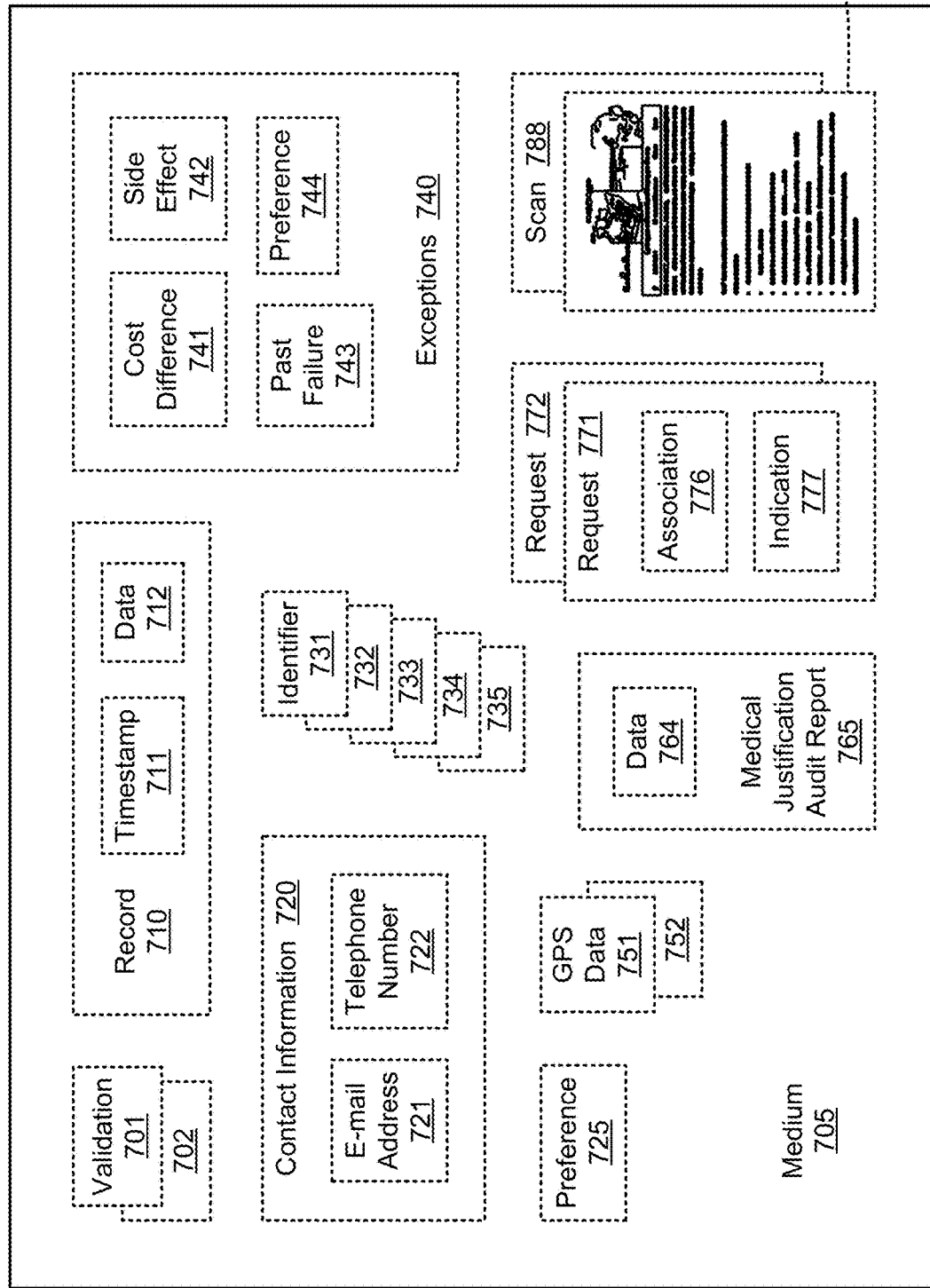

With reference now to FIG. 7, shown is another example of a system 7 (a network subsystem, e.g.) in which one or more technologies may be implemented. One or more media 705 are configured to bear one or more instances of validations 701, 702; records 710 (comprising timestamps 711 or other data 712 manifesting measurement or observation events, e.g.); e-mail addresses 721, telephone numbers 722, or other contact information 720 (of a care provider or administrator, e.g.); preferences 725 (of users of devices 305 as described below, e.g.); identifiers 731, 732, 733, 734, 735 (of devices or individuals, e.g.); coded or other digitally expressed exceptions 740 affecting treatment decisions (cost differences 741, side effects 742, past failures 743, or patient preferences 744, e.g.); global positioning system (GPS) data 751, 752 (of devices or individuals as described below, e.g.); data 764 comprising medical justification audit reports 765; indications 777 comprising requests 771, 772 (signaling an association 776 between a caregiver or patient and various indications 681-689 described below, e.g.); and scans 788, 789 (of documents supporting a course of treatment, e.g.).

Several variants described herein refer to device-detectable "implementations" such as one or more instances of computer-readable code, transistor or latch connectivity layouts or other geometric expressions of logical elements, firmware or software expressions of transfer functions implementing computational specifications, digital expressions of truth tables, or the like. Such instances can, in some implementations, include source code or other human-readable portions. Alternatively or additionally, functions of implementations described herein may constitute one or more device-detectable outputs such as decisions, manifestations, side effects, results, coding or other expressions, displayable images, data files, data associations, statistical correlations, streaming signals, intensity levels, frequencies or other measurable attributes, packets or other encoded expressions, or the like from invoking or monitoring the implementation as described herein.

In some embodiments, a "state" of a component may comprise "available" or some other such state-descriptive labels, an event count or other such memory values, a partial depletion or other such physical property of a supply device, a voltage, or any other such conditions or attributes that may change between two or more possible values irrespective of device location. Such states may be received directly as a measurement or other detection, in some variants, and/or may be inferred from a component's behavior over time. A distributed or other composite system may comprise vector-valued device states, moreover, which may affect dispensations or departures in various ways as exemplified herein.

"Received," "particular," "wearable," "portable," "precedent," "stationary," "audible," "conditional," "explicit," "prior," "extrinsic," "mobile," "specific," "partly," "local," "between," "passive," "associated," "effective," "single," "wireless," "any," "within," "automatic," "proximate," "remote," "common," "selective," "explicit," "resident," "employed," "detectable," "multiple," "in a vicinity," "visible," "objective," "matching," "artificial," "institutional," "medical," or other such descriptors herein are used in their normal yes-or-no sense, not as terms of degree, unless context dictates otherwise. "Compliant," for example, is used in its normal yes-or-no sense except in contexts that describe degrees of compliance with particularity (quantifying "how well" a regimen has been followed, e.g.). In light of the present disclosure those skilled in the art will understand from context what is meant by "vicinity," by being "in" or "at" a detection region, by "remote," and by other such positional descriptors used herein. Terms like "processor," "center," "unit," "computer," or other such descriptors herein are used in their normal sense, in reference to an inanimate structure. Such terms do not include any people, irrespective of their location or employment or other association with the thing described, unless context dictates otherwise. A "hospital" may refer merely to a facility (one or more brick-and-mortar buildings, e.g.) adapted for administering medical care, for example, except in contexts that describe an abstract institution with particularity (relating to whether such institutions have "admitted" a patient, e.g.). "For" is not used to articulate a mere intended purpose in phrases like "circuitry for" or "instruction for," moreover, but is used normally, in descriptively identifying special purpose circuitry or code.

In some embodiments a "manual" occurrence includes, but is not limited to, one that results from one or more actions consciously taken by a device user in real time. Conversely an "automatic" occurrence is not affected by any action consciously taken by a device user in real time except where context dictates otherwise.

In some embodiments, "signaling" something can include identifying, contacting, requesting, selecting, or indicating the thing. In some cases a signaled thing is susceptible to fewer than all of these aspects, of course, such as a task definition that cannot be "contacted."

In some embodiments, "status indicative" data can reflect a trend or other time-dependent phenomenon indicating some aspect of a subject's condition. Alternatively or additionally, a status indicative data set can include portions that have no bearing upon such status. Although some types of distillations can require authority or substantial expertise (e.g. making a final decision upon a risky procedure or other course of treatment), many other types of distillations can readily be implemented without undue experimentation in light of teachings herein.

In some embodiments, "causing" events can include triggering, producing or otherwise directly or indirectly bringing the events to pass. This can include causing the events remotely, concurrently, partially, or otherwise as a "cause in fact," whether or not a more immediate cause also exists.

Some descriptions herein refer to an "indication whether" an event has occurred. An indication is "positive" if it indicates that the event has occurred, irrespective of its numerical sign or lack thereof. Whether positive or negative, such indications may be weak (i.e. slightly probative), definitive, or many levels in between. In some cases the "indication" may include a portion that is indeterminate, such as an irrelevant portion of a useful photograph.

With reference now to FIG. 8, shown is another example of a system 8 (a subsystem of one or more networks 290, 890 described herein, e.g.) in which one or more technologies may be implemented. A desktop scanner 878 is configured to transmit a scan 811 of a hardcopy 877 (of a medical journal article, e.g.) to a local system 841 (comprising a display 810 and keyboard 846, e.g.) on one or more networks 290, 890 described herein. One such network 890 comprises a records archive 820 accessible by one or more retrieval modules 825 operable by a remote requestor 893 (remote from local system 841, e.g.).

With reference now to FIG. 14, shown is a high-level logic flow 14 of an operational process. Intensive operation 42 describes causing an electronic record of a first protocol for a particular condition to be annotated with a scan of a document (e.g. configuration module 326 amending a digital record 569 of the first protocol to include a reference to or a copy of a digital scan 811 of a hard copy 877 in response to input module 314 receiving the reference to or the copy of the digital scan 811). This can occur, for example, in a context in which record 569 reflects patient 250 being admitted or having been admitted to hospital 201 for the treatment of a particular condition 170 by a specific protocol 120, in which network 290 is linked to network 890, in which one or more instances of device 305 reside on network 890 (implementing a computer workstation comprising system 841, e.g.), in which one or more input modules 311-319 receive the digital scan 811 as an automatic response to scanner 878 receiving the hard copy 877, and in which configuration module 326 fully implements the annotation (directly to a remote instance of record 569, e.g.) without any manual input (as an additional automatic response to scanner 878 receiving the hard copy 877, e.g.). Alternatively, input module 314 may be configured to confirm that a caregiver wants such annotation or to permit the caregiver to tune the annotation (by adding related notes or orders or by annotating other records 561-569, 3191-3197 with the same scan 811, e.g.). In some variants, for example, the local user can confirm that the changes made to a local instance of record 569 (including a locally indicated or displayed scan 811, e.g.) should be written to a remote records archive 820 (into a data component 127 specifically associated with the protocol 120 and with the condition 170, e.g.) by responding affirmatively to a query 572 like "save changes to the current record?"

Extensive operation 61 describes retrieving the electronic record of the first protocol after the electronic record of the first protocol is annotated with the scan of the document partly based on an indication of a first patient undergoing the first protocol and partly based on an indication of an institutional readmission (e.g. retrieval module 825 retrieving record 569 based on indications that patient 250 was treated for the particular condition 170 at hospital 201 and was released and later readmitted for the same condition 170). This can occur, for example, in a context in which record 569 includes a symptom identifier 512 or other indication 681 of the specific medical condition 170, in which record 569 also includes a color scan 811 of content 431 pertaining to the medical condition 170 presented in the form of a hard copy 877 (a research study provided by the patient 250 or a family member, e.g.), and in which such later readmission (for the particular condition or for a treatment of some harm to the patient resulting from a medical error that occurred during the prior hospitalization, e.g.) would otherwise trigger a reduction in payment for the "first" protocol or for other hospital services. In some contexts, for example, a Multidrug-Resistant Staphylococcus Aureus (MRSA) diagnosis that appears during a patient's hospital stay, or some other hospital-acquired condition, may be indicative of such medical error. Alternatively or additionally, such content 431 (in one or more media 105, 405 residing on network 890, e.g.) may pertain to one or more medical protocols 120, 130 under prospective consideration for treating the patient 250 and may be retained (as evidence of diligent decision-making or of why a course of treatment was not selected, e.g.).

With reference now to FIG. 9, shown is another example of a system 9 (e.g. a subsystem of one or more networks 290, 990) in which one or more technologies may be implemented. A desktop system 941 is configured to display (to a caregiver 991 or other authorized entity, e.g.) one or more instances of studies 931, records 932, forms 933, or other such indications relating to a patient 992. Such records 932 may include various data components 127, 136, 148 relating to therapies (actually or potentially) being performed upon one or more patients 250, 992 as described herein. In some contexts, one or more such records 932 may be retrieved from or saved to records archive 920 (by one or more retrieval modules 925 in an implementation of device 305 described above, e.g.). Alternatively or additionally, a regional network 990 (e.g. for one or more hospitals 201, 202) containing such archives may be accessed (by a remote requestor 993, e.g.) as described herein.

With reference now to FIG. 15, shown is a high-level logic flow 15 of an operational process. Intensive operation 35 describes obtaining an indication that a particular condition was treated in a first patient with a first protocol (e.g. input module 316 receiving a medical record 932 or other specific indication 935 that protocol 120 was used for treating condition 170 in patient 250). This can occur, for example, in a context in which one or more such indications 935 comprise a data component 127 associated with protocol 120 and with condition 170, in which a second patient 992 or her caregiver 991 has access to some or all of the data component 127 (including the specific indication 935, e.g.), and in which condition 170 is described in data component 127 with a pathology identifier 511 ("fibromyalgia," e.g.) that has also been assigned to the "second" patient 992. In some variants, for example, one or more such data components 126-128, 136-138 may reside in one or more regional records archives 820, 920 accessible to authorized caregivers 991. Alternatively or additionally, one or more such indications 935 may be obtained from a published research study 931 (as a hard copy 877 to be scanned, e.g.) or entered into an online form 933 (with an identifier of a hospital 201 or a physician or protocol data 450 or other background information known to caregiver 991 about the "first" patient 250 or his/her prior treatment, e.g.).

Intensive operation 43 describes causing a record of a second patient to include the indication that the particular condition was treated in the first patient with the first protocol (e.g. configuration module 323 modifying a medical record 562 of the "second" patient 992 by including one or more specific indications 935 that protocol 120 was used for treating condition 170 in one or more prior patients 250, with or without identifying any particular "first" patient 250). This can occur, for example, in a context in which protocol 120 is not yet established as the preferred treatment for treating condition 170; in which the "first" and "second" patients have one or more attributes 470 (gender 471 or general age 472 or race 473, e.g.) in common; in which record 562 identifies one or more such attributes 470 but does not include other information that identifies the "first" patient 250. In addition to such considerations relating to patient privacy, tracking such information may be helpful in relation to other regulatory considerations. Under the healthcare system in the United States, for example, Section 4302 of Public Law 111-148 (the "Patient Protection and Affordable Care Act," sometimes called "Obamacare") "[r]equires federally conducted or supported healthcare programs or surveys to collect and report demographic data, including ethnicity, sex, primary language, and disability status, as well as data at the smallest geographic level possible, such as state or local, etc."

Referring again to FIGS. 1 & 9, moreover, in some contexts a caregiver 991 may determine a circumstance of the "second" patient falls into one or more identifiable exceptions 740 to a general practice of treating condition 170 with a more conventional protocol 140. In a context in which the conventional protocol 140 is characterized by one or more generally preferred drugs 141 and associated dosages 142, practice groups or facilities or modes (in-patient at hospital 201, e.g.), or frequencies of treatment (daily or weekly, e.g.), an unconventional protocol 120 may be warranted for one or more reasons of cost difference 741 (protocol 140 being too expensive for continued use, e.g.); side effects 742 (an allergy to drug 141 or drug interaction risk, e.g.); past failure 743 (having been ineffective for treating condition 170 in patient 992, e.g.); or a documented preference 744 (manifested by a waiver from "second" patient 992, e.g.). In some variants, therefore, it may be preferable for configuration module 323 to be operable for modifying medical record 562 to include such exceptions 740 in circumstance (optionally by querying caregiver 991 for such information, e.g.).

Extensive operation 62 describes retrieving the record of the second patient selectively in response to an association between the second patient and an indication of an institutional readmission after the record of the second patient includes the indication that the particular condition was treated in the first patient with the first protocol (e.g. retrieval module 925 requesting and providing medical record 562 in response to a remote requestor 993 initiating a medical justification audit report 765 indicating that the "second" patient 992 underwent multiple in-patient treatments for condition 170 during separate hospital stays). This can occur, for example, in a context in which operations 35 and 43 had both been performed; in which the retrieval is "selective" insofar that each instance of operation 62 retrieves less than all such records 561-569, 3191-3197 (of billing, e.g.); in which caregiver 991 has reasonably and correctly relied upon the indication 935 as precedent (that the particular condition 170 was treated in the "first" patient 250 with protocol 120, e.g.) in her decision to recommend or administer protocol 120 to the "second" patient 992 in hospital 201; in which it is not self-evident that such administration was reasonable in the absence of the specific indication 935; and in which protocol 120 is ultimately not permanently effective at eradicating the particular condition 170. In the event that the "second" patient 992 is readmitted to hospital 202 later for further treatment of the particular condition 170 and that such readmission would otherwise trigger a reduction in payment for the services of caregiver 991 or of hospital 201, remembering and reacquiring the particular condition 170 (or some other adequate justification) may become an onerous and crucial task. In some contexts, a medical justification audit report 765 may include data 764 (where available) supporting care decisions made on behalf of many individuals each of whom was readmitted (hospitalized more than once for a particular condition, e.g.). Alternatively or additionally, in some contexts, such an association 776 (between the "second" patient 992 and an indication 777 of apparently-excessive institutional readmissions, e.g.) may be established by an electronic request 771 (received from remote requestor 993 and directly invoking retrieval module 925, e.g.). More generally, such actions taken with reference to one or more criteria are "selective" (as used in FIGS. 59-62 below, e.g.) if at least one of the criteria is used as a determinant in deciding which data components (records, e.g.) will not be included in or affected by the action.

Figure 10:
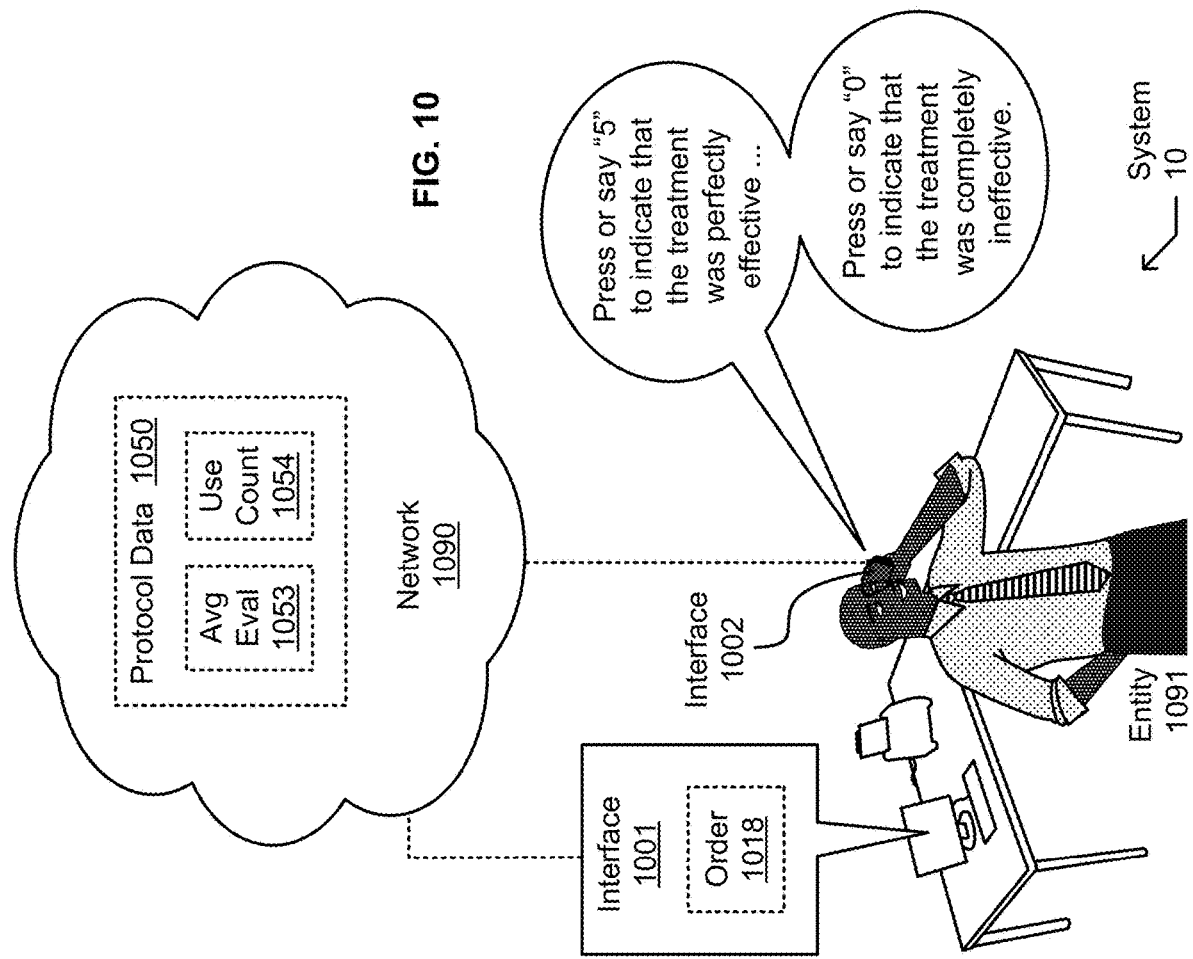

With reference now to FIG. 10, shown is another example of a system 10 in which one or more technologies may be implemented. One interface 1001 (e.g. a desktop system 841, 941) is configured for use (e.g. by a physician, administrator, or other authorized entity 1091) in entering and transmitting an order 1018 or other such content (of a protocol 130 or condition 170, e.g.) via one or more networks 1090 as described above. The one or more networks 1090 are also configured to contact entity 1091 (using contact information 720 for the same interface 1001 or another interface 1002 associated with the same entity 1091, e.g.) under some conditions as described herein, such as to request an indication of the effectiveness of a treatment (protocol 130, e.g.) that the entity might have tried or witnessed recently. In some contexts, this permits protocol data 1090 (average evaluations 1053 or use counts 1054, e.g.) to be generated or updated (on various instance of media 105, 405, 505, 605, 705 in network 1050, e.g.).

Figure 16:
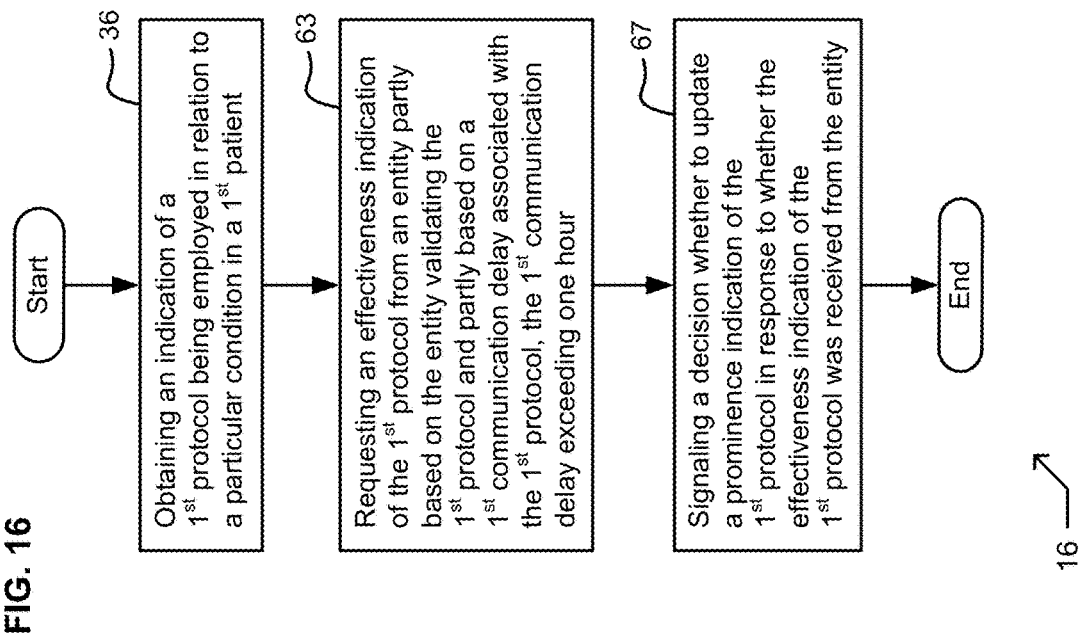
FIG. 16 depicts a high-level logic flow of an operational process (described with reference to FIG. 10, e.g.).

With reference now to FIG. 16, shown is a high-level logic flow 16 of an operational process. Intensive operation 36 describes obtaining an indication of a first protocol being employed in relation to a particular condition in a first patient (e.g. input module 313 receiving a record 564 indicating that an order 1018 was placed for a particular drug 141 or protocol 140 prescribed or purchased for the treatment of a particular condition 170 in patient 250). This can occur, for example, in a context in which device 305 includes one or more media 105 (on network 1090, e.g.) bearing an average evaluation 1053, use count 1054, or other such quantified protocol data 1050 as described below (as a data component 147 associated with the particular condition 170 and with the particular drug 141 or protocol 140, e.g.). In some contexts, moreover, input module may receive the indication as an inquiry into the prospect of treating condition 170 with one or more protocols 130, 140 and may record such inquiries in record 564. Alternatively or additionally, input module 313 and request module 332 may be configured to perform operation 36 jointly by initiating communication with someone generally familiar with the protocol 140 (a nurse or pharmacist who can administer the particular drug 141 or protocol 140, e.g.).

Extensive operation 63 describes requesting an effectiveness indication of the first protocol from an entity partly based on the entity validating the first protocol and partly based on a first communication delay associated with the first protocol, the first communication delay exceeding one hour (e.g. request module 331 asking one or more entities 1091 who validated the particular protocol for an effectiveness indicator 456 signaling how effective the particular protocol was for the treatment of condition 170 in patient 250). This can occur, for example, in a context in which an entity 1091 signals one or more validations 701, 702 of the treatment by prescribing, purchasing, administering, or authorizing the particular drug 141 or protocol 140 for the treatment of condition 170 in patient 250 and in which one or more data components 127, 137, 147 define respective communication delays 542, 543, 544 so that request module 331 transmits a query (by telephone or e-mail, e.g.) to the entity 1091 (practitioner or patient, e.g.) only after the treatment has probably failed or started to work. In a context in which a 10-day course of an antibiotic (as protocol 130, e.g.) would be expected to alleviate a fever (as condition 160, e.g.) in a few hours or days, for example, a corresponding communication delay 543 of about 5 days (within an order of magnitude, e.g.) will be appropriate for obtaining a score 455 (on a 0-5 scale, e.g.) or other effectiveness indicator 456 as a delayed automatic response to the ordering or administration of the antibiotic. In less urgent contexts, moreover, an expected delivery time (in hours or days, e.g.) may be included for some of the communication delays 541-544 (those for which a drug 141 or other material component of a protocol 140 is delivered to a patient's home 289, e.g.). Alternatively or additionally, request module 331 may be configured to send the same request to a particular entity 1091 via more than one interface 1001, 1002 (using both an e-mail address 721 and a telephone number 722 associated with a single identified entity 1091, e.g.).

In light of teachings herein, numerous existing techniques may be applied for configuring special-purpose circuitry or other structures effective for transmitting queries or other information requests as described herein without undue experimentation. See, e.g., U.S. Pat. No. 8,073,013 ("Method and apparatus for collecting survey data via the internet"); U.S. Pat. No. 7,962,359 ("Method and system for collecting and disseminating survey data over the internet"); U.S. Pat. No. 7,836,073 ("Method and system for transmitting pre-formulated query to database"); U.S. Pat. No. 7,590,547 ("Method for transmitting an anonymous request from a consumer to a content or service provider through a telecommunication network"); U.S. Pat. No. 7,529,214 ("Mobile node for transmitting a request for information which specifies a transfer device to be used"); U.S. Pat. No. 6,807,532 ("Method of soliciting a user to input survey data at an electronic commerce terminal"); U.S. Pat. No. 6,513,014 ("Method and apparatus for administering a survey via a television transmission network").

Extensive operation 67 describes signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol (e.g. statement module 382 incrementing a use count 1054 in response to receiving a Facebook-style "like" signal from a patient 250 who used the protocol). This can occur, for example, in a context in which the patient 250 was the "entity" contacted in operation 63 (via contact information 720, e.g.); in which the patient 250 was sent a request for such a "like" signal after protocol 140 had enough time (to fail or start working, e.g.), in which a total count of such "like" signals is a "prominence indication" (of protocol 140, e.g.), in which the communication delay and the "first" patient's identity are recorded but not published, and in which a new best practice could not otherwise win widespread recognition within a year of someone devising the practice. In some contexts, for example, a nurse or other care provider familiar with one or more protocols 120, 130 (as they apply to condition 160, e.g.) can designate one or more corresponding delays (based on a success, when a difference is typically seen, or on a side effect onset or other symptom change distribution, e.g.). In a context in which protocol 120 comprises a spinal fusion, for example, a corresponding delay 2226 may be between 6 and 12 months. (See FIG. 22.) In a context in which protocol 130 comprises administering an antihypertensive (for condition 170, e.g.), a corresponding delay 2237 may be on the order of 1.0 months (within an order of magnitude, e.g.). Alternatively or additionally, statement module 382 may perform operation 67 by transmitting an average evaluation 1053 computed based on effectiveness-indicative numerical scores 455 received from each of several entities 1091. This can occur, for example, in a context in which multiple entities have each responded to a corresponding query 573 (like "We need to know how effective you thought this treatment was on a zero-to-five scale . . . please press or say '5' to indicate that the treatment was perfectly effective . . . please press or say '0' to indicate that the treatment was completely ineffective," e.g.) transmitted by request module 331 and in which such an average (as a rolling or inception-to-date average, e.g.) is a "prominence indication" of the treatment or other protocol.

Figure 11:
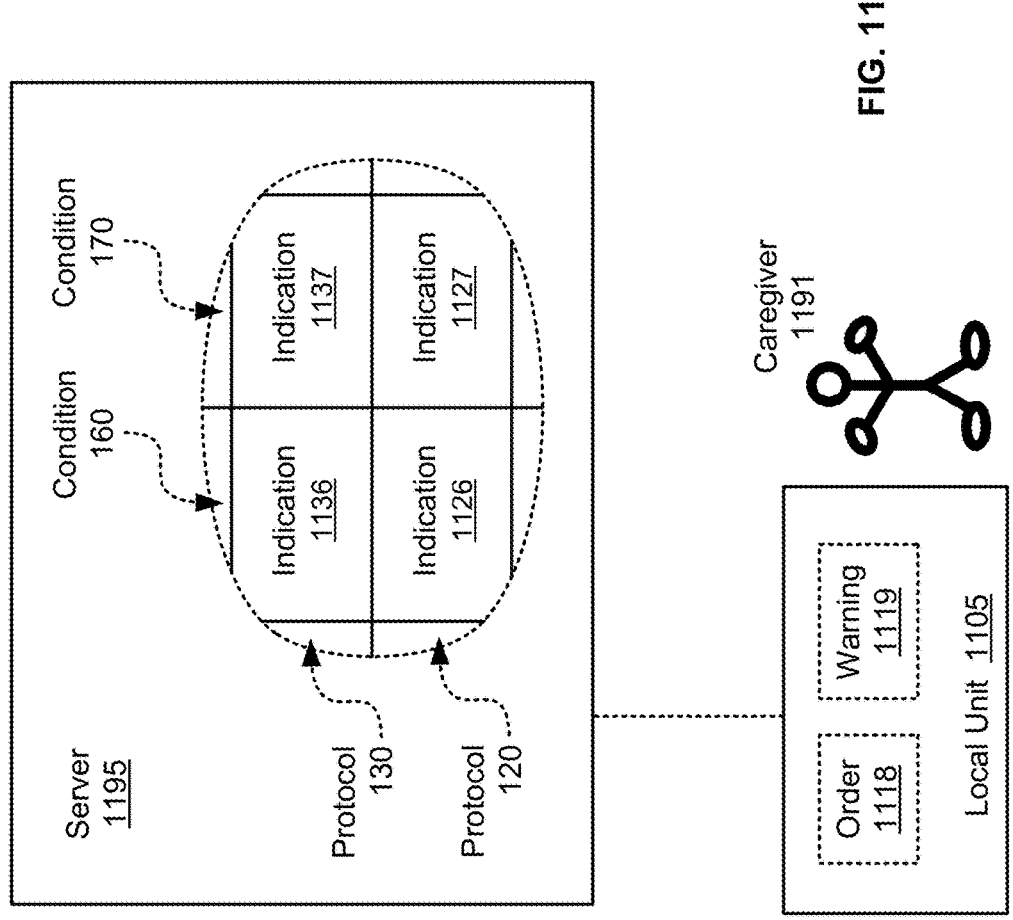

With reference now to FIG. 11, shown is another example of a system 11 (a subsystem of one or more networks described above, e.g.) in which one or more technologies may be implemented. A local unit 1105 owned or used by a caregiver 1191 may be configured to receive one or more orders 1018, 1118 or other indications 1126, 1127, 1136, 1137 each comprising corresponding data components 126, 127, 136, 137 that each relate to a corresponding specific combination of a condition 160, 170 and protocol 120, 130 for its treatment, as shown. In some contexts, one or more servers 1195 (residing in networks described herein, e.g.) or local circuitry may provide selective feedback (one or more warnings 1119, e.g.) relating to some such combinations (selected by caregiver 1191, e.g.).

Figure 17:
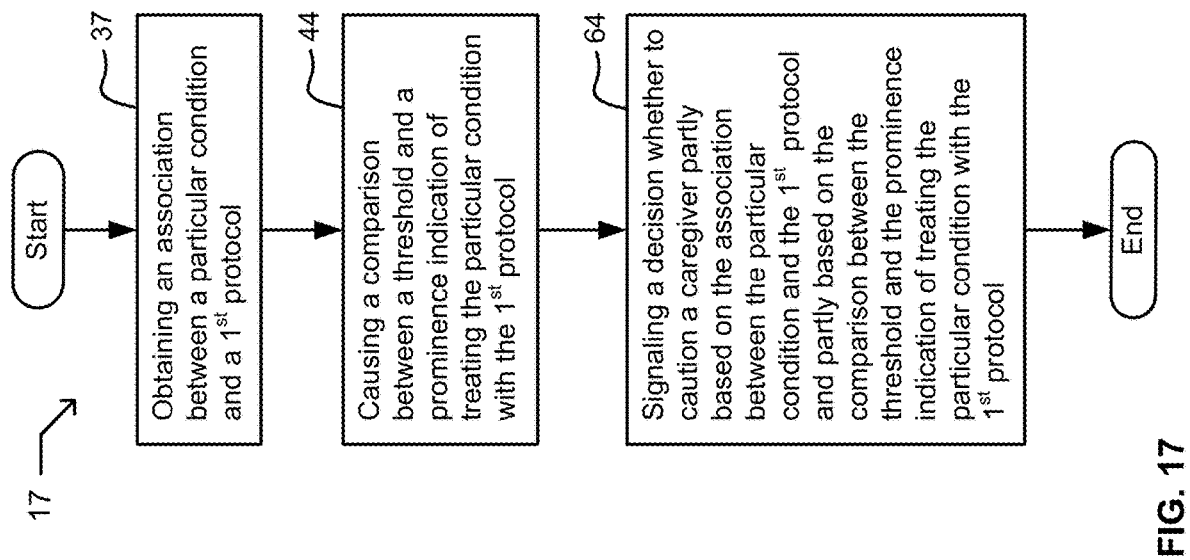
FIG. 17 depicts a high-level logic flow of an operational process (described with reference to FIG. 11, e.g.).

With reference now to FIG. 17, shown is a high-level logic flow 17 of an operational process. Intensive operation 37 describes obtaining an association between a particular condition and a first protocol (e.g. input module 311 receiving a record 563 indicating that an order 1118 was placed for a particular drug or protocol 130 prescribed or purchased for the treatment of a particular condition 160). This can occur, for example, in a context in which the protocol 130 includes administering prednisone daily by ingestion and in which the particular condition 160 is Bell's palsy, bone pain, carpal tunnel syndrome, muscular dystrophy, pulmonary fibrosis, or certain other off-label uses of prednisone. In some contexts, moreover, such protocols 120, 130, 140 may include other drugs or non-medicinal components (physical therapy or surgery, e.g.). Moreover input module 311 may, in some variants, be configured to be invoked by one or more queries 571-574 or other structured dialogs (permitting an expert system 393 to interact with a physician or other caregiver 1191 via local unit 1105, e.g.).

In light of teachings herein, numerous existing techniques may be applied for configuring special-purpose circuitry or other structures effective for searching for therapies or conditions that may apply to a patient as described herein without undue experimentation. See, e.g., U.S. Pat. No. 8,008,285 ("Droxidopa and pharmaceutical composition thereof for the treatment of fibromyalgia"); U.S. Pat. No. 8,005,687 ("System, method and computer program product for estimating medical costs"); U.S. Pat. No. 7,979,289 ("System and method for intelligent management of medical care"); U.S. Pat. No. 7,860,552 ("CNS assay for prediction of therapeutic efficacy for neuropathic pain and other functional illnesses"); U.S. Pat. No. 7,797,145 ("Animal health diagnostics"); U.S. Pat. No. 7,552,039 ("Method for sample processing and integrated reporting of dog health diagnosis"); U.S. Pat. No. 7,490,048 ("Apparatus and method for processing and/or for providing healthcare information and/or healthcare-related information"); U.S. Pat. No. 7,346,523 ("Processing an insurance claim using electronic versions of supporting documents"); U.S. Pat. No. 6,704,595 ("Automated method for diagnosing and monitoring the outcomes of atrial fibrillation"); and U.S. Pat. No. 6,014,626 ("Patient monitoring system including speech recognition capability").

Intensive operation 44 describes causing a comparison between a threshold and a prominence indication of treating the particular condition with the first protocol after the association between then particular condition and the first protocol is obtained (e.g. invocation module 373 triggering comparator 391 to generate an output 195 by comparing a prominence indication 1136 with a threshold 191). This can occur, for example, in a context in which one or more devices 305 (including media 105, 405, 505, 705, e.g.) reside in server 1195 and in which response module 351 selects the threshold 191 according to who initiates the association (as a function of a user identifier 523 of a specific caregiver 1191 or caregiver type, e.g.) or to what condition 160 or protocol 130 has been associated. In some contexts, for example, more esteemed caregivers or less hazardous conditions and protocols may warrant a threshold 192 corresponding to a lower prominence (signaling less scrutiny and more latitude in the caregiver's choice of treatment protocols, e.g.). Alternatively or additionally, invocation module 373 may trigger a comparison implemented in a formula (as a subtraction, e.g.). In some contexts, moreover, a less-prominent protocol may be requested by a patient 250 or warranted by the patient's situation. Alternatively or additionally, invocation module 373 may be configured to trigger a storage operation in which one or more instances of prominence indications 1136; thresholds 191; comparison results; quantifications of reputation or scrutiny or latitude (characterizing caregiver 1191, e.g.); or other output 195 are stored in one or more records 569-569, 671-675 as described herein (e.g. in a data component 136-138, 146-148 relating to an elected protocol 130, 140).

Extensive operation 64 describes signaling a decision whether to caution a caregiver partly based on the association between the particular condition and the first protocol and partly based on the comparison between the threshold and the prominence indication of treating the particular condition with the first protocol (e.g. response module 356 transmitting an "obscure treatment option" warning 1119 to caregiver 1191 if the threshold 191 exceeds the prominence indication 1136 and otherwise not transmitting any such warning). This can occur, for example, in a context in which server 1195 is on several networks 290, 890, 990; in which searching various records archives 820, 920 can take several minutes or hours to determine a prominence indication 1136; in which local unit 1105 includes an e-mail or other text message display capability operable to deliver such warnings; in which a hospital 201 or field of practice uses a standard numerical threshold for all prominence indication comparisons; and in which the caregiver 1191 would otherwise select among several protocols 120, 130 for the particular condition(s) 160, 170 without knowing which of them had recently become popular in the caregiver's field of practice. In a context in which higher numerical indications 1126 signify more prominence and in which a threshold is set at 4, for example, such threshold may be met (sufficient to avoid triggering a cautionary message to caregiver 1191, e.g.) by determining either that 4 instances of condition 160 had been treated with protocol 120 (for an implementation incorporating a use count 1054, e.g.) or that one or more entities indicated the effectiveness of treating condition 160 with protocol 120 with an average evaluation of at least 4 (for an implementation incorporating an average evaluation 1053, e.g.). Alternatively or additionally, response module 356 may be configured to implement a conditional decision to caution a caregiver 1191 with one or more of a font effect (a bolding or bright color selectively applied for lower-prominence therapies, e.g.), audible warning 1119 (a tone, e.g.), or modal dialog box (displaying a message like "are you sure you want to order this unconventional treatment?" at local unit 1105 before finalizing order 1118, e.g.).

Figure 12:
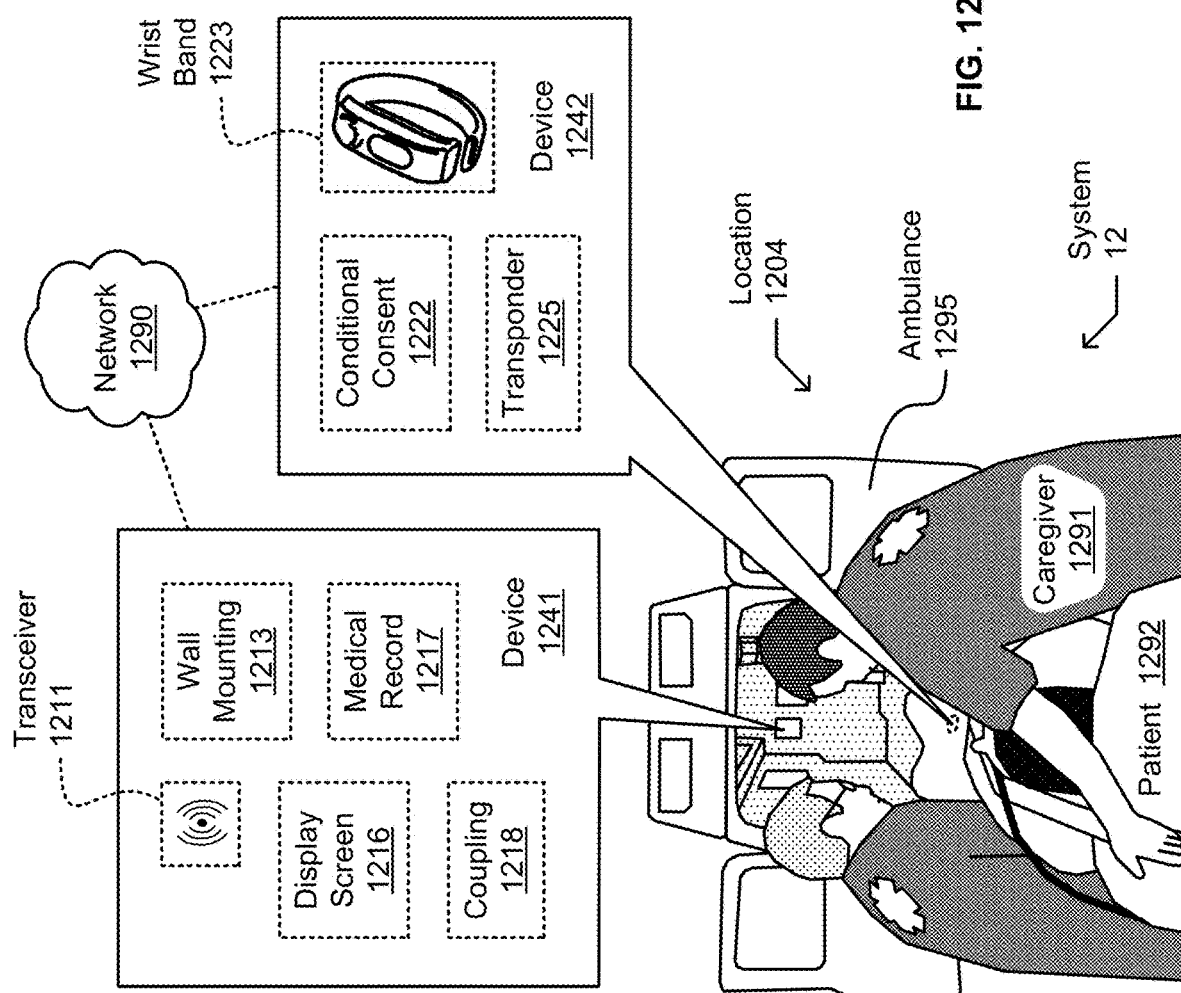

With reference now to FIG. 12, shown is another example of a system 12 (e.g. a subsystem of one or more networks 290, 890, 990, 1090, 1290) in which one or more technologies may be implemented. A motor vehicle or other device 1241 associated with a care administration space (a location 1204 inside or near ambulance 1295 configured to permit one or more caregivers 1291 to treat a patient 1292 in trauma, e.g.) may include one or more instances of wireless transceivers 1211, wall mountings 1213, display screens 1216, or couplings 1218 to external power. Also in some contexts, as described below, device 1241 may be configured to obtain and present one or more medical records 1217 (comprising one or more data components 126, 128 relating to an emergency protocol 120 or to a specific patient 1292 relayed via display screen 1216, e.g.). This can occur, for example, in a context in which a wrist band 1223 or other device 1242 worn or held by patient 1292 contains one or more implementations of conditional consent 1222 (configured by patient 1292 prior to an emergency, e.g.) or transponders 1225 as described below.

Figure 18:
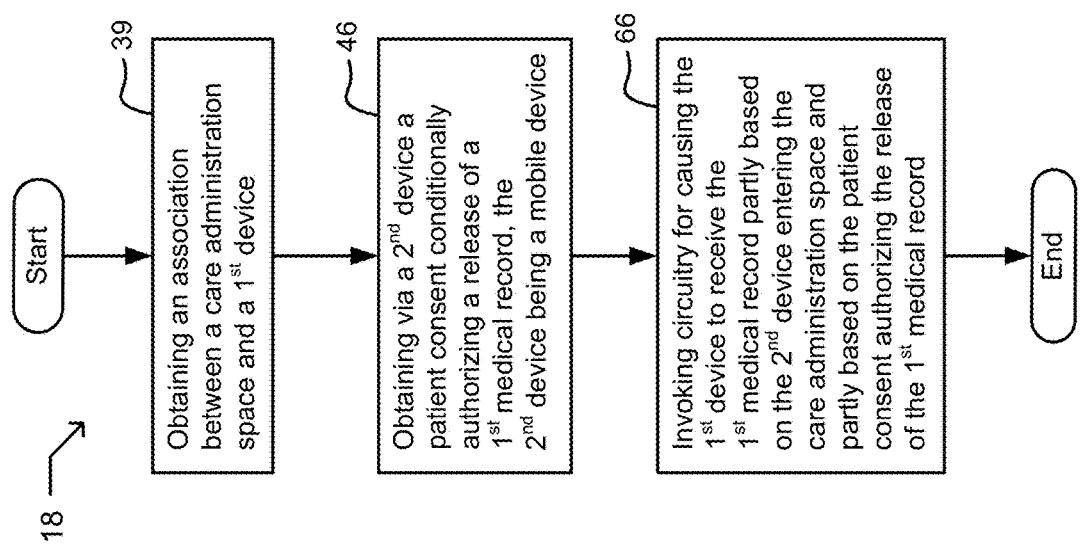
FIG. 18 depicts a high-level logic flow of an operational process (described with reference to FIG. 12, e.g.).

With reference now to FIG. 18, shown is a high-level logic flow 18 of an operational process. Intensive operation 39 describes obtaining an association between a care administration space and a first device (e.g. configuration module 322 making a record 568 in which an identifier 734 of the "first" device 242, 1241 is associated with an identifier 732 of an ambulance 1295 or other location 204 allocated to providing patients 250 medical care). This can occur, for example, in a context in which "first" device 242, 1241 includes a wall mounting 1213 fixing it in relation to the care administration space; in which the "first" device includes a wireless transmitter 394 or transceiver 1211 detectable by a "second" device as described below; and in which the care administration space is defined by the effective range of the wireless transmitter 394 or transceiver 1211. In some contexts, for example, such locations 204 may include an emergency room or urgent care clinic. Alternatively or additionally, a regional server 1195 or other stationary device in network 1290 may be configured to obtain GPS data 751 indicating a current position of an ambulance 1295 or other mobile care administration space that may then be compared with GPS data 752 indicating a current position of a device held or worn by patient 250 (e.g. through network 1290 in lieu of direct wireless transmission between proximate devices 1241, 1242). In some contexts, moreover, the "first" device may comprise an external power coupling 1218 configured to power the "first" device for an indefinite period (via a vehicle battery or similar source that is maintained daily, e.g.).

In light of teachings herein, numerous existing techniques may be applied for configuring special-purpose circuitry or other structures effective for configuring a device for direct or indirect wireless communication as described herein without undue experimentation. See, e.g., U.S. Pat. No. 7,986,940 ("Automatic wireless network linking method with security configuration and device thereof"); U.S. Pat. No. 7,940,744 ("System, apparatus and method for automated wireless device configuration"); U.S. Pat. No. 7,929,950 ("Dynamically configurable IP based wireless device and wireless networks"); U.S. Pat. No. 7,916,707 ("Identity-based wireless device configuration"); U.S. Pat. No. 7,885,687 ("Device for updating configuration information in a wireless network"); U.S. Pat. No. 7,778,752 ("System for connecting a telematics device to a vehicle using a wireless receiver configured to transmit diagnostic data"); U.S. Pat. No. 7,681,231 ("Method to wirelessly configure a wireless device for wireless communication over a secure wireless network"); U.S. Pat. No. 7,643,828 ("Method and apparatus for fast link setup in a wireless communication system"); U.S. Pat. No. 7,616,594 ("Wireless device discovery and configuration"); and U.S. Pat. No. 7,233,745 ("Field device configured for wireless data communication").

Intensive operation 46 describes obtaining via a second device a patient consent conditionally authorizing a release of a first medical record, the second device being a mobile device (e.g. input module 315 receiving pre-emergency input 551 from or about a patient 492 that includes a conditional consent 1222 permitting a release of the one or more medical records 567, 1217 of the patient's to a caregiver 991, 1291 that is contingent upon the occurrence of an emergency). This can occur, for example, in a context in which the patient 492 (who can, in some instances, be the same individual as one or more other identified patients depicted herein, e.g.) enters such pre-emergency input 551 (by a menu selection, e.g.) using a handheld device (the "second" device 1242, e.g.); in which the "occurrence of an emergency" is manifested as the "second" device entering the "care administration space" (e.g. location 204, 1204); and in which the authorization to release the "first" medical record would otherwise be much slower (due to trauma, e.g.). In some contexts, for example, the "first" device may be configured to include one or more media 105, 505 bearing such contingently-releasable medical records 1217 for most or all registered patients 992, 1292 (patients enrolled in registry 109, e.g.) in a region (county or state, e.g.) so that the "first" and "second" devices 1241, 1242 may easily interact directly and locally (not via network 1290, e.g.) with or without network 1290 being online. Alternatively or additionally, the "second" device may include a wrist band 1223 wearable by an at-risk patient 1292 (e.g. one suffering from dementia, epilepsy, or other medical conditions that make it more likely that a patient may be unable to consent to a records transfer).

Extensive operation 66 describes invoking circuitry for causing the first device to receive the first medical record partly based on the second device entering the care administration space and partly based on the patient consent authorizing the release of the first medical record (e.g. invocation module 372 causing display screen 1216 of device 1241 to display medical record 1217 as an automatic response to the "second" device 1242 entering the care administration space and partly based on the prior configuration of above-described conditional consent 1222 (in operation 46, e.g.). In some contexts, for example, such configuration may have been implemented by a non-emergency caregiver 991 who provides the patient with the "second" device 1242. Alternatively or additionally, in some contexts, a local entity (a hospital 201 or ambulance company, e.g.) may own the first device, a patient may own the second device, and a third entity may own the invoked "circuitry."

In light of teachings herein, numerous existing techniques may be applied for configuring special-purpose circuitry or other structures effective for identifying wireless devices in a region of interest as described herein without undue experimentation. See, e.g., U.S. Pat. No. 7,903,905 ("Pen-shaped scanning device having a region identity sensor"); U.S. Pat. No. 7,869,807 ("Method of managing a code identifying a wireless device with conflict minimized in a wireless telecommunications system"); U.S. Pat. No. 7,319,876 ("System and method for using equipment identity information in providing location services to a wireless communication device"); U.S. Pat. No. 7,295,120 ("Device for verifying a location of a radio-frequency identification (RFID) tag on an item"); U.S. Pat. No. 6,791,477 ("Method and apparatus for identifying waypoints and providing keyless remote entry in a handheld locator device"); U.S. Pat. No. 6,693,512 ("Device location and identification system"); and U.S. Pat. No. 6,392,747 ("Method and device for identifying an object and determining its location").

Figure 13:
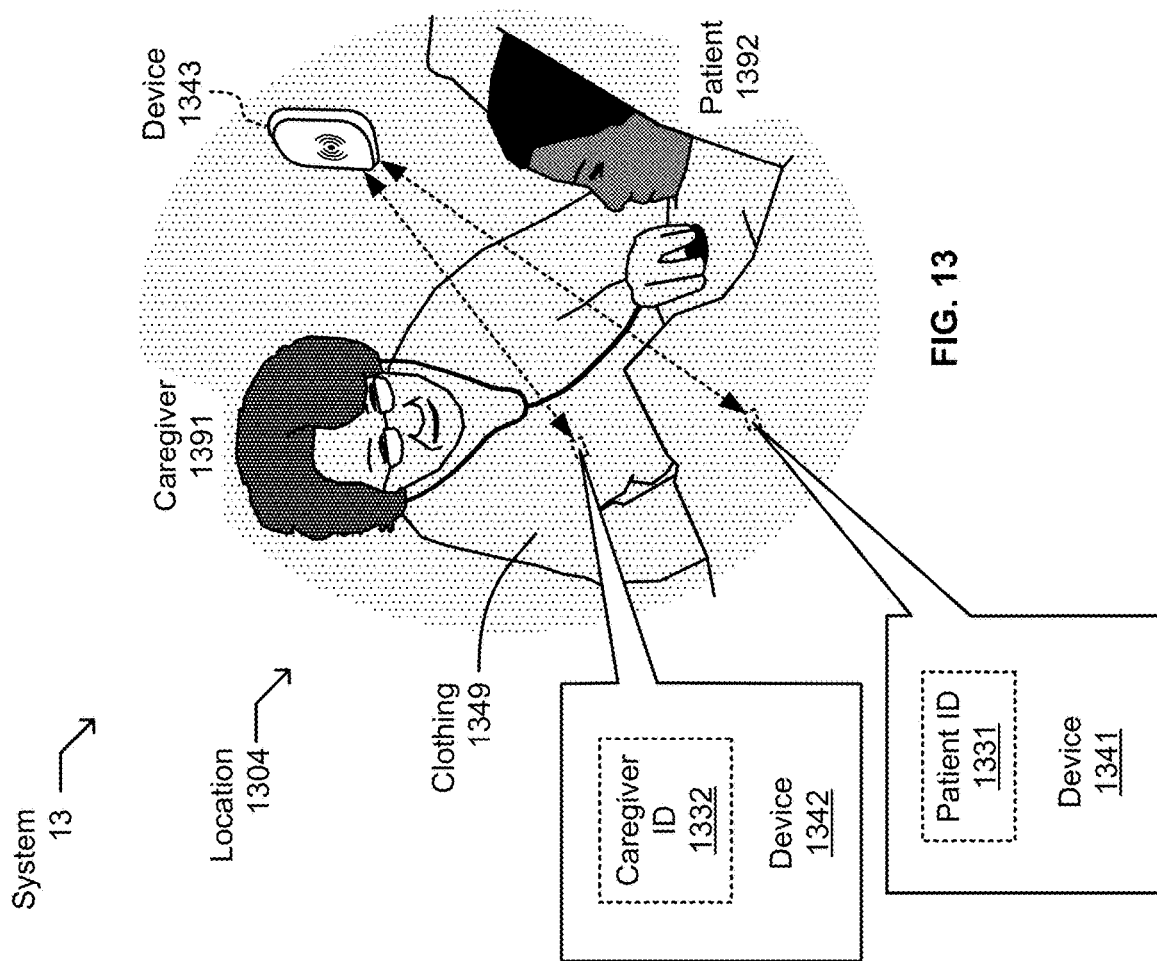

With reference now to FIG. 13, shown is another example of a system 13 (e.g. a subsystem of one or more networks 290, 890, 990, 1090, 1290) in which one or more technologies may be implemented. As shown, caregiver 1391 wears a device 1342 (on a lanyard or clothing 1349, e.g.) configured to include a caregiver identifier 1332 that identifies her. Likewise patient 1331 wears a device 1341 configured to include a patient identifier 1331 that identifies him (on a gown or wrist band 1223, e.g.). In some variants, such wearable devices 1341, 1342 are configured to interact wirelessly (either with one another or with a wall-mounted device 1343, e.g.) as an automatic response to being in a common location (e.g. at location 1204, 1304).

Figure 19:
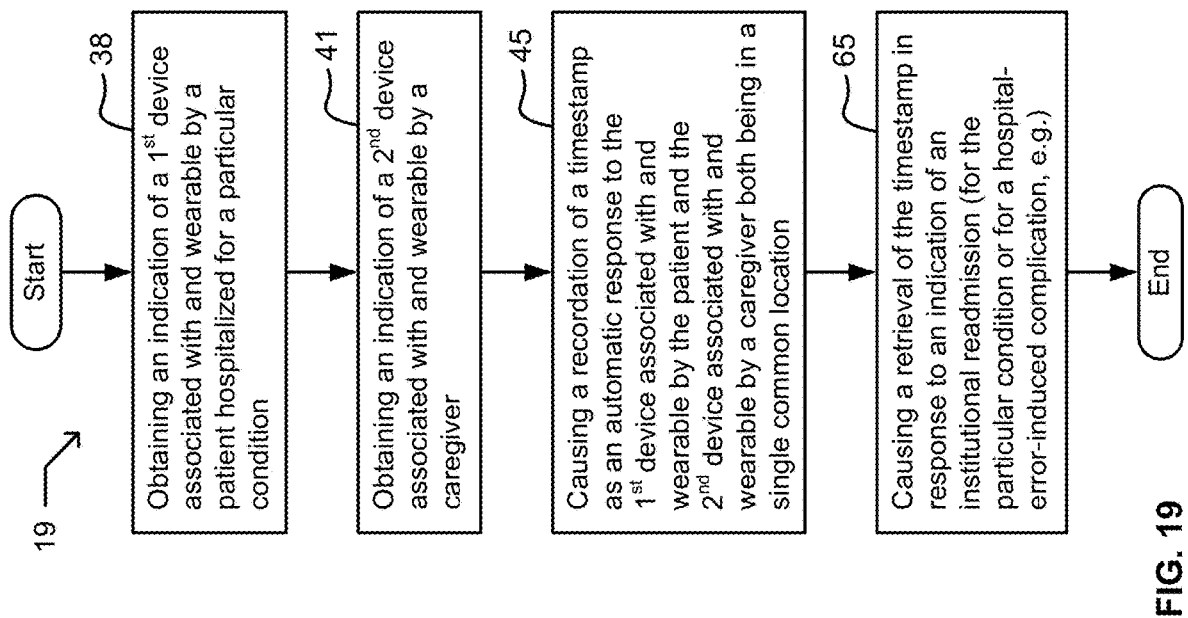
FIG. 19 depicts a high-level logic flow of an operational process (described with reference to FIG. 13, e.g.).

With reference now to FIG. 19, shown is a high-level logic flow 19 of an operational process. Intensive operation 38 describes obtaining an indication of a first device associated with and wearable by a patient hospitalized for a particular condition (e.g. configuration module 322 associating a specific patient 1392 with a patient identifier 1331 on an article wearable by a patient 1392 who has been admitted to hospital 201 for a specific pathology 181 or complaint 513). This can occur, for example, in a context in which the article (a wrist band 1223, e.g.) is assigned to patient 1392 upon checking in to the hospital; in which configuration module 322 was invoked at that time (at patient intake, e.g.); and in which one or more instances of device 305 reside on one or more networks described herein (in a wall-mounted device 1343 or server 1195 of hospital 201, e.g.). Alternatively or additionally, a stationary device 1343 may perform operation 38 by detecting a device 1341 associated with patient 1392 in a given location 1304 (entering his hospital room, e.g.).

Intensive operation 41 describes obtaining an indication of a second device associated with and wearable by a caregiver (e.g. configuration module 321 associating a specific caregiver 1391 with a caregiver identifier 1332 on an article wearable by the caregiver). This can occur, for example, in a context in which the article (on a badge or lanyard or in a wrist band or article of clothing 1349, e.g.) was assigned to caregiver 1391 upon arriving at the facility and in which configuration module 321 was invoked at that time. Alternatively or additionally, a stationary device 1343 (mounted on a wall, e.g.) may perform operation 41 by detecting a device 1342 associated with caregiver 1391 in a given location 1304 (entering her patient's hospital room, e.g.).

Intensive operation 45 describes causing a recordation of a timestamp as an automatic response to the first device associated with and wearable by the patient and the second device associated with and wearable by a caregiver both being in a single common location (e.g. configuration module 324 storing a timestamp 711 indicating when both caregiver 1391 and patient 1392 were together in location 1304). This can occur, for example, in a context in which timestamp 711 is generated from a digital clock 392; in which record 710 is initially aggregated at one or more devices 1341-1343 locally, in which one or more records archives 820, 920 later received record 710 in a batch data aggregation process, and in which the "single common location" is a hospital room or a detection range of one or more devices 1341-1343. In some implementations, for example, device 1341 may include one or more configuration modules 321-326 as described herein and may be configured to perform operations 38, 41, and 45 (in lieu of device 1343, e.g.). Alternatively or additionally, in some variants, device 1342 may likewise include one or more configuration modules 321-326 as described herein and may be configured to implement device 305 (e.g. operable to perform operations 38, 41, and 45).

Extensive operation 65 describes causing a retrieval of the timestamp in response to an indication of an institutional readmission after the recordation of the timestamp indicating the first device associated with and wearable by the patient and the second device associated with and wearable by the caregiver both having been in the single common location (e.g. response module 352 retrieving a record 710 including such timing data 453 from one or more records archives 820, 920 in response to a request 581 indicative of patient 1392 being readmitted to one or more hospitals 201, 202 for the same specific pathology 181 or complaint 513). This can occur, for example, in a context in which such readmission for the particular condition would otherwise trigger a reduction in payment for one or more prior hospitalizations. In some contexts, for example, one or more remote requestors 893, 993 may have initiated a prior instance of operation 65 (performed by a remote instance of invocation module 371, e.g.) in which an entity's request 581 for records included a readmission-indicative report type 521 (having a name that includes "readmission," e.g.), a readmission-indicative request authorization 522 (from an agency that monitors excessive readmissions, e.g.), a query reciting or prompted by readmission, or other such explicit or implicit indications 525 of readmission that might have been avoidable if a prior hospitalization or treatment had been executed correctly. Alternatively or additionally, response module 352 may be configured to perform operation 65 by retrieving and transmitting such a timestamp-containing record 710 (indicative of when the first and second devices 1341, 1342 were both in the single common location 1304, e.g.) to one or more remote requestors 893, 993.

With reference now to FIG. 20, shown is context in which one or more technologies may be implemented. System 2000 may include two or more devices 2005, 2015 having a linkage 2011 therebetween as described herein. In various embodiments, device 2005 may include one or more instances of lookup modules 2021, 2022; update modules 2028, 2029; detection modules 2041, 2042, 2043, 2044, 2045, 2046; cameras 2053 or other sensors 2054; or processors 2055 as described below. Alternatively or additionally, device 2005 may comprise a machine 2030 (configured for vending or other dispensations of drugs 141, foods, or other goods 691, e.g.); a battery or other on-board power supply 2058; or one or more speakers 2057 (configured to manifest a warning 1119 or other audio data 2257 as described below, e.g.). In various implementations, device 2015 may likewise include one or more instances of food containers (refrigerators or cupboards 2071, e.g.); actuators 2072 (of a dispenser, e.g.); exercise machines 2073 (relating to one or more regimens 2331-2339, e.g.); handhelds 2074 (telephones, e.g.); detectable structures 2075 (transponder or barcode, e.g.); adhesives 2077; wristbands 2078; or buttons 2079. Alternatively or additionally, device 2015 may comprise medical equipment 2080 (devices configured for imaging or measurement, e.g.). One or more of devices 2005, 2015 may be configured to implement an instance of device 305 and to include one or more media depicted herein. See FIGS. 1, 4-7 and 21-26.

With reference now to FIG. 21, shown is context in which one or more technologies may be implemented. System 2100 includes one or more data-handling media 2105 (residing in an instance of device 305, e.g.) operably coupled with one or more search engines 2198 on the various networks described herein. Medium 2105 may include one or more instances of search terms 2110 (e.g. comprising criteria 2101, 2102); names 2111, audit identifiers 2112, or other such indications 2113; search results 2130; values 2161, 2162; or queries 2171, 2172 as described below.

Figure 22:
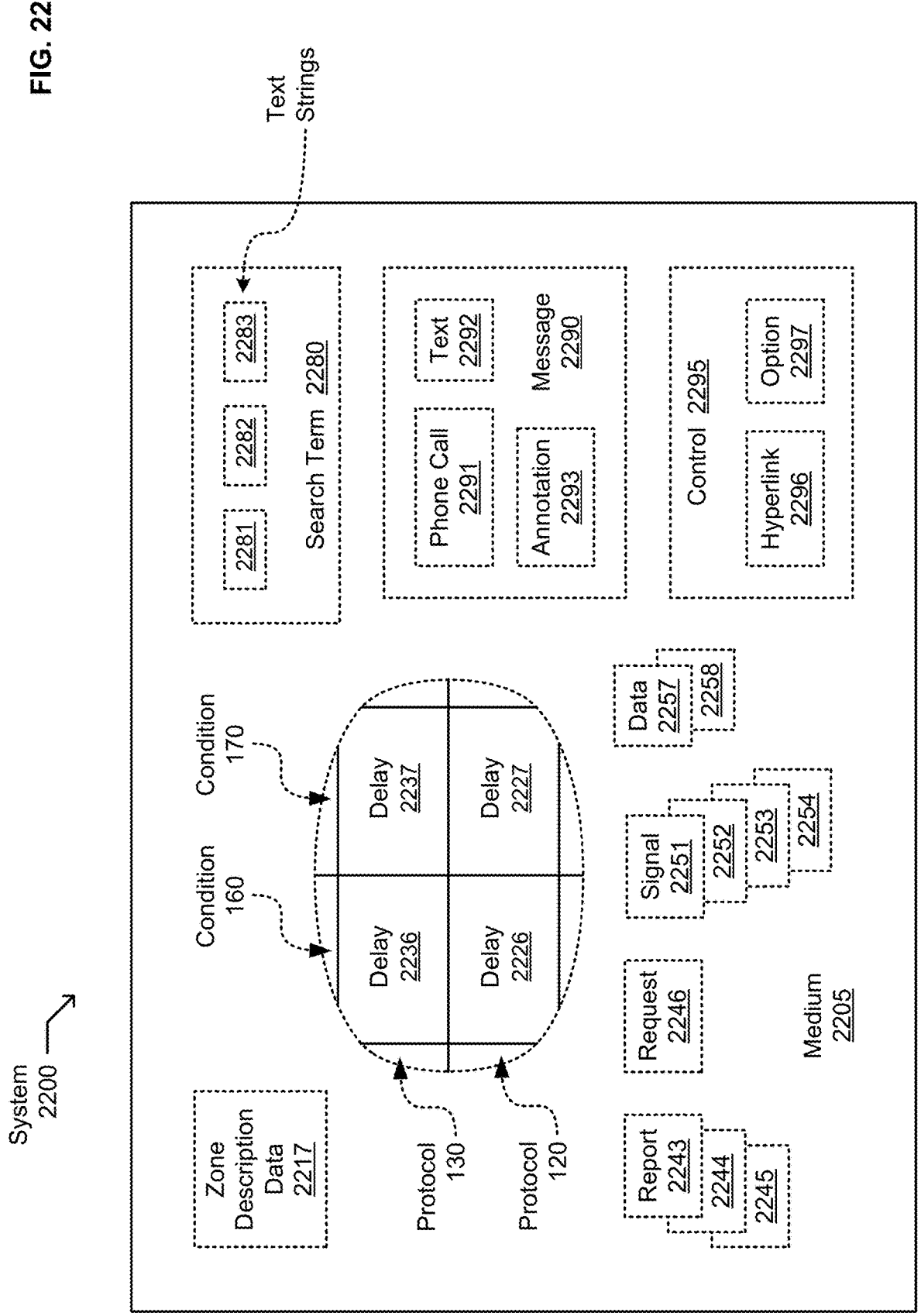

With reference now to FIG. 22, shown is context in which one or more technologies may be implemented. System 2200 may (optionally) include one or more data-handling media 2205 (configured to transmit or store data, e.g.) residing in an instance of device 305 or otherwise on a network 290 as described above. In some variants, medium 2205 may bear one or more instances of zone description data 2217 (e.g. representing one or more service zones 207, 208 or other locations 204, 1204, 1304); data components 126, 127, 136, 137 (in tabular form, e.g.); reports 2243, 2244, 2245; requests 2246; signals 2251, 2252, 2253, 2254 (comprising audio data 2257 or other encoded data 2258, e.g.); search terms 2280 (comprising one or more text strings 2281, 2282, 2283 connected by logical operators, e.g.); messages 2290 (comprising phone calls 2291, text 2292, and annotations 2293 as described below, e.g.); and hyperlinks 2296, menu options 2297, or other such controls 2295 (comprising one or more interfaces 1001, 1002 or other devices described above, e.g.). In some contexts, data component 126 (as described above) may include one or more delays 2226 corresponding specifically to the handling of condition 160 with protocol 120; data component 127 (as described above) may include one or more delays 2227 corresponding specifically to the handling of condition 170 with protocol 120; data component 136 (as described above) may include one or more delays 2236 corresponding specifically to the handling of condition 160 with protocol 130; and data component 137 (as described above) may include one or more delays 2237 corresponding specifically to the handling of condition 170 with protocol 130. Moreover in some variants each instance of audio data 2257 may include one or more timestamps 711 as well as other data 712 (transcripts or labels of patient interview clips, recorded physician remarks, concurrent diagnostic data 490, or other events encoded as text 2292 or other annotations 2293 relating to raw auditory data with which they are archived, e.g.).

Figure 23:
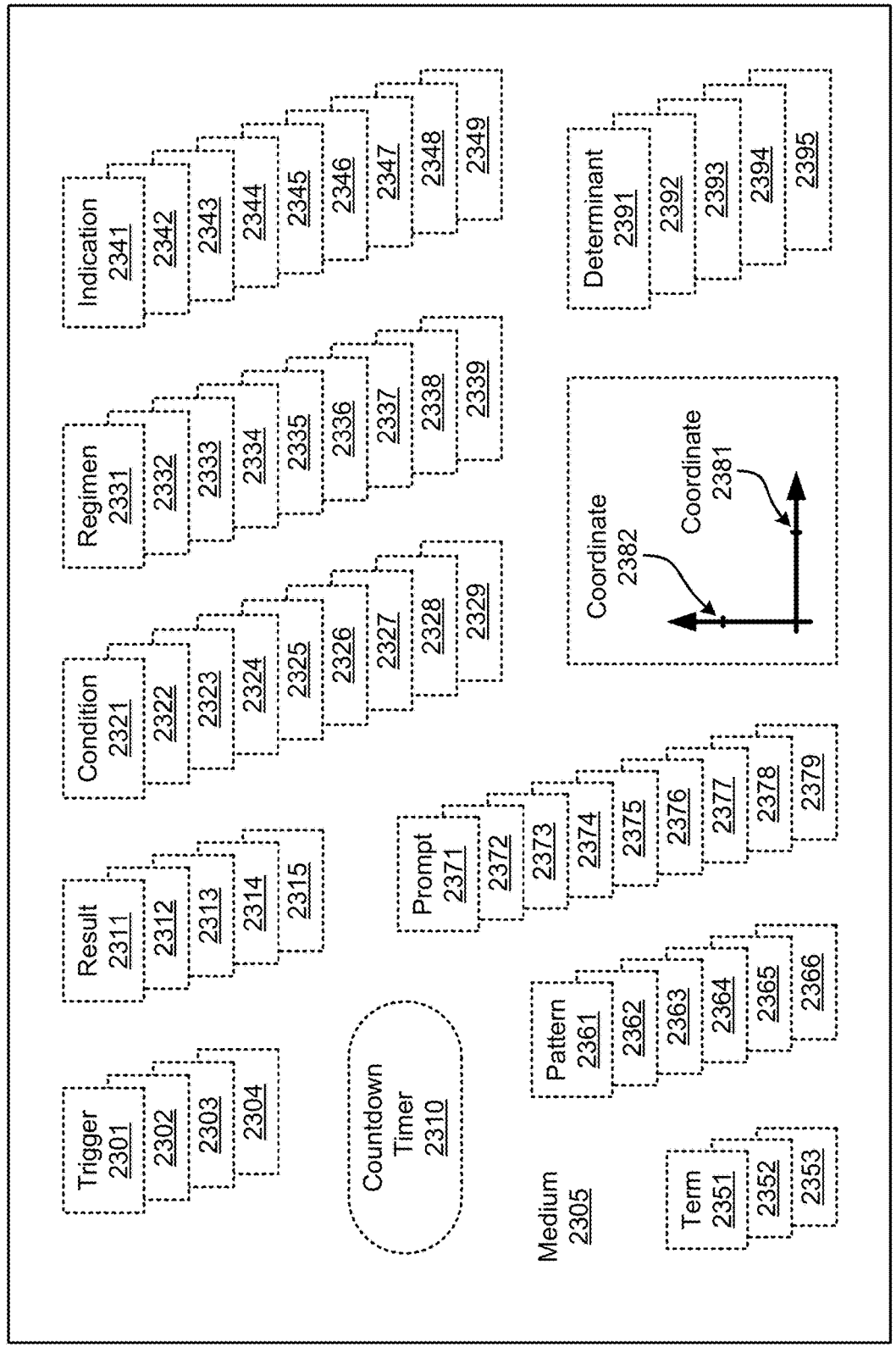

With reference now to FIG. 23, shown is context in which one or more technologies may be implemented. System 2300 may include one or more data-handling media 2305 (configured to transmit or store data, e.g.) residing in an instance of device 305 or otherwise on a network 290 as described above. In some variants, medium 2305 may bear one or more instances of triggers 2301, 2302, 2303, 2304; countdown timers 2310; results 2311, 2312, 2313, 2314, 2315; conditions 2321, 2322, 2323, 2324, 2325, 2326, 2327, 2328, 2329; regimens 2331, 2332, 2333, 2334, 2335, 2336, 2337, 2338, 2339; indications 2341, 2342, 2343, 2344, 2345, 2346, 2347, 2348, 2349; terms 2351, 2352, 2353; patterns 2361, 2362, 2363, 2364, 2365, 2366; prompts 2371, 2372, 2373, 2374, 2375, 2376, 2377, 2378, 2379; coordinates 2381, 2382; or other such user interaction content or programmatic determinants 2391, 2392, 2393, 2394, 2395 affecting automatic decisions as described herein.

Figure 24:
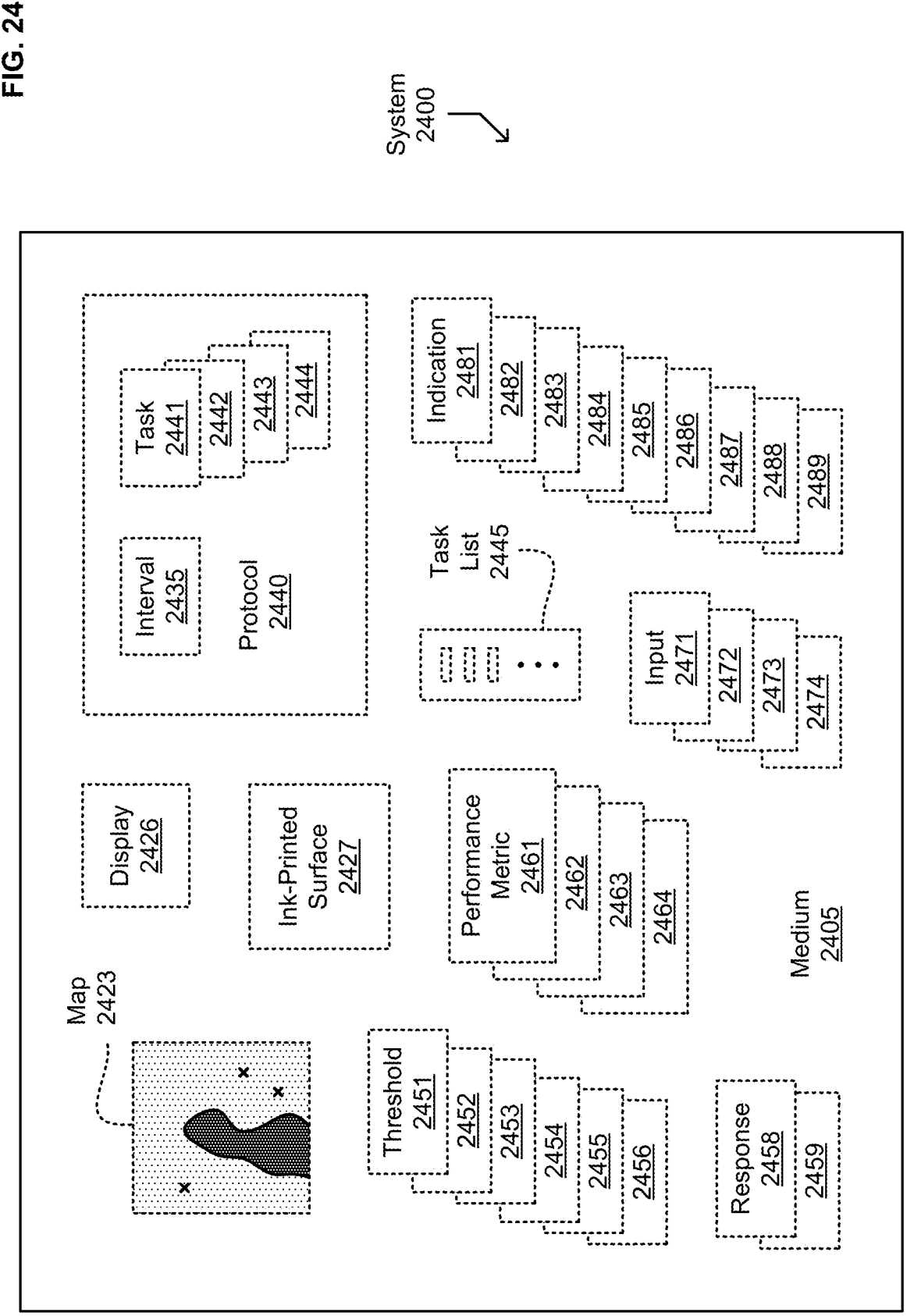

With reference now to FIG. 24, shown is context in which one or more technologies may be implemented. System 2400 may include one or more data-handling media 2405 (configured to transmit or store data, e.g.) residing in an instance of device 305 or otherwise on a network 290 as described above. In some variants, medium 2405 may bear one or more instances of maps 2423 or similar positional graphics; screen displays 2426 or ink-printed surfaces 2427; protocols 2440 or other task lists 2445 (comprising one or more time intervals 2545 associated with one or more tasks 2441, 2442, 2443, 2444, e.g.); thresholds 2451, 2452, 2453, 2454, 2455, 2456; responses 2458, 2459; performance metrics 2461, 2462, 2463, 2464; inputs 2471, 2472, 2473, 2474; or other indications 2481, 2482, 2483, 2484, 2485, 2486, 2487, 2488, 2489 (as user interaction content or programmatic determinants affecting automatic decisions as described herein, e.g.).

Figure 25:
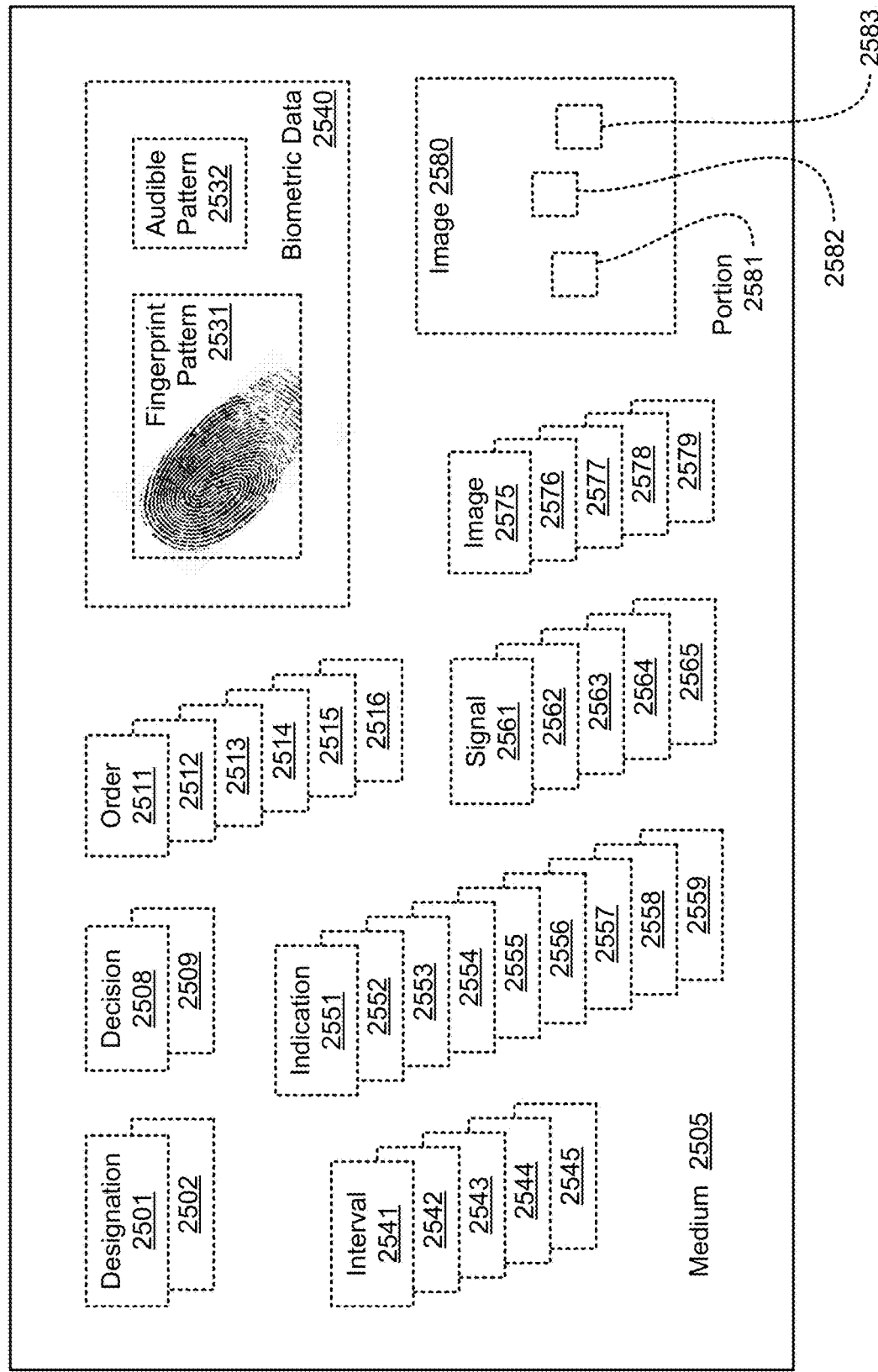

With reference now to FIG. 25, shown is context in which one or more technologies may be implemented. System 2500 may include one or more data-handling media 2505 (configured to present or otherwise transmit data, e.g.) residing in an instance of device 305 or otherwise on a network 290 as described above. In some variants, medium 2505 may bear one or more instances of designations 2501, 2502; decisions 2508, 2509; orders 2511, 2512, 2513, 2514, 2515, 2516; biometric data 2540 (comprising a fingerprint pattern 2531 or audible pattern 2532, e.g.); intervals 2541, 2542, 2543, 2544, 2545; indications 2551, 2552, 2553, 2554, 2555, 2556, 2557, 2558, 2559; signals 2561, 2562, 2563, 2564, 2565; or images 2575, 2576, 2577, 2578, 2579, 2580 (comprising respective image portions 2581, 2582, 2583 and a remainder, e.g.).

Figure 26:
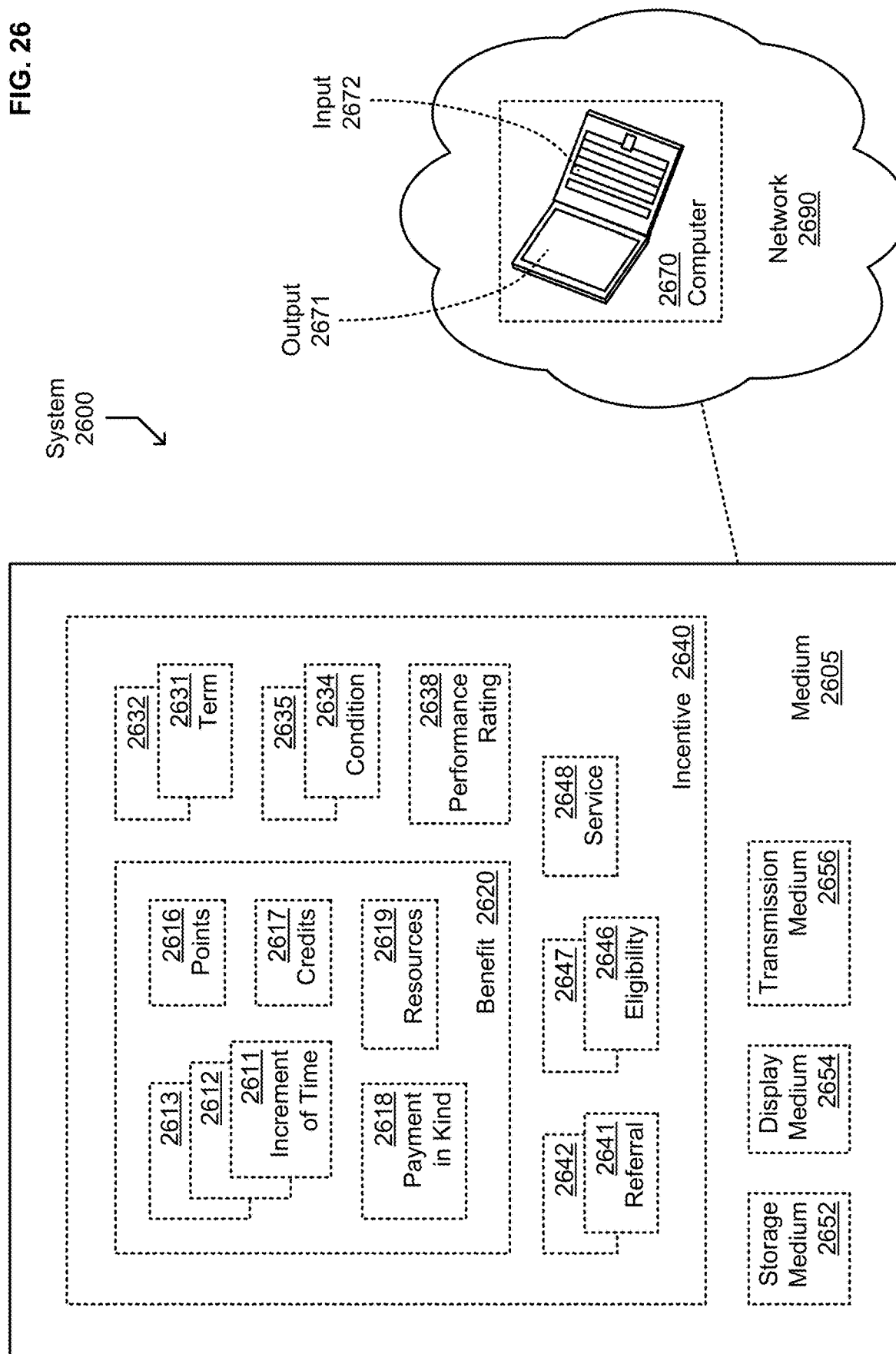

With reference now to FIG. 26, shown is a system 2600 in which one or more technologies may be implemented. System 2600 may include one or more incentives 2640 represented or manifested (as voltage levels or magnetization states comprising digital expressions, e.g.) on magnetic or other storage media 2652, display media 2654, transmission media 2656, or other media 2605. In some contexts, such expressions may explicitly associate an actual (accomplished) or prospective incentive 2640 that is physical and tangible: a card or other device-readable medium granting a membership or other temporary access for one or more increments 2611, 2612, 2613 of time; cash or other certificates indicative of points 2616, credits 2617 or other physical media of exchange; medications, nutritional supplements, exercise equipment, or other goods transferred as payments in kind 2618; or other such resources 2619 directly manifesting a physical, tangible benefit 2620 as (at least part of) the incentive. Alternatively or additionally, such incentives can include one or more discounts or other terms 2631, 2632 or conditions 2634, 2635; performance ratings 2638 or favorable referrals 2641, 2642; policies, rebates, or other eligibilities 2646, 2647; or supplemental therapies or other such services 2648. In some contexts, as exemplified below, a combination of such incentives may be necessary or helpful for motivating qualified patients to comply with a testing or treatment regimen 2331-2339 or for motivating others to explain or otherwise facilitate an individual's participation or enrollment in a testing or treatment program. Alternatively or additionally, one or more of the above-described devices may include medium 2605 and may access or be accessed by a network 2690. In some contexts, for example, a portable computer 2670 or similar user interface 1001 residing in network 2690 may comprise one or more outputs 2671 or inputs 2672 (operable for entering or accessing one or more orders 2511-2516 or other user data, e.g.) as shown.

In light of teachings herein, numerous existing techniques may be applied for identifying and administering tangible or other incentives effectively to motivate individuals to suggest or elect products or programs as described herein without undue experimentation. See, e.g., U.S. Pat. No. 7,739,115 ("Script compliance and agent feedback"); U.S. Pat. No. 7,668,747 ("System and method for providing incentives to purchasers"); U.S. Pat. No. 7,653,594 ("Targeted incentives based upon predicted behavior"); U.S. Pat. No. 7,624,051 ("Method and system for forming a list-based value discovery network"); U.S. Pat. No. 7,555,444 ("Dynamic time-of-purchasing-decision incentive system and method"); U.S. Pat. No. 7,433,834 ("Apparatus and method for facilitating transactions"); U.S. Pat. No. 7,389,245 ("Method and apparatus for providing incentives to physicians"); U.S. Pat. No. 7,376,700 ("Personal coaching system for clients with ongoing concerns such as weight loss"); U.S. Pat. No. 7,373,318 ("Information recommendation apparatus and information recommendation system"); U.S. Pat. No. 7,016,854 ("Loyalty link method and apparatus with audio performance for integrating customer information with dealer management information"); U.S. Pat. No. 6,988,132 ("System and method for identifying and establishing preferred modalities or channels for communications based on participants' preferences and contexts"); U.S. Pat. No. 6,952,678 ("Method, apparatus, and manufacture for facilitating a self-organizing workforce"); U.S. Pat. No. 6,901,347 ("Availability, reliability or maintainability index including outage characterization"); U.S. Pat. No. 6,739,508 ("Evaluation apparatus with voting system, evaluation method with voting system, and a computer product"); U.S. Pat. No. 6,699,124 ("Amusement game incentive points system"); U.S. Pat. No. 6,561,811 ("Drug abuse prevention computer game"); and U.S. Pat. No. 5,537,314 ("Referral recognition system for an incentive award program").

Figure 27:
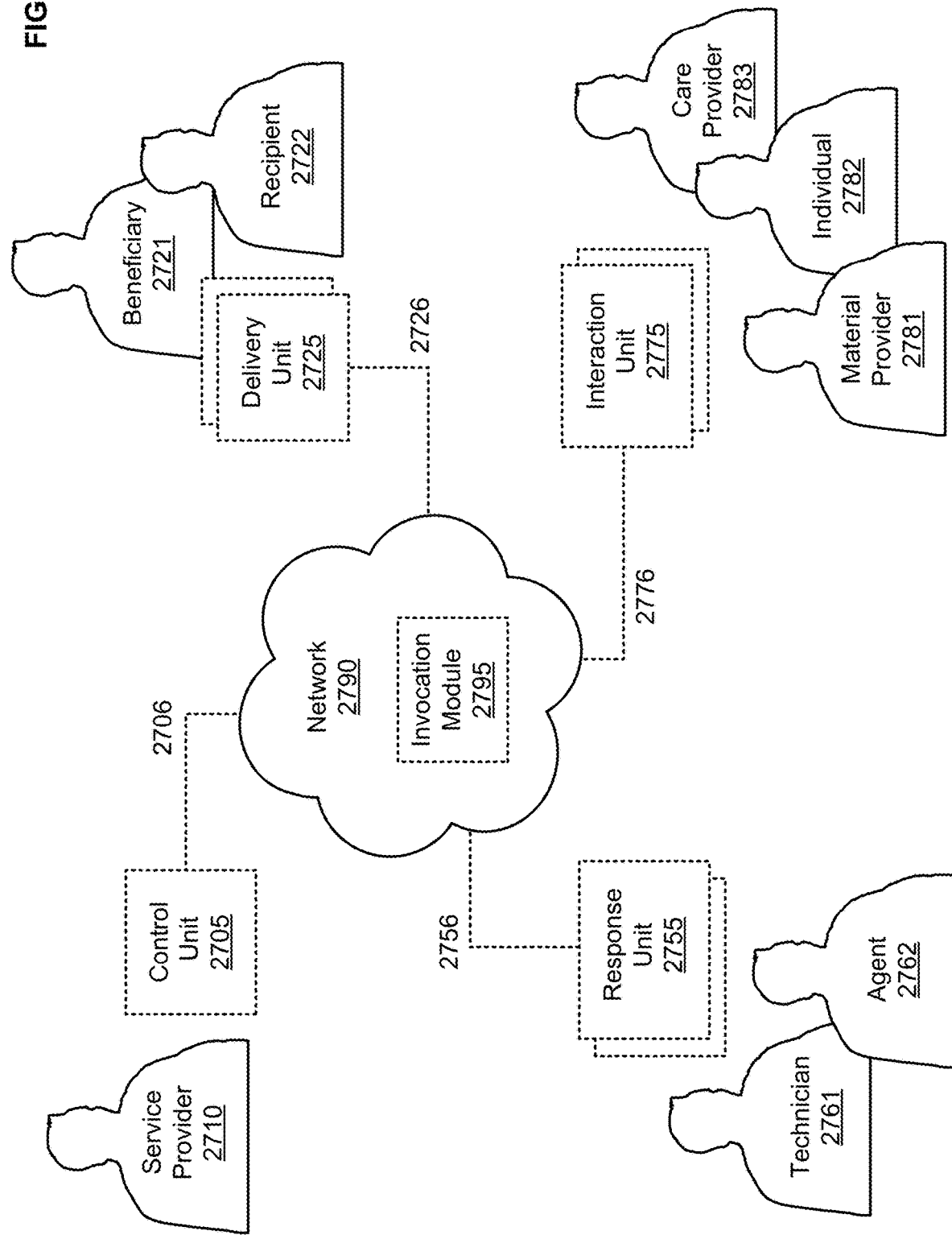
FIG. 27 depicts another exemplary environment in which one or more technologies may be implemented via one or more networked devices.

With reference now to FIG. 27, shown is a network 2790 having wireless signal paths or other suitable linkages 2706, 2726, 2756, 2776 providing access among several parties. An insurer, policymaker, program enrollment coordinator, or similar service provider 2710 may have access through a control unit 2705, for example, implementing a local display module or other media 2605 as described herein. One or more support technicians 2761, program enrollment coordinators, or other such agents 2762 may similarly access or provide data through network 2790 via servers or other response units 2755 implementing media 2605. Individuals 2782 prospectively or actually participating in a therapeutic or monitoring regimen 2331-2339 as described herein may similarly communicate with others on network 2790 via a portable or other local interaction unit 2775. Material providers 2781 or care providers 2783 having regular opportunities to interact personally with such individuals 2782 may likewise have local interaction units 2775 operable for indicating compliance, enrollment, or similar events to be tracked pursuant to therapeutic components (products or other requirements of a prescribed regimen, e.g.) or artificial incentives 2640 as described herein. Alternatively or additionally, correspondence or incentive deliveries to one or more beneficiaries 2721 or other recipients 2722 may occur automatically via one or more delivery units 2725 as described herein. Any such control units 2705, delivery units 2725, response units 2755, or interaction units 2775 may (optionally) include one or more storage media 2652, display media 2654, transmission media 2656 or other modules indicating, delivering, or otherwise manifesting one or more (artificial) incentives 2640 as described herein. In some variants, moreover, such devices or networks 2790 may include one or more invocation modules 371-374, 2795 (for facilitating one or more flows, e.g.) as described herein.

Figure 28:
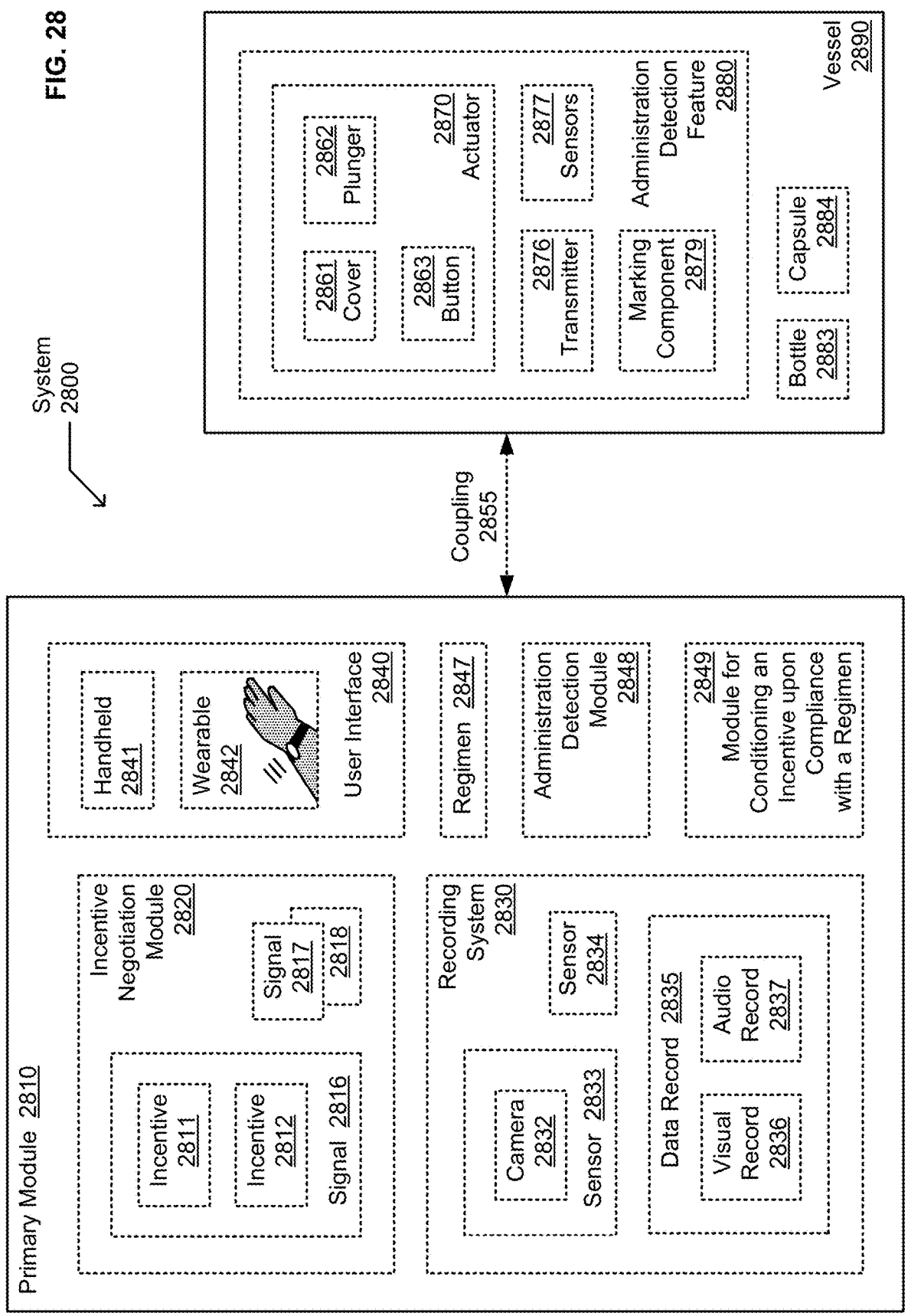
FIG. 28 depicts another exemplary environment in which one or more technologies may be configured to operate between or among respective devices.

With reference now to FIG. 28, shown is a system 2800 in which one or more technologies may be implemented. A bottle 2883, capsule 2884, or other vessel 2890 may include one or more plungers 2862, slidable or other covers 2861, buttons 2863, removable caps, or other actuators 2870. Such administration detection features 2880 may be configured effectively to permit one or more primary modules 2810 to monitor administrations (of a therapy, e.g.) within a vicinity of a vessel 2890, transdermal delivery device, iontophoretic device, patch with microprotrusions, dispenser, or other such object (variants of articles depicted below in FIGS. 29-47, e.g.). In some variants, for example, one or more transmitters 2876 on such dispensers permit periodic or occasional notifications (via a wireless or other coupling 2855 with a primary module 2810, e.g.) of such administrations (detected via one or more sensors 2877 of the vessel 2890, e.g.) or a remaining quantity of material (nominally or actually) available for dispensation. Alternatively or additionally, a colorant or other marking component 2879 permits direct optical or auditory monitoring (of a vessel or material, e.g.) within a vicinity of the dispenser or of a recipient 2722 of the therapy. Such systems may likewise include or otherwise interact with a vessel 2890 or other object containing one or more bioactive materials or other therapeutic components: medications, nutraceuticals, placebos, inhalants, inoculants or other such materials.

In some variants, a service delivery unit may include one or more primary modules 2810 having one or more instances of incentive negotiation modules 2820, recording systems 2830, user interfaces 2840, regimens 2847, administration detection modules 2848, modules for conditioning an incentive upon compliance with a regimen 2849, or administration detection features 2880 as described herein. In some contexts, for example, incentive negotiation module 2820 may handle one or more instances of signals 2816 indicative of one or more incentives 2811, 2812. Alternatively or additionally, such a module may handle one or more signals 2817 indicative of enrollment certification or signals 2818 indicative of informed consent (from an individual participating in a program described herein, e.g.). Recording system 2830 may include a camera 2832 or other sensor 2833 (capable of capturing a visual record 2836 or other data record 2835 confirming an administration or other relevant event as described herein, e.g.). An auditory sensor 2834 may likewise capture an audio record 2837 or other data record 2835 confirming a notification, enrollment, acceptance, transfer, or other relevant event as described herein. See also U.S. patent application Ser. No. 13/066,444 ("Cost-effective resource apportionment technologies suitable for facilitating therapies").

Figure 29:
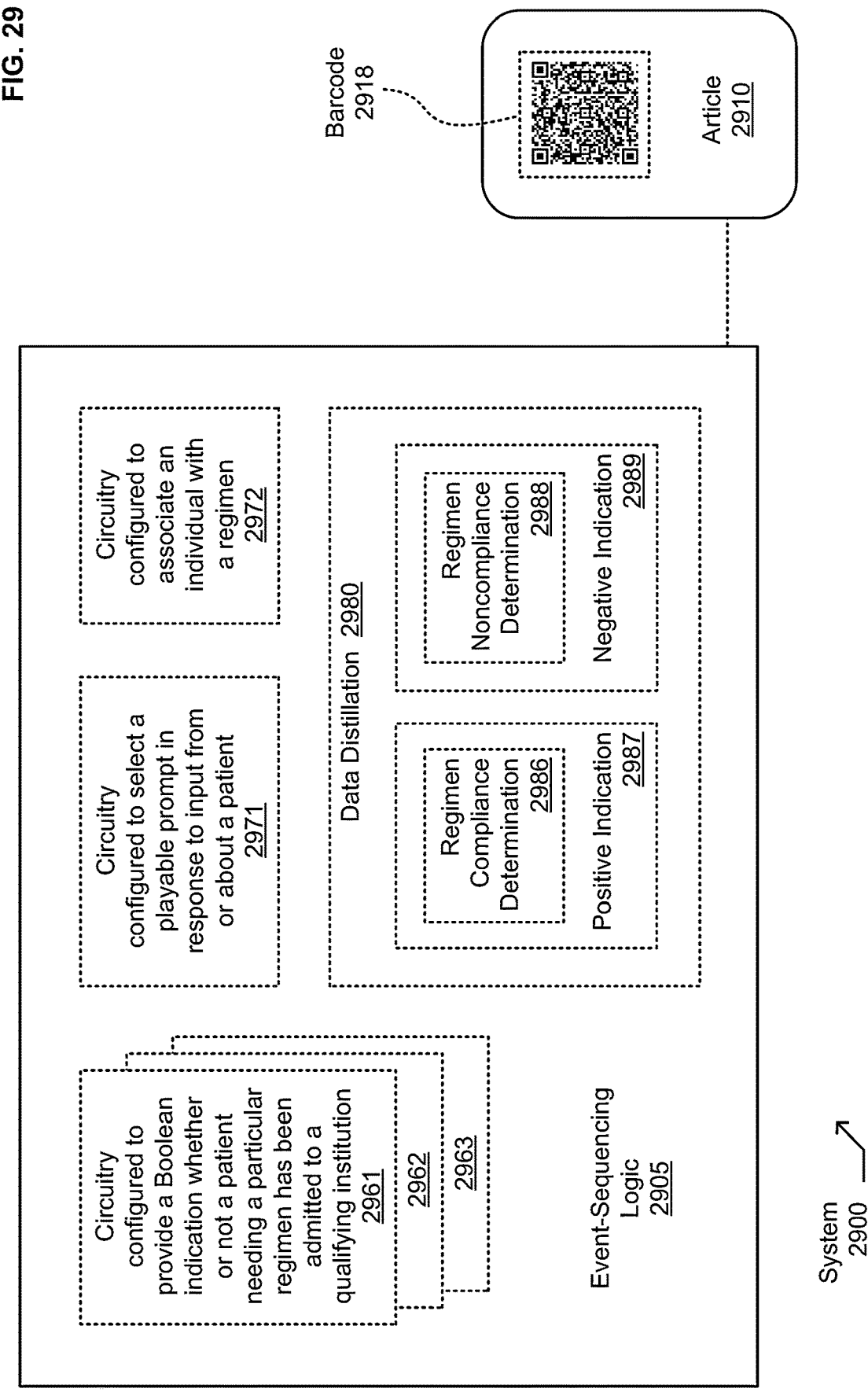
FIG. 29 depicts another exemplary environment in which local event-sequencing logic is configured to observe or interact with a uniquely identifiable article.

With reference now to FIG. 29, shown is a system 2900 in which one or more technologies may be implemented. Local event-sequencing logic 2905 (comprising control unit 2705 or interaction unit 2775, e.g.) may be configured to interact with or monitor or otherwise detect one or more articles 2910 having an RFID transponder 397 or ink-printed surface 2427 or other device-readable feature (barcode 2918, e.g.). As variously described above, for example, such articles may comprise a patient identifier 1331, caregiver identifier 1332, wearable article (wristband 2078, e.g.), or other such device or system. In some contexts, moreover, article 2910 may comprise a device 2005 that includes one or more cameras 2053 or other sensors 2054 or special-purpose circuitry (for remote interaction via network 290, e.g.) as described herein. Alternatively or additionally, local event-sequencing logic 2905 may itself comprise one or more instances of special-purpose transistor-based circuitry 2961, 2962, 2963 configured to provide a Boolean indication whether or not a patient needing a particular regimen has been admitted to a qualifying institution; special-purpose transistor-based circuitry 2971 configured to select a playable prompt in response to input from or about a patient; or special-purpose transistor-based circuitry 2972 configured to associate an individual with a regimen. Alternatively or additionally, local event-sequencing logic 2905 may comprise one or more regimen compliance determinations 2986 or other compliance-positive indications 2987; regimen non-compliance determinations 2988 or other compliance-negative indications 2989; or other such data distillations 2980 as described herein (with reference to media, e.g.) at FIG. 1, 4-7, or 21-26 or in U.S. patent application Ser. No. 13/199, 051 ("Systematic distillation of status data relating to regimen compliance").

Figure 30:
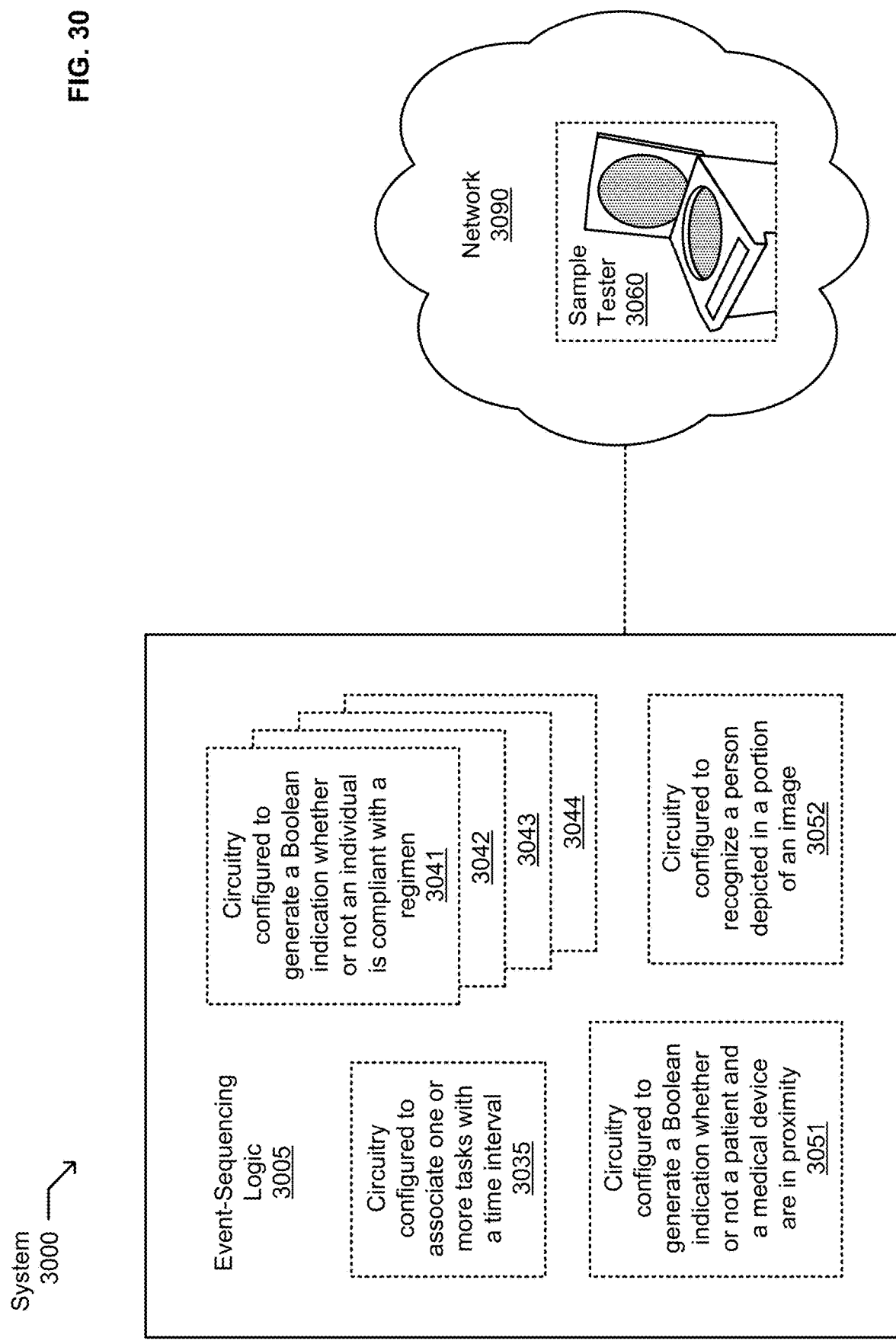
FIG. 30 depicts another exemplary environment in which local event-sequencing logic is configured to receive a signal from a sample tester or other networked device.

With reference now to FIG. 30, shown is a system 3000 in which one or more technologies may be implemented. Local event-sequencing logic 3005 (operably coupled with and local to event-sequencing logic 2905, e.g.) may be configured to interact with a sample tester 3060 (configured to perform a compliance-monitoring or other diagnostic test upon a blood or other fluid sample from a patient, e.g.) or other medical equipment 2080 residing in network 3090. As variously described herein, for example, such tests may be required by one or more regimens 2331-2339 or orders 2511-2516 (prescribed or placed by a physician or other care provider 2783, e.g.). In some contexts, moreover, local event-sequencing logic 3005 may be configured to receive measurements or other results from sample tester 3060 (as determinants 2391-2395 or other indications 2341-2349 relating to decisions described herein, e.g.). Alternatively or additionally, local event-sequencing logic 3005 may comprise one or more instances of special-purpose transistor-based circuitry 3035 configured to associate one or more tasks with a time interval; special-purpose transistor-based circuitry 3041, 3042, 3043, 3044 configured to generate a Boolean indication whether or not an individual is compliant with a regimen; special-purpose transistor-based circuitry 3051 configured to generate a Boolean indication whether or not a patient and a medical device are in proximity; special-purpose transistor-based circuitry 3052 configured to recognize a person depicted in a portion of an image; or other relevant data as described herein with reference to FIG. 1, 4-7, or 21-26.

Figure 31:
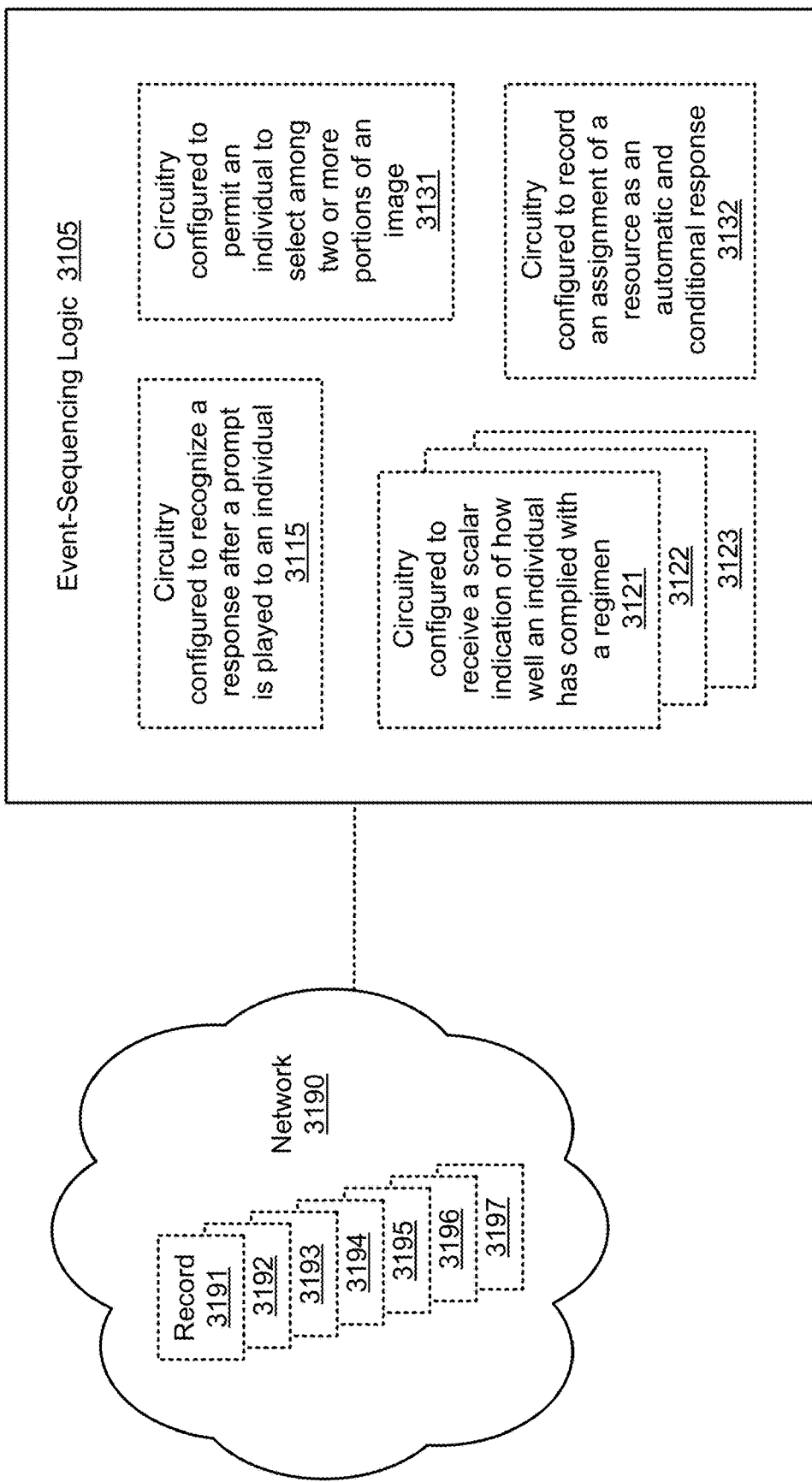
FIG. 31 depicts another exemplary environment in which local event-sequencing logic is configured to receive a signal from a network on which several records reside.

With reference now to FIG. 31, shown is a system 3100 in which one or more technologies may be implemented. Local event-sequencing logic 3105 (operably coupled with and local to local event-sequencing logic 2905, e.g.) may be configured to access one or more records 3191-3197 residing (remotely, e.g.) in network 3190. As variously described herein, for example, such records may include medical history data or other background data (provided by or useful to material providers 2781 or care providers 2783, e.g.). Alternatively or additionally, local event-sequencing logic 3105 may comprise one or more instances of special-purpose transistor-based circuitry 3115 configured to recognize a response after a prompt is played to an individual; special-purpose transistor-based circuitry 3121, 3122, 3123 configured to receive a scalar indication of how well an individual has complied with a regimen; special-purpose transistor-based circuitry 3131 configured to configured to permit an individual to select among two or more portions of an image; or special-purpose transistor-based circuitry 3132 configured to record an assignment of a resource as an automatic and conditional response as described below.

Figure 32:
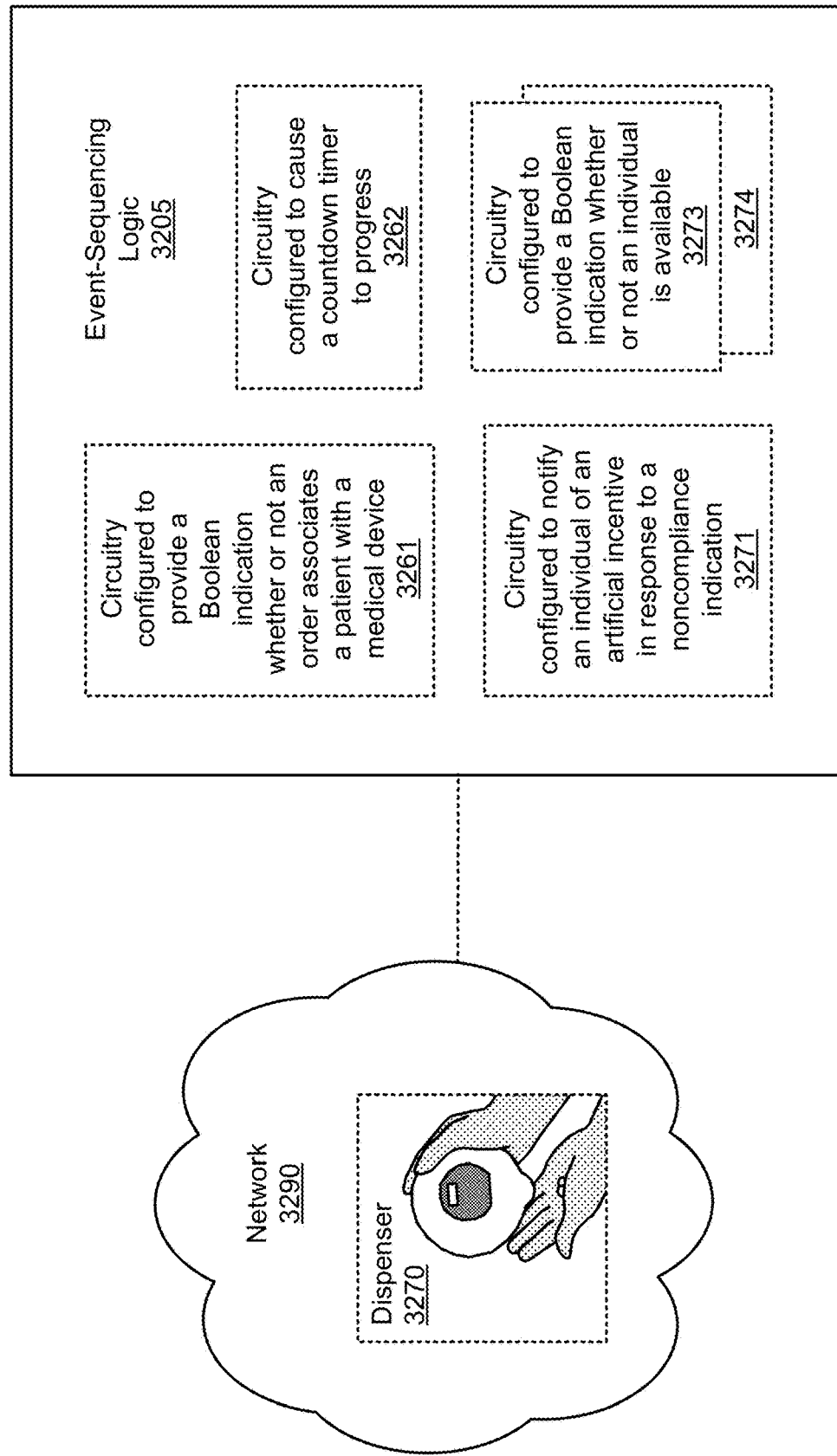
FIG. 32 depicts another exemplary environment in which local event-sequencing logic is configured to communicate to or from a dispenser or other networked device.

With reference now to FIG. 32, shown is a system 3200 in which one or more technologies may be implemented. Local event-sequencing logic 3205 (resident in delivery unit 2725 or interaction unit 2775, e.g.) may be configured to monitor or control a portable material dispenser 3270 (configured to perform a compliance-monitoring or incentive implementation task described below, e.g.) or both. As variously described herein, for example, such tasks may signify a component of regimen compliance (dispensing a drug 141 on time, e.g.) or may manifest an incentive (candy dispensed as a payment in kind 2618 for enticing a patient or provider to cooperate, e.g.). Alternatively or additionally, local event-sequencing logic 3205 may comprise one or more instances of special-purpose transistor-based circuitry 3261 configured to provide a Boolean indication whether or not an order associates a patient with a medical device; special-purpose transistor-based circuitry 3262 configured to cause a countdown timer to progress; special-purpose transistor-based circuitry 3271 configured to notify an individual of an artificial incentive in response to a noncompliance indication; or special-purpose transistor-based circuitry 3273, 3274 configured to provide a Boolean indication whether or not an individual is available as described herein. See FIG. 34.

Figure 33:
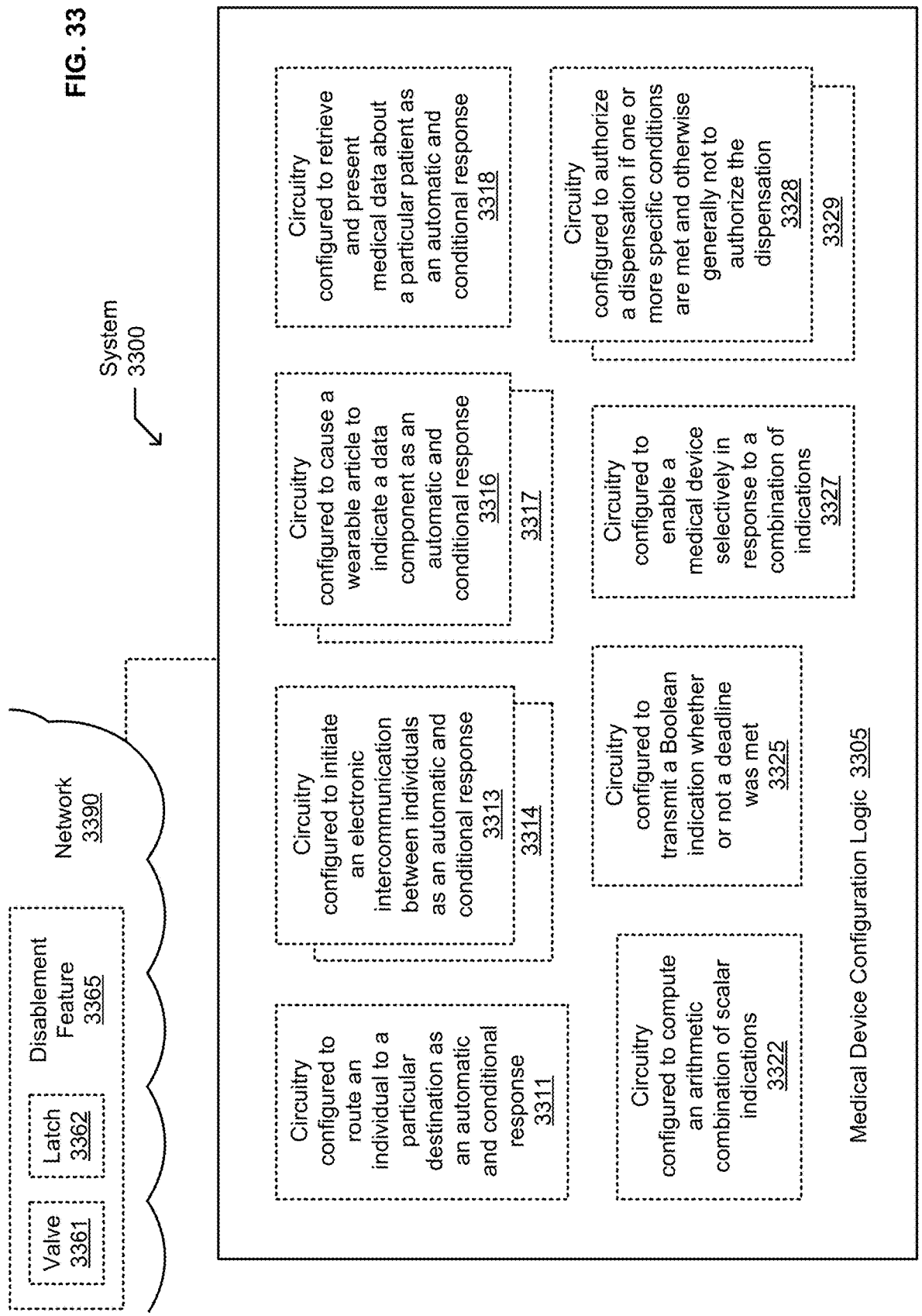
FIG. 33 depicts another exemplary environment in which medical device configuration logic is configured to control a disablement feature or other component of a medical device.

With reference now to FIG. 33, shown is a system 3300 in which one or more technologies may be implemented. In some variants, medical device configuration logic 3305 (operably coupled with one or more instances of event-sequencing logic described above, e.g.) may be configured to control one or more instances of an electrical or electro-mechanical disablement feature 3365 (a valve 3361 or fuse or latch 3362 configured to enable/disable a primary function of medical equipment 2080 or other devices depicted herein, e.g.) in network 3390. As variously described herein, for example, such features may prevent a dispensation or other material transfer under some circumstances as described below. In some contexts, moreover, medical device configuration logic 3305 may be configured to display or otherwise transmit decisions, determinants, and user data via one or more media (depicted at FIG. 1, 4-7, or 21-26, e.g.). Alternatively or additionally, medical device configuration logic 3305 may comprise one or more instances of special-purpose transistor-based circuitry 3311 configured to route an individual to a particular destination as an automatic and conditional response; special-purpose transistor-based circuitry 3313, 3314 configured to initiate an electronic intercommunication between individuals as an automatic and conditional response; special-purpose transistor-based circuitry 3316, 3317 configured to cause a wearable article to indicate a data component as an automatic and conditional response; special-purpose transistor-based circuitry 3318 configured to retrieve and present medical data about a particular patient as an automatic and conditional response; special-purpose transistor-based circuitry 3322 configured to compute an arithmetic combination of scalar indications; special-purpose transistor-based circuitry 3325 configured to transmit a Boolean indication whether or not a deadline was met; special-purpose transistor-based circuitry 3327 configured to enable a medical device selectively in response to a combination of indications; or special-purpose transistor-based circuitry 3328, 3329 configured to authorize a dispensation if one or more specific conditions are met and otherwise generally not to authorize the dispensation. As explained below, moreover, some or all such logic may be configured to respond to device-detectable environmental or remote data irrespective of real-time local user input. See FIGS. 48-62.

Figure 34:
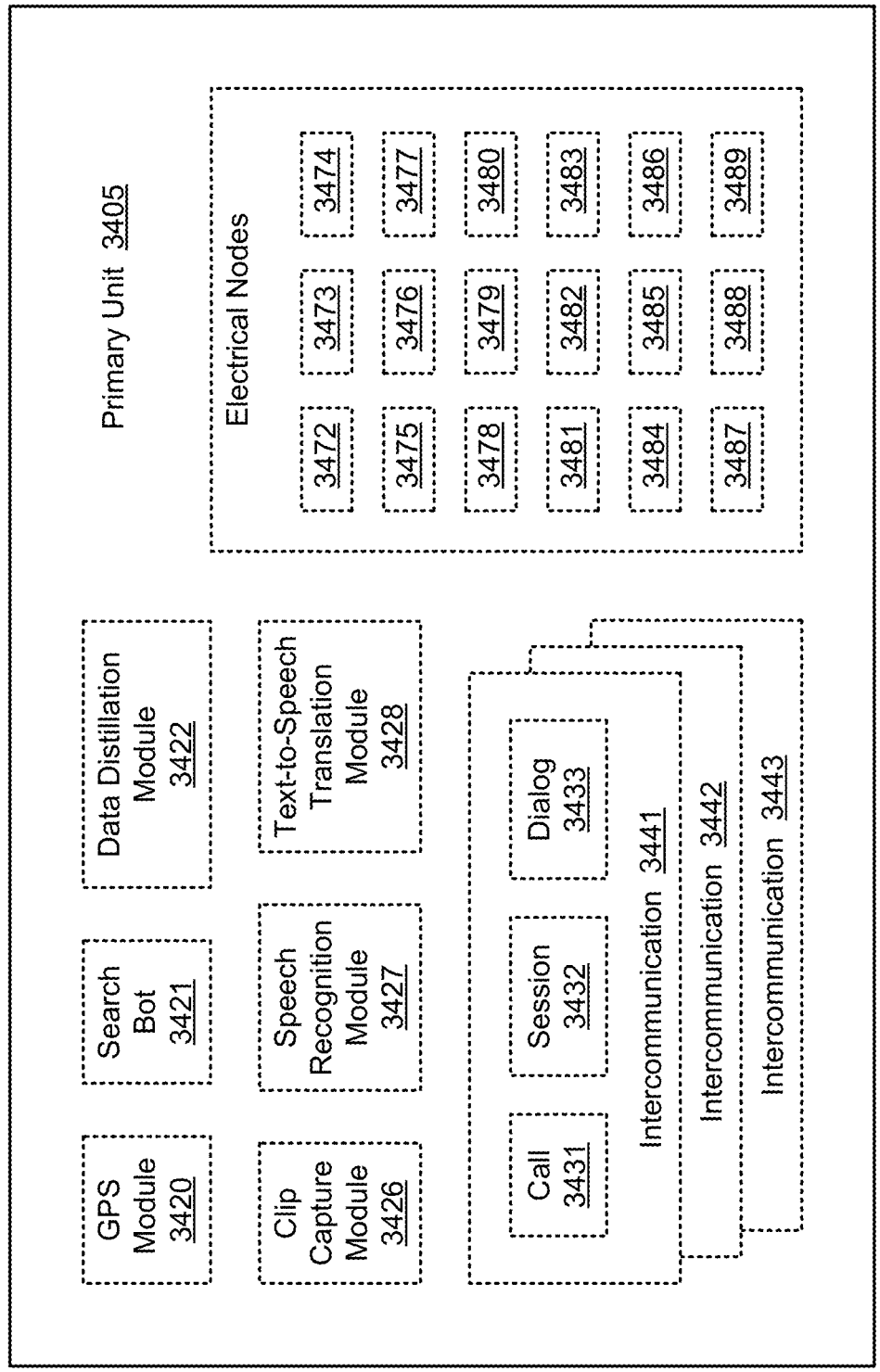
FIG. 34 depicts another exemplary environment in which one or more technologies may be configured to operate a primary unit (one or more chips, e.g.) having one or more electrical nodes.

With reference now to FIG. 34, shown is a system 3400 in which one or more technologies may be implemented (in a server or other network subsystem, e.g.). In some variants, primary unit 3405 may comprise one or more instances of global positioning system (GPS) modules 3420 (configured to generate coordinates 2381, 2382 in some variants, e.g.), search bots 3421, data distillation modules 3422, clip capture modules 3426, speech recognition modules 3427, or text-to-speech translation modules 3428. Such modules may reside in one or more application-specific integrated circuits (ASICs), for example, or in a general purpose processor 2055 configured to execute special-purpose software (within a device 305 or system described above, e.g.). Alternatively or additionally, primary unit 3405 may implement a channel or other structure (comprising a linkage 2011 between devices, e.g.) within which one or more intercommunications 3441, 3442, 3443 (comprising a call 3431, session 3432, dialog 3433, or other bidirectional communication as described herein, e.g.) may exist as described below. In some variants, moreover, such logic may comprise one or more electrical nodes 3472, 3473, 3474, 3475, 3476, 3477, 3478, 3479, 3480, 3481, 3482, 3483, 3484, 3485, 3486, 3487, 3488, 3489 (each expressing a yes-or-no decision or other Boolean value, e.g.). In some contexts, for example, such nodes may each comprise a forked or other signal path adjacent one or more logic gates, for example, the Boolean value manifested as either a "low" or "high" voltage according to a complementary metal-oxide-semiconductor (CMOS), emitter-coupled logic (ECL), or other common semiconductor configuration protocol.

Figure 35:
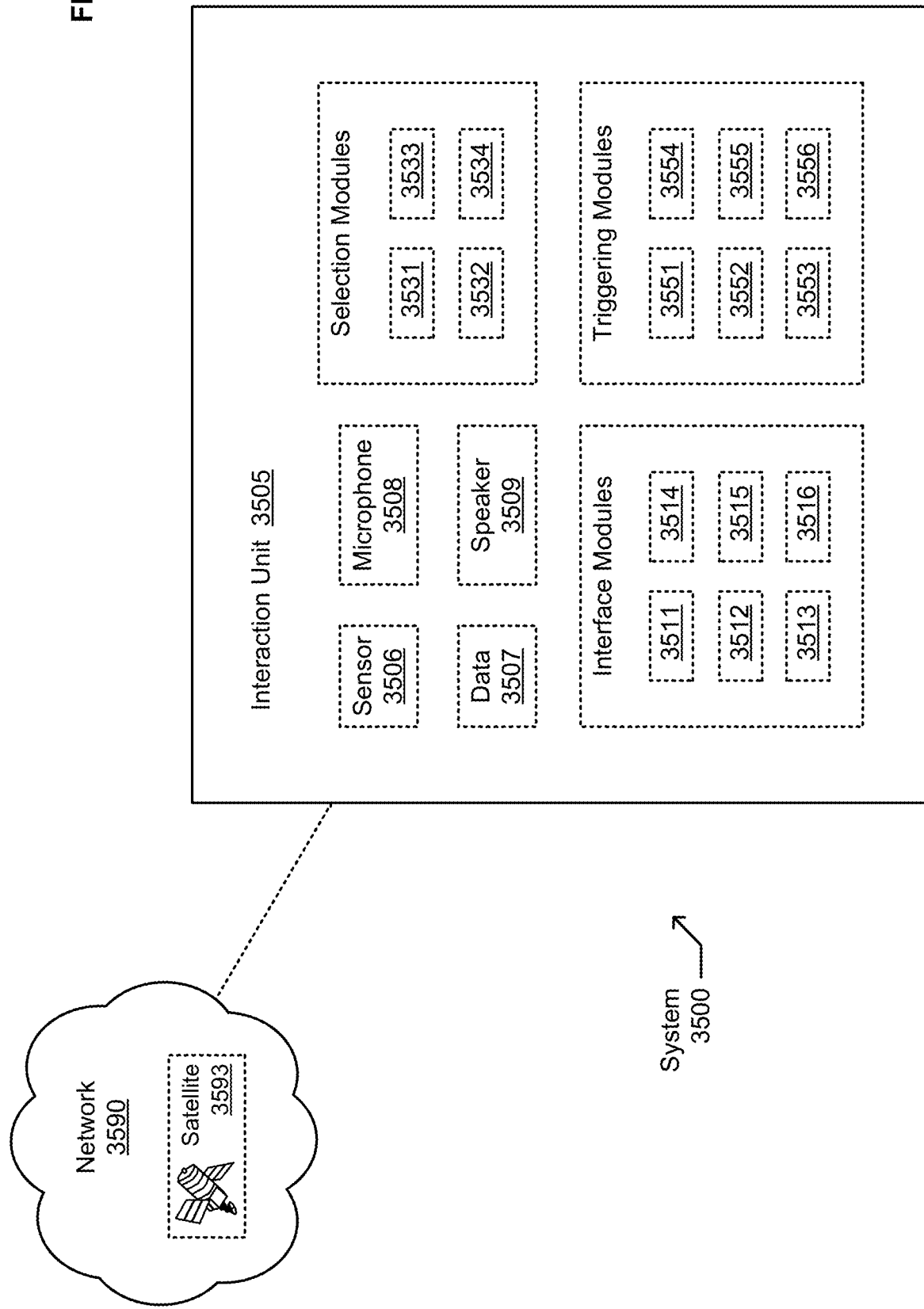
FIG. 35 depicts another exemplary environment in which one or more technologies may be configured to communicate with or via a satellite.

With reference now to FIG. 35, shown is a system 3500 in which one or more technologies may be implemented. In some variants, interaction unit 3505 (implemented local to an individual 2782 or service provider 2710, e.g.) may be configured to communicate via one or more instances of a satellite 3593 or other remote communication device in network 3590 (to one or more other networks described herein, e.g.). In some contexts, such interaction units 2775 may comprise one or more sensors 3506 (such as a microphone 3508, e.g.) or speakers 3509 or other components operable for handling data 3507 (for or from a patient, e.g.). Alternatively or additionally, interaction unit 3505 may comprise one or more instances of special-purpose interface modules 3511, 3512, 3513, 3514, 3515, 3516; selection modules 3531, 3532, 3533, 3534; or triggering modules 3551, 3552, 3553, 3554, 3555, 3556 as described below. As explained below, moreover, some or all such logic may be configured to respond to device-detectable environmental or remote data irrespective of real-time local user input. See FIGS. 48-62.

Figure 36:
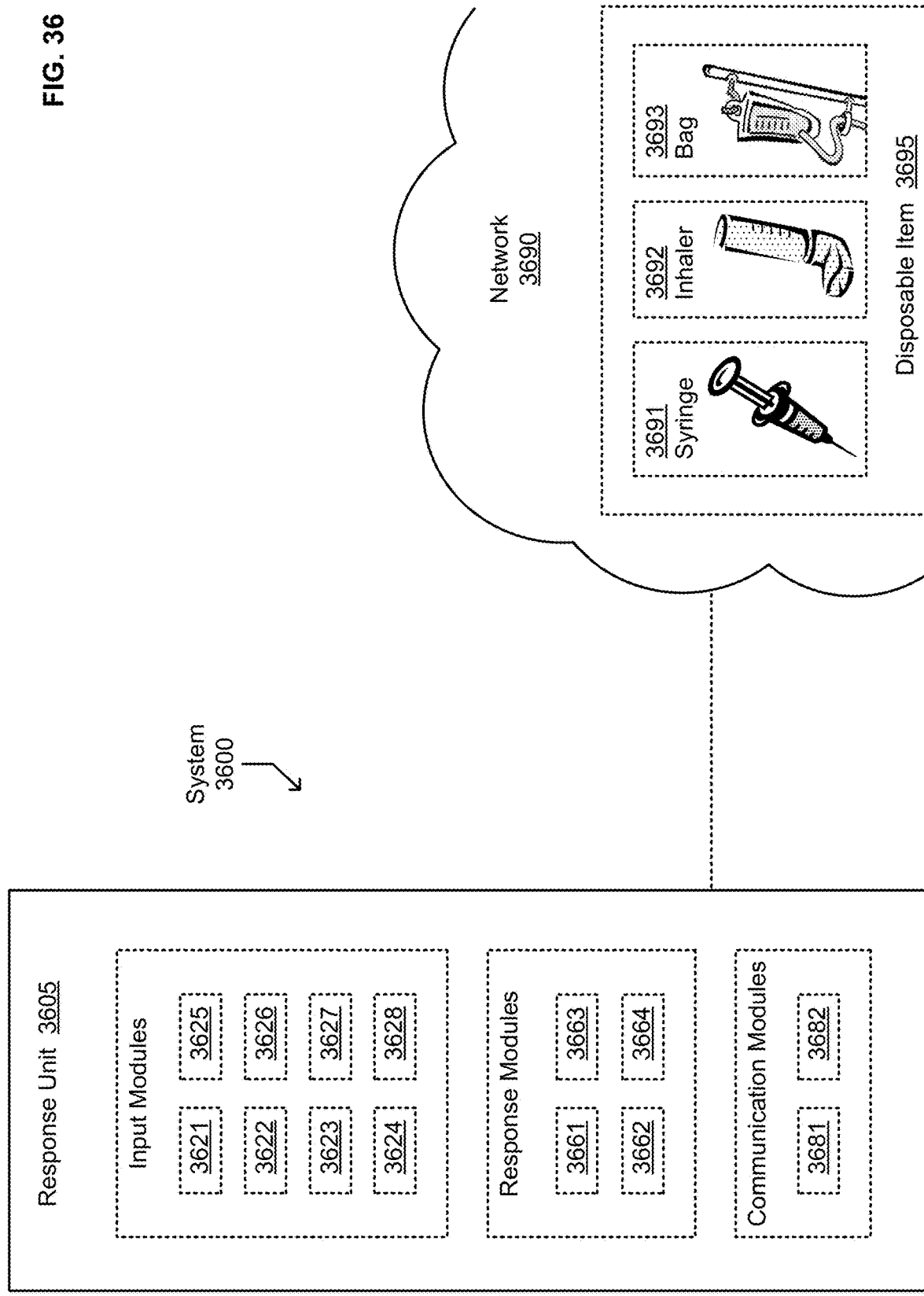
FIG. 36 depicts another exemplary environment in which one or more technologies may be configured to actuate, disable, or otherwise control a disposable item.

With reference now to FIG. 36, shown is a system 3600 in which one or more technologies may be implemented. In some variants, response unit 3605 (implemented local to a technician 2761 or care provider 2783, e.g.) may be configured to interact with an article 2910 (a sample tester 3060 or dispenser 3270 or other device 305 with a disablement feature 3365, e.g.) in or via network 3690. In some variants such articles may comprise a disposable item 3695 (a syringe 3691 or inhaler 3692 or infusion bag 3693 configured to be used only once, e.g.). Alternatively or additionally, response unit 3605 may comprise one or more input modules 3621, 3622, 3623, 3624, 3625, 3626, 3627, 3628; response modules 3661, 3662, 3663, 3664; communication modules 3681, 3682 or other control circuitry as described below.

With reference now to FIG. 37, shown is a system 3700 in which one or more technologies may be implemented. In some variants, a computer 2670 or other data-handling device 3705 may comprise one or more configuration modules 3701, 3702, 3703, 3704; detection modules 3741, 3742, 3743, 3744, 3745, 3746 (implementing a comparator 391 configured to apply one or more patterns 2361-2366, e.g.); computation modules 3771, 3772, 3773, 3774; or authorization modules 3791, 3792, 3793, 3794 as described below. In some contexts, for example, data-handling device 3705 may be implemented in a handheld device 305 (operably coupled to an earpiece 3749 or other wearable output device, e.g.) that also includes one or more cameras 3707 or other input devices (microphone 3708, e.g.) accessible to user 3780. Moreover such implementations may have particular utility in an institutional setting (comprising a stationary device 3760 mounted in a ceiling of a hallway 3709, e.g.). See FIG. 38.

Figure 38:
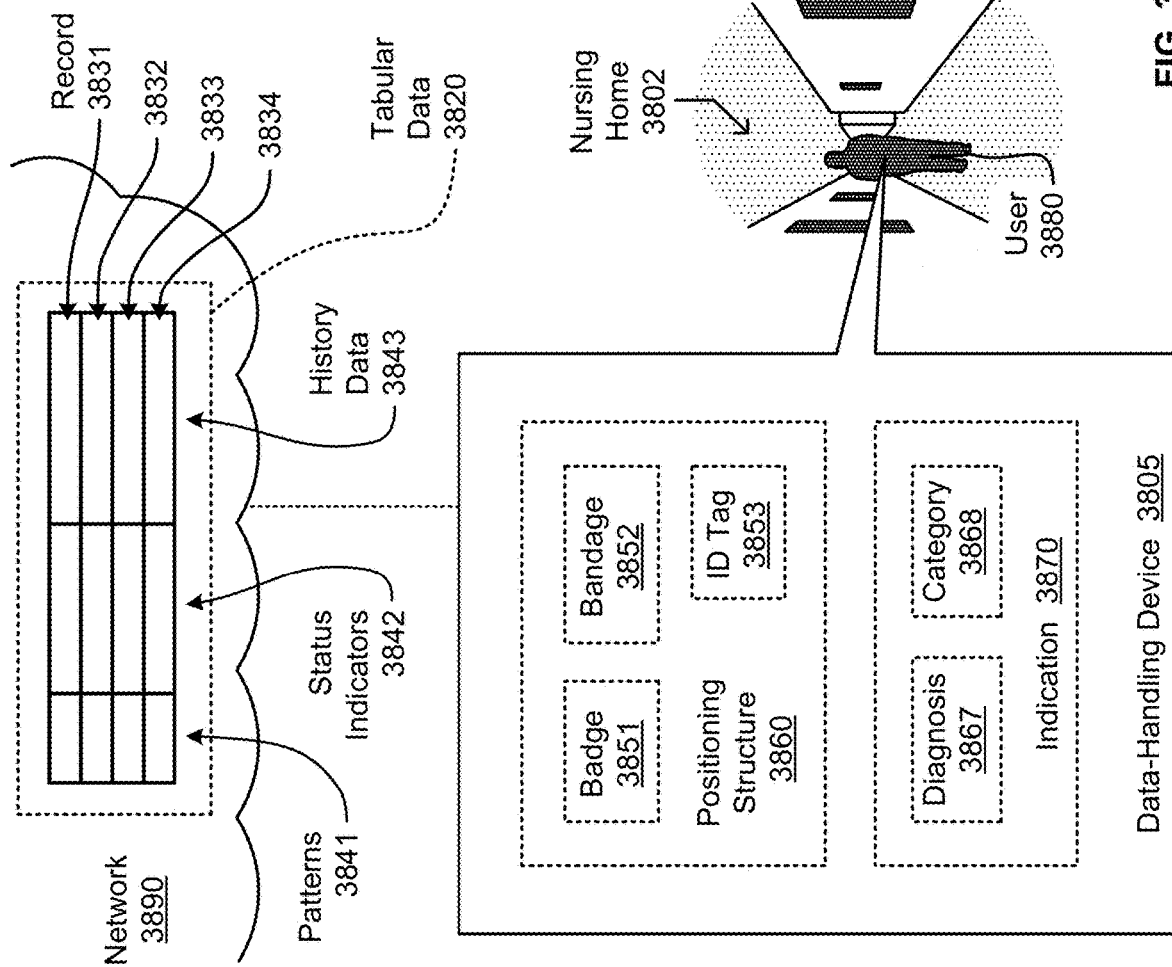
FIG. 38 depicts another exemplary environment in which one or more technologies may be configured to implement a data-handling device (in a wearable article, e.g.).

With reference now to FIG. 38, shown is an example of a data-handling device 3805 (worn or carried by a user 3880 in a nursing home 3802, e.g.) operably coupled (through a wireless or other linkage, e.g.) with one or more networks 3890 described herein. In some contexts, for example, tabular data 3820 resident (on a server, e.g.) on network 3890 may (optionally) include several records 3831-3834 each of which includes one or more status indicators 3842 or history data 3843 (or both) designated by one or more record-designating patterns 3841 (uniquely identifying each respective record, e.g.). In some variants data-handling device 3805 may include one or more badges 3851, bandages 3852, identification tags 3853, or other positioning structures 3860 and may include one or more diagnoses 3867, categories 3868, or other indications 3870 (relating to user 3880 as a healthcare recipient 2722, e.g.). Alternatively or additionally data-handling device 3805 may comprise an unpowered article 2910 with a barcode or other passive feature readable by local event-sequencing logic 2905 or other circuitry described herein.

Figure 48:
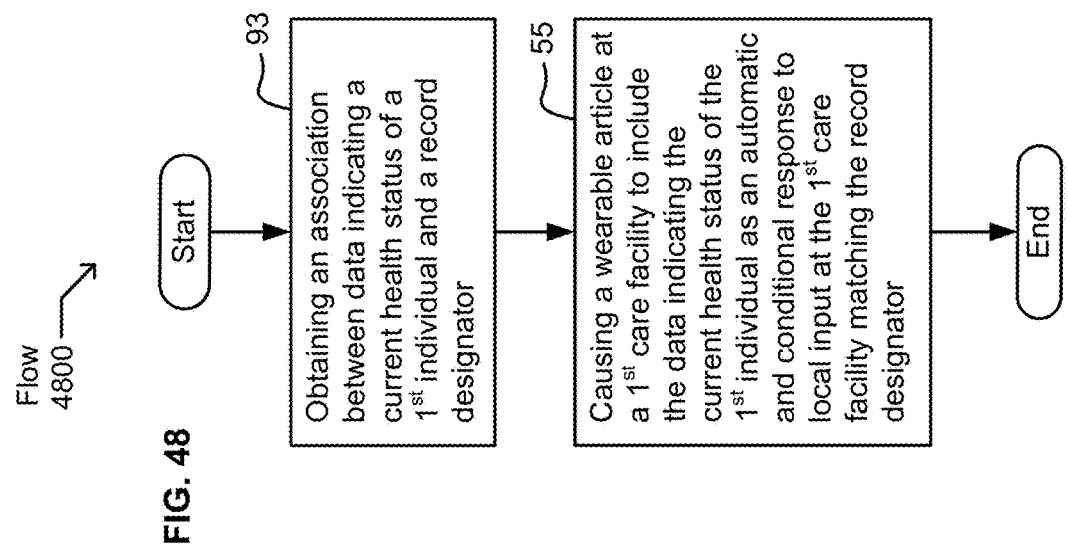
FIG. 48 depicts a high-level logic flow of an operational process (described with reference to FIG. 38, e.g.).

With reference now to FIG. 48, shown is a high-level logic flow 4800 of an operational process. Intensive operation 93 describes obtaining an association between data indicating a current health status of a first individual and a record designator (e.g. interface module 3513 creating or updating a specific record 3831 associating one or more patient health status indicators 3842 with one or more record serial numbers, patient names, or other data patterns 3841 that serve to designate that specific record 3831) This can occur, for example, in a context in which user 3880 is the "first" individual; in which each of the patterns 3841 within available tabular data 3820 uniquely identifies a corresponding one of the records 3831-3834; in which some or all of the status indicators 3842 include a test result 2315, image 2578, data distillation 2980 (diagnosis 3867, computed negative indication 2989 of regimen compliance, evaluation, or patient category 3868 assigned or entered by a physician or other care provider 2783, e.g.), or other health status indication 3870 that is "current" (at most about a week old and not superseded by a newer item of the same type, e.g.); and in which one or more such records 3831-3834 may also include medical history data 3843 (non-current indicia, e.g.) pertaining to the first individual. This can occur, for example, in a context in which interface module 3513 comprises a telephone menu or website (accessed using a handheld interface 1002, e.g.) via which one or more other users 3780 (caregivers, e.g.) may provide various information as described herein (with reference to media of FIGS. 21-26, e.g.) that interface module 3513 then stores as tabular data 3820 (on a network server, e.g.) indexed by respective designation patterns 3841.

In light of teachings herein, numerous existing techniques may be applied for configuring special-purpose circuitry or other structures effective for managing the accounting for a hospital or other medical provider as described herein without undue experimentation. See, e.g., U.S. Pat. No. 8,065, 162 ("Provider data management and claims editing and settlement system"); U.S. Pat. No. 7,962,350 ("Payment of health care insurance claims using short-term loans"); U.S. Pat. No. 7,860,732 ("Medicare pharmacy calculator II"); U.S. Pat. No. 7,827,234 ("Privacy entitlement protocols for secure data exchange, collection, monitoring and/or alerting"); U.S. Pat. No. 7,805,318 ("Using a non-profit organization to satisfy medicare out-of-pocket/troop and product replacement"); U.S. Pat. No. 7,464,043 ("Computerized method and system for obtaining, storing and accessing medical records"); U.S. Pat. No. 7,433,827 ("System and method for displaying a health status of hospitalized patients"); U.S. Pat. No. 7,263,493 ("Delivering electronic versions of supporting documents associated with an insurance claim"); U.S. Pat. No. 6,655,545 ("Medical code system"); and U.S. Pat. No. 6,000,828 ("Method of improving drug treatment").

In light of teachings herein, numerous existing techniques may be applied for configuring special-purpose circuitry or other structures effective for retrieving data based on a medical condition as described herein without undue experimentation. See, e.g., U.S. Pat. No. 7,844,470 ("Treatment order processing system suitable for pharmacy and other use"); U.S. Pat. No. 7,739,126 ("Method, system, and computer program product for physician efficiency measurement and patient health risk stratification"); U.S. Pat. No. 7,707, 047 ("Method and system for generating personal/individual health records"); U.S. Pat. No. 7,664,659 ("Displaying clinical predicted length of stay of patients for workload balancing in a healthcare environment"); U.S. Pat. No. 7,640,175 ("Method for high-risk member identification"); U.S. Pat. No. 7,624,027 ("Method and system for automated medical records processing"); U.S. Pat. No. 7,613,620 ("Physician to patient network system for real-time electronic communications and transfer of patient health information"); U.S. Pat. No. 7,444,291 ("System and method for modeling of healthcare utilization"); and U.S. Pat. No. 6,266,645 ("Risk adjustment tools for analyzing patient electronic discharge records").

Extensive operation 55 describes causing a wearable article at a first care facility to include the data indicating the current health status of the first individual as an automatic and conditional response to local input at the first care facility matching the record designator (e.g. triggering module 3554 transmitting a status-indicative wireless signal 2563 to data-handling device 3805 if and only if a detection module 3746 detects one or more recognizable patterns 3841 of user input 2473 from user 3880). This can occur, for example, in a context in which one or more interface modules 3513 in nursing home 3802 include or are operably coupled with detection module 3746; in which detection module 3746 is configured to determine whether or not user input 2473 (auditory, optical, keyed, or other data entered by a user, e.g.) includes any instances of a pattern 3841 designating one of the active records 3831-3834 of available tabular data 3820; in which data-handling device 3805 is configured to store any status indicator 3842 received from triggering module 3554; and in which status-indicative customization of wearable articles would otherwise incur unnecessary delay or user participation. In some contexts, such devices may be configured to be activated by coming into contact with (the skin of) user 3880 and to detect whether it has ever been removed since activation. Alternatively or additionally, data-handling device 3805 may indicate the "current health status" by virtue of a (passive or other radio frequency or ultrasound) identification tag 3853 (previously customized, e.g.) wirelessly detectable by a data handling device in the same vicinity (within hallway 3709, e.g.). In some contexts, moreover, invocation module 2795 may be configured to coordinate flow 4800 automatically (without further input from any user local to the wearable article, e.g.).

In light of teachings herein, numerous existing techniques may be applied for configuring special-purpose circuitry or other structures effective for permitting an identification of a person by a wearable article as described herein without undue experimentation. See, e.g., U.S. Pat. No. 8,068,008 ("Emergency responder credentialing system and method"); U.S. Pat. No. 8,049,597 ("Systems and methods for securely monitoring an individual"); U.S. Pat. No. 8,039,093 ("Method for preparing tamperproof ID documents"); U.S. Pat. No. 7,988,043 ("Fraud prevention in issuance of identification credentials"); U.S. Pat. No. 7,979,286 ("Patient-interactive healthcare management"); U.S. Pat. No. 7,975, 913 ("Discernment card and a discernment card business system using the discernment card"); U.S. Pat. No. 7,481, 370 ("Removable patient identification strap for blood recipient verification"); and U.S. Pat. No. 6,748,687 ("Multi-web business form having moisture proof wristband, identification labels and web joint").

Figure 39:
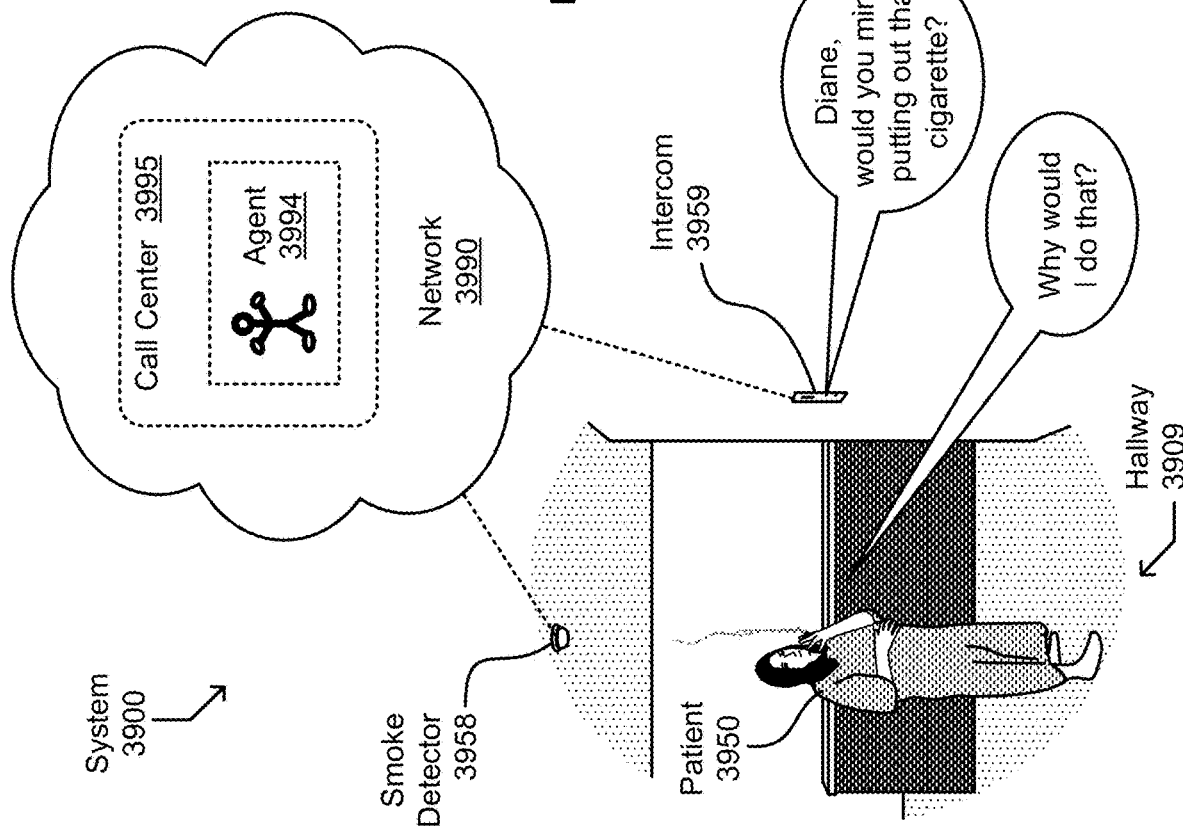
FIG. 39 depicts another exemplary environment in which one or more technologies may be configured to implement a local device via which a call center may communicate with a patient, e.g.).

With reference now to FIG. 39, shown is a system 3900 in which one or more technologies may be implemented. A pregnant patient 3950 who is smoking in a hallway 3909 (at her home or at a healthcare facility that is "local" to her, e.g.). Her actions are monitored via a network 3990 that comprises one or more agents 3994 (at a remote call center 3995, e.g.) who are authorized to monitor and interact with patient 3950 via one or more devices (smoke detector 3958 and intercom 3959 respectively as shown, e.g.) in her vicinity.

Figure 49:
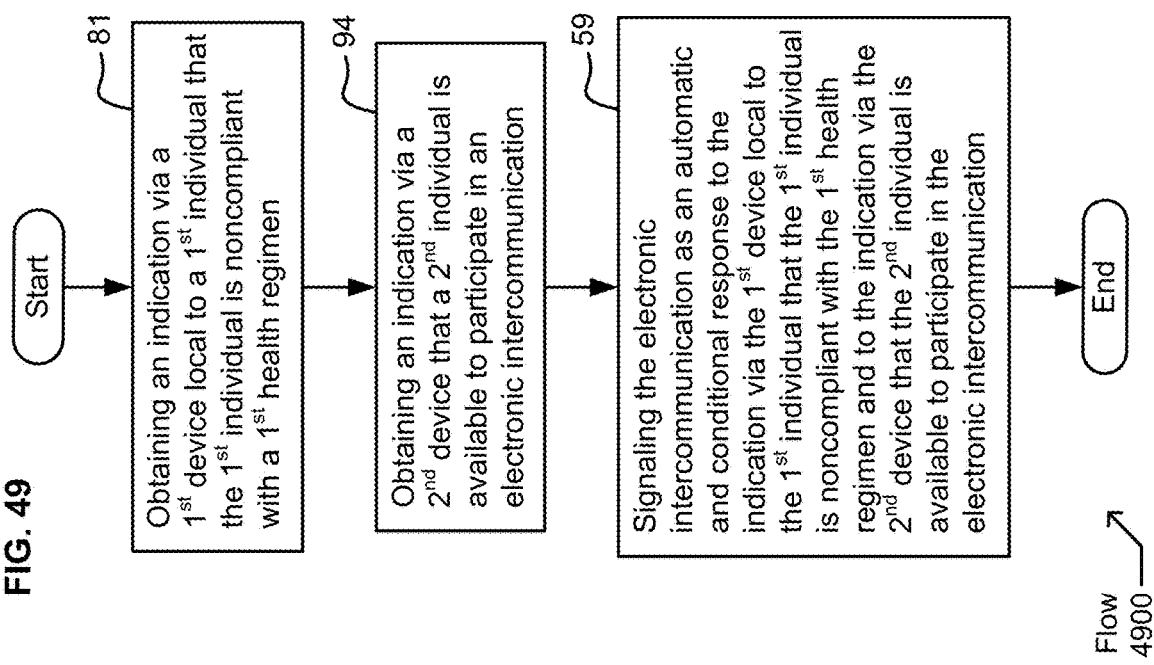
FIG. 49 depicts a high-level logic flow of an operational process (described with reference to FIG. 39, e.g.).

With reference now to FIG. 49, shown is a high-level logic flow 4900 of an operational process. Intensive operation 81 describes obtaining an indication via a first device local to a first individual that the first individual is noncompliant with a first health regimen (e.g. detection module 3741 generating a regimen noncompliance determination 2988 or other negative indication 2989 of compliance with a pregnancy regimen 2331). This can occur, for example, in a context in which system 2900 implements intercom 3959 or resides in network 3990; in which the "first" device comprises at least one of a smoke detector 3958 or computer 2670 or other data-handling device 3705 in the same room with patient 3950 (in a hallway 3909 or other location 204 associated with patient 3950, e.g.); and in which the "indication via the first device" is a result 2314 of a cigarette smoke concentration indication 2481 exceeding a corresponding threshold 2451 (indicating that someone is smoking in hallway 3909, e.g.) or a cigarette smoke detection frequency indication 2482 exceeding a corresponding threshold 2452 (corresponding to cigarette smoke being detected via smoke detector 3958 one day per week, e.g.). Alternatively or additionally, in some variants, one or more configuration modules 3701-3704, detection modules 3741-3746, computation modules 3771-3774, or authorization modules 3791-3794 may reside in a smoke detector 3958, intercom 3959, kiosk, or other stationary device 3760 as described herein. Alternatively or additionally, pregnancy regimen 2331 may include one or more medicinal, dietary, measurement, reporting, or other health-related regimen components with which patient 3950 or her local caregivers (nurses, e.g.) may or may not comply. In some contexts, for example, such thresholds 2451-2453 or other compliance determinants 2393 may be defined (via a control unit 2705 operated by a specialty service provider 2710, e.g.) with reference to one or more other indications 2483 (relating to the individual and received via a camera 2832 or other sensor 2833 residing in interaction unit 2775, e.g.) specific to a particular regimen 2331 (as defined by a specialist, e.g.).

In light of teachings herein, numerous existing techniques may be applied for configuring special-purpose circuitry or other structures effective for associating an entity (user or device, e.g.) with another entity as described herein without undue experimentation. See, e.g., U.S. Pat. No. 8,023,485 ("Method, system and device for realizing user identity association"); U.S. Pat. No. 7,979,585 ("System and method to associate a private user identity with a public user identity"); U.S. Pat. No. 7,970,660 ("Identifying associations between items and email-address-based user communities"); U.S. Pat. No. 7,941,505 ("System and method for associating a user with a user profile in a computer network environment"); U.S. Pat. No. 7,894,812 ("Automatic over-the-air updating of a preferred roaming list (PRL) in a multi-mode device, based on an account association between the device and a wireless local area network (WLAN) access point"); U.S. Pat. No. 7,743,099 ("Associating multiple visibility profiles with a user of real-time communication system"); U.S. Pat. No. 7,716,378 ("System and method to associate a private user identity with a public user identity"); U.S. Pat. No. 7,703,691 ("Multiple device and/or user association"); U.S. Pat. No. 7,627,577 ("System and method for maintaining an association between a distribution device and a shared end user characteristic"); U.S. Pat. No. 6,473,824 ("Dynamic association of input/output device with application programs").

In light of teachings herein, numerous existing techniques may be applied for configuring special-purpose circuitry or other structures effective for generating indications of patient compliance or noncompliance as described herein without undue experimentation. See, e.g., U.S. Pat. No. 8,032,399 ("Treatment regimen compliance and efficacy with feedback"); U.S. Pat. No. 7,917,377 ("Patient data mining for automated compliance"); U.S. Pat. No. 7,599,892 ("Method for secure diagnostic screening, servicing, treatment, and compliance monitoring for sleep apnea in truck drivers"); U.S. Pat. No. 7,417,205 ("Medical item thermal treatment systems and method of monitoring medical items for compliance with prescribed requirements"); U.S. Pat. No. 6,926,667 ("Patient compliance monitor"); U.S. Pat. No. 6,790,668 ("Monitoring patient compliance and bio-availability of drugs by deproteinizing body fluids"); U.S. Pat. No. 6,380,858 ("Systems and methods for monitoring patient compliance with medication regimens"); U.S. Pat. No. 6,161,095 ("Treatment regimen compliance and efficacy with feedback"); U.S. Pat. No. 6,124,136 ("Method of monitoring compliance with methadone treatment program"); and U.S. patent application Ser. No. 13/199,053 ("Systematic distillation of status data relating to regimen compliance").

Intensive operation 94 describes obtaining an indication via a second device that a second individual is available to participate in an electronic intercommunication (e.g. interface module 3511 receiving an indication 2484 via one or more response units 2755, 3605 that one or more qualified agents 294, 3994 are online). This can occur, for example, in a context in which such agents can each press a button 2079 (on an office phone, e.g.) at their workstations to generate such availability indications 2484, 2485 when they start or resume working or when they accept a particular work task. In some variants, for example, a work task 2441 becomes available to one or more call center agents 294, 3994 as an automatic and conditional response to a negative indication 2989 of compliance (a current or recent condition 2321 signaling a patient's failure to report within a prescribed interval, e.g.) and interface module 3511 assigns the work task 2441 (of participating in the electronic intercommunication, e.g.) in response to the first-arriving indication 2485 (from whichever of the eligible call center agents 294, 3994 signals availability first, e.g.) by invoking communication module 3681.

In light of teachings herein, numerous existing techniques may be applied for configuring special-purpose circuitry or other structures effective for facilitating the operation of a call center or otherwise initiating communications as described herein without undue experimentation. See, e.g., U.S. Pat. No. 8,069,213 ("Method of controlling access to network resources using information in electronic mail messages"); U.S. Pat. No. 7,860,935 ("Conditional communication"); U.S. Pat. No. 7,783,023 ("Systems and methods for providing unified collaboration systems with conditional communication handling"); U.S. Pat. No. 7,484,048 ("Conditional message delivery to holder of locks relating to a distributed locking manager"); U.S. Pat. No. 7,042,338 ("Alerting a care-provider when an elderly or infirm person in distress fails to acknowledge a periodically recurrent interrogative cue"); U.S. Pat. No. 6,307,937 ("Method and apparatus for an adapter card providing conditional access in a communication system"); and U.S. Pat. No. 6,108,709 ("System for sending an e-mail message to a first type of terminal based upon content thereof and selected conditions and selectively forwarding it to a second type of terminal").

Extensive operation 59 describes signaling the electronic intercommunication as an automatic and conditional response to the indication via the first device local to the first individual that the first individual is noncompliant with the first health regimen and to the indication via the second device that the second individual is available to participate in the electronic intercommunication (e.g. communication module 3681 initiating a telephone call 3431, text chat session 3432, or other electronic intercommunication 3441 as a real-time response to hybrid indication 2485). This can occur, for example, in a context in which each such indication 2485 signifies both the first individual's apparent noncompliance and the second individual's availability to participate, at least; in which one or more of the above-described systems and media (of FIG. 1-13 or 20-38, e.g.) reside in network 3990; and in which a timely and selective response to various types of device-detectable regimen noncompliance would not otherwise be cost-effective. In some contexts in which an initial negative indication 2989 of compliance comes from a vessel 2890 containing medication (not having been used on schedule, e.g.), for example, incentive acceptance module 2820 may transmit a signal 2816 that indicates one or more incentives 2811, 2812 with the negative indication 2989 of compliance. Such incentives 2811 may include a flat fee or per-minute fee for participating in the electronic intercommunication, for example, which incentives are implemented as another automatic and conditional response to a hybrid indication 2485 (generally signifying the first individual's apparent noncompliance and the second individual's availability to participate, e.g.). In some contexts, moreover, invocation module 2795 may be configured to coordinate flow 4900 automatically (activating intercom 3959 without further input from call center 3995 or from any user local to patient 3950, e.g.).

In light of teachings herein, numerous existing techniques may be applied for configuring special-purpose circuitry or other structures effective for implementing a conditional message as described herein without undue experimentation. See, e.g., U.S. Pat. No. 7,932,837 ("Conditional aircraft cabin warning and signalling system for determining the cabin status"); U.S. Pat. No. 7,002,454 ("System and method for warning an operator of a vehicle if the vehicle is operating in a condition that may result in drive belt failure"); U.S. Pat. No. 6,452,487 ("System and method for warning of a tip over condition in a tractor trailer or tanker"); U.S. Pat. No. 6,437,707 ("Detecting a low performance takeoff condition for aircraft for use with ground proximity warning systems"); U.S. Pat. No. 6,373,392 ("Alert device for providing a warning of a baby's condition which may lead to the onset of SIDS"); U.S. Pat. No. 6,310,556 ("Apparatus and method for detecting a low-battery power condition and generating a user perceptible warning"); U.S. Pat. No. 6,310,554 ("Severe weather detection apparatus and method of detecting and warning of severe weather conditions"); and U.S. Pat. No. 6,211,791 ("Warning system for excessive apparent temperature conditions").

In light of teachings herein, numerous existing techniques may be applied for configuring special-purpose circuitry or other structures effective for implementing a device-initiated phone call or other audible notification as described herein without undue experimentation. See, e.g., U.S. Pat. No. 8,041,017 ("Emergency call service with automatic third party notification and/or bridging"); U.S. Pat. No. 7,650,811 ("Shifting device"); U.S. Pat. No. 7,508,298 ("Automatic crash notification using prerecorded messages"); U.S. Pat. No. 7,493,281 ("Automatic notification of irregular activity"); U.S. Pat. No. 7,469,155 ("Handheld communications device with automatic alert mode selection"); U.S. Pat. No. 7,181,192 ("Handheld portable automatic emergency alert system and method"); U.S. Pat. No. 7,076,235 ("Automatic notification of personal emergency contacts from a wireless communications device"); U.S. Pat. No. 6,442,485 ("Method and apparatus for an automatic vehicle location, collision notification, and synthetic voice"); and U.S. Pat. No. 6,112,074 ("Radio communication system with automatic geographic event notification").

Figure 40:
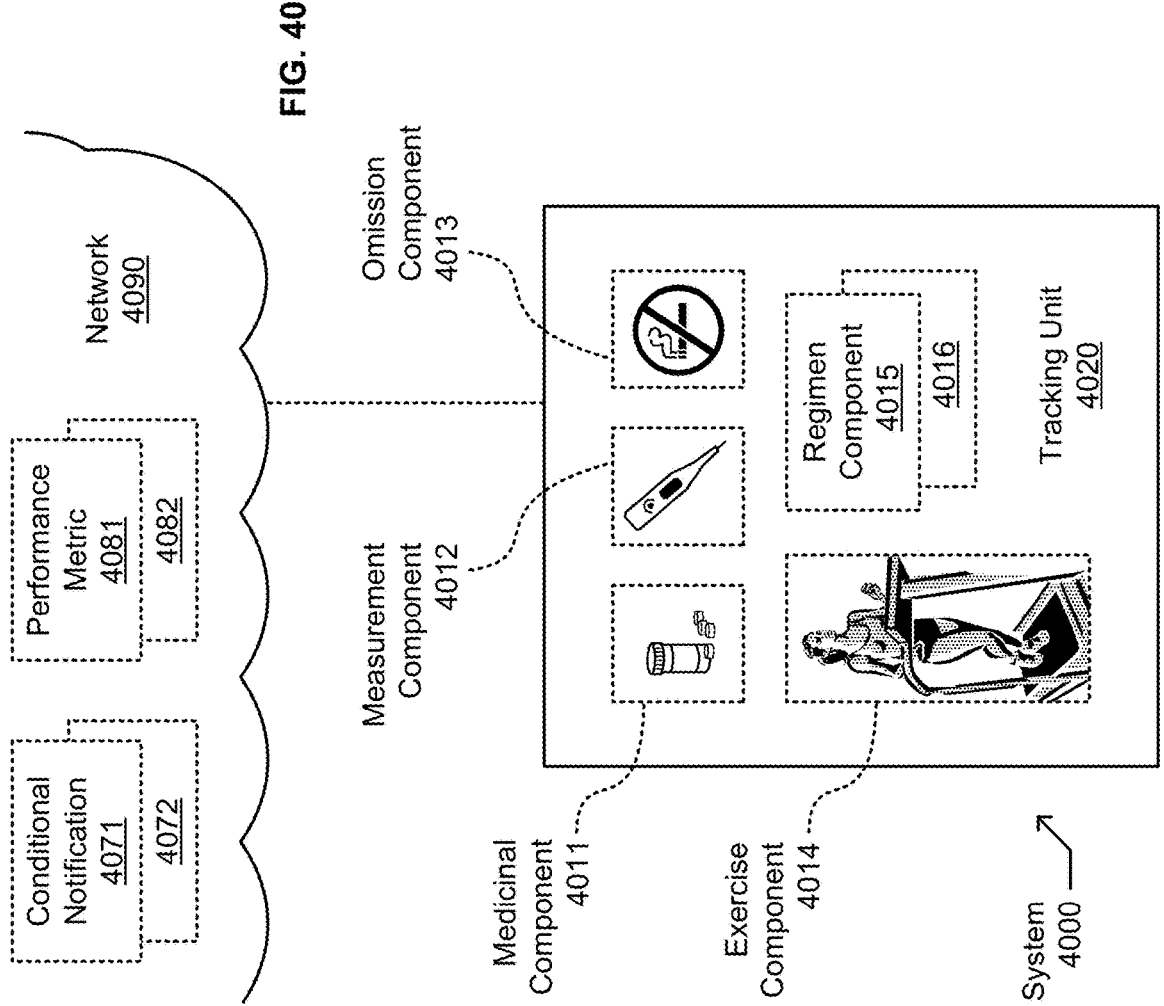
FIG. 40 depicts another exemplary environment in which one or more technologies may be configured to implement a tracking unit useful for monitoring compliance with a health regimen.

With reference now to FIG. 40, shown is another example of a system 4000 in which one or more technologies may be implemented. One or more tracking units 4020 (implemented in device 305 or near a healthcare recipient, e.g.) is configured to implement a health-related regimen 2331-2339 comprising one or more medicinal components 4011, measurement components 4012, omission components 4013, exercise components 4014, or other regimen components 4015, 4016. In some variants, such tracking may result in one or more conditional notifications 4071, 4072 or performance metrics 4081, 4082 being generated (via local event-sequencing logic in tracking unit 4020 or medical device configuration logic 3305 in network 4090, e.g.) as described below.

Figure 50:
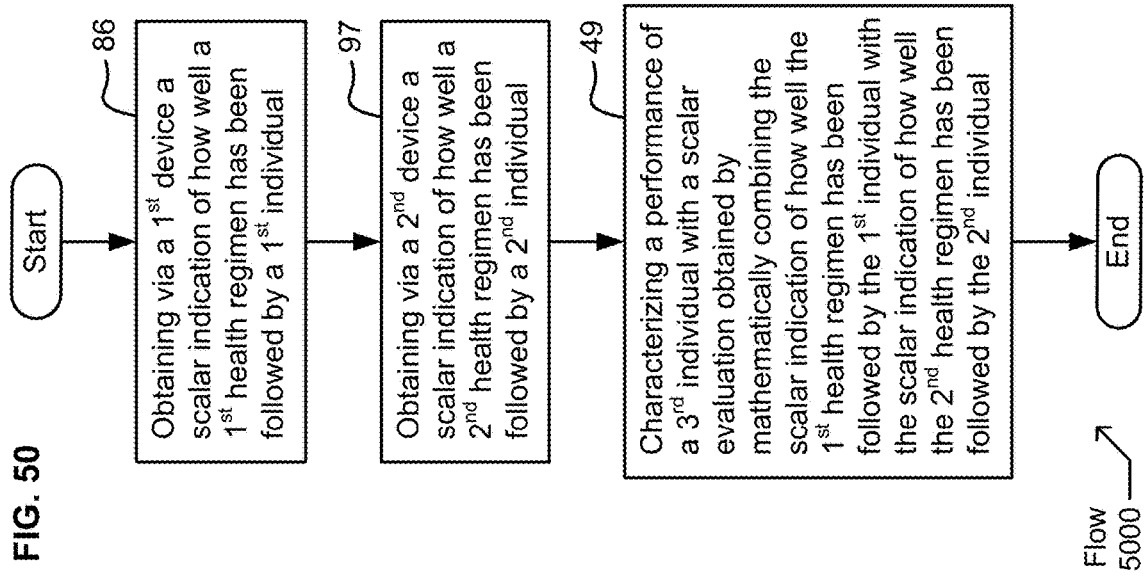
FIG. 50 depicts a high-level logic flow of an operational process (described with reference to FIG. 40, e.g.).

With reference now to FIG. 50, shown is a high-level logic flow 5000 of an operational process. Intensive operation 86 describes obtaining via a first device a scalar indication of how well a first health regimen has been followed by a first individual (e.g. interface module 3512 receiving via tracking unit 4020 a percentage or other quantified indication 2343 of how well patient 3950 has complied with pregnancy regimen 2331). This can occur, for example, in a context in which patient 3950 is the "first" patient; in which smoke detector 3958 and interaction unit 3505 are each instances of the "first" device; in which an obstetrician has defined required and suggested parameters for respective components of pregnancy regimen 2331; in which one or more tracking units 4020 on or near patient 3950 are configured (by a programmer or other technician 2761, e.g.) to derive such quantified indications 2343 (positively or negatively indicative of compliance, e.g.) from sensor data local to patient 3950 or from user input 2473, and in which the pregnancy regimen 2331 includes one or more omission components 4013 (not smoking, e.g.). In some contexts, for example, quantified indication 2343 may include an occurrence count (of detected regimen violations, e.g.), a rate (of calories consumed per day or of intercommunications or other events required by a reporting regimen component, e.g.), or a concentration (of detected metabolites indicative of compliance or noncompliance as measured by sample tester 3060, e.g.). In some variants, two or more such quantified indications 2343, 2344 may respectively reflect the performance by a patient 3950 and her provider (caregiver 991, e.g.) in regard to their respective regimens 2331, 2339 or regimen components.

In light of teachings herein, numerous existing techniques may be applied for applying various provider-specified criteria (relating to counts or dosages or other quantifications provided by a physician or other service provider, e.g.) to device-detectable health-indicative data (for determining success, eligibility, or some other threshold event, e.g.) as described herein without undue experimentation. See, e.g., U.S. Pat. No. 7,488,291 ("Methods for detecting and monitoring sleep disordered breathing using an implantable medical device"); U.S. Pat. No. 7,487,774 ("Adaptive patient trigger threshold detection"); U.S. Pat. No. 7,465,551 ("Method of determining cytokine dosage for improving myelosuppressive state"); U.S. Pat. No. 7,366,571 ("Neurostimulator with activation based on changes in body temperature"); U.S. Pat. No. 7,246,619 ("Snore detecting method and apparatus"); U.S. Pat. No. 7,223,246 ("Diagnosis of the presence of cochlear hydrops using observed auditory brainstem responses"); U.S. Pat. No. 7,177,684 ("Activity monitor and six-minute walk test for depression and CHF patients"); U.S. Pat. No. 7,132,238 ("Method of determining a chemotherapeutic regimen based on ERCC1 expression"); U.S. Pat. No. 7,107,095 ("Device for and method of rapid noninvasive measurement of parameters of diastolic function of left ventricle and automated evaluation of the measured profile of left ventricular function at rest and with exercise"); U.S. Pat. No. 7,054,688 ("Heart stimulator with evoked response detector and an arrangement for determining the stimulation threshold"); U.S. Pat. No. 7,047,083 ("Method and apparatus for identifying lead-related conditions using lead impedance measurements"); U.S. Pat. No. 6,988,498 ("Administration of CPAP treatment pressure in presence of apnea"); U.S. Pat. No. 6,978,177 ("Method and apparatus for using atrial discrimination algorithms to determine optimal pacing therapy and therapy timing"); U.S. Pat. No. 6,671,548 ("Implantable stimulation device and method for discrimination atrial and ventricular arrhythmias"); U.S. Pat. No. 6,336,048 ("Implantable active medical device enslaved to at least one physiological parameter").

Intensive operation 97 describes obtaining via a second device a scalar indication of how well a second health regimen has been followed by a second individual (e.g. input module 3625 receiving via device 1242 an event count or other indication 2346 quantitatively describing how well patient 1292 has complied with a personalized regimen 2332 having an exercise component 4014). This can occur, for example, in a context in which an accelerometer aboard device 1242 generates indication 2346 as a count of how many steps patient 1292 takes each day. Alternatively or additionally, in some contexts, a service provider (a programmer or other technician 2761, e.g.) may define required and suggested parameters for respective regimen components of a personalized regimen 2332 and configure one or more tracking units 4020 (comprising device 1242, e.g.) to derive such compliance-related quantified indications 2346 (event counts or time intervals or measurements, e.g.). In a context in which regimen 2332 includes an omission component 4013 relating to alcohol consumption, for example, such tracking units 4020 may include a breathalyzer. Alternatively or additionally, regimen 2332 may require a regimen component 4016 of daily reporting (implemented as a conditional notification 4071 or other data upload from a portable tracking unit 4020, e.g.).

Extensive operation 49 describes characterizing a performance of a third individual with a scalar evaluation obtained by mathematically combining the scalar indication of how well the first health regimen has been followed by the first individual with the scalar indication of how well the second health regimen has been followed by the second individual (e.g. computation module 3771 generating a median performance metric 4081 across two or more scalar indications 2343-2349 of regimen compliance performance by or on behalf of patients 250, 1292, 3950 in a given patient category). This can occur, for example, in a context in which the patient category is defined as whichever patients (in a particular service zone 208 or records archive 820, e.g.) have been served repeatedly by a particular provider (a material provider 2781 or care provider 2783 or corporate entity, e.g.) during the past year; in which performance metric 2461 (quantified indication 2343, e.g.) reflects recent behavior of a particular patient 3950 (in relation to regimen 2331, e.g.); in which performance metric 2462 (quantified indication 2346, e.g.) reflects recent behavior of patient 1292 (in relation to regimen 2332, e.g.); in which performance metric 2463 reflects recent behavior of patient 250 (in relation to regimen 2332, e.g.); and in which computation module 3771 derives performance metric 4081 as the median of these performance metrics 2461-2463. In some contexts, for example, such component performance metrics 2461-2463 express similar respective percentages (negatively indicative of compliance, e.g.). Alternatively or additionally, an alternative performance metric 4082 may be derived using one or more other component performance metrics 2464 relating to other patients 992, 1392 or relating to other regimen components 4015, 4016 or relating to other regimens 2333-2338 or components thereof or relating to other periods of time (a week or a month, e.g.); or other modes of mathematical combination (ranking or other common statistical operations, e.g.).

In light of teachings herein, numerous existing techniques may be applied for configuring special-purpose circuitry or other structures effective for calculating and disseminating metrics as described herein without undue experimentation. See, e.g., U.S. Pat. No. 8,078,606 ("Rank-based estimate of relevance values"); U.S. Pat. No. 8,069,080 ("Methods for generating healthcare provider quality and cost rating data"); U.S. Pat. No. 8,065,669 ("Apparatus for automatically converting numeric data to a processor efficient format for performing arithmetic operations"); U.S. Pat. No. 8,046,371 ("Scoring local search results based on location prominence"); U.S. Pat. No. 7,949,643 ("Method and apparatus for rating user generated content in search results"); U.S. Pat. No. 7,865,171 ("Method and system for rating notification"); U.S. Pat. No. 7,826,965 ("Systems and methods for determining a relevance rank for a point of interest"); U.S. Pat. No. 7,730,005 ("Issue tracking system using a criteria rating matrix and workflow notification"); U.S. Pat. No. 7,630,913 ("Automated processing of medical data for disability rating determinations"); and U.S. Pat. No. 6,832,245 ("System and method for analyzing communications of user messages to rank users and contacts based on message content").

Figure 41:
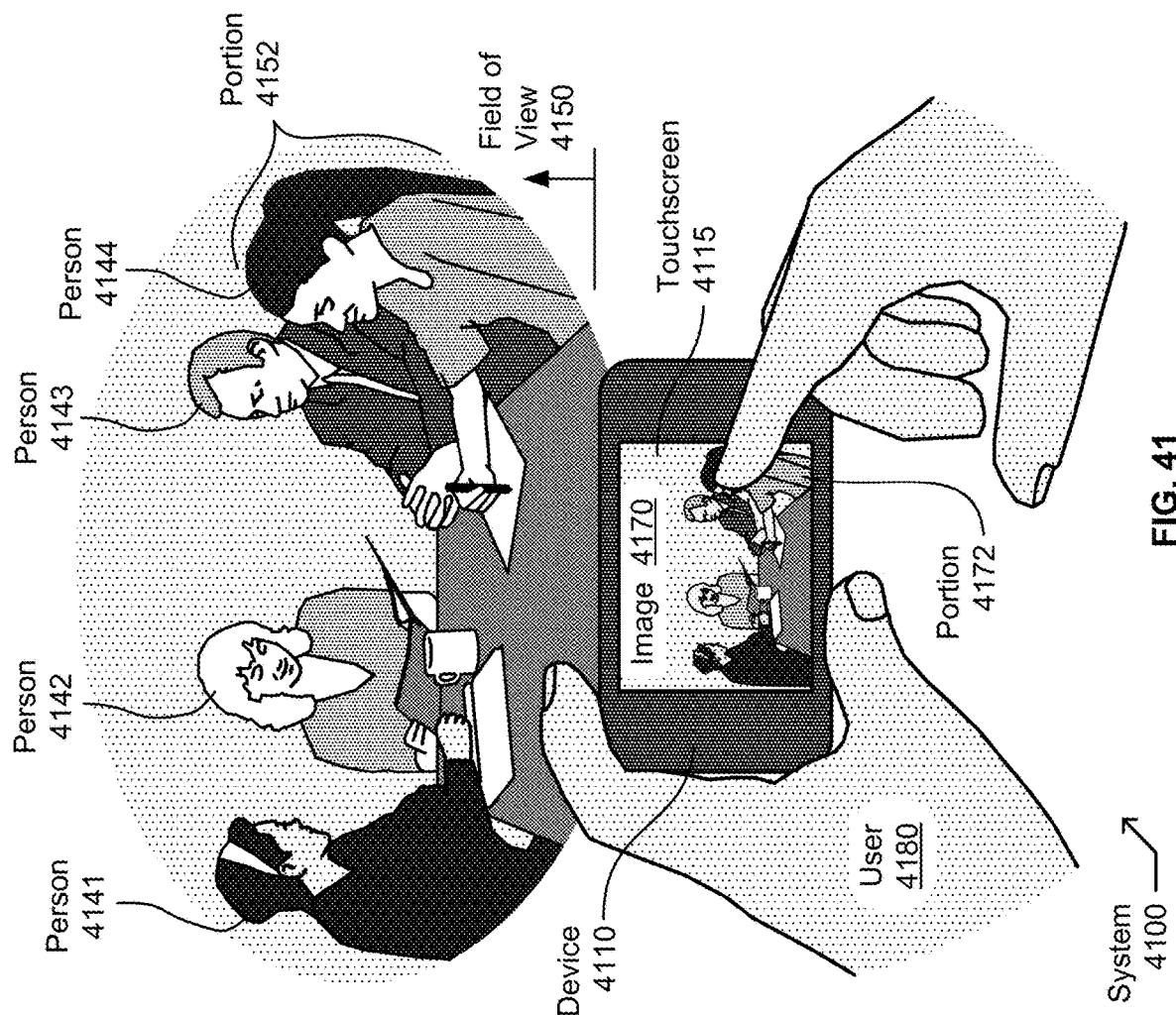
FIG. 41 depicts another exemplary environment in which one or more technologies may be configured to implement a device (a handheld having a touchscreen, e.g.) by which a user may designate an individual (patient, e.g.).

With reference now to FIG. 41, shown is another example of a system 4100 in which one or more technologies may be implemented. A local user 4180 and a handheld device 4110 each have a field of view 4150 within which several people 4141, 4142, 4143, 4144 are visible. A portion 4172 of an image 4170 (depicting person 4144, e.g.) shown on a touchscreen 4115 of the device 4110 captures a corresponding portion 4152 of the field of view 4150 so that, in some contexts, user 4180 can designate a patient (person 4144, e.g.) selectively (by touching portion 4172, e.g.). In some contexts, such designation can trigger closer tracking (supplemental capture of facial image data or other biometric data 2540 to facilitate recognition or detection of devices on person 4144, e.g.) or other device-assisted investigation concerning that patient and her medical status, as described below.

Figure 51:
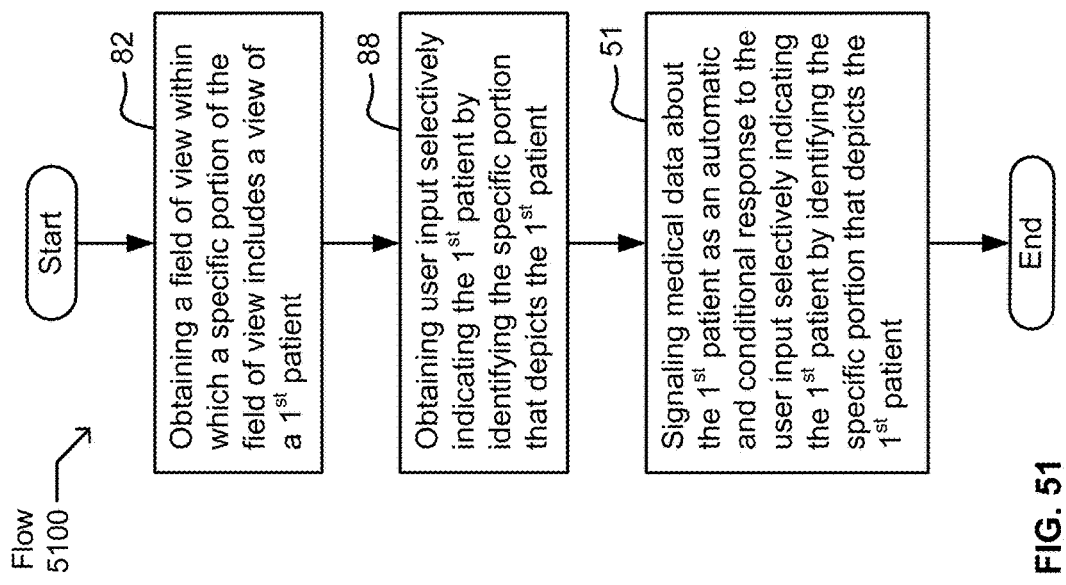
FIG. 51 depicts a high-level logic flow of an operational process (described with reference to FIG. 41, e.g.).

With reference now to FIG. 51, shown is a high-level logic flow 5100 of an operational process. Intensive operation 82 describes obtaining a field of view within which a specific portion of the field of view includes a view of a first patient (e.g. detection module 3744 receiving an image 4170 of which a lower-right portion 4172 depicts the "first" patient). This can occur, for example, in a context in which the first patient is person 4144; in which device 4110 is a handheld device comprising a camera 2053 via which image 4170 was captured; and in which detection module 3744 is configured to distinguish one person 4144 from another in (a raw version of) the image 4170. In some variants, for example, detection module 3744 may reside within device 4110 and be configured to highlight image features (with blinking brackets or similar visible markings, e.g.) of one or more individuals visible within image 4170 that detection module 3744 identifies (as human faces or figures, e.g.) in an enhanced version of image 4170 (visible to user 4180, e.g.).

In light of teachings herein, numerous existing techniques may be applied for configuring special-purpose circuitry or other structures effective for locating symbols, faces, or other shapes in field of view as described herein without undue experimentation. See, e.g., U.S. Pat. No. 8,295,556 ("Apparatus and method for determining line-of-sight direction in a face image and controlling camera operations therefrom"); U.S. Pat. No. 8,259,169 ("Eye-gaze detecting device and eye-gaze detecting method"); U.S. Pat. No. 8,188,880 ("Methods and devices for augmenting a field of view"); U.S. Pat. No. 8,045,805 ("Method for determining whether a feature of interest or an anomaly is present in an image"); U.S. Pat. No. 7,986,828 ("People detection in video and image data"); U.S. Pat. No. 7,912,288 ("Object detection and recognition system"); U.S. Pat. No. 7,903,880 ("Image processing apparatus and method for detecting a feature point in an image"); U.S. Pat. No. 7,856,142 ("Methods and systems for detecting character content in a digital image"); U.S. Pat. No. 7,787,692 ("Image processing apparatus, image processing method, shape diagnostic apparatus, shape diagnostic method and program"); U.S. Pat. No. 7,715,659 ("Apparatus for and method of feature extraction for image recognition"); U.S. Pat. No. 7,682,025 ("Gaze tracking using multiple images"); U.S. Pat. No. 7,630,544 ("System and method for locating a character set in a digital image"); U.S. Pat. No. 7,590,275 ("Method and system for recognizing a candidate character in a captured image"); U.S. Pat. No. 7,572,008 ("Method and installation for detecting and following an eye and the gaze direction thereof"); U.S. Pat. No. 7,526,123 ("Estimating facial pose from a sparse representation"); U.S. Pat. No. 7,454,067 ("Symbol classification depending on cluster shapes in difference image"); U.S. Pat. No. 7,403,656 ("Method and apparatus for recognition of character string in scene image"); U.S. Pat. No. 6,700,604 ("Image capturing method and apparatus for determining a shape of an object").

Intensive operation 88 describes obtaining user input selectively indicating the first patient by identifying the specific portion that depicts the first patient (e.g. interface module 3516 receiving auditory or touchscreen input 2472 indicating person 4144 from user 4180 after operation 82). This can occur, for example, in a context in which such input 2472 includes coordinates 2381, 2382 indicating a position on touchscreen 4115 within a portion 4172 of image 4170 that was touched by user 4180; in which user 4180 intends or perceives that such input is "selective" insofar that it indicates less than all of the field of view (image 4170, e.g.); in which the specific portion 4172 depicts only one patient (person 4144, e.g.); and in which other people depicted in image 4170 (if there are any) are therefore not "selectively indicated" by such input. In some contexts, for example, ambiguous input (spanning two or more portions of image 4170 respectively identifying two or more persons 4143, 4144 depicted therein, e.g.) may not register (may not trigger interface module 3516 to take any action perceptible to user 4180, e.g.) or may cause interface module 3516 to prompt user 4180 to specify which person user 4180 intends to designate (by asking the user for a menu selection or by zooming in on part of the image 4170 that depicts them to prompt a more precise designation via touchscreen 4115, e.g.). Alternatively or additionally, interface module 3516 may be configured to provide (via a speaker or touchscreen 4115 of device 4110, e.g.) one or more unique patient designations 2501, 2502 (patient names or birthdates or serial numbers retrieved from corresponding institutional records 3191-3197, e.g.) by which user 4180 may resolve that person 4144 has been identified correctly (in a variant in which interface module 3516 uses a voice menu confirmation or other protocol for prompting user 4180 for clarification, e.g.). Alternatively or additionally, interface module 3516 may be configured to extract such institutional data by a direct detection (via a passive wireless linkage 2776 or line of sight, e.g.) of a data-handling device 3805 (an interaction unit 2775, e.g.) worn by person 4144 (individual 2782, e.g.).

In light of teachings herein, numerous existing techniques may be applied for configuring special-purpose circuitry or other structures effective for highlighting detected features in displays or other visual media as described herein without undue experimentation. See, e.g., U.S. Pat. No. 7,911,482 ("Method and system for efficient annotation of object trajectories in image sequences"); U.S. Pat. No. 7,853,586 ("Highlighting occurrences of terms in documents or search results"); U.S. Pat. No. 7,639,396 ("Editing of digital images, including (but not limited to) highlighting and shadowing of image areas"); U.S. Pat. No. 7,555,159 ("Image highlight correction using illumination specific HSV color coordinate"); U.S. Pat. No. 7,119,814 ("System and method for annotation on a moving image").

In light of teachings herein, numerous existing techniques may be applied for configuring special-purpose circuitry or other structures effective for comparing a face or other informational element with a database of similar items as described herein without undue experimentation. See, e.g., U.S. Pat. No. 8,000,528 ("Method and apparatus for authenticating printed documents using multi-level image comparison based on document characteristics"); U.S. Pat. No. 7,949,191 ("Method and system for searching for information on a network in response to an image query sent by a user from a mobile communications device"); U.S. Pat. No. 7,908,518 ("Method, system and computer program product for failure analysis implementing automated comparison of multiple reference models"); U.S. Pat. No. 7,856,137 ("Apparatus and method for verifying image by comparison with template image"); U.S. Pat. No. 7,831,559 ("Concept-based trends and exceptions tracking"); U.S. Pat. No. 7,787,693 ("Text detection on mobile communications devices"); U.S. Pat. No. 7,644,055 ("Rule-based database object matching with comparison certainty"); U.S. Pat. No. 7,443,787 ("Cluster system, cluster member, and failure recovery method and program thereof"); U.S. Pat. No. 6,424,729 ("Optical fingerprint security verification using separate target and reference planes and a uniqueness comparison scheme"); U.S. Pat. No. 6,167,398 ("Information retrieval system and method that generates weighted comparison results to analyze the degree of dissimilarity between a reference corpus and a candidate document"); U.S. Pat. No. 6,134,014 ("Apparatus and method of inspecting phase shift masks using comparison of a mask die image to the mask image database").

Extensive operation 51 describes signaling medical data about the first patient as an automatic and conditional response to the user input selectively indicating the first patient by identifying the specific portion that depicts the first patient (e.g. triggering module 3552 automatically causing medical history data 3843 pertaining to person 4144 to be transmitted if and only if interface module 3516 successfully obtains input 2472 as described above). This can occur, for example, in a context in which one or more interface modules 3511-3516 are operably coupled to triggering modules 3551-3556 as described herein; in which record 3834 pertains specifically to person 4144; and in which other tabular data 3820 from the same source is not accessible to triggering module 3552. In some contexts, for example, such input 2472 comprises a pattern 3841 uniquely designating such record 3834. Alternatively or additionally, triggering module 3552 may trigger an acquisition or retrieval of one or more status indicators 3842 (current images 2575, measurements, regimens 2335, query responses 2459, or unfilled medical orders 2511, e.g.) pertaining to person 4144 (via a data-handling device 3805 worn by person 4144, e.g.). This can occur, for example, in a context in which device 4110 resides in networks 2790, 3590 and implements interaction unit 3505; and in which a healthcare provider (user 4180, e.g.) could not otherwise manage a crowded environment (numerous patients in a clinic or office or cafeteria, e.g.) effectively. In some contexts, moreover, invocation module 2795 may be configured to coordinate flow 5100 automatically (without further input from any user local to the first patient, e.g.).

In light of teachings herein, numerous existing techniques may be applied for configuring special-purpose circuitry or other structures effective for extracting an indication that a patient (mammal, e.g.) was treated for a particular condition as described herein without undue experimentation. See, e.g., U.S. Pat. No. 8,073,711 ("Method and system for obtaining health-related records and documents using an online location"); U.S. Pat. No. 8,065,347 ("Managing protocol amendments in electronically recorded clinical trials"); U.S. Pat. No. 7,972,274 ("System and method for analyzing a patient status for congestive heart failure for use in automated patient care"); U.S. Pat. No. 7,935,055 ("System and method of measuring disease severity of a patient before, during and after treatment"); U.S. Pat. No. 7,899,764 ("Medical ontologies for machine learning and decision support"); U.S. Pat. No. 7,552,039 ("Method for sample processing and integrated reporting of dog health diagnosis"); U.S. Pat. No. 7,533,353 ("Electronic system for collecting and automatically populating clinical order information in an acute care setting"); and U.S. Pat. No. 7,069,085 ("Method and apparatus to produce, maintain and report information related to patient treatment using medical devices").

In light of teachings herein, numerous existing techniques may be applied for configuring special-purpose circuitry or other structures effective for annotating an electronic record as described herein without undue experimentation. See, e.g., U.S. Pat. No. 7,941,009 ("Real-time computerized annotation of pictures"); U.S. Pat. No. 7,913,162 ("System and method for collaborative annotation using a digital pen"); U.S. Pat. No. 7,847,970 ("System and method for reception analysis and annotation of prescription data"); U.S. Pat. No. 7,546,524 ("Electronic input device system and method using human-comprehensible content to automatically correlate an annotation of a paper document with a digital version of the document"); U.S. Pat. No. 7,373,342 ("Including annotation data with disparate relational data"); U.S. Pat. No. 7,286,894 ("Hand-held computer device and method for interactive data acquisition analysis annotation and calibration"); U.S. Pat. No. 7,269,787 ("Multi-document context aware annotation system"); U.S. Pat. No. 7,263,493 ("Delivering electronic versions of supporting documents associated with an insurance claim"); U.S. Pat. No. 6,839,403 ("Generation and distribution of annotation overlays of digital X-ray images for security systems"); U.S. Pat. No. 6,721,921 ("Method and system for annotating documents using an independent annotation repository"); U.S. Pat. No. 6,594,519 ("Distributed real time catalog-based annotation and documentation system for cardiology procedures"); U.S. Pat. No. 6,575,901 ("Distributed real time replication-based annotation and documentation system for cardiology procedures"); U.S. Pat. No. 6,397,181 ("Method and apparatus for voice annotation and retrieval of multimedia data").

Figure 42:
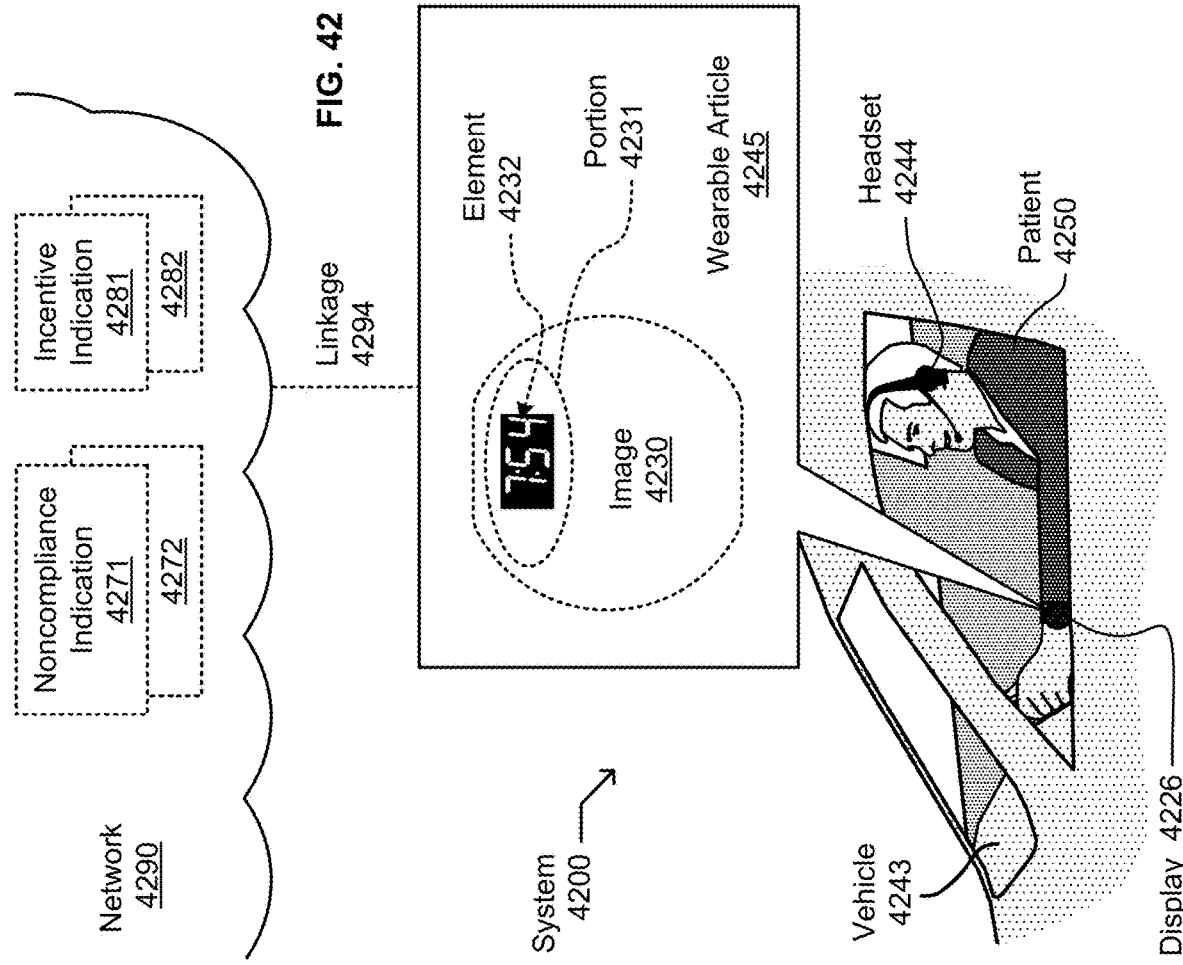
FIG. 42 depicts another exemplary environment in which one or more technologies may be configured to notify an individual (patient, e.g.) of a remaining portion of a time interval (associated with a task, e.g.) or of an artificial incentive (for participating in the task, e.g.).

With reference now to FIG. 42, shown is another example of a system 4200 in which one or more technologies may be implemented in one or more devices 305 (in a vicinity of patient 4250, e.g.) having a wireless linkage 4294 with network 4290. In some variants one or more regimen noncompliance indications 4271, 4272 relating to patient 4250 trigger conditional or other incentive indications 4281, 4282 being communicated (via a display 2426, 4226 of a vehicle 4243 or glasses or other wearable article 4245, e.g.) to patient 4250 (via, e.g.). See FIG. 52. Alternatively or additionally one or more such devices may comprise one or more elements 4232 (in a respective portion 2581, 4231 of one or more images 2580, 4230 each implementing a countdown timer 2310, e.g.) to indicate a remaining portion (7 minutes and 54 seconds, e.g.) of one or more time intervals 2543, 2544 associated with respective tasks (starting an intercommunication or arriving at a location, e.g.). See FIG. 57.

Figure 52:
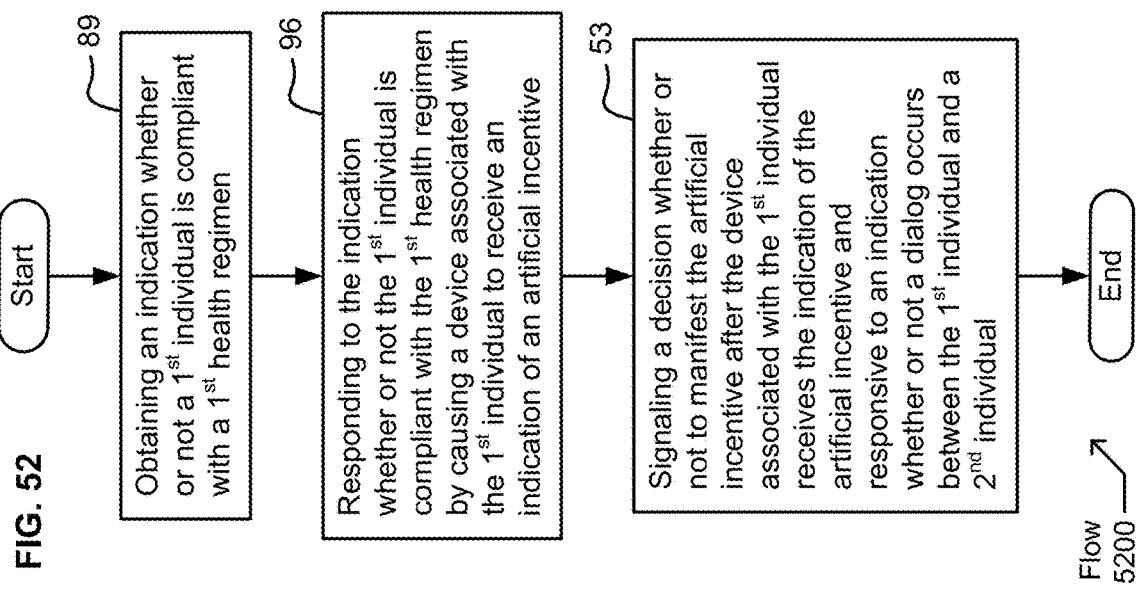
FIG. 52 depicts a high-level logic flow of an operational process (described with reference to FIG. 42, e.g.).

With reference now to FIG. 52, shown is a high-level logic flow 5200 of an operational process. Intensive operation 89 describes obtaining an indication whether or not a first individual is compliant with a first health regimen (e.g. input module 3624 failing to receive an indication 2349 that patient 4250 took a medication or measurement within a time interval 2545 required by a component 4015 of his therapeutic regimen 2336). This can occur, for example, in a context in which a medicinal component 4011 or measurement component 4012 required that such medication or measurement be administered daily; in which another component 4015 of regimen 2336 required that the indication 2349 of such administration (from an administration detection module 2848 or an administration detection feature 2880 directly or indirectly coupled with input module 3624, e.g.) be received within a prescribed time interval (between 11 am and 1 pm, e.g.) each day; in which the effectiveness of regimen 2336 depends heavily upon such timely administration; and in which such indication 2349 was not received or was received early or late today. In some contexts, for example, such reporting may be implemented via a wearable device (headset 4244, e.g.) or other device associated with patient 4250.

Intensive operation 96 describes responding to the indication whether or not the first individual is compliant with the first health regimen by causing a device associated with the first individual to receive an indication of an artificial incentive (e.g. triggering module 3551 responding to the absence of the indication 2349 by causing a wearable article 4245 or other device associated with patient 4250 to receive an indication 2553 of a particular payment in kind 2618 or other benefit 2620 available to patient 4250 or to another recipient 2722 in exchange for participating in a one-minute telephone call 3431 or similar electronic intercommunication 3443). This can occur, for example, in a context in which patient 4250 and his care provider 2783 are busy people (prone to exhibit imperfect compliance and intermittent followthrough and availability, e.g.); in which triggering module 3551 associates patient 4250 with one or more wearable articles 4245 (headsets 4244, e.g.) or handhelds 2074 or vehicles 4243 operable for communicating the benefit 2620; and in which such benefit 2620 is not large enough to motivate regimen noncompliance but is generally large enough to motivate the patient 4250 to participate in such a dialog 3433. Alternatively or additionally, triggering module 3551 may be configured to associate his care provider 2783 or another recipient 2722 with a delivery unit 2725 operable for communicating another incentive 2640 (penalty for failing to participate in the dialog 3433, e.g.). In some contexts, for example, a wearable article associated with patient 4250 (headset 4244, e.g.) or a data-handling device 3705 associated with another recipient 2722 in his household, e.g.) may be configured to announce "please be advised that your home's cable television service will be turned off if [patient X] does not call Dr. Smith's office before 2 pm" (via speaker 3509, e.g.) or to sound a reward-indicative ringtone (a cash register "ching-ching" sound, e.g.) signaling that answering the call will trigger a lottery eligibility 2646 or other positive incentive 2640. This can occur, for example, in a context in which such message recipients have configured such ringtones on their own devices or are otherwise aware of what such ringtones signify; in which such persons have cognitive or other behavioral attributes that make independent timely compliance uncertain; in which adequately ensuring compliance with regimen 2336 would otherwise require that patient 4250 be hospitalized; and in which a service provider 2710 (insurer, e.g.) designs such artificial incentives and timely notifications (comprising regimen 2336, e.g.) as a cost-effective alternative to hospitalization.

In light of teachings herein, numerous existing techniques may be applied for configuring special-purpose circuitry or other structures effective for motivating or monitoring voluntary participation in information management protocols as described herein without undue experimentation. See, e.g., U.S. Pat. No. 8,056,118 ("Systems and methods for universal enhanced log-in, identity document verification, and dedicated survey participation"); U.S. Pat. No. 7,828,554 ("System for delivering an educational program to a remote site and for monitoring participation therein"); U.S. Pat. No. 6,807,532 ("Method of soliciting a user to input survey data at an electronic commerce terminal"); and U.S. patent application Ser. No. 13/066,442 ("Cost-effective resource apportionment technologies suitable for facilitating therapies").

Extensive operation 53 describes signaling a decision whether or not to manifest the artificial incentive after the device associated with the first individual receives the indication of the artificial incentive and responsive to an indication whether or not a dialog occurs between the first individual and a second individual (e.g. authorization module 3792 placing an electronic order 2512 as an automatic and conditional response to an indication 2487 from caregiver 1391 that patient 4250 did not call her office by 2 pm today, the electronic order 2512 directing that cable television service for home 289 be turned off). This can occur, for example, in a context in which patient 4250 lives in home 289; in which service provider 2710 pays for the cable television service for home 289; in which caregiver 1391 is the "second" individual (Dr. Smith or her assistant, e.g.); in which triggering module 3551 responds to the absence of the indication 2349 of compliance by transmitting a message 2290 to caregiver 1391 (via an email or other app resident on device 1342, e.g.) asking whether patient 4250 called Dr. Smith's office by 2 pm; and in which Dr. Smith is motivated to receive the call and to respond truthfully and promptly to the message 2290 because she understands regimen 2336. In some contexts, moreover, invocation module 2795 may be configured to coordinate flow 5200 automatically (without further input from any user local to the first individual, e.g.).

In light of teachings herein, also, numerous existing techniques may be applied for configuring special-purpose circuitry or other structures effective for determining whether someone has accepted a telephone call as described herein without undue experimentation. See, e.g., U.S. Pat. No. 7,680,260 ("Detecting a voice mail system answering a call"); U.S. Pat. No. 7,386,101 ("System and method for call answer determination for automated calling systems"); U.S. Pat. No. 7,260,205 ("Call waiting using external notification and presence detection"); U.S. Pat. No. 6,738,613 ("Telephone set having automatic incoming-call acknowledgement detection"); U.S. Pat. No. 6,697,456 ("Speech analysis based answer detection for IP based telephones"); U.S. Pat. No. 6,650,751 ("Answer detection for IP based telephones using passive detection"); and U.S. Pat. No. 6,111,946 ("Method and system for providing answer supervision in a switched telephone network").

Figure 43:
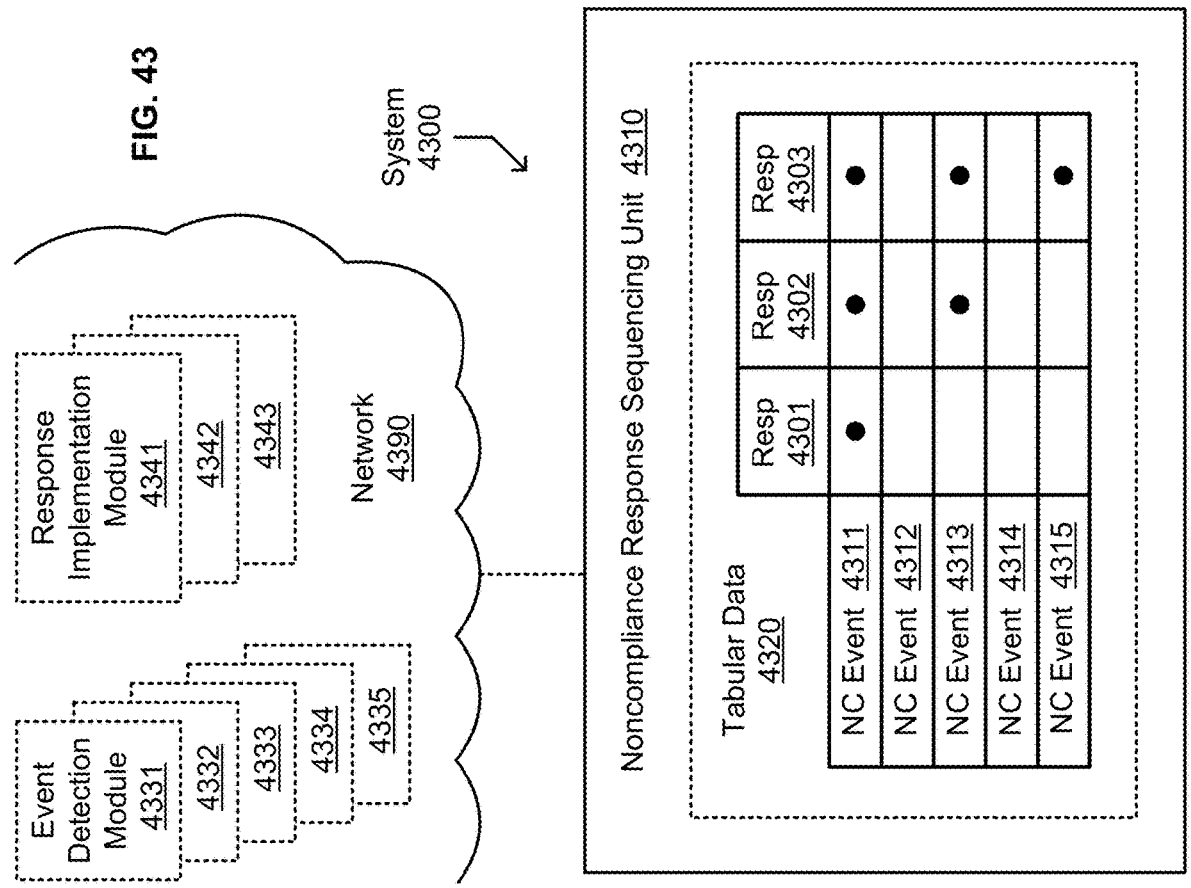
FIG. 43 depicts another exemplary environment in which one or more technologies may be configured to implement a tiered response to a health regimen that is not followed.

With reference now to FIG. 43, shown is another example of a system 4300 in which one or more technologies may be implemented. A noncompliance response sequencing unit 4310 (implemented in control unit 2705, e.g.) comprises tabular data 4320 (configured by service provider 2710 or technician 2761, e.g.). Two or more event detection modules 4331, 4332, 4333, 4334, 4335 (implemented in one or more tracking units 4020 local to one or more patients, e.g.) each respectively correspond to a device-detectable noncompliance event 4311, 4312, 4313, 4314, 4315 relating to one or more regimens 2331-2339 prescribed for said patient(s). Tabular data 4320 associates two or more of these noncompliance events 4311, 4313, 4315 each with a respective response 4301, 4302, 4303 that can be implemented by a respective response implementation module 4341, 4342, 4343 (local to one or more patients or providers, e.g.). See FIG. 53. Response implementation module 4341 will be triggered in response to a noncompliance event 4311 being detected (irrespective of other events 4313-4315 being detected or not, e.g.), for example, whereas response implementation module 4343 will be triggered only if several noncompliance events 4311, 4313, 4315 are detected.

Figure 53:
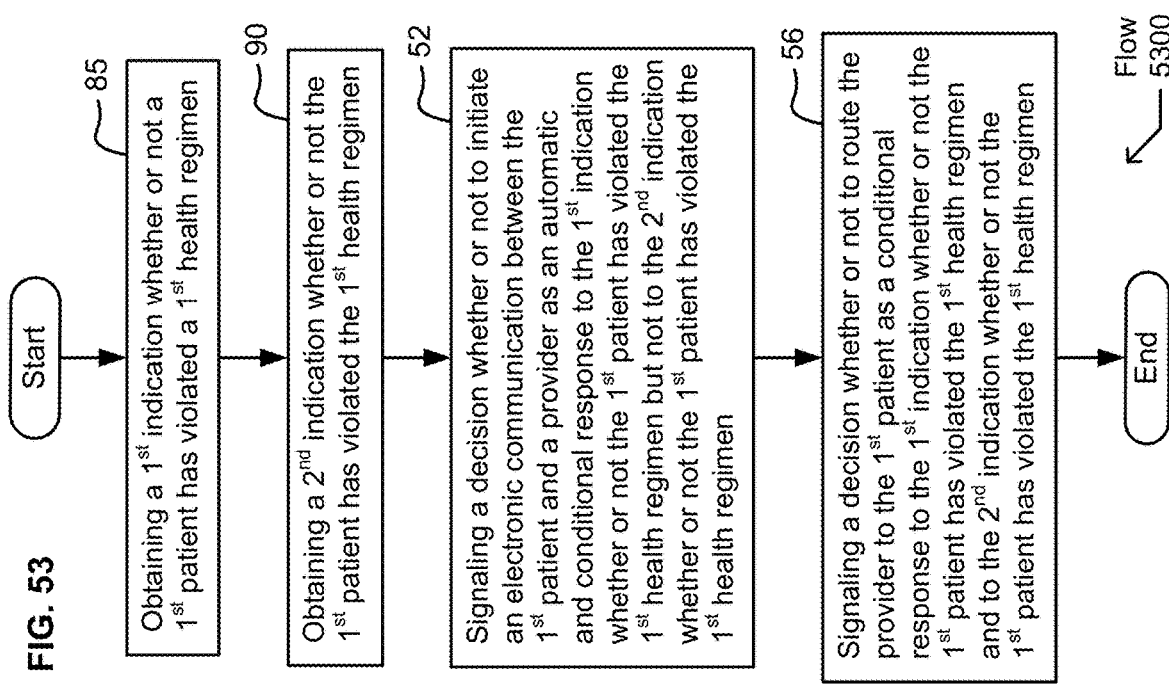
FIG. 53 depicts a high-level logic flow of an operational process (described with reference to FIG. 43, e.g.).

With reference now to FIG. 53, shown is a high-level logic flow 5300 of an operational process. Intensive operation 85 describes obtaining a first indication whether or not a first patient has violated a first health regimen (e.g. input module 3626 receiving an indication 2555 that the "first" patient has failed to complete a particular task 2442 required by regimen 2337 within an allowable time period). This can occur, for example, in a context in which regimen 2337 is designed to address a serious eating disorder (anorexia nervosa, e.g.) for which the first patient 250 has been admitted (by hospital 202, e.g.); in which the failure to complete task 2442 has been recognized (as noncompliance-indicative event 4311, e.g.) by an event detection module 4331 that transmits the "first" indication 2555; and in which system 4300 resides in network 290. In some contexts, for example, task 2442 may include the first patient ordering breakfast every morning by 10 am. Alternatively or additionally, triggering module 3556 may be configured to generate an order 2513 (requesting that the first patient be weighed every day, e.g.) as an automatic and conditional response to one or more such noncompliance-indicative events 4311, 4312 being signaled to input module 3626.

In light of teachings herein, numerous existing techniques may be applied for configuring special-purpose circuitry or other structures effective for selecting and applying thresholds or other criteria as described herein without undue experimentation. See, e.g., U.S. Pat. No. 8,069,236 ("Flow control of events based on threshold, grace period, and event signature"); U.S. Pat. No. 8,061,592 ("Overdraft threshold analysis and decisioning"); U.S. Pat. No. 8,005,685 ("Ranking air travel search results based upon user criteria"); U.S. Pat. No. 7,976,171 ("Projector cooling system with time dependent temperature threshold"); U.S. Pat. No. 7,898,995 ("Dynamic adjustment of inactivity timer threshold for call control transactions"); U.S. Pat. No. 7,894,448 ("Proving that a user profile satisfies selection criteria for targeted data delivery"); U.S. Pat. No. 7,849,398 ("Decision criteria for automated form population"); U.S. Pat. No. 7,742,193 ("Method for inspecting prints identifying differences exceeding a threshold"); U.S. Pat. No. 7,624,447 ("Using threshold lists for worm detection"); U.S. Pat. No. 7,592,859 ("Apparatus to compare an input voltage with a threshold voltage"); and U.S. Pat. No. 7,536,301 ("System and method for implementing real-time adaptive threshold triggering in acoustic detection systems").

Intensive operation 90 describes obtaining a second indication whether or not the first patient has violated the first health regimen (e.g. input module 3627 receiving an indication 2556 that the first patient has not complied with an omission component 4013 of regimen 2337). This can occur, for example, in a context in which regimen 2337 prohibits certain behaviors comprising at least one noncompliance-indicative event 4315 reported to have occurred via an event detection module 4335 (implemented in a questionnaire app completed by one or more care providers 2783, e.g.) that transmits indication 2556. In some contexts, for example, such behaviors may include inducing vomiting or failing to maintain a body weight above a particular threshold 2456 (5% below a weight of patient 250 measured upon admission to hospital 202, e.g.).

Extensive operation 52 describes signaling a decision whether or not to initiate an electronic communication between the first patient and a provider as an automatic and conditional response to the first indication whether or not the first patient has violated the first health regimen but not to the second indication whether or not the first patient has violated the first health regimen (e.g. triggering module 3553 transmitting an order 2514 to agent 294 as an automatic response 4301 to one or more noncompliance-indicative events 4311 received from event detection module 4331). This can occur, for example, in a context in which a work order 2514 calls for agent 294 to send a therapeutic message 2290 (advice or encouragement in a periodic email or text message to patient 250, e.g.) or to conduct telephonic counseling with patient 250; in which triggering module 3553 initiates such therapeutic responses as a direct response to an indication 2555 of minor noncompliance received via input module 3626 and without regard to any other noncompliance indications 2556 (or lack thereof) received via input module 3627. (It should be noted that, for semantic reasons relating to antecedent basis, flow 5300 is not presented in a most likely sequence of occurrence: more typically operation 52 will precede or overlap operation 90.)

Extensive operation 56 describes signaling a decision whether or not to route the provider to the first patient as a conditional response to the first indication whether or not the first patient has violated the first health regimen and to the second indication whether or not the first patient has violated the first health regimen (e.g. authorization module 3791 implementing a recommended response 4303 of placing an order 2515 or request that caregiver 1391 visit patient 250 every other day if two particular conditions 2326, 2327 are present and otherwise not transmitting any such order or request). This can occur, for example, in a context in which regimen 2337 includes such response 4303 as a conditional response to such conditions; in which "the provider" is a corporation that employs agent 294 and caregiver 1391; in which condition 2327 (manifested as a voltage level of a particular electrical node 3487, e.g.) comprises a particular indication 2555 (of a "minor" noncompliance-indicative event 4311, e.g.) received via input module 3626; in which condition 2326 (manifested as a voltage level of one or more other electrical nodes 3488, e.g.) comprises another particular indication 2556 (of a "major" noncompliance-indicative event 4315, e.g.) received via input module 3627; and in which a measured response to minor or moderate instances of regimen noncompliance would not otherwise occur. In some contexts, for example, regimen 2337 may include an intermediate programmatic response 4302 of an extra telephonic or in-person visit scheduled (as another instance of operation 52 or 56, e.g.) in response to an indication 2554 of an intermediate noncompliance-indicative event 4313 (a physician's notation or utterance recognized by event detection module 4333 of patient 250 exercising to excess or consuming over-the-counter laxatives, e.g.). In some contexts "the provider" may comprise a single individual (caregiver 1391, e.g.) who can participate in the electronic communication and also be routed to patient 250 (at home 289 or a room in hospital 202, e.g.) respectively pursuant to operations 52 and 56. In some variants, moreover, authorization module 3791 may be configured to "route the provider to the first patient" by generating a task list 2445 or map 2423 (from which caregiver 1391 may conduct her work, e.g.) that designates a location of a home 289 or hospital room (including a residential address or room number, e.g.) at which patient 250 is residing. In some contexts, moreover, invocation module 2795 may be configured to coordinate flow 5300 automatically (without further input from any user via network 4390, e.g.).

In light of teachings herein, numerous existing techniques may be applied for configuring special-purpose circuitry or other structures effective for routing an entity as described herein without undue experimentation. See, e.g., U.S. Pat. No. 8,290,701 ("Vehicle route selection based on energy usage"); U.S. Pat. No. 8,255,147 ("Air traffic control"); U.S. Pat. No. 8,155,811 ("System and method for optimizing a path for a marine vessel through a waterway"); U.S. Pat. No. 8,140,592 ("Delivery operations information system with route adjustment feature and methods of use"); U.S. Pat. No. 8,027,784 ("Personal GPS navigation device"); U.S. Pat. No. 8,005,488 ("Automatic service vehicle hailing and dispatch system and method"); U.S. Pat. No. 8,000,892 ("Pedestrian mapping system"); U.S. Pat. No. 7,693,653 ("Vehicle routing and path planning"); U.S. Pat. No. 7,653,457 ("Method and system for efficient package delivery and storage"); U.S. Pat. No. 7,587,369 ("Trusted and secure techniques, systems and methods for item delivery and execution"); and U.S. Pat. No. 7,487,114 ("System and method for associating aerial images, map features, and information").

Figure 44:
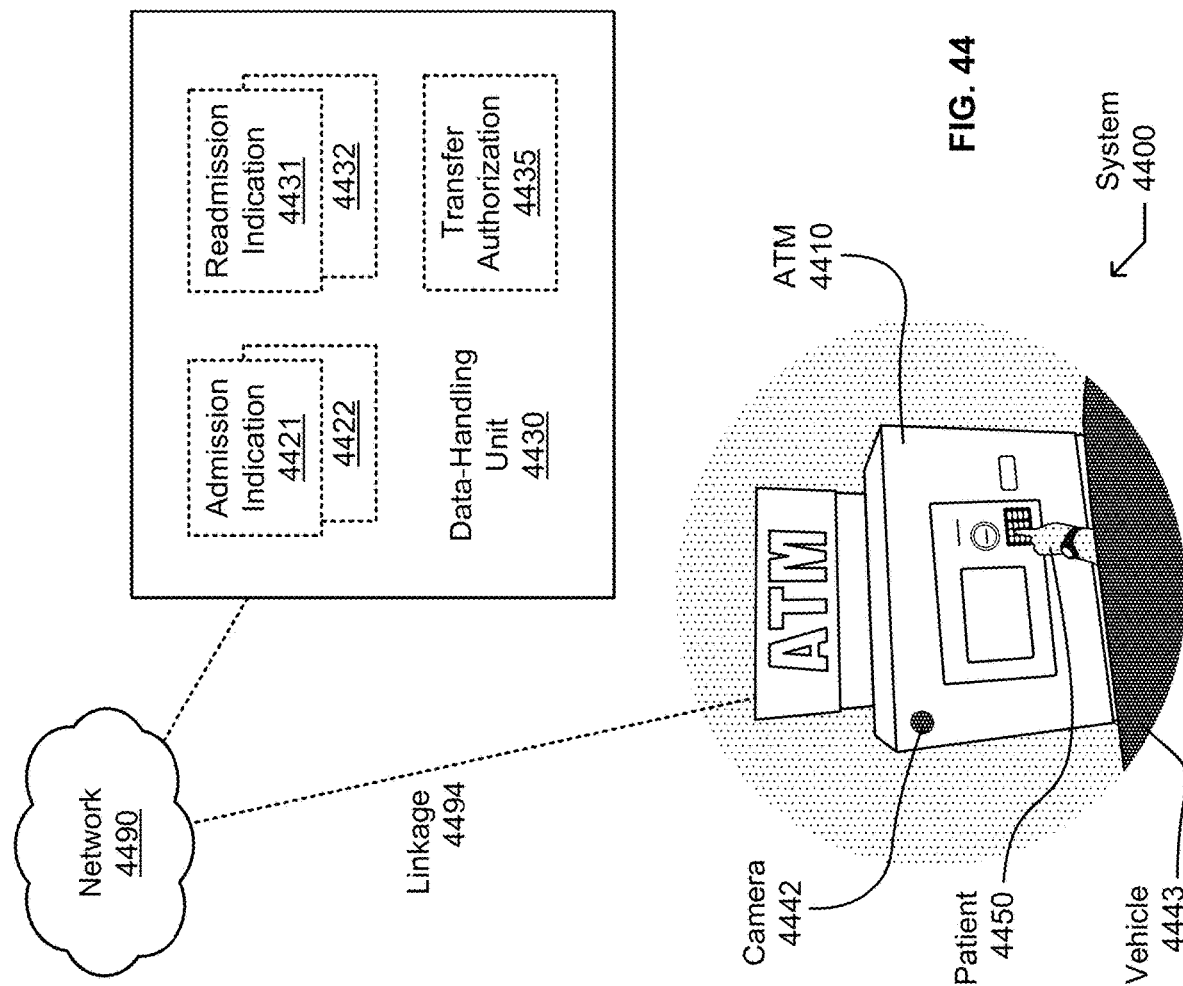
FIG. 44 depicts another exemplary environment in which one or more technologies may be configured to implement an artificial incentive (dispensed item, e.g.) to an individual (patient released from a hospital, e.g.).

With reference now to FIG. 44, shown is another example of a system 4400 in which one or more technologies may be implemented. A data-handling unit 4430 interacts with an automated teller machine (ATM) 4410 via one or more linkages 4494 and network 4490. Data-handling unit 4430 (residing in control unit 2705, e.g.) may handle one or more admission indications 4421, 4422 (relating to a hospital or other institution having admitted a patient or not, e.g.); readmission indications 4431, 4432 (relating to the patient having been readmitted or not, e.g.); or transfer authorizations 4435 (relating to an item or other incentive that may be dispensed to the patient or not, e.g.). In some contexts, ATM 4410 may interact with a patient 4450 who is in a field of view of a camera 4442 and is operating a passenger vehicle 4443, as described below.

Figure 54:
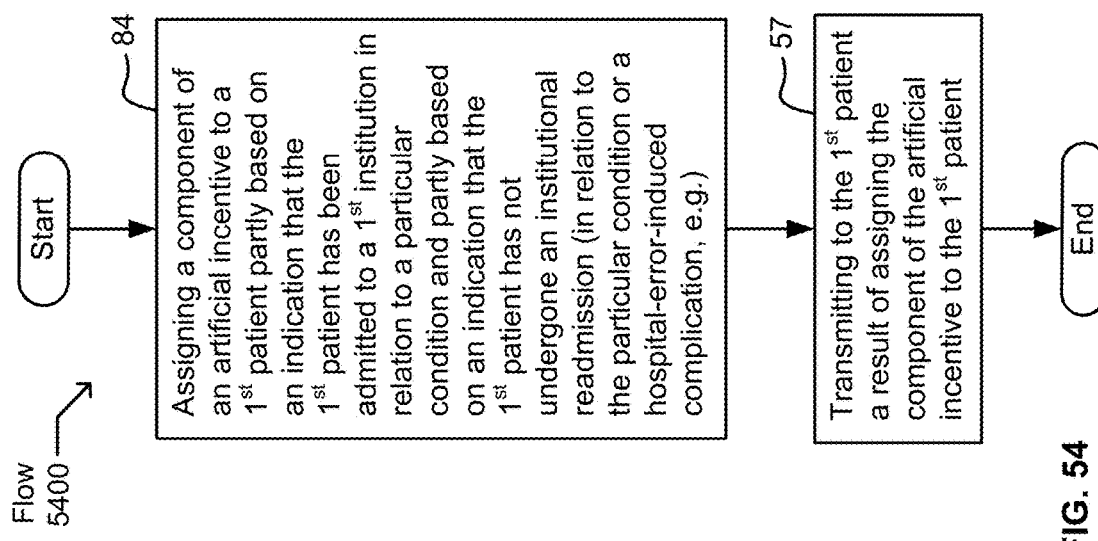
FIG. 54 depicts a high-level logic flow of an operational process (described with reference to FIG. 44, e.g.).

With reference now to FIG. 54, shown is a high-level logic flow 5400 of an operational process. Intensive operation 84 describes assigning a component of an artificial incentive to a first patient partly based on an indication that the first patient has been admitted to a first institution in relation to a particular condition and partly based on an indication that the first patient has not undergone an institutional readmission (e.g. selection module 3533 assigning a daily cash allowance or similar tangible benefit 2620 to patient 4450 only if both conditions are met). This can occur, for example, in a context in which the "first" institution is a psychiatric hospital; in which the particular condition comprises a pathology (clinical depression, e.g.); in which data distillation module 3422 generates one or more admission indications 4421, 4422 (from a search result comprising record 3191, e.g.) that patient 4450 has been admitted to the psychiatric hospital in relation to the particular condition; in which data distillation module 3422 likewise generates a readmission indication 4431 (from a search result comprising record 3192, e.g.) that patient 4450 has not since been admitted to any known hospital or a readmission indication 4432 (from a search result comprising record 3193, e.g.) that patient 4450 has not since been admitted to any participating regional hospital for any "avoidable" medical treatment related to the particular condition (a drug overdose or wound apparently inflicted by the patient 4450, e.g.); and in which search bot 3421 refreshes such records regularly (hourly or daily, e.g.) by searching all records of a network of regional hospitals near ATM 4410 (using one or more identifiers of patient 4450, e.g.). In some contexts, for example, selection module 3533 may perform operation 84 by designating a $20 cash credit (in lieu of a service 2648 or other available incentive 2640, e.g.) for patient 4450 whenever both conditions are met. Alternatively or additionally, selection module 3533 may be configurable (by a caregiver or patient 4450 having access to interaction unit 3505, e.g.) so that such conditions will result in a designation of an alternative incentive component (a payment in kind 2618, e.g.). In some variants, moreover, such assignment may be contingent upon a patient's location (visiting an ATM or caregiver 991, e.g.) or upon one or more other determinants 2393 (fulfillment of one or more medicinal components 4011, measurement components 4012, or other regimen components 4016 described herein, e.g.).

In light of teachings herein, numerous existing techniques may be applied for configuring special-purpose circuitry or other structures effective for establishing which patients have been admitted and treated for a particular condition as described herein without undue experimentation. See, e.g., U.S. Pat. No. 7,996,074 ("System and method for providing closely-followed cardiac therapy management through automated patient care"); U.S. Pat. No. 7,991,485 ("System and method for obtaining, processing and evaluating patient information for diagnosing disease and selecting treatment"); U.S. Pat. No. 7,942,817 ("Patient monitoring and treatment medical signal interface system"); U.S. Pat. No. 7,827,043 ("Method using a global server for providing patient medical histories to assist in the delivery of emergency medical services"); U.S. Pat. No. 7,698,154 ("Patient-controlled automated medical record, diagnosis, and treatment system and method"); U.S. Pat. No. 7,395,216 ("Using predictive models to continuously update a treatment plan for a patient in a health care location"); U.S. Pat. No. 7,395,214 ("Apparatus, device and method for prescribing, administering and monitoring a treatment regimen for a patient"); U.S. Pat. No. 7,204,805 ("Patient conditional diagnosis, assessment and symptom tracking system"); U.S. Pat. No. 7,069,085 ("Method and apparatus to produce, maintain and report information related to patient treatment using medical devices"); U.S. Pat. No. 6,726,634 ("System and method for determining a condition of a patient"); U.S. Pat. No. 6,405,165 ("Medical workstation for treating a patient with a voice recording arrangement for preparing a physician's report during treatment"); and U.S. Pat. No. 6,338,039 ("Method for automated collection of psychotherapy patient information and generating reports and treatment plans").

Extensive operation 57 describes transmitting to the first patient a result of assigning the component of the artificial incentive to the first patient partly based on the indication that the first patient has been admitted to the first institution in relation to the particular condition and partly based on the indication that the first patient has not undergone the institutional readmission (e.g. authorization module 3793 transmitting a transfer authorization 4435 to ATM 4410 so that any of the above-referenced $20 cash credits assigned by selection module 3533 will automatically be dispensed whenever patient 4450 transacts business at a qualifying ATM 4410 until and unless patient 4450 undergoes an institutional readmission deemed "avoidable" by service provider 2710). This can occur, for example, in a context primary unit 3405 and interaction unit 3505 are operably coupled to a computer 2670 or other data-handling device 3705 (implemented in network 4490, e.g.); in which the result 2311 of the assignment includes a dispensation trigger 2304 being transmitted to ATM 4410 (implementing the transfer authorization 4435 as an immediate cash dispensation, e.g.); in which service provider 2710 is an auditor (having authority to implement a clawback or other payment reduction under applicable state laws or Medicare regulations or policies internal to an accountable care organization, e.g.) or agent 2762 thereof; and in which any institutional readmissions being thus categorized as "avoidable" would otherwise be much more costly for a provider (of health insurance or care, e.g.) to address. Alternatively or additionally, one or more other transfer authorizations 4435 (authorizing a transfer of points 2616, credits 2617, payments in kind 2618, or other resources 2619, e.g.) may affect event-sequencing structures (in network 4490, e.g.) to implement other benefits 2620 (for one or more readmission indications 4431, 4432 being negatively indicative of readmission, e.g.). This can occur, for example, in a context in which such benefits 2620 are a sufficient incentive 2640 for qualifying patients 4450 (released from a hospital 202 and at risk for a much-more-costly hospital readmission, e.g.) generally to maintain a physician-specified home care or other therapeutic or monitoring regimen 2333 well enough to avoid such readmission but in which such benefits are not so large as to cause physician bribes or similar overt corruption to become common. In some contexts, moreover, invocation module 2795 may be configured to coordinate flow 5400 automatically (without further input from any user local to patient 4450, e.g.).

In light of teachings herein, numerous existing techniques may be applied for configuring special-purpose circuitry or other structures effective for causing a vending machine actuation or other item delivery as described herein without undue experimentation. See, e.g., U.S. Pat. No. 8,068,933 ("Products and processes for vending a plurality of products via defined groups"); U.S. Pat. No. 8,041,454 ("Automated business system and method of vending and returning a consumer product"); U.S. Pat. No. 8,002,144 ("Drive system for a vending machine dispensing assembly"); U.S. Pat. No. 7,844,363 ("Vending machine apparatus to dispense herbal medications and prescription medicines"); U.S. Pat. No. 7,783,379 ("Automated vending of products containing controlled substances"); U.S. Pat. No. 7,753,091 ("Device and method for controlling the filling of a cup by a vending machine"); U.S. Pat. No. 7,536,360 ("Electronic purchase of goods over a communications network including physical delivery while securing private and personal information of the purchasing party"); U.S. Pat. No. 7,272,571 ("Method and apparatus for effective distribution and delivery of goods ordered on the World-Wide-Web"); U.S. Pat. No. 6,799,165 ("Apparatus and methods for inventory, sale, and delivery of digitally transferable goods"); and U.S. Pat. No. 6,536,189 ("Computerized, monitored, temperature affected, delivery system for perishable goods").

Figure 45:
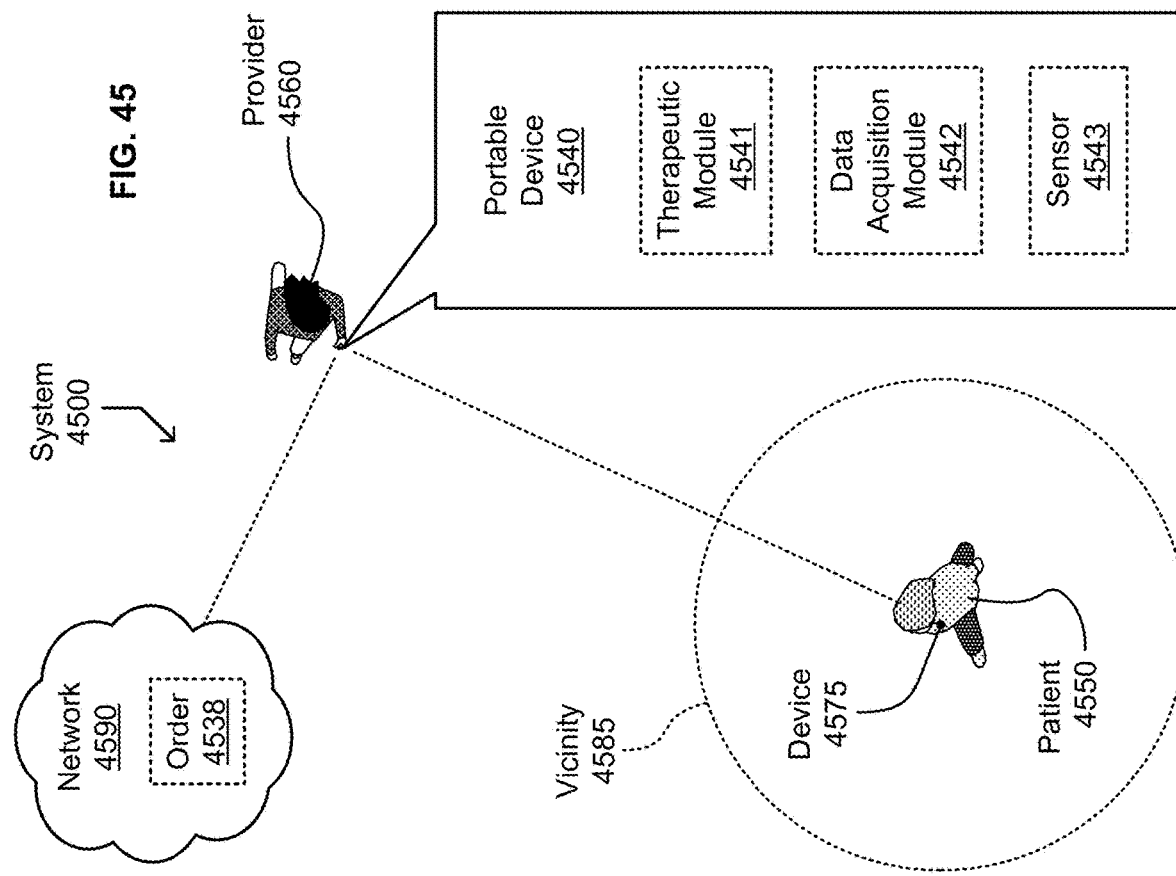
FIG. 45 depicts another exemplary environment in which one or more technologies may be configured to determine whether a medical device is in a vicinity of a patient.

With reference now to FIG. 45, shown is another example of a system 4500 in which one or more technologies may be implemented. A wearable or handheld device 4575 borne by or associated with patient 4550 is configured to observe or be observed by a portable device 4540 borne by or associated with a healthcare provider 4560. Portable device 4540 may include one or more (instances of) therapeutic modules 4541 (an inhaler 3692 or transfusion bag 3693, e.g.); medical data acquisition modules 4542 (sample extraction or measurement or imaging or other diagnostic medical equipment 2080, e.g.); or other sensors 2833 (configured to detect whether portable device 4540 is in the same room with or otherwise within a particular vicinity 4585 of patient 4550, e.g.). In some embodiments, one or more primary functions of portable device 4540 will remain disabled (by a failsafe or other disablement feature 3365 thereof, e.g.) until an order 4538 associates patient 4550 with portable device 4540 and until portable device 4540 is in the vicinity 4585 of patient 4550. Alternatively or additionally, one or both devices may be operably coupled (via a wireless linkage 2776, e.g.) with one or more networks 2790, 4590 described herein.

Figure 55:
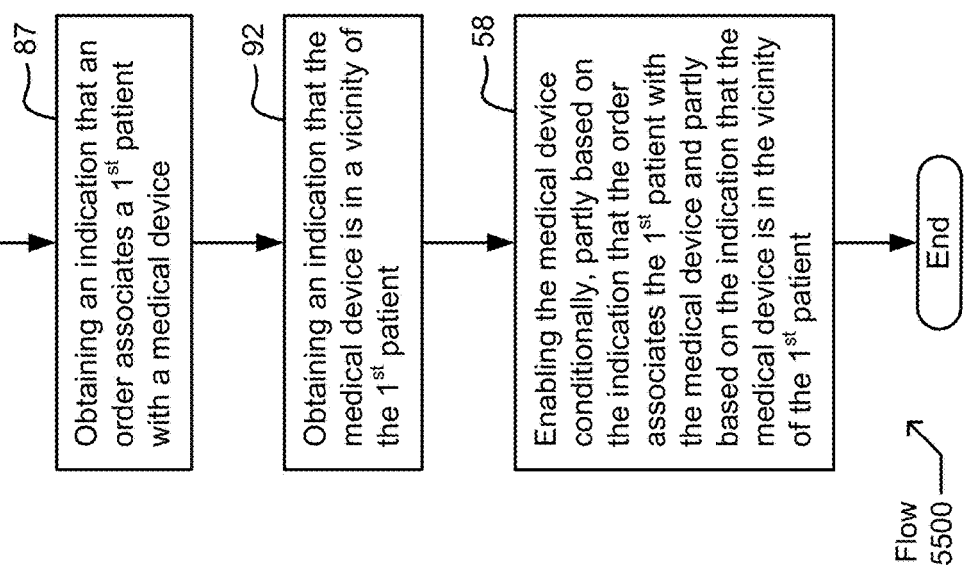
FIG. 55 depicts a high-level logic flow of an operational process (described with reference to FIG. 45, e.g.).

With reference now to FIG. 55, shown is a high-level logic flow 5500 of an operational process. Intensive operation 87 describes obtaining an indication that an order associates a first patient with a medical device (e.g. input module 3628 being operated by a caregiver 991 to upload an order 4538 allocating a portable device 4540 or other medical equipment 2080 or material to be used for or by patient 4550 to the one or more networks 2790, 4590). This can occur, for example, in a context in which the medical device is associated with a therapeutic component or measurement component 4012 of a particular regimen 2338; in which response unit 3605 resides in system 941 or network 4590; and in which caregiver 991 generates the order 4538 by prescribing regimen 2338 to patient 4550. In some contexts, for example, the portable device 4540 may comprise a syringe 3691 or other disposable item 3695. Alternatively or additionally, the portable device 4540 may comprise a drug dispenser 3270 configured (as a therapeutic module 4541, e.g.) to facilitate a medicinal component 4011 of regimen 2338. In some contexts, moreover, input module 3628 may transmit an affirmative decision 2508 (to network 4090, e.g.) to associate the particular medical device with patient 4550 after transmitting an automated prompt 2379 (like "Please press or say '1' to confirm that X should be used to perform Y upon patient Z" expressed via speaker 2057, e.g.) to caregiver 991 and as a direct and conditional response to receiving an affirmative reply ("1," e.g.).

Intensive operation 92 describes obtaining an indication that the medical device is in a vicinity of the first patient (e.g. one or more sensors 3506, 4543 generating an indication 2488 that portable device 4540 is within a vicinity 4585 of patient 4550). This can occur, for example, in a context in which another portable device 4575 is carried or worn by patient 4550; in which portable device 4540 approaches patient 4550 or in which patient 4550 approaches portable device 4540; in which such approach or proximity is detected by the one or more sensors 3506, 4543 (optically or by radio frequency or other short range communication between devices, e.g.); and in which a de facto vicinity 4585 (of patient 4550, e.g.) is established by an effective range of the one or more sensors 3506, 4543 of one portable device detecting the other portable device. Alternatively or additionally, the medical device may include an authorization module 3794 (including a speech recognition module 3427 or otherwise capable of recognizing biometric data 2540 of patient 4550, e.g.) configured to generate the indication 2488 of proximity between the medical device and patient 4550 conditionally (as a selective response to recognizing an utterance or other audible pattern 2532 detected at portable device 4540, e.g.) in sensor data received (via camera 3707 or microphone 3708, e.g.) from a nearby patient 4550.

In light of teachings herein, numerous existing techniques may be applied for configuring special-purpose circuitry or other structures effective for determining by wireless communication which devices are in a region as described herein without undue experimentation. See, e.g., U.S. Pat. No. 8,064,884 ("System and method for provisioning a wireless device to only be able to access network services within a specific location"); U.S. Pat. No. 8,010,126 ("Surveying wireless device users by location"); U.S. Pat. No. 7,983,677 ("Location-based wireless messaging for wireless devices"); U.S. Pat. No. 7,979,086 ("Virtual visitor location register for a wireless local area network"); U.S. Pat. No. 7,809,378 ("Location visit detail services for wireless devices"); U.S. Pat. No. 7,548,158 ("First responder wireless emergency alerting with automatic callback and location triggering"); U.S. Pat. No. 7,539,500 ("Using cell phones and wireless cellular systems with location capability for toll paying and collection"); U.S. Pat. No. 7,385,516 ("Location visit confirmation services for wireless devices"); U.S. Pat. No. 7,068,992 ("System and method of polling wireless devices having a substantially fixed and/or predesignated geographic location"); and U.S. Pat. No. 6,957,076 ("Location specific reminders for wireless mobiles").

In light of teachings herein, numerous existing techniques may be applied for configuring special-purpose circuitry or other structures effective for computing a difference between locations as described herein without undue experimentation. See, e.g., U.S. Pat. No. 8,044,798 ("Passive microwave speed and intrusion detection system"); U.S. Pat. No. 8,026, 850 ("Apparatus and method for computing location of a moving beacon using time difference of arrival and multi-frequencies"); U.S. Pat. No. 7,962,283 ("Deviation-correction system for positioning of moving objects and motion tracking method thereof"); U.S. Pat. No. 7,778,792 ("Systems and methods for location, motion, and contact detection and tracking in a networked audiovisual device"); U.S. Pat. No. 7,775,329 ("Method and detection system for monitoring the speed of an elevator car"); U.S. Pat. No. 7,671,795 ("Wireless communications device with global positioning based on received motion data and method for use therewith"); U.S. Pat. No. 7,647,049 ("Detection of high velocity movement in a telecommunication system"); U.S. Pat. No. 7,460,052 ("Multiple frequency through-the-wall motion detection and ranging using a difference-based estimation technique"); U.S. Pat. No. 7,242,462 ("Speed detection methods and devices"); U.S. Pat. No. 6,985,206 ("Baseball pitch speed measurement and strike zone detection devices"); U.S. Pat. No. 6,400,304 ("Integrated GPS radar speed detection system").

In light of teachings herein, numerous existing techniques may be applied for configuring special-purpose circuitry or other structures effective for determining whether a device is in a location or region as described herein without undue experimentation. See, e.g., U.S. Pat. No. 8,019,168 ("Motion detecting device and search region variable-shaped motion detector"); U.S. Pat. No. 8,000,723 ("System of utilizing cell information to locate a wireless device"); U.S. Pat. No. 7,986,237 ("Location management method using RFID series"); U.S. Pat. No. 7,932,830 ("Method of assigning and deducing the location of articles detected by multiple RFID antennae"); U.S. Pat. No. 7,605,688 ("Vehicle location determination system using an RFID system"); U.S. Pat. No. 7,573,369 ("System and method for interrogating and locating a transponder relative to a zone-of-interest"); U.S. Pat. No. 7,525,425 ("System and method for defining an event based on relationship between an object location and a user-defined zone"); U.S. Pat. No. 7,046,162 ("Method and apparatus to locate a device in a dwelling or other enclosed space"); and U.S. Pat. No. 6,205,326 ("Method for determining when a communication unit is located within a preferred zone").

Extensive operation 58 describes enabling the medical device conditionally, partly based on the indication that the order associates the first patient with the medical device and partly based on the indication that the medical device is in the vicinity of the first patient (e.g. configuration module 3704 transmitting a trigger 2302 to the medical device in response to either a positive indication 2488 or an affirmative decision 2508, whichever is received later). This can occur, for example, in a context in which the medical device is a portable device 4540 that include an electromechanical disablement feature 3365 (a valve 3361 or latch 3362, e.g.) that prevents one or more therapeutic modules 4541 (a syringe 3691 or inhaler 3692 or bag 3693, e.g.) or data acquisition modules 4542 thereof from functioning (administering a drug 141 or diagnostic protocol, e.g.) until portable device 4540 receives trigger 2302 (a wireless device enablement signal 2562, e.g.); and in which configuration module 3704 includes an "AND" gate configured to transmit the trigger 2302 and to receive the indication 2488 and decision 2508 upon which it is based. Some variants of configuration module 3704 may respond to one or more other Boolean values also in some variants, such as in a configuration in which one or more additional determinants 2394, 2395 as described above are also configured as "AND" gate inputs. Alternatively or additionally, in some implementations, one or more inputs of configuration module 3704 may be latched independently (configured to remain "set" once activated, for example, so that trigger 2302 might be transmitted even if indication 2488 and decision 2508 are manifested as positive signals that do not overlap in time, e.g.). In some contexts, moreover, invocation module 2795 may be configured to coordinate flow 5500 automatically (without further input from any user local to the medical device, e.g.).

In light of teachings herein, numerous existing techniques may be applied for configuring special-purpose circuitry or other structures effective for implementing an equipment failsafe as described herein without undue experimentation. See, e.g., U.S. Pat. No. 8,083,406 ("Diagnostic Delivery Service"); U.S. Pat. No. 8,070,739 ("Liquid drug transfer devices for failsafe correct snap fitting onto medicinal vials"); U.S. Pat. No. 8,068,917 ("Fail-safe programming for implantable medical device"); U.S. Pat. No. 7,752,058 ("Portable terminal and health management method and system using portable terminal"); U.S. Pat. No. 7,696,751 ("Method and apparatus for ferrous object and/or magnetic field detection for MRI safety"); U.S. Pat. No. 7,438,072 ("Portable field anesthesia machine and control therefore"); U.S. Pat. No. 7,087,036 ("Fail safe system for operating medical fluid valves"); U.S. Pat. No. 7,034,934 ("Anti-carcinogenic lights and lighting"); U.S. Pat. No. 6,768,420 ("Vehicle compartment occupancy detection system"); and U.S. Pat. No. 6,366,809 ("Defibrillator battery with memory and status indication gauge").

Figure 46:
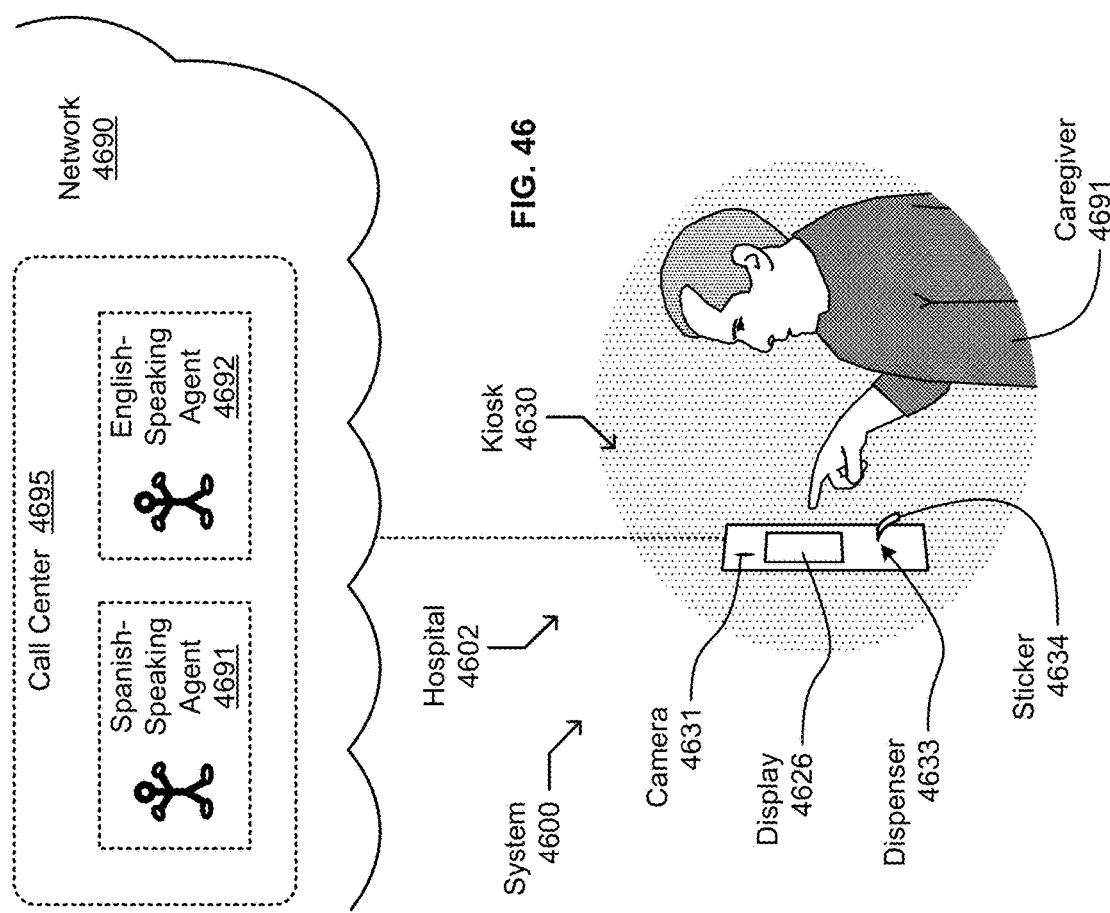
FIG. 46 depicts another exemplary environment in which one or more technologies may be configured to operate a dispenser at a patient care facility.

With reference now to FIG. 46, shown is another example of a system 4600 in which one or more technologies may be implemented. A wall-mounted intercom 3959 or other kiosk 4630 configured to facilitate patient intake (at a hospital 4602 or clinic, e.g.) may interact various patients 3950, 4250 or caregivers 4691. In some variants, kiosk 4630 may include one or more dispensers 4633 configured to dispense a wearable article (a sticker 4634, wristband, facemask, or other such article 2910, e.g.) customized with patient data (in a magnetic strip or ink-printed surface 2427 thereof, e.g.) as described below. Kiosk 4630 may likewise include one or more inputs (a camera 4631 or button 2079 or microphone 3508, e.g.) and one or more other outputs (a display 4626 configured to provide video or other visual prompts recognizable by a deaf caregiver 4691, e.g.) to facilitate usage with a monolingual or other user who requires a particular protocol for effective intercommunication. A speaker 3509 may be provided, for example, to facilitate auditory intercommunications (with a Spanish-speaking agent 4691 or an English-speaking agent 4692 at a remote call center 4695, e.g.) via network 4690. Alternatively or additionally, kiosk 4360 may be adapted to display one or more countdown timers 2310 each relating to a task of apparent urgency (a remaining portion of a two-minute time interval associated with emergency personnel arriving at kiosk 4630 or a longer interval 2544 associated with maintenance personnel arriving at kiosk 4630, e.g.) made evident by kiosk input data. See FIGS. 56-57.

Figure 56:
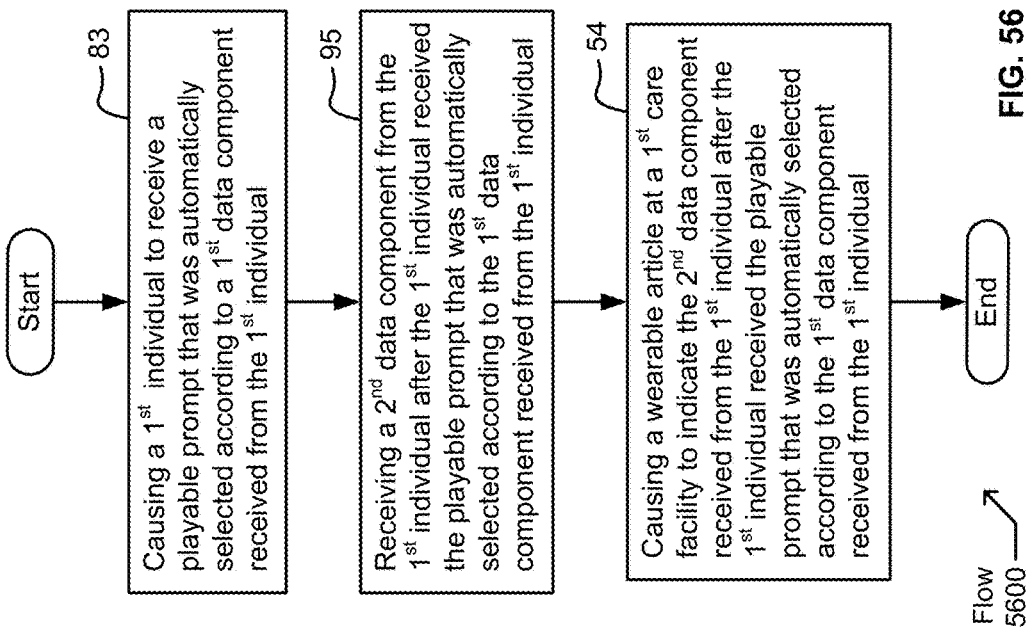
FIG. 56 depicts a high-level logic flow of an operational process (described with reference to FIG. 46, e.g.).

With reference now to FIG. 56, shown is a high-level logic flow 5600 of an operational process. Intensive operation 83 describes causing a first individual to receive a playable prompt that was automatically selected according to a first data component received from the first individual (e.g. response module 3664 causing one or more audio or video prompts 2376, 2377 to be played to a patient or to his caregiver via a kiosk 4630 in a hospital 4602). This can occur, for example, in a context in which medium 2305 and response unit 3605 implement a telephonic or other voice menu system (resident in kiosk 4630 or in network 4690, e.g.); in which the "first" data component is a spoken term 2351 ("a dose," e.g.) detected by microphone 3508; in which a speech recognition module 3427 (along a signal path between microphone 3508 and selection module 3531 and operably coupled thereto, e.g.) recognizes the spoken term (as being on an English or Spanish word list associated with one or more call centers 295, 4695 within network 4690, e.g.); in which network 290 overlaps network 4690; and in which selection module 3531 indicates at least one resource (call center 4695, e.g.) in response to speech recognition module 3427 providing an indication 2489 that the spoken term seems to be in English. In some contexts, for example, each such resource selection may manifest a decision to present one or more corresponding playable prompts 2376, 2377 (like "Press or say 'two' for English," e.g.) to the first individual (via a speaker 3509 of kiosk 4630 or of a handheld 2841 or other user interface 2840, e.g.). Alternatively or additionally, speech recognition module 3427 may be configured to detect local physicians' names, symptom descriptors, or other probative terms 2352, 2353 (particular to a local medical practice or other specific context, e.g.) based upon which selection module 3531 can select a suitable prompt 2378. In some variants, moreover, selection module 3531 may also select such prompts in response to one or more other determinants 2391, 2392 (whether or not the first individual's voice manifests distress or whether an English-speaking agent 4692 is apparently online, e.g.)

In light of teachings herein, numerous existing techniques may be applied for configuring special-purpose circuitry or other structures effective for querying a user and recognizing a reply as described herein without undue experimentation. See, e.g., U.S. Pat. No. 8,041,570 ("Dialogue management using scripts"); U.S. Pat. No. 8,015,006 ("Systems and methods for processing natural language speech utterances with context-specific domain agents"); U.S. Pat. No. 8,005,263 ("Hand sign recognition using label assignment"); U.S. Pat. No. 7,996,519 ("Detecting content and user response to content"); U.S. Pat. No. 7,983,611 ("Mobile device that presents interactive media and processes user response"); U.S. Pat. No. 7,912,201 ("Directory assistance dialog with configuration switches to switch from automated speech recognition to operator-assisted dialog"); U.S. Pat. No. 7,778,816 ("Method and system for applying input mode bias"); U.S. Pat. No. 7,415,414 ("Systems and methods for determining and using interaction models"); U.S. Pat. No. 7,346,555 ("Method and apparatus for client-in-charge business transaction processing"); U.S. Pat. No. 7,313,515 ("Systems and methods for detecting entailment and contradiction").

In light of teachings herein, numerous existing techniques may also be applied for configuring special-purpose circuitry or other structures effective for recognizing voiced and other auditory signals as described herein, or an absence thereof, without undue experimentation. See, e.g., U.S. Pat. No. 8,036,735 ("System for evaluating performance of an implantable medical device"); U.S. Pat. No. 8,014,562 ("Signal processing of audio and video data, including deriving identifying information"); U.S. Pat. No. 8,005,672 ("Circuit arrangement and method for detecting and improving a speech component in an audio signal"); U.S. Pat. No. 7,957,966 ("Apparatus, method, and program for sound quality correction based on identification of a speech signal and a music signal from an input audio signal"); U.S. Pat. No. 7,899,677 ("Adapting masking thresholds for encoding a low frequency transient signal in audio data"); U.S. Pat. No. 7,856,289 ("Method and apparatus for conserving power consumed by a vending machine utilizing audio signal detection"); U.S. Pat. No. 7,809,559 ("Method and apparatus for removing from an audio signal periodic noise pulses representable as signals combined by convolution"); U.S. Pat. No. 7,580,832 ("Apparatus and method for robust classification of audio signals, and method for establishing and operating an audio-signal database, as well as computer program"); U.S. Pat. No. 7,557,728 ("Using audio to detect changes to the performance of an application").

Intensive operation 95 describes receiving a second data component from the first individual after the first individual received the playable prompt that was automatically selected according to the first data component received from the first individual (e.g. detection module 3743 receiving and recognizing an utterance of "two" from patient 4250 after the prompt 2377 of "Press or say 'two' for English"). This can occur, for example, in a context in which (an instance of) a computer 2670 or other data-handling device 3705 (implemented in network 4490, e.g.) includes interaction unit 3505 and in which detection module 3743 is configured to recognize a limited set of possible responses (keyed-in or spoken digits, e.g.). Alternatively or additionally, detection module 3743 may be configured to recognize other medical intake data 3507 as the "second" data component (vital signs, patient or caregiver responses 2458 to diagnostic questions, audio or video clips of patient 4250, images 2577, or other diagnostic or authorization data from or about the first individual, e.g.) via other modes of input (a keyboard 846 or camera 4631 or similar sensors of a data-handling device 3705, e.g.).

In light of teachings herein, numerous existing techniques may be applied for configuring special-purpose circuitry or other structures effective for conducting a structured dialogue with a patient or caregiver as described herein without undue experimentation. See, e.g., U.S. Pat. No. 8,065,250 ("Methods and apparatus for predictive analysis"); U.S. Pat. No. 8,024,179 ("System and method for improving interaction with a user through a dynamically alterable spoken dialog system"); U.S. Pat. No. 7,610,556 ("Dialog manager for interactive dialog with computer user"); U.S. Pat. No. 7,539,656 ("System and method for providing an intelligent multi-step dialog with a user"); U.S. Pat. No. 7,461,000 ("System and methods for conducting an interactive dialog via a speech-based user interface"); and U.S. Pat. No. 7,114,954 ("Interaction education system for teaching patient care").

Extensive operation 54 describes causing a wearable article at a first care facility to indicate the second data component received from the first individual after the first individual received the playable prompt that was automatically selected according to the first data component received from the first individual (e.g. configuration module 3702 causing a wearable sticker 4634 or wrist band 1223 at the "first" care facility to include intake data 3507 from or about patient 4250). This can occur, for example, in a context in which the first care facility is an ambulance 1295 or nursing home or hospital 4602; in which the first individual is a caregiver 4691 or patient 4250; in which the configuration module 3702 transmits a trigger 2301 that includes at least the "second" data component; and in which such effective patient intake could not otherwise be automated. In some variants, for example, an on-site machine (dispenser 4633, e.g.) may encode such information in or on the wearable article (in a barcode or magnetic stripe, e.g.) in response to such a trigger. In some contexts, moreover, invocation module 2795 may be configured to coordinate flow 5600 automatically (without further input from any user local to hospital 4602, e.g.).

With reference now to FIG. 47, shown is another example of a system 4700 in which one or more technologies may be implemented. A stationary or other countdown timer 4740 is mounted on a wall in a vicinity (hospital room 4704, e.g.) of one or more patients 4750. As shown, for example, countdown timer 4740 is configured so that a counterclockwise-moving element (relative to an interior of room 4704, e.g.) has a position 4747 that manifests a remaining time interval 2541 (about 22 minutes, e.g.). In various implementations, countdown timer 4740 is controlled by one or more modules (of an interaction unit 3505 resident in network 4790, e.g.) having access to one or more protocol definitions 4771,

4772, 4773 each comprising one or more records 4761, 4762, 4763 having one or more task definition components 4781 (specifying what needs doing, e.g.) mapped to one or more corresponding timing components 4782 (specifying when it is to be done, e.g.). In a context in which a task definition component 4781 comprises responding to an activation of a call control 4730 in some device-detectable manner, for example, a timing component 4782 may specify a standard time interval (thirty minutes, e.g.) within which it is expected that at least one corresponding task (authorized personnel resetting a call switch within room 4704 or activating an intercom in room 4704, e.g.) will be complete.

With reference now to FIG. 57, shown is a high-level logic flow 5700 of an operational process. Intensive operation 91 describes identifying a first health regimen associated with a first individual, the first health regimen including one or more healthcare-related tasks associated with a time interval (e.g. interface module 3514 receiving an order 2516 or other manifestation of a decision 2509 about a caregiver 991 having prescribed one or more regimens 2338, 2339 including one or more timing components 4782 for the treatment of patient 4750). This can occur, for example, in a context in which caregiver 991 enters the order 2516 directly via system 941; in which regimen 2338 is defined to include at least one task 2443 (a medicinal component 4011 manifested in one or more records 4761, 4762, e.g.) having a task definition component 4781 and a timing component 4782; in which protocol definition 4771 calls for either a caregiver 1391 to administer an injection of a first steroid or dose (as a task definition 4781 of record 4761, e.g.) or for patient 4750 to ingest a second steroid or dose (as a task definition 4781 of record 4762, e.g.); and in which the corresponding time interval ends at 1 pm. This can occur, for example, either in a context in which the nominal time of administration is 1 pm (as a strict formal designation 2501 of the time interval ending, e.g.) or in which records 4761-4763 allow for a one hour margin (in which the nominal time of administration is at noon as an informal designation 2502, e.g.). Alternatively or additionally, some or all such records 4761-4763 may be derived from an input module 3623 configured for optical character recognition upon a scan of a hard copy 877 (entered via scanner 878, e.g.).

In light of teachings herein, numerous existing techniques may be applied for determining and recording whether scheduled events are happening within a given interval of time as described herein without undue experimentation. See, e.g., U.S. Pat. No. 7,369,476 ("Device for reading from or writing to optical recording media having a control unit for a data slicer"); U.S. Pat. No. 7,335,106 ("Closed-loop system for displaying promotional events and granting awards for electronic video games"); U.S. Pat. No. 7,330,101 ("Prescription compliance device and method of using device"); U.S. Pat. No. 7,293,645 ("Method for monitoring hand hygiene compliance"); U.S. Pat. No. 7,287,031 ("Computer system and method for increasing patients compliance to medical care instructions"); U.S. Pat. No. 7,271,728 ("Method for assessing improvement in hand hygiene practices"); U.S. Pat. No. 7,170,823 ("Medical dispenser, a blister card for use in the dispenser and a method of dispensing medical doses"); U.S. Pat. No. 6,973,371 ("Unit dose compliance monitoring and reporting device and system"); U.S. Pat. No. 6,882,278 ("Apparatus and methods for monitoring compliance with recommended hand-washing practices"); U.S. Pat. No. 6,655,583 ("Medical billing method and system"); U.S. Pat. No. 6,514,200 ("Patient compliance monitor"); U.S. Pat. No. 6,375,038 ("Dispenser having timing means, multisensory output and means of tracking usage number"); U.S. Pat. No. 6,371,931 ("Reflex tester and method for measurement of range of motion and peripheral vision"); U.S. Pat. No. 6,198,695 ("Event monitoring device"); U.S. Pat. No. 6,198,383 ("Prescription compliance device and method of using device").

Extensive operation 60 describes causing a countdown timer to indicate a remaining portion of the time interval associated with the one or more healthcare-related tasks visibly in a vicinity of the first individual (e.g. interface module 3515 configuring a countdown timer 4740 to depict or support one or more physical or virtual elements at a position 4747 that visibly manifests a remaining time interval 2541 in the vicinity of patient 4750). This can occur, for example, in a context in which "the vicinity" substantially comprises an interior of the patient's room 4704 or vehicle 4243 (that includes an article held or worn by patient 4750, e.g.); in which the remaining time interval 2541 is manifested as a shrinking area or difference (a wedge or arc of a needle or dial relative to an ending position, e.g.); in which the remaining time interval 2541 has a conspicuous visual expiration indicator (a vertical position or digital zero or empty hourglass, e.g.); and in which patient 4750 would otherwise manifest inappropriate indifference (by failing to note past compliance lapses and future regimen requirements, e.g.) or anxiety (by repeatedly activating call control 4730 needlessly, e.g.) about the various tasks of his health regimens.

Extensive operation 50 describes signaling a Boolean indication of whether or not any of the one or more healthcare-related tasks associated with the time interval were performed within the time interval after the countdown timer has indicated the remaining portion of the time interval associated with the one or more healthcare-related tasks visibly in the vicinity of the first individual (e.g. communication module 3682 recording a Boolean indication 2557 signifying that task 2443 was not completed on time). This can occur, for example, in a context in which "any" refers to at least one of the one or more healthcare-related tasks associated with the time interval; in which countdown timer 4740 indicated the remaining time interval 2541 in room 4704 throughout the interval; in which regimen 2338 called for the timely completion of task 2443 (or lack thereof) to be recorded (in records archive 920, e.g.) as a performance metric 4082 (for patient 4750 or caregiver 1391 or her employer, e.g.); and in which evaluation of regimens and service providers 2710 (insurers or caregivers 991 who prescribe regimens, e.g.) over a period of months or years would otherwise lack objectivity. In some contexts, moreover, the institutional presence of flow 5700 and countdown timers (in a care facility or home care network, e.g.) may provide such caregivers 991 better latitude to establish (by a suitable invocation of operation 91 for configuring protocol definition 4772, e.g.) which timing components 4782 of each new regimen are to be observed strictly (those for which interface module 3515 and communication module 3682 are both invoked, e.g.) and which are to be observed more casually (without operation 50 or without operation 60, e.g.) or not at all. In some contexts, moreover, invocation module 2795 may be configured to coordinate flow 5700 automatically (without further input from any user local to patient 4750, e.g.).

In light of teachings herein, numerous existing techniques may be applied for configuring special-purpose circuitry or other structures effective for implementing an automatic timestamp and recordation as described herein without undue experimentation. See, e.g., U.S. Pat. No. 8,000,979

("Automated patient management system"); U.S. Pat. No. 7,844,837 ("Electronic device and timer therefor with tamper event time stamp features and related methods"); U.S. Pat. No. 7,643,465 ("Method for insertion of time stamp into real time data within a wireless communications network"); U.S. Pat. No. 7,289,651 ("Image reporting method and system"); U.S. Pat. No. 7,283,566 ("Method and circuit for generating time stamp data from an embedded-clock audio data stream and a video clock"); U.S. Pat. No. 7,257,158 ("System for transmitting video images over a computer network to a remote receiver"); U.S. Pat. No. 7,100,210 ("Hood intrusion and loss of AC power detection with automatic time stamp"); U.S. Pat. No. 6,893,396 ("Wireless internet bio-telemetry monitoring system and interface"); and U.S. Pat. No. 6,656,122 ("Systems and methods for screening for adverse effects of a treatment").

In light of teachings herein, numerous existing techniques may be applied for configuring special-purpose circuitry or other structures effective for determining whether specific input has been received from a person within a particular time interval as described herein without undue experimentation. See, e.g., U.S. Pat. No. 8,055,240 ("Method of notifying a caller of message confirmation in a wireless communication system"); U.S. Pat. No. 8,045,693 ("Message reception confirmation method, communications terminal and message reception confirmation system"); U.S. Pat. No. 7,707,624 ("System for, and method of, proving the transmission, receipt and content of a reply to an electronic message"); U.S. Pat. No. 7,483,721 ("Communication device providing diverse audio signals to indicate receipt of a call or message"); U.S. Pat. No. 7,283,807 ("Method and telecommunication system for indicating the receipt of a data message"); U.S. Pat. No. 7,031,734 ("System and method for confirming short message service (SMS) message reception in mobile communication terminal"); U.S. Pat. No. 7,020,458 ("Method and telecommunication system for indicating the receipt of a data message"); U.S. Pat. No. 6,553,341 ("Method and apparatus for announcing receipt of an electronic message"); and U.S. Pat. No. 6,122,485 ("Method and system for confirming receipt of a message by a message reception unit").

Figure 58:
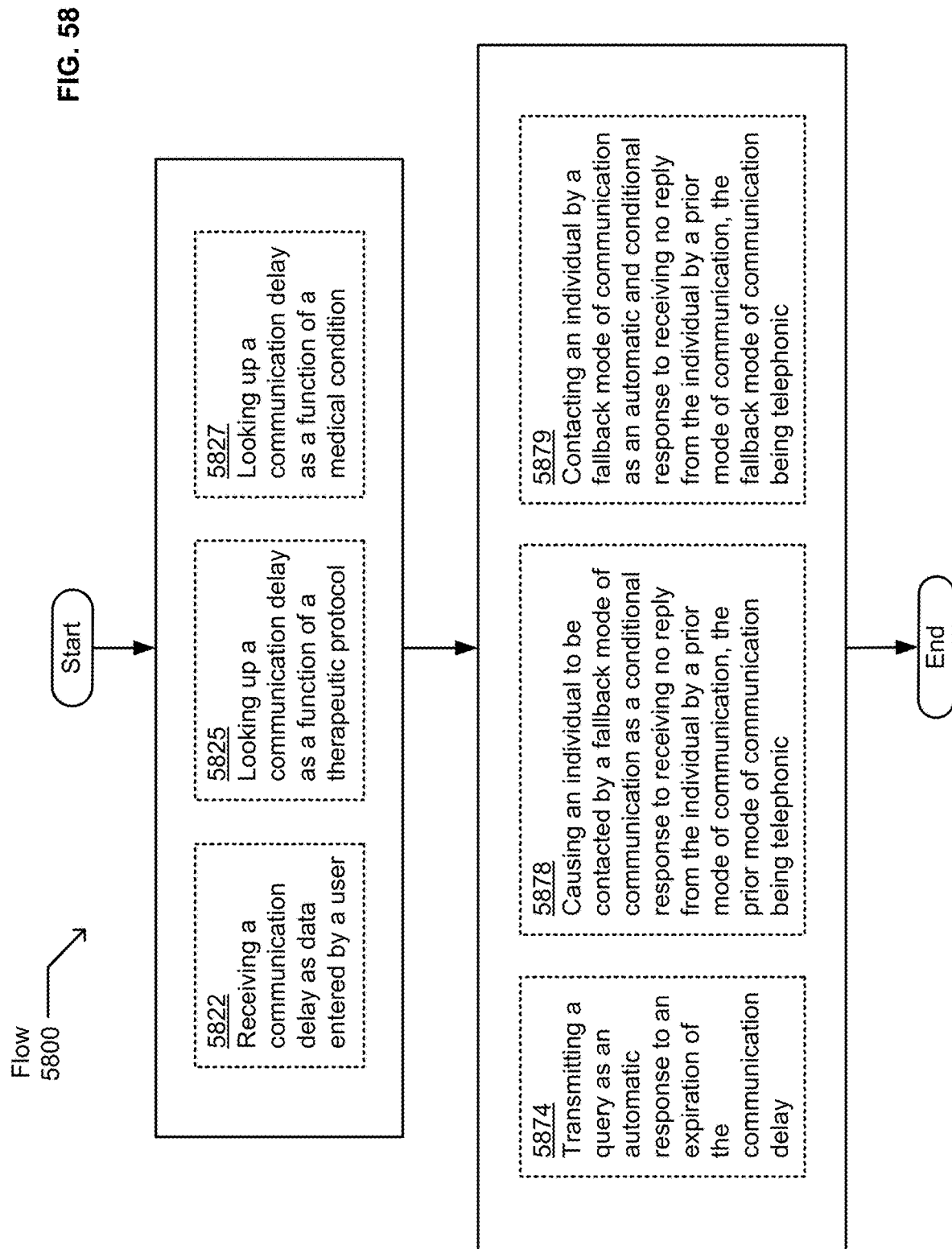
FIG. 58 depicts variants of earlier-presented flows (in any of FIG. 14-19 or 48-57).

With reference now to flow 5800 of FIG. 58 and to other flows described above, in some variants, one or more of operations 5822, 5825 may be performed in conjunction with intensive operations described above or in preparation for one or more extensive operations described above. Alternatively or additionally, one or more of operations 5874, 5878, 5879 may likewise be performed in response to one or more intensive operations described above or in conjunction with extensive operations described above.

Operation 5822 describes receiving a communication delay as data entered by a user (e.g. input module 312 receiving data 2258 that includes delay 2237 from an end user device 2015 or system 841, 941). This can occur, for example, in a context in which input module 312 comprises transistor-based circuitry having an event-sequencing structure; in which the user 3780 is a caregiver or patient 4250 who operates an implementation of device 305 (data-handling device 3705, e.g.); in which input module 312 can accept such data 2258 as a user preference 725 (e.g. by asking "when should we contact you?"); in which delay 2237 comprises an integer number of days; and in which means for performing one or more intensive operations 35-46, 81-97 as described above include an implementation of device 305. Alternatively or additionally, one or more input modules 311-319 may be configured to obtain other such data 2258 as described herein. In one such configuration, for example, input module 317 may be configured to let the user enter an e-mail address 721, telephone number 722, or other contact information 720 manifesting one or more of the user's preferences 725 (to be used in operation 5874 described below, e.g.).

Operation 5825 describes looking up a communication delay as a function of a therapeutic protocol (e.g. lookup module 2021 returning delay 2237 selectively in response to an indication that protocol 130 is being used for treating someone). This can occur, for example, in a context in which lookup module 2021 comprises transistor-based circuitry having an event-sequencing structure; in which means for performing one or more intensive operations 35-46, 81-97 as described above include an implementation of device 2005; in which a data component 127 associated with a different therapeutic protocol 120 includes a communication delay 2227 of 2.0 hours (as a digital expression, e.g.); in which one or more data components 137, 138 specifically associated with therapeutic protocol 130 each includes a communication delay 2237 that is more than 2.0 hours; and in which an appropriate entity (a caregiver 1391 or expert consultant, e.g.) has determined that such a communication delay 2237 will be more effective (than a shorter delay 2227, e.g.) following a triggering event (an order or administration, e.g.) for eliciting participation from a population of patients or caregivers who adopt a therapeutic protocol 130. In some contexts, for example, a table of suitable communication delays 2226, 2236, 2227, 2237 may be estimated (by a survey of experienced nurses or physician's assistants, e.g.) as a median time within which each given condition 160, 170 typically produces a detectable change in symptoms (relating to each respective protocol, e.g.). In some contexts, moreover, a slightly longer period (by 1% to 50% or 1-3 standard deviations across a survey distribution, e.g.) may be preferable. Alternatively or additionally, the lookup result (communication delay 2237, e.g.) may depend as a function of a medical condition (being shorter than a communication delay 2236 associated with the same protocol 130 but a different condition 160, e.g.). Such a configuration of tabular data 3820 may be useful, for example, in a context in which protocol 130 (taking an angiotensin-converting enzyme inhibitor, e.g.) typically provides a faster detectable response in treating condition 170 (shortness of breath, e.g.) than in treating condition 160 (leg swelling, e.g.).

In light of teachings herein, numerous existing techniques may be applied for configuring special-purpose circuitry or other structures effective for implementing lookup functions as described herein without undue experimentation. See, e.g., U.S. Pat. No. 7,940,982 ("Method and apparatus for color space conversion using per-color selection of look-up table density"); U.S. Pat. No. 7,921,088 ("Logical operations encoded by a function table for compressing index bits in multi-level compressed look-up tables"); U.S. Pat. No. 7,916,137 ("Generation of 3D look-up tables for image processing devices"); U.S. Pat. No. 7,847,989 ("Method for conversion of a colour space using separate chromatic and luminance look-up tables"); U.S. Pat. No. 7,706,034 ("Multi-Dimensional look-up table generation via adaptive node selection based upon color characteristics of an input image"); U.S. Pat. No. 7,558,961 ("Systems and methods for embedding messages in look-up tables"); U.S. Pat. No. 7,370,069 ("Numerical value conversion using a look-up table for coefficient storage"); U.S. Pat. No. 7,346,642 ("Arithmetic processor utilizing multi-table look up to obtain reciprocal operands"); and U.S. Pat. No. 6,981,080 ("Look-up table based USB identification").

Operation 5827 describes looking up a communication delay as a function of a medical condition (e.g. lookup module 2022 selecting delay 2237 in response to an indication that a patient 4250 is being treated for condition 170). This can occur, for example, in a context in which lookup module 2022 comprises transistor-based circuitry having an event-sequencing structure; in which a data component 136 associated with a different condition 160 (pathology, e.g.) includes a communication delay 2236 of 2.0 calendar months (as a digital expression, e.g.); in which one or more data components 137, 147 specifically associated with medical condition 170 each includes a communication delay 2237 that is less than 2.0 calendar months; and in which an appropriate entity (a specialist or other physician, e.g.) has determined that such a communication delay 2237 will be more effective (than a longer delay 2236, e.g.) following a triggering event (an estimated delivery time, e.g.) for eliciting participation from a population of caregivers 991, 4691 or patients 3950, 4250, 4450, 4550 who treat or suffer from medical condition 170. Alternatively or additionally, the lookup result (data component 137, e.g.) may depend as a function of a therapeutic protocol (having a communication delay 2237 longer than that of a data component 127 associated with the same condition 170 but a different protocol 120, e.g.). Such a configuration of tabular data may be useful, for example, in a context in which treating condition 170 (back pain, e.g.) with protocol 130 (a particular weightlifting exercise in a sauna, e.g.) will not generally permit an evaluation of treatment effectiveness as soon as that of protocol 120 (medication, e.g.).

Operation 5874 describes transmitting a query as an automatic response to an expiration of the communication delay (e.g. statement module 381 transmitting one or more queries 571-574 relating to protocol 120 or to condition 160 only after waiting for a time interval specified by delay 2226). This can occur, for example, in a context in which one or more of operations 5822, 5825, 5827 have been performed; in which statement module 381 comprises transistor-based circuitry having an event-sequencing structure; in which a prior communication (such as an input 551-552 or query 571-574 or request 581, 582 or order 1018, 1118, 2511-2516 or intercommunication 3441-3443) or other event described herein tolled the beginning of the time interval and in which means for performing one or more extensive operations 49-67 as described above include an implementation of device 305. Alternatively or additionally, in various embodiments, statement module 381 may be configured to trigger one or more other operations (extensive operations 49-67, e.g.) as described herein upon such expiration.

Operation 5878 describes causing an individual to be contacted by a fallback mode of communication as a conditional response to receiving no reply from the individual by a prior mode of communication, the prior mode of communication being telephonic (e.g. response module 354 taking no action if a reply 555 to a phone call 2291 is received before an expiration of delay 541 but otherwise initiating another message 2290 to the individual). This can occur, for example, in a context in which response module 354 comprises transistor-based circuitry having an event-sequencing structure; in which the delay 541 is on the order of ten seconds (within an order of magnitude, e.g.); in which the reply 555 may take the form of a key press or utterance (as indicated in FIG. 10, e.g.) during the phone call 2291; and in which the fallback mode of communication includes a delivery (by a fax or other machine 2030 installed in the individual's home 289 or office or by an automatically placed order to a third party with delivery instructions, e.g.) of a physical article (in which message 2290 comprises one or more instance of reminder letters or goods 691, e.g.) to the individual. Alternatively or additionally, in a context in which a foreseeable reply 555 may take the form of a return phone call 2291, e-mail message (containing specific text 2292, or online session 3432 (via the Internet, e.g.), the delay 541 may be on the order of one hour or one week (within 1 or 2 orders of magnitude, e.g.).

Operation 5879 describes contacting an individual by a fallback mode of communication as an automatic and conditional response to receiving no reply from the individual by a prior mode of communication, the fallback mode of communication being telephonic (e.g. response module 355 taking no action if a reply 555 to a prior message 2290 is received within a time interval 538 but otherwise initiating a phone call 2291 to the individual). This can occur, for example, in a context in which response module 355 comprises transistor-based circuitry having an event-sequencing structure; in which the prior message 2290 (comprising text 2292 or a phone query 571, e.g.) was sent by a request module 331, 332 as described above; in which the prior message 2290 included a hyperlink 2296, menu option 2297, or other such control 2295 configured to facilitate the individual providing input 552 to response module 355 without the need to include any direct communication with other individuals; in which the time interval 538 began when the prior message 2290 was sent; in which response module 355 infers the "receiving no reply from the individual" if the time interval 538 ends without such input 552; and in which means for performing one or more extensive operations 49-67 as described above include an implementation of device 305. In some implementations, for example, the time interval 538 may be on the order of 3.0 days or of 3.0 months (within an order of magnitude, e.g.). Alternatively or additionally, response module 355 may be configured (as an auto-dialer, e.g.) to initiate a phone call 2291 or other intercommunication 3441-3443 between a call center 295 and the individual (a caregiver or patient 4250, e.g.) as an automatic response partly based on the time interval 538 having expired and partly based on an immediate availability of a call center agent 294 (manifested as an indication 684 of the agent's current status, e.g.).

Figure 59:
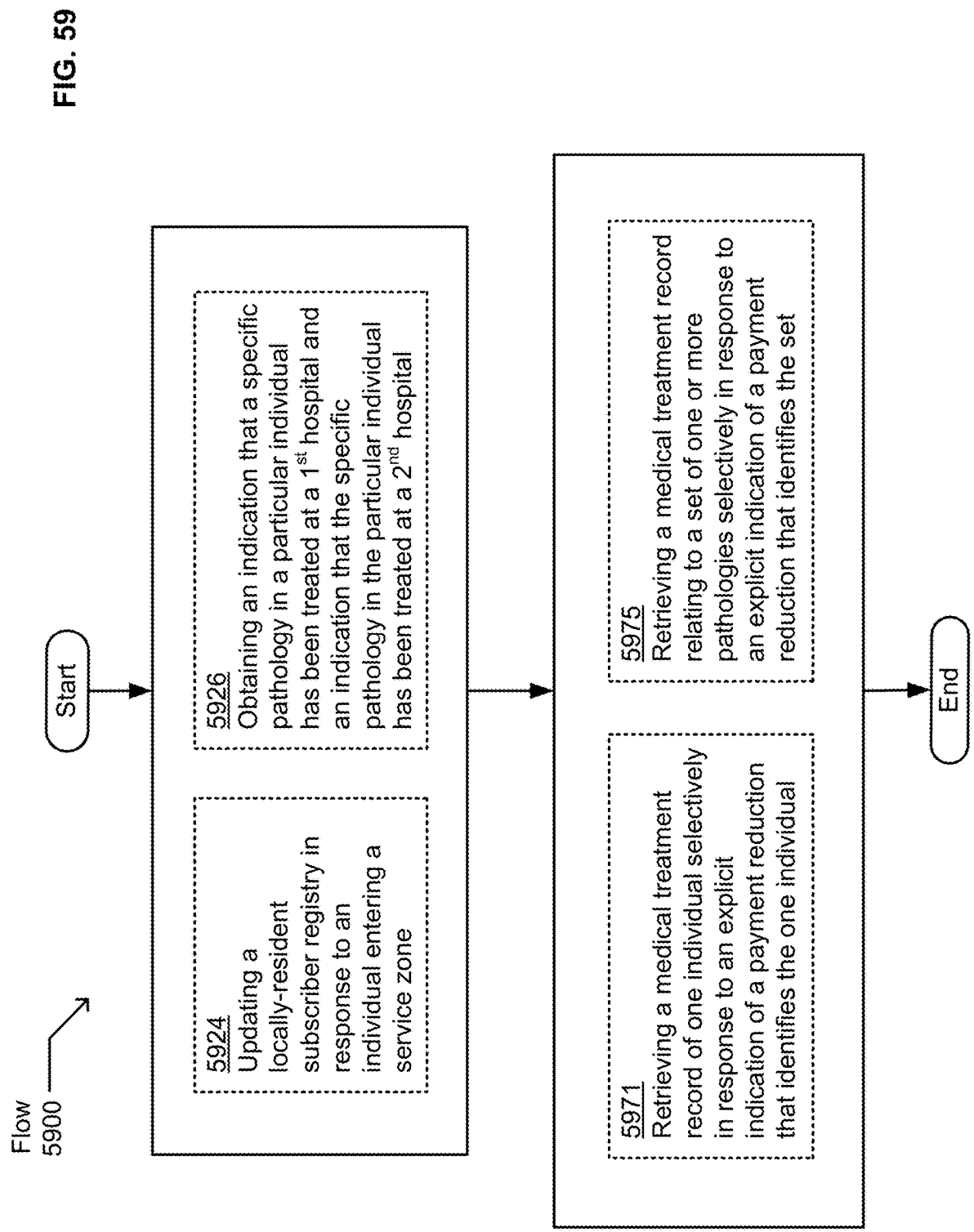
FIG. 59 likewise depicts variants of earlier-presented flows (in any of FIG. 14-19 or 48-58).

With reference now to flow 5900 of FIG. 59 and to other flows described above, in some variants, one or more of operations 5924, 5926 may be performed in conjunction with intensive operations described above or in preparation for one or more extensive operations described above. Alternatively or additionally, one or more of operations 5971, 5975 may likewise be performed in response to one or more intensive operations described above or in conjunction with extensive operations described above.

Operation 5924 describes updating a locally-resident subscriber registry in response to an individual entering a service zone (e.g. update module 2028 adding an identifier 733 of the individual to a registry 109 stored on a medium 105 in service zone 207 in response to an indication 683 that the individual has entered service zone 207). This can occur, for example, in a context in which update module 2028 comprises transistor-based circuitry having an event-sequencing structure; in which the individual is a patient 1392, 4250 as described herein; in which service zone 207 is a defined region (a county or metropolitan area, e.g.); in which device 2005 is on network 290; in which device 2015 is held or worn by patient 4250; in which detection module 2042 detects that patient 4250 has entered service zone 207 by comparing zone description data 2217 (defining service zone 207, e.g.) with GPS data 752 indicating a current position of device 2015; in which detection module 2042 responds by passing the indication 683 to update module 2028; and in which means for performing one or more intensive operations 35-46, 81-97 as described above include an implementation of device 2005. Alternatively or additionally, one or more detection modules 2042, 3741-3746 may be configured to determine whether the individual has entered service zone 207 simply by detecting whether device 2015 is within a direct operating range of device 2005. See FIG. 45.

Operation 5926 describes obtaining an indication that a specific pathology in a particular individual has been treated at a first hospital and an indication that the specific pathology in the particular individual has been treated at a second hospital (e.g. retrieval module 343 extracting a first record 671 indicating that patient 4450 was first treated at hospital 201 for pathology 181 and a second record 672 indicating that the same patient 4250 was later treated at hospital 202 for the same pathology 181). This can occur, for example, in a context in which retrieval module 343 comprises transistor-based circuitry having an event-sequencing structure; in which retrieval module 343 comprises one or more of the means for performing intensive operations 35-46, 81-97 as described above; in which retrieval module 343 has access to one or more records archives 820, 920 pertaining to treatments at both hospitals 201, 202; in which the institutional readmission (whichever was later, e.g.) and some suspect conditions (those that are not objectively verifiable or even supported by evidence, e.g.) or protocols (those that signal possible caprice or ulterior motivation on the part of a patient or caregiver 4691, e.g.) together suggest a possibility of fraud or neglect that might warrant a clawback or payment reduction for one or more hospitalizations or protocols; in which the records 671, 672 identify one or more protocols 130, 140 performed in relation to the specific pathology 181; and in which such records 671, 672 pertaining to the particular individual (patient 4450, e.g.) both identify pathology 181 in an identical or sufficiently similar manner. Such a context can exist, for example, where retrieval module 343 automatically recognizes identical or related pathology identifiers 511 in use at both hospitals 201, 202. Alternatively or additionally, a user 3780 who invokes retrieval module 343 (an auditor who has some cause to suspect fraud or abuse, e.g.) may provide two or more instances of pathology identifiers 511 (expressed as text strings 2281, 2282 of a search term, e.g.) that are considered related, optionally with a name or other identifiers of the particular individual (as another text string 2283 of the search term, e.g.).

Operation 5971 describes retrieving a medical treatment record of one individual selectively in response to an explicit indication of a payment reduction that identifies the one individual (e.g. retrieval module 341 extracting whichever billing or other records 561-569, 3191-3197 contain data components 127, 137, 147 pertaining to treatment of a medical condition 170 of a specific patient 4250 at hospital 202 in response to an explicit indication 2113 of a potential or actual payment reduction identifying the specific patient 4250). This can occur, for example, in a context in which retrieval module 341 comprises transistor-based circuitry having an event-sequencing structure; in which means for performing one or more extensive operations 49-67 as described above include an implementation of device 305 (configured to include medical device configuration logic 3305, e.g.); in which the specific patient 4250 has been identified by name 2111; in which the payment reduction is indicated "explicitly" insofar that the indication 2113 includes an audit identifier 2112 that CMS (Centers for Medicare & Medicaid Services, a federal agency within the United States Department of Health and Human Services) associates with payment reductions so that hospitals 201, 202 recognize the significance of the audit; in which one or more such records 561-569, 3191-3197 reside in archive 820; and in which such retrieval is "selective" insofar that medical treatment records of other individuals in the same archive 820 are not included in the retrieval. This can occur, for example, in a context in which one or more remote requestors 893, 993 (federal regulators, e.g.) have singled out an individual (patient 4250, e.g.) suspected of "excess" institutional readmissions. Under the healthcare system in the United States, for example, Section 3025 of Public Law 111-148 (the "Patient Protection and Affordable Care Act," sometimes called "Obamacare") states that, " . . . beginning on or after Oct. 1, 2012, in order to account for excess readmissions in the hospital, the Secretary [of Health and Human Services] shall reduce the payments that would otherwise be made to such hospital . . . ."

Operation 5975 describes retrieving a medical treatment record relating to a set of one or more pathologies selectively in response to an explicit indication of a payment reduction that identifies the set (e.g. retrieval module 342 generating a report 2245 comprising numerous data components 127, 128, 137, 138 relating particularly to a list or set 107 of one or more medical conditions to be extracted from one or more records archives 820, 920 as an automatic response to a report request 2246 that effectively identifies which medical conditions are being audited pursuant to a potential or actual payment reduction). This can occur, for example, in a context in which retrieval module 342 comprises transistor-based circuitry having an event-sequencing structure; in which at least one such condition 180 comprises a pathology 181 associated with one or more specific text strings 2282, 2283 (e.g. "addict" or "stress disorder" listed in the subset of data components 127, 128, 137, 138 comprising the report 2245) and in which the potential or actual payment reduction is implicitly evident in a report type 521 (a readmission audit, e.g.), a request authorization 522 (identifying a federal agency or other office responsible for identifying or preventing payment reductions, e.g.), a user identifier 523 (of a remote requestor 893, 993 who works for Medicare or Medicaid, e.g.), or other such indications 525; in which each data component in records archives 820, 920 includes one or more instances of records 561-569, 3191-3197 described herein; and in which such retrieval is "selective" in that it excludes some records (in data component 126, e.g.) that reside in one or more records archives 820 based on their relation to a medical condition 160 that is not of interest. Alternatively or additionally, in some contexts, retrieval module 342 may implement operation 5975 by executing a request (using search term 2280, e.g.) that sets forth one or more pathological conditions 160 (e.g. "injur" or "lacerat" expressed in an "ANDNOT" clause of a search term 2110, 2280) that are to be excluded from the report 2245.

Figure 60:
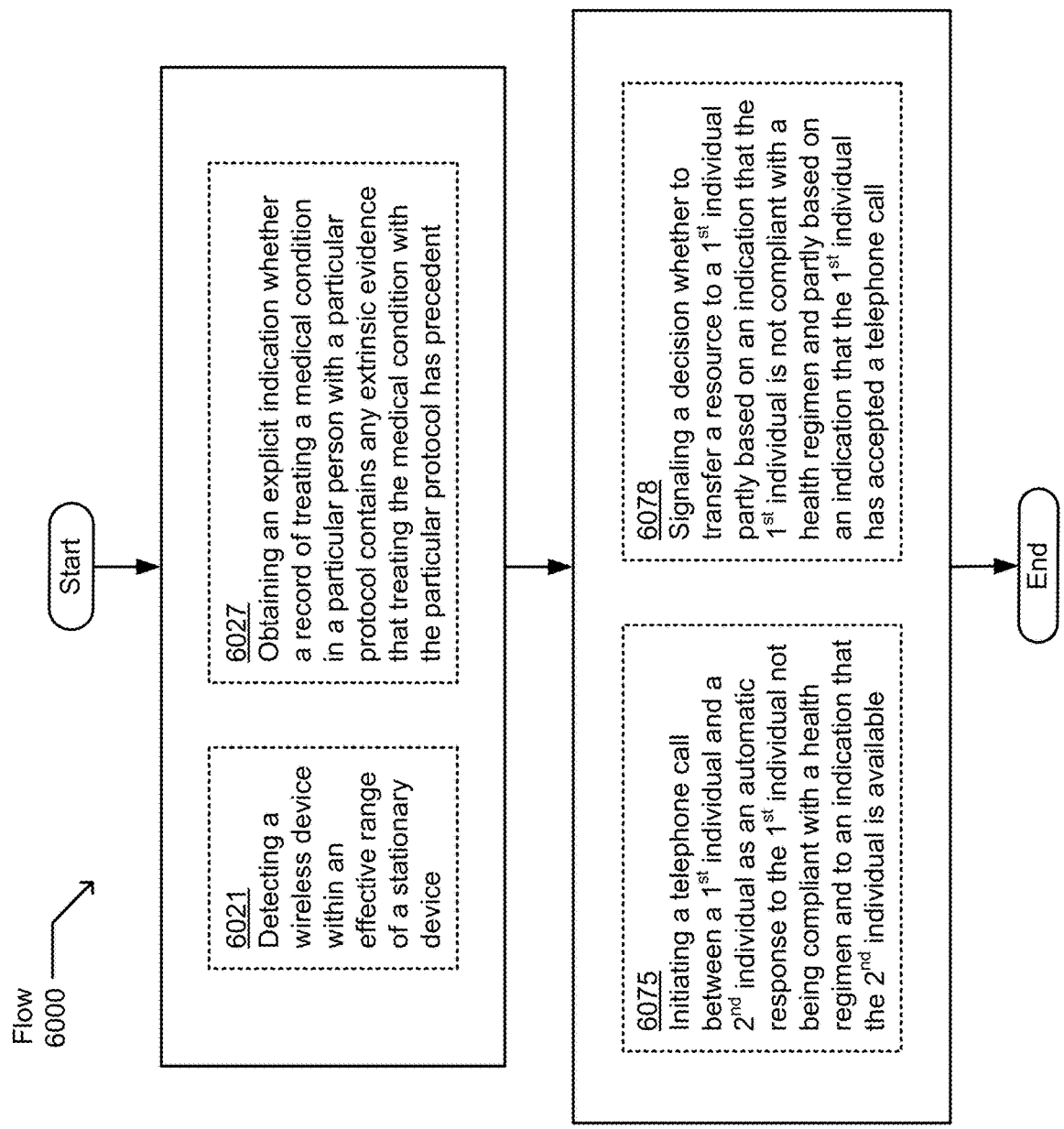
FIG. 60 likewise depicts variants of earlier-presented flows (in any of FIG. 14-19 or 48-59).

With reference now to flow 6000 of FIG. 60 and to other flows 14-19, 5800, 5900 described above, in some variants, one or more of operations 6021, 6027 may be performed in conjunction with intensive operations described above or in preparation for one or more extensive operations described above. Alternatively or additionally, one or more of operations 6075, 6078 may likewise be performed in response to one or more intensive operations described above or in conjunction with extensive operations described above.

Operation 6021 describes detecting a wireless device within an effective range of a stationary device (e.g. detection module 2046 determining that device 2015 is within an effective range of device 2005 by establishing a wireless linkage 2011 with device 2015). This can occur, for example, in a context in which detection module 2046 comprises transistor-based circuitry having an event-sequencing structure; in which means for performing one or more intensive operations 35-46, 81-97 as described above include an implementation of device 2005 as a stationary device that also implements device 242 (affixed to a building or other stationary structure, e.g.); in which device 2015 includes one or more media as described above and an implementation of device 305 that does not have a power supply (comprising a passive RFID transponder 397, e.g.); and in which device 2015 is configured to respond to a wireless signal from device 2005 by transmitting a unique wireless signal 2254 recognizable to detection module 2046 if device 2015 is within the effective range (linkage 2011, e.g.) of device 2005. Alternatively or additionally, in some contexts, device 2015 may comprise a passive USID transponder 398 in a system configured as described above, mutatis mutandis.

Operation 6027 describes obtaining an explicit indication whether a record of treating a medical condition in a particular person with a particular protocol contains any extrinsic evidence that treating the medical condition with the particular protocol has precedent (e.g. configuration module 325 receiving one or more yes/no values 2161, 2162 from physicians or other caregivers 991, 1191 in response to one or more queries 2171, 2172 directed to whether a patient's records 671-675 included suitable annotations 2293 of extrinsic evidence in support of any unconventional protocols 130, 140 prescribed or used by the patient 4250). This can occur, for example, in a context in which configuration module 325 comprises transistor-based circuitry having an event-sequencing structure; in which means for performing one or more intensive operations 35-46, 81-97 as described above include an implementation of device 305; in which configuration module 325 directs such a query to caregivers 991, 1191 who are editing one or more data components 126, 136, 146 of the patient's medical record 674 (relating to one or more protocols 120, 130, 140 being performed, e.g.); in which configuration module 325 is configured to recognize one or more protocols 120 as conventional (standard or normal or common, e.g.); and in which configuration module 325 is configured to accept such evidentiary content 432 (scans 811 or references or annotations 2293, e.g.) documenting any applicable precedent (research studies or reports or prominence indications or anecdotal data, e.g.). In some contexts, configuration module 325 may require such content 432 or an affirmation of its existence (as value 2161, e.g.) before permitting such records 674 to be saved, for example, or before permitting any order for other protocols 130, 140 (for non-emergency treatments, e.g.) to be placed. Alternatively or additionally, configuration module 325 may be operable to send a notification message 2290 to another entity 1091 (a hospital administrator, e.g.) as an automatic response to any unconventional protocol 140 being ordered by any caregiver at a particular hospital 202 unless one or more such values 2161, 2162 are received (concerning extrinsic evidence and precedent, e.g.). In some contexts, moreover, configuration module 325 is itself configurable by such entities 1091 such that each can control what kinds of notice they receive (by selectively subscribing to receive notices of unprecedented protocols 140 being used with or without subscribing to receive notices of unconventional-but-precedented protocols 130 being used, e.g.).

In light of teachings herein, numerous existing techniques may be applied for configuring special-purpose circuitry or other structures effective for searching a collection of health-related treatments as described herein without undue experimentation. See, e.g., U.S. Pat. No. 8,010,664 ("Hypothesis development based on selective reported events"); U.S. Pat. No. 7,991,485 ("System and method for obtaining, processing and evaluating patient information for diagnosing disease and selecting treatment"); U.S. Pat. No. 7,970,552 ("Diagnostic system for selecting nutrition and pharmacological products for animals"); U.S. Pat. No. 7,959,568 ("Advanced patient management for identifying, displaying and assisting with correlating health-related data"); U.S. Pat. No. 7,853,626 ("Computational systems for biomedical data"); U.S. Pat. No. 7,630,762 ("Medical device with resuscitation prompts depending on elapsed time"); U.S. Pat. No. 7,485,095 ("Measurement and analysis of trends in physiological and/or health data"); U.S. Pat. No. 7,181,375 ("Patient data mining for diagnosis and projections of patient states"); and U.S. Pat. No. 6,665,558 ("System and method for correlation of patient health information and implant device data").

Operation 6075 describes initiating a telephone call between a first individual and a second individual as an automatic response to the first individual not being compliant with a health regimen and to an indication that the second individual is available (e.g. response module 358 creating a teleconference session or other phone call 2291 that includes patient 250 and agent 294 in response to an indication 686 that patient 250 is currently not compliant with one or more components 651, 652, 4011-4016 of one or more health regimens 650, 2331-2339 contemporaneously with an indication 687 of agent 294 being available to participate in the phone call 2291). This can occur, for example, in a context in which response module 358 comprises transistor-based circuitry having an event-sequencing structure; in which means for performing one or more extensive operations 49-67 as described above include an implementation of device 305; in which agent 294 provides indication 687 explicitly and directly to response module 358 (by clicking an "available" button on a desktop system 841, 941 that implements an auto-dialer, e.g.); in which such components 651, 652 include at least one of a requirement (to use an exercise machine or take particular drugs 141 or nutraceuticals, e.g.) or a restriction (to refrain from smoking, e.g.); and in which one or more devices 2005, 2015 (comprising one or more sensors 2054, e.g.) signal compliance or noncompliance with the regimen(s). A sensor activation can signal noncompliance with a regimen component 651 that forbids snacking during certain hours, for example, by detecting a kitchen cupboard 2071 opening. Alternatively or additionally, an implementation of sensor 2054 can detect compliance with a regimen component 652 that requires a task (medication or exercise, e.g.) to be performed during a particular time interval 538 by detecting a movement in something associated with the task (an exercise machine 2073 or drug dispenser actuator 2072 or "task done" button 2079 on a handheld 2074, e.g.).

In light of teachings herein, numerous existing techniques may be applied for configuring special-purpose circuitry or other structures effective for detecting a movement of some or all of a device as described herein without undue experimentation. See, e.g., U.S. Pat. No. 8,082,122 ("Mobile device having a motion detector"); U.S. Pat. No. 7,973,820 ("Motion detector and image capture device, interchangeable lens and camera system including the motion detector"); U.S. Pat. No. 7,967,141 ("Device for the automatic detection of the movement of objects"); U.S. Pat. No. 7,887,493 ("Implantable device employing movement sensing for detecting sleep-related disorders"); U.S. Pat. No. 7,826,310 ("Acoustic navigation device and method of detecting movement of a navigation device"); U.S. Pat. No. 7,635,846 ("Motion detector device with rotatable focusing views and a method of selecting a specific focusing view"); U.S. Pat. No. 7,511,260 ("Encoder device for detecting movement"); U.S. Pat. No. 7,454,299 ("Device and method for detecting an end of a movement of a valve piston in a valve"); and U.S. Pat. No. 6,920,699 ("Device for and method for detecting a relative movement between two machine parts which are movable relative to one another").

Operation 6078 describes signaling a decision whether to transfer a resource to a first individual partly based on an indication that the first individual is not compliant with a health regimen and partly based on an indication that the first individual has accepted a telephone call (e.g. response module 357 transferring credits 693 into an account 616 of patient 4250 in response to an indication 685 that patient 4250 participated in a phone call 2291 with call center 295 about one or more health regimens 650, 2331-2339). This can occur, for example, in a context in which response module 357 comprises transistor-based circuitry having an event-sequencing structure; in which an agent 294 of call center 295 participates in the phone call 2291; in which the resource (incentive 694, e.g.) is effective (large enough, e.g.) to motivate a particular patient 4250 sometimes to take the call but not large enough to motivate the patient to violate the regimen; and in which a primary purpose of call center 295 is to initiate such telephone calls in response to one or more signals 2253 (a device-generated notification or webcam feed, e.g.) directly or indirectly indicating that a patient 4250 is apparently noncompliant with a time-critical component 651 (relating to dosages of an antibiotic, e.g.) of regimen. This can occur, for example, in a context in which patient 4250 complies with the regimen component 651 in a portion of the patient's home 289 that the call center agent 294 can monitor (via a camera 2053, microphone, or other sensor 2054, e.g.); in which patient 4250 has been informed of the incentives 694; in which an instance of device 305, 2005 as described above resides in the patient's home 289 and on one or more networks described above; and in which response module 357 performs operation 6078 by causing food or other goods 691 to be provided to patient 4250 (delivered to the patient's home 289 by a third-party supplier who receives an order 618 from response module 357, e.g.) as an automatic response to patient 4250 accepting the phone call from call center 295. Alternatively or additionally, an instance of device 305 may be configured to deliver such goods 691 (in a dispensing machine 2030 at the patient's home, e.g.).

With reference now to flow 6100 of FIG. 61 and to other flows 14-19, 5800, 5900, 6000 described above, in some variants, one or more of operations 6121, 6123 may be performed in conjunction with intensive operations described above or in preparation for one or more extensive operations described above. Alternatively or additionally, one or more of operations 6174, 6177 may likewise be performed in response to one or more intensive operations described above or in conjunction with extensive operations described above.

Operation 6121 describes causing a locally-resident subscriber registry to be updated (e.g. invocation module 371 triggering update module 2028 to remove an identifier 733 of the individual from a registry 109 stored on a medium 105 in service zone 207 in response to an indication 683 that the individual is not in service zone 207). This can occur, for example, in a context in which update module 2028 comprises transistor-based circuitry having an event-sequencing structure; in which the individual is a patient 4250, 1292 as described herein; in which service zone 207 is a defined region (a county or metropolitan area, e.g.); in which device 2005 is on network 290; in which device 2015 is held or worn by patient 4250; in which invocation module 371 detects that patient 4250 left service zone 207 by receiving an indication that patient 4250 is now in another service zone 208 (at home 289, e.g.); and in which invocation module 371 responds by transmitting a request 772 for the removal of the individual from the registry 109. Alternatively or additionally, invocation module 371 and detection module 2044 may be configured jointly to determine whether the individual is still in service zone 207 simply by detecting whether device 2015 (worn or carried by the individual, e.g.) is within a direct operating range of device 2005. Alternatively or additionally, invocation module 371 may be configured to invoke one or more other functional modules as described with reference to flows herein.

Operation 6123 describes determining whether a portable device is in a vicinity of another device (e.g. detection module 2041 detecting whether two devices 2005, 2015 are close enough that a sensor 2054 in one can directly detect a transponder 1225 or other detectable structure 2075 of the other). This can occur, for example, in a context in which detection module 2041 comprises transistor-based circuitry having an event-sequencing structure; in which means for performing one or more intensive operations 35-46, 81-97 as described above include an implementation of device 2005; in which one or both devices 2005, 2015 implement an instance of device 305; in which detection module 2041 is configured to receive a signal 2252 from sensor 2054; in which such detection is "direct" insofar that a wireless linkage 2011 between the devices 2005, 2015 consists of free space or other passive media (air, e.g.); and in which one or both devices 2005, 2015 are portable (configured to be worn or carried in one hand, e.g.). In some contexts, for example, a camera 2053 can transmit a signal 2252 (image, e.g.) indicating a detectable structure 2075 (a barcode or other visible feature that is unique to device 2015, e.g.) that detection module 2041 is configured to recognize. Alternatively or additionally, one or more other devices 241, 242 may be configured (e.g. as a tower or satellite or wall-mounted device 1343, e.g.) to perform operation 6123 by detecting both devices 2005, 2015 in a common location 204, 1304 simultaneously and the two devices are "in a vicinity" of one another insofar that both are within 50 meters of the same point (e.g. at a "third" device 241, 242).

Operation 6174 describes responding to an event with an audible notification (e.g. response module 353 causing speaker 2057 to signal a caregiver 1291, 1391 or other entity 1091 when one or more intensive operations 35-46, 81-97 are completed). This can occur, for example, in a context in which response module 353 comprises transistor-based circuitry having an event-sequencing structure; in which a device 305 or system 841, 941 described above includes an implementation of device 2005. Alternatively or additionally, response module 353 may comprise one or more of the means for performing extensive operations 49-67 as described above.

Operation 6177 describes responding to a payment-reduction event relating to a first medical treatment by causing a selective retrieval of one or more records that lack any prominence indication relating to the first medical treatment from an archive that includes at least one prominence indication relating to a second medical treatment (e.g. response module 352 responding to a request 582 for records 565, 566 indicating that protocol 120 was administered but that lack any prominence indications 1126, 1127 relating to protocol 120). This can occur, for example, in a context in which response module 352 comprises transistor-based circuitry having an event-sequencing structure; in which request 582 comprises a message from an entity that pays for at least some of the first medical treatment (Medicare or Medicaid, e.g.) such as remote requestor 893 (an auditor or regulator, e.g.); in which a report type 521, request authorization 522, or other such indication 525 signals a potential or actual payment-reduction event (manifesting a reduction that has resulted or may result from a failure to justify the use of protocol 120 in treating one or more specific medical conditions 160, e.g.) and in which a single order 1018 for protocol 120 does not constitute a "prominence indication" for purposes of determining whether the use of protocol 120 itself should be scrutinized (made subject to a payment reduction, e.g.). Alternatively or additionally, response module 352 may invoke one or more retrieval modules 825, 925 configured to access at least one records archive 920 that contains a prominence indication 1137 (average evaluation 1053 or use count 1054, e.g.) for another protocol 130.

In light of teachings herein, numerous existing techniques may be applied for configuring special-purpose circuitry or other structures effective for identifying records relating to an unjustified action as described herein without undue experimentation. See, e.g., U.S. Pat. No. 7,793,835 ("System and method for identity-based fraud detection for transactions using a plurality of historical identity records"); U.S. Pat. No. 7,668,843 ("Identification of anomalous data records"); U.S. Pat. No. 7,650,321 ("Two classifier based system for classifying anomalous medical patient records"); U.S. Pat. No. 7,493,281 ("Automatic notification of irregular activity"); U.S. Pat. No. 6,944,599 ("Monitoring and automatic notification of irregular activity in a network-based transaction facility"); and U.S. Pat. No. 6,636,592 ("Method and system for using bad billed number records to prevent fraud in a telecommunication system").

With reference now to flow 6200 of FIG. 62 and to other flows 14-19, 5800, 5900, 6000, 6100 described above, in some variants, one or more of operations 6224, 6229 may be performed in conjunction with intensive operations described above or in preparation for one or more extensive operations described above. Alternatively or additionally, one or more of operations 6272, 6273, 6276 may likewise be performed in response to one or more intensive operations described above or in conjunction with extensive operations described above.

Operation 6224 describes detecting a passive wireless transponder within a vicinity of a vehicle (e.g. detection module 2043 receiving a return signal 2251 from a passive device implementing a radio frequency identification transponder 397 or an ultrasound identification transponder 398). This can occur, for example, in a context in which detection module 2043 comprises transistor-based circuitry having an event-sequencing structure; in which medium 2205 comprises the passive device (a semiconductor chip or other device lacking a power supply 2058, e.g.); in which one or more detection modules 2041-2046 reside aboard an ambulance 1295 (in device 1241, e.g.) or other vehicle (in device 241, e.g.); and in which means for performing one or more intensive operations 35-46, 81-97 as described above include an implementation of device 2005. Alternatively or additionally, detection module 2043 (implemented in a stationary device 242, e.g.) may be configured to perform operation 6224 by detecting a passive wireless transponder that is aboard the vehicle (in device 1241, e.g.).

Operation 6229 describes obtaining an indication whether an individual is compliant with a health regimen (e.g. input module 318 receiving timing data 453 relating to when a patient is taking medications at home). This can occur, for example, in a context in which input module 318 comprises transistor-based circuitry having an event-sequencing structure; in which one or more caregivers 991, 1191 prescribe a home care regimen 650 and in which one or more particular components 652 of the regimen (antibiotics or other medications, e.g.) are crucial to a favorable outcome for a specific patient 4250. Alternatively or additionally, input module 318 may be configured to provide additional data relevant to a determination of regimen compliance (raw data 712 with one or more timestamps 711 from a sensor 2054 in the patient's home 289, e.g.) into the patient's record 673. This can occur, for example, in a context in which there are one or more indications 685 (diagnostic data 490 or protocol data 450, e.g.) that an institutional readmission has resulted from a behavior of a patient 4250 or at-home caregiver and not from anything that occurred earlier (while in-patient at hospital 201, e.g.).

Operation 6272 describes triggering a search of a particular records archive by providing a selective search criterion, one that results in an exclusion of a first element in the particular records archive and an inclusion of a second element in the particular records archive (e.g. retrieval module 344 transmitting a search term 2110 to search engine 2198 that searches records archive 820 and generates a search result 2130 that excludes one or more data components 138 therein and includes one or more other data components 126 therein). This can occur, for example, in a context in which retrieval module 344 comprises transistor-based circuitry having an event-sequencing structure; in which search term 2110 identifies one or more selective inclusion criteria 2101 (e.g. words or codes identifying condition 160) and one or more selective exclusion criteria 2102 (e.g. words or codes identifying protocols 130, 140). Alternatively or additionally, retrieval module 344 may be configured to trigger a search of other search records archive 920 (by invoking retrieval module 925, e.g.) and to include the result 2130 (in report 2244, e.g.).

In light of teachings herein, numerous existing techniques may be applied for configuring special-purpose circuitry or other structures effective for performing selective data retrieval as described herein without undue experimentation. See, e.g., U.S. Pat. No. 8,068,603 ("Focused retrieval of selected data in a call center environment"); U.S. Pat. No. 7,966,532 ("Method for selectively retrieving column redundancy data in memory device"); U.S. Pat. No. 7,203,633 ("Method and system for selectively storing and retrieving simulation data utilizing keywords"); U.S. Pat. No. 6,519,327 ("System and method for selectively retrieving messages stored on telephony and data networks"); U.S. Pat. No. 6,421,726 ("System and method for selection and retrieval of diverse types of video data on a computer network"); U.S. Pat. No. 6,185,573 ("Method and system for the integrated storage and dynamic selective retrieval of text, audio and video data"); U.S. Pat. No. 6,137,914 ("Method and format for storing and selectively retrieving image data"); and U.S. Pat. No. 6,094,573 ("System and a method for selective data retrieval from a remote database on basis of caller line identification and user specific access codes").

Operation 6273 describes transmitting a real-time notification to a first person as an automatic response to an interface in a vicinity of a second person detecting a particular event relating to the second person (e.g. update module 2029 transmitting one or more records 561-569, 3191-3197, 671-675 or other data components 136-138 to the "first" person upon detecting an input 551, 552 or other action taken by the "second" person). This can occur, for example, in a context in which update module 2029 comprises transistor-based circuitry having an event-sequencing structure; in which the "first" person is a caregiver 991, 1191, 1291 or patient 992, 4250 or administrator (a call center agent 294 or other entity 1091, e.g.); in which the interface comprises one or more of the above-described devices; in which such data components 136-138 relate to the "second" person or to device 2005; in which the "particular event" comprises device 2015 entering a detection range of something carried or worn by the "second" person (manifesting the vicinity of the 2nd person, e.g.); and in which means for performing one or more extensive operations 49-67 as described above include an implementation of device 2005. Alternatively or additionally, update module 2029 may be configured to transmit such a notification (using an e-mail address 721 or telephone number 722, e.g.) in response to a "particular event" occurring within device 305 (comprising one or more computation or detection events described herein or a combination thereof, e.g.). In some contexts, for example, update module 2029 may be configured to respond to one or more records 561-569, 3191-3197, 671-675 as described herein being saved without a prominence indication or annotation 2293 (in a context in which the "second" person is a caregiver failing to document an unconventional treatment being ordered, e.g.).

Operation 6276 describes implementing a failsafe preventing medical equipment from operating until an order associating the medical equipment with a patient is received and until an indication is received that the patient is in a vicinity of the medical equipment (e.g. detection module 2045 enabling medical equipment 2080 to function only after receiving a report 2243 or other indication 688 that an authorized caregiver has generated such an order and only after detecting that the specific patient 1392, 4250 is in a vicinity of the medical equipment 2080). This can occur, for example, in a context in which detection module 2045 comprises transistor-based circuitry having an event-sequencing structure; in which one or more orders 1018, 618 as described above call for particular diagnostic data 490 in relation to patient 4250; in which such orders explicitly or implicitly identify the equipment 2080 (corresponding to a particular biometric 481, test result 482, computed tomography scan 483, or other image 484, e.g.) in association with the patient for whom they are to be obtained; in which detection module 2045 is configured to determine whether a location or device that includes a patient identifier 731, 1331 is in a vicinity of the equipment 2080; and in which detection module 2045 receives indication 688 via input module 314. This can occur, for example, in a context in which one or more detection modules 2041-2046 are mounted on the equipment 2080 or in the same room (as a stationary instance of equipment 2080, e.g.). In some contexts, moreover, a single device 305 or room (office or server room, e.g.) or facility (hospital 201, e.g.) may be configured to contain an entire system described herein. Alternatively or additionally, an instance of detection module 2045 configured to detect equipment 2080 may reside on the specific patient 4250 or in a location associated with the patient 4250 (in the patient's room, e.g.). Alternatively or additionally, module 314 may be configured to receive other data (one or more of indications 681-687, e.g.) on data-handling media as described herein (at FIG. 4-7 or 21-26, e.g.).

Referring again to the flow variants of FIGS. 48 and 58-62 described above, intensive operation 93 may (optionally) be performed by a special purpose interface module 3513 implemented as circuitry 3044 having an event-sequencing structure (an arrangement of transistors and voltage levels in one or more semiconductor chips, e.g.) configured to generate a Boolean indication (implemented as a voltage level of a particular electrical node 3484, e.g.) whether or not user 3780 is compliant with one or more regimens 2332-2336. This can occur, for example, in a context in which such circuitry can determine apparent regimen compliance (positively or otherwise) based upon raw data (from a sample tester 3060 or camera 3707 or other sensors described herein, e.g.) or upon one or more test records 3196 (received from a technician 2761 who tests a fluid sample from user 3780, e.g.). In some variants, for example, one or more such test records 3196 may be associated with a record designation pattern 3841 (comprising a character or phoneme sequence naming user 3780 or his caregiver and designating a specific record 3831 thereof, e.g.). Alternatively or additionally, tabular data 3820 may include one or more recognizable human face patterns, fingerprint patterns 2531, retinal scan patterns, recognizable human voice or other audible patterns 2532, or other such biometric data 2540 as a pattern 3841 that effectively designates another record 3832. Alternatively or additionally, tabular data 3820 may include one or more serial numbers as a pattern 3841 (recited during a telephonic intake session or other electronic intercommunication with caregiver 4691 before his arrival at hospital 4602, e.g.) that effectively designates another record 3833.

In light of teachings herein, numerous existing techniques may be applied for configuring special-purpose circuitry or other structures effective for recognizing whether content matches a pattern as described herein without undue experimentation. See, e.g., U.S. Pat. No. 8,005,875 ("Automatic data transmission in response to content of electronic forms satisfying criteria"); U.S. Pat. No. 7,949,191 ("Method and system for searching for information on a network in response to an image query sent by a user from a mobile communications device"); U.S. Pat. No. 7,941,124 ("Methods of providing messages using location criteria and related systems and computer program products"); U.S. Pat. No. 7,689,705 ("Interactive delivery of media using dynamic playlist generation subject to restrictive criteria"); U.S. Pat. No. 7,668,647 ("Computer method and apparatus for filling in an entry field using geographical proximity and character criteria"); U.S. Pat. No. 7,580,952 ("Automatic digital image grouping using criteria based on image metadata and spatial information"); U.S. Pat. No. 7,394,011 ("Machine and process for generating music from user-specified criteria"); U.S. Pat. No. 7,127,493 ("Optimizing server delivery of content by selective inclusion of optional data based on optimization criteria").

Also in such variants, extensive operation 55 may be performed by a special purpose configuration module 3702 implemented as or operably coupled with circuitry 3317 having an event-sequencing structure configured to cause a wearable article to indicate a data component as an automatic and conditional response (operably coupled with a sticker-printing dispenser 4633 or other machine at the "first" care facility that can configure a wrist band 1223, badge 3851, item of clothing, sticker 4634, or other such article to include the data indicating the current health status, e.g.). This can occur, for example, in a context in which the wearable article displays (via a screen display 2426 or ink-printed surface 2427 thereof, e.g.) at least some of the designated record (indicating the current health status as one or more coded colors or barcodes 2918, e.g.) and in which (an instance of) a computer 2670 or other data-handling device 3705 resides in one or more networks 3890 accessible to the first care facility. Moreover a wall-mounted kiosk 4630 or other stationary device 3760 (in nursing home 3802, e.g.) configured to recognize the wearable article may, in some contexts, reside in network 3890.

Referring again to the flow variants of FIGS. 49 and 58-62 described above, intensive operation 81 may be performed by a special purpose detection module 3741 implemented as or operably coupled with circuitry 3041 having an event-sequencing structure (an arrangement of transistors and voltage levels in one or more semiconductor chips, e.g.) configured to generate a Boolean indication (implemented as a voltage level of a particular electrical node 3485 or a magnetic configuration of a storage element on a disk drive, e.g.) whether or not an individual is compliant with a regimen 2331-2339. This can occur, for example, in a context in which detection module 3741 is operably coupled with one or more of an administration detection module 2848 (configured to detect compliance with a medicinal component 4011, e.g.); a sample tester 3060 or other measurement equipment (configured to detect compliance with one or more medicinal components 4011 or measurement components 4012 or omission components 4013, e.g.); specially-configured cupboards 2071 or smoke detectors 3958 or other environmental sensors 2054 (configured to detect compliance with a dietary or other omission component 4013, e.g.); exercise machines 2073 (configured to detect compliance with an exercise component 4014, e.g.); or other such special-purpose monitoring equipment 2080. In some contexts, for example, such a noncompliance indication 2483 may comprise a percentage of events (of detection, e.g.) that were indicative of compliance being less than 100% or falling below a threshold 2453 defined by a service provider 2710 (consultant or insurance provider, e.g.).

Also in such variants, intensive operation 94 may (optionally) be performed by a special purpose interface module 3511 implemented as or operably coupled with circuitry 3273 having an event-sequencing structure configured to provide a local Boolean indication (implemented as a voltage level of a particular electrical node 3486, e.g.) whether or not an individual is available (at one or more remote call centers, e.g.). This can occur, for example, in a context in which a "high" voltage signifies that the "second" individual is available to participate in the electronic intercommunication 3442 and in which a "low" voltage signifies that the second individual may or may not be available to participate in the electronic intercommunication 3442. Alternatively or additionally, interface module 3511 may be configured to generate a negative indication 2486 of availability as an automatic and conditional response to a signal 2565 (from a remote call center 295, e.g.) indicating that an earpiece 3749 or other data-handling device 3705 (configured to permit agent 3994 to speak to patient 3950 or hear her reply, e.g.) is offline or that a stationary zone (a workstation or office in call center 3995, e.g.) is unoccupied.

Also in such variants, extensive operation 59 may be performed by a special purpose communication module 3681 implemented as or operably coupled with circuitry 3314 having an event-sequencing structure (including an arrangement of transistors and voltage levels in one or more semiconductor chips, e.g.) configured to initiate an electronic intercommunication 3441 (telephone call 3431, e.g.) between the first and second individuals as an automatic and conditional response to a particular combination of voltage levels of respective electrical nodes 3485, 3486. This can occur, for example, in a context in which communication module 3681 initiates such a telephone call 3431 by auto-dialing a handheld 2074 associated with the first individual or in which communication module 3681 automatically activates intercom 3959 so that agent 3994 and patient 3950 can converse. Moreover in some variants a particular agent 3994 may be able to maintain a ranked position so that another available agent 294 will not be selected to participate in the intercommunication 3441 with a particular first individual while agent 3994 is available, perhaps fostering an effective rapport with particular patients over time.

Referring again to the flow variants of FIGS. 50 and 58-62 described above, intensive operation 86 may be performed by a special purpose interface module 3512 implemented as circuitry 3121 having an event-sequencing structure (an arrangement of transistors and voltage levels in one or more semiconductor chips, e.g.) configured to receive a scalar indication 2345 (a quantification from computation module 3772 expressed via two or more electrical nodes 3472-3473, e.g.) of how well patient 992 has complied with a regimen 2334 that includes a medicinal component 4011. This can occur, for example, in a context in which (an instance of) a computer 2670 or other data-handling device 3705 including a medium 2305 that resides in or on several networks 2790, 3190 3590, 4090 and in which computation module 3772 generates the scalar indication 2345 as an inverse (reciprocal, e.g.) of another such compliance-indicative quantification described herein (e.g. indications 2343, 2344) or as a sum or other aggregation of such values or as an inverse thereof.

Also in such variants, intensive operation 97 may be performed by a special purpose input module 3625 implemented as or operably coupled with circuitry 3122 having an event-sequencing structure configured to receive from care provider 2783 (a personal trainer, e.g.) a scalar indication 2346 (a ranking relative to other clients, e.g.) of how well a particular individual 2782 is currently complying with an exercise component 4014 of a personalized regimen 2332. This can occur, for example, in a context in which one or more available records 3191-3197 provide contact information relating to providers who have recently served the second individual (individual 2782, e.g.); in which individual 2782 has requested or otherwise authorized that such providers periodically provide regimen compliance information (by subscribing or enrolling, e.g.) pursuant to program requirements (that facilitate flow 5000, e.g.) of a provider network; and in which the "second" device is a handheld device (owned by care provider 2783, e.g.) running a data-gathering app implementing such program requirements (automatically gathering scalar indications that may be missing or out-of-date, e.g.). In some contexts, for example, a program may provide that such evaluations become part of the particular individual's medical record 3195 without a specific notification to the individual so that the individual will not have an occasion to exert pressure in regard to such ranking Also in such variants, extensive operation 49 may be performed by a special purpose computation module 3771 implemented as circuitry 3322 having an event-sequencing structure configured to compute a result 2312 of arithmetically combining two or more scalar indications 2343-2349 (a weighted average having normalizing coefficients and offsets so that each summand, for example, is effectively expressed as a percentage). In some contexts, for example, a technician 2761 configures invocation module 2795 to identify which scalar indications to include in the mathematical combination (by executing a search of all available records 3191-3197, e.g.) to determine which patients (having various regimens 2331-2339, e.g.) are currently being served by a particular entity (caregiver 991, e.g.) and thereby to obtain two or more scalar indications (by extracting or requesting such scalar values, e.g.) suitable for use by computation module 3771. Alternatively or additionally, invocation module 2795 may be configured to transmit such results 2312 (as a conditional notification 4072 to service provider 2710, e.g.) under one or more conditions 2302 (in response to result 2312 exceeding a maximum threshold 2455 or falling below a minimum threshold 2454, e.g.) defined by organizational management (relating to a class of caregivers, e.g.). Such embodiments may establish a meaningful advance over conventional monitoring, for example, in contexts in which diverse health regimens are in use and in which distinguishing between excellent and mediocre compliance facilitation strategies by respective service providers 2710 would not otherwise achieve much objectivity.

Referring again to the flow variants of FIGS. 51 and 58-62 described above, intensive operation 82 may be performed by a special purpose detection module 3744 implemented as circuitry 3052 having an event-sequencing structure (an arrangement of transistors and voltage levels in one or more semiconductor chips, e.g.) configured to recognize a person 4144 depicted in a portion 4172 of an image 4170. This can occur, for example, in a context in which detection module 3744 is configured to execute facial recognition software (1) to define the portion 4172 that corresponds to a shape or color region generally recognizable as a person's face or (2) to determine a particular patient designation 2502 by matching the face visible within portion 4172 with facial parameters of known patients (or both).

In light of teachings herein, numerous existing techniques may be applied for configuring special-purpose circuitry or other structures effective for recognizing faces or other three-dimensional structures as described herein without undue experimentation. See, e.g., U.S. Pat. No. 7,925,058 ("Iris recognition system and method using multifocus image sequence"); U.S. Pat. No. 7,873,189 ("Face recognition by dividing an image and evaluating a similarity vector with a support vector machine"); U.S. Pat. No. 7,860,281 ("Method for the automatic recognition of an object in an image"); U.S. Pat. No. 7,778,483 ("Digital image processing method having an exposure correction based on recognition of areas corresponding to the skin of the photographed subject"); U.S. Pat. No. 7,706,068 ("Image three-dimensional recognition apparatus"); U.S. Pat. No. 7,664,339 ("Image processing method for object recognition and dynamic scene understanding"); U.S. Pat. No. 7,345,574 ("Image recognition facilitated movable barrier operations method and apparatus"); U.S. Pat. No. 7,239,275 ("Methods and systems for tracking signals with diverse polarization properties"); U.S. Pat. No. 7,092,566 ("Object recognition system and process for identifying people and objects in an image of a scene"); U.S. Pat. No. 7,062,073 ("Animated toy utilizing artificial intelligence and facial image recognition"); U.S. Pat. No. 6,831,993 ("Vehicle security systems and methods employing facial recognition using a reflected image").

Also in such variants, intensive operation 88 may be performed by a special purpose interface module 3516 implemented as or operably coupled with circuitry 3131 having an event-sequencing structure (including an arrangement of transistors and voltage levels in one or more semiconductor chips as described herein and operably coupled with a user interface comprising a screen display 2426 and a user input, e.g.) configured to permit an individual (user 3780, e.g.) to select among two or more portions 2581, 2582 of an image 2580 (visible on screen display 2426, e.g.) via auditory or touchscreen input 2472. This can occur, for example, in a context in which the image portion 2582 selected by user 3780 depicts the first patient (user 3880, e.g.) or in a context in which user 3780 validates or otherwise selects image portion 2582 verbally (by speaking "yes" or "option three" into microphone 3708, e.g.).

Also in such variants, extensive operation 51 may be performed by a special purpose triggering module 3552 implemented as or operably coupled with circuitry 3318 having an event-sequencing structure (including an arrangement of transistors and voltage levels in one or more semiconductor chips as described herein and operably coupled with a remote server or other network resource containing patient records 3191-3197, e.g.) configured to retrieve and present medical data about the first patient (user 3880 or person 4144, e.g.) as an automatic and conditional response (to user input 2471, 2472 selectively indicating the first patient, e.g.). This can occur, for example, in a context in which such medical data includes tabular data 3820 or other indications 2341-2349 pertaining to the indicated patient as described herein; in which (an instance of) a computer 2670 or other data-handling device 3705 (implemented in network 3890, e.g.) includes several storage or other media described above (in FIGS. 21-26, e.g.); and in which such "signaling" of operation 51 includes presenting such medical data visually (via screen display 2426 or ink-printed surface 2427, e.g.) or audibly (via earpiece 3749 or speaker 2057, e.g.). In some contexts, moreover, such medical data may include health status indicators 3842 derived from secondary sources (from Facebook or similar social networking websites, e.g.) on network 3890. Alternatively or additionally, such "signaling" may include transmitting the medical data to a handheld or wearable data-handling device used by the first patient (user 3880, e.g.) or by another entity (user 3780, e.g.).

In some implementations of flow 5100, a camera 2053 (comprising a stationary device 3760 or portable data-handling device 3705, e.g.) and a person (user 3780, e.g.) may perform operation 82 concurrently (in a hallway 3709 in which the first patient is visible, e.g.). This can occur, for example, in a context in which the first patient is in view of both user 3780 and camera 2053; in which another camera 3707 obtains an image 2579 of user 3780 (at about the same time, e.g.) as the user input 2471; and in which interface module 3516 includes a computation module 3773 configured to process such user input (images 2579, 2580, e.g.) to determine who user 3780 was pointing or looking at (as a particular portion 4152 of a direct field of view 4150, e.g.) as the selective indication. Alternatively or additionally, a detection module 3742 operably coupled to triggering module 3552 may be configured to identify some all persons 4141-4144 visible within an image 4170 or other field of view 4150 (one by one, e.g.) and to indicate continuously which such visible persons are fully identified (with green blinking brackets on touchscreen 4115, e.g.) or are not fully identified (with red or yellow blinking brackets on touchscreen 4115, e.g.) even before user input 2471, 2472 selectively indicating the "first patient" is obtained. In some variants, for example, triggering module 3552 may pre-fetch the "medical data about the first patient" to a local data-handling device 3705 in anticipation of receiving such user input 2471, 2472. In some variants, data-handling device 3705 may be configured to forego operation 88 (conditionally) in contexts in which a particular field of view 4150 includes only one patient (fully identified by detection module 3742, e.g.). Alternatively or additionally, in some embodiments, data-handling device 3705 may include a mode control switch (implemented as a voltage level of a particular electrical node 3483 that selectively enables or disables triggering module 3552 from performing operation 51, e.g.) accessible to user 3780 (so that data-handling device 3705 may continue to perform telephonic or other communication functions whether or not flow 5100 is fully implemented, e.g.). Moreover a wall-mounted kiosk 4630 or other stationary device 3760 configured to interact with device 4110 may, in some contexts, reside on network 2790.

Referring again to the flow variants of FIGS. 52 and 58-62 described above, intensive operation 89 may be performed by a special purpose input module 3624 implemented as or operably coupled with circuitry 3044 having an event-sequencing structure (an arrangement of transistors and conductors in one or more semiconductor chips, e.g.) configured to generate a Boolean indication 2551 (implemented as a voltage level of a particular electrical node 3476, e.g.) whether or not patient 992 and her caregiver 991 are compliant with regimen 2334. This can occur, for example, in a context in which detection module 3745 is configured to generate indication 2551 by comparing one or more scalar indications 2343-2345 against a minimum threshold 2454 (0.9 or 90%, e.g.) positively indicative of compliance or against a maximum acceptable failure/violation rate (threshold 2455, e.g.) permitted by regimen 2334.

Also in such variants, intensive operation 96 may be performed by a special purpose triggering module 3551 implemented as or operably coupled with circuitry 3271 having an event-sequencing structure (including an arrangement of transistors and voltage levels in one or more semiconductor chips, e.g.) configured to notify patient 992 or her caregiver 991 of an artificial incentive 2640 in response to a negative indication 2989 of compliance with regimen 2334. This can occur, for example, in a context regimen 2334 includes a training component, measurement component 4012, record keeping component, or other component in which caregiver 991 participates and in which triggering module 3551 responds to one or more positive indications 2987 or negative indications 2989 of compliance by causing a system 941 belonging to caregiver 991 to receive an electronic message 2290 (email or SMS text or voice message, e.g.) that includes an indication 2552 of the artificial incentive 2640 (one or more points 2616 or credits 2617 or other resources 2619, e.g.) offered in exchange for participating in a dialog 3433 (with an agent 3994 of call center 3995, e.g.). Alternatively or additionally, triggering module 3551 may be configured to initiate a text chat session 3432 (with patient 992 or caregiver 991 via a service like "Instant Messenger" or on a handheld device, e.g.) with a bot-generated remark like "Hey, great job on keeping up with [regimen X]. You are eligible for [prize Y] if you take a quick survey. Are you interested?" Or in response to a regimen noncompliance determination 2988 triggering module 3551 may (optionally) be configured to initiate the dialog 3433 with a bot-generated remark like "Say, we have concerns about [regimen X] and we really need to talk to you. In fact, we'll give you [prize Y] just for having a chat with us. Are you interested?" In such contexts, for example, the dialog 3433 may be established when the remark recipient (patient 992 or her caregiver 991, e.g.) provides a device-detectable affirmative reply (to agent 3994, e.g.). In light of teachings herein, those skilled in the art will recognize various determinants 2394 suitable for establishing whether or when such dialog 3433 is adequately completed (agent 3994 accepting another task without signaling that the dialog 3433 was inadequate, each participant saying or texting at least twenty words, agent 3994 entering five or more responses to survey questions during the dialog, dialog 3433 lasting at least a minute, or other such device-detectable events manifested in user input 2471, e.g.).

Also in such variants, extensive operation 53 may be performed by a special purpose authorization module 3792 implemented as or operably coupled with circuitry 3328 having an event-sequencing structure (including an arrangement of transistors and voltage levels in one or more semiconductor chips, e.g.) configured to authorize a dispensation of one or more tangible benefits 2620 (to patient 992 or her caregiver 991, e.g.) if two specific conditions 2323, 2324 are met and otherwise generally not to authorize the dispensation. This can occur, for example, in a context in which condition 2323 (manifested as a voltage level of a particular electrical node 3481, e.g.) comprises a regimen compliance determination 2986 (signaling that patient 992 and her caregiver 991 are currently compliant with regimen 2334, e.g.) or other compliance-positive indication 2987; in which condition 2324 (manifested as a voltage level of one or more other electrical nodes 3482, e.g.) comprises one or more determinants 2394 signaling that dialog 3433 occurred; in which authorization module 3792 is configured to authorize a physical dispensation (of a drug via dispenser 3270 or of currency via ATM 4410 or of other items via a machine 2030 mounted on a wall in a nursing home 3802, e.g.) responsive to such conditions 2323, 2324; and in which timely communication about regimen compliance with intermittently available patients or caregivers would not otherwise occur. In some contexts, for example, authorization module 3792 may implement a partial withholding or other conditional access to a recreational drug (scotch, e.g.) or other treat (imported chocolates, e.g.) as an effective artificial incentive as described herein. Alternatively or additionally, in some embodiments, one or more other conditions 2325 as described herein (the first individual being present for the dispensation, e.g.) may enable such dispensations. Alternatively or additionally, in some embodiments, one or more other conditions 2328 as described herein (the first individual refusing to receive the dispensation, e.g.) may disable such dispensations.

Referring again to the flow variants of FIGS. 53 and 58-62 described above, intensive operation 85 may be performed by a special purpose input module 3626 implemented as circuitry 3042 having an event-sequencing structure (an arrangement of transistors and voltage levels in one or more semiconductor chips, e.g.) configured to generate a Boolean indication (implemented as a voltage level of a particular electrical node 3474, e.g.) whether or not patient 4250 is compliant with a minor requirement of regimen 2337 (violations of which are unlikely to have any precipitous consequences, e.g.) as described above. Also in such variants, intensive operation 90 may be performed by a special purpose input module 3627 implemented as or operably coupled with circuitry 3043 having an event-sequencing structure configured to generate a Boolean indication (implemented as a voltage level of a particular electrical node 3475, e.g.) whether or not patient 4250 is compliant with a major requirement of regimen 2337 (violations of which are deemed by service provider 2710 to be likely to result in a major medical consequence or in a loss of coverage, e.g.) as described above.

Also in such variants, extensive operation 52 may be performed by a special purpose triggering module 3553 implemented as or operably coupled with circuitry 3313 having an event-sequencing structure configured to initiate one or more electronic intercommunications 3441-3443 (involving one or more caregivers 1291, 1391 or their employer as described above, e.g.) automatically or otherwise as described above (as a real-time response to at least two "less significant" conditions 2324-2326 being present but irrespective of at least one "more significant" condition 2327 being present or not, e.g.).

Also in such variants, extensive operation 56 may be performed by a special purpose authorization module 3791 implemented as or operably coupled with circuitry 3311 having an event-sequencing structure configured to route one or more caregivers 1291, 1391 or their employer to a device associated with patient 4250 (a vehicle 4243 or wearable article 4245 or handheld 2074, e.g.) as an automatic and conditional response to a "more significant" condition 2327 being present as described above. In some variants, moreover, such routing (dispatching an ambulance 1295, e.g.) may be conditional upon one or more additional determinants 2395 (patient 4250 failing to respond to several consecutive attempts to initiate electronic intercommunications 3441-3443 or other conditions 2329 as described above, e.g.).

Referring again to the flow variants of FIGS. 54 and 58-62 described above, intensive operation 84 may be performed by a special purpose response module 3663 (a logic gate, e.g.) operably coupled (through respective input signal paths, e.g.) to receive input from two other response modules 3661, 3662. This can occur, for example, in a context in which hospital 202 was a "qualifying" institution into which patient 4250 was previously admitted (because he needed angioplasty for congestive heart failure, e.g.); in which response module 3662 is implemented as circuitry 2962 having an event-sequencing structure configured to provide a Boolean indication 2342 (implemented as a voltage level of a particular electrical node 3477, e.g.) whether or not patient 4250 has yet experienced an institutional readmission (in relation to the congestive heart failure or to an infection from the angioplasty procedure or to some other hospital-error-induced complication, e.g.); and in which response module 3661 is implemented as circuitry 2961 having an event-sequencing structure configured to provide a Boolean indication 2341 whether or not patient 4250 has ever been admitted to a qualifying institution (implemented as a voltage level representative of a "true" value to indicate that such admission had occurred, e.g.) operatively coupled with circuitry 3132 having an event-sequencing structure configured to record an assignment of a resource 2619 as an automatic and conditional response (as described in operation 84, e.g.). This can occur, for example, in a context in which such indication 2342 is inverted (implemented as a voltage level representative of a "false" value to indicate that such readmission had occurred, e.g.); in which response module 3663 comprises an AND gate; in which a smaller (zero-value or negative, e.g.) artificial incentive will be selected if the AND gate output is "false"; and in which a larger artificial incentive will be selected if the AND gate output is "true."

Also in such variants, extensive operation 57 may be performed by a special purpose authorization module 3793 implemented as or operably coupled with circuitry 3329 having an event-sequencing structure (an arrangement of transistors and voltage levels in one or more semiconductor chips, e.g.) configured to authorize a dispensation if one or more specific conditions are met and otherwise generally not to authorize the dispensation. This can occur, for example, in a context in which such structure further comprises a vending machine 2030, ATM 4410, slot machine, or other electromechanical interaction unit 2775 capable of dispensing food, currency, or other resources 2619 directly to patient 4250 and in which such incentives 2640 would not otherwise be appropriately tailored (cost-effective, e.g.) for motivating patient 4250 and others similarly situated to be proactive and diligent in avoiding such readmission. Alternatively or additionally, one or more other flows described herein (for responding to noncompliance events or interacting with patients, e.g.) may be used concurrently to notify patient 4250 of applicable circumstances (reasons to follow a health regimen, e.g.) or to adjust the incentive regimen so that the particular patient 4250 will be more inclined to comply. In some instances, for example, such patients 4250 may respond best to a negative incentive such as one in which a result 2313 of assigning "the component of the artificial incentive" may comprise a trigger 2306 that temporarily limits the capabilities of one or more devices 2005, 2015 (establishing a maximum number of hours per day that a TV or phone will operate or a maximum speed at which a vehicle 4243 or data download will operate, e.g.) as a conditional response to an institutional readmission (resulting from health regimen noncompliance, e.g.). Even in contexts in which authorization module 3793 cannot feasibly control such devices 2005, 2015 in real time, for example, such negative-incentive results 2313 may be implemented by a suitable implementation of operation 57 in which an order is transmitted to a specialty service provider (mechanic, e.g.) to modify the device (by installing a speed governor, e.g.). See FIG. 53.

Referring again to the flow variants of FIGS. 55 and 58-62 described above, intensive operation 87 may be performed by a special purpose input module 3628 implemented as circuitry 3261 having an event-sequencing structure (an arrangement of transistors and voltage levels in one or more semiconductor chips, e.g.) configured to provide a Boolean indication 2559 (implemented as a voltage level of a particular electrical node 3478, e.g.) whether or not an order 4538 associates the first patient with the medical device. This can occur, for example, in a context in which the "first" patient is a patient 4550 who might suffer harm if the regimen 2338 prescribed to her is not followed correctly; in which the medical device would otherwise present a significant hazard to another particular patient 1292 (who has a heart condition or allergy or similar vulnerability, e.g.); or in which the medical device is expensive and subject to degradation (disposable, e.g.). Some implementations of operation 87 may cause one such medical device to be associated with a particular list of two or more patients 4550, 4750. Other implementations of operation 87 may cause the first patient 4550 to be associated with two or more such medical devices 2005, 2015 (operably coupled via a network 4590 or via a direct linkage 2011, e.g.). In some variants, configuration module 3704 may be authorized to cause one or more such assignments to be undone selectively (when the therapy or measurement is complete or the medical device is used or when the order is cancelled, e.g.).

Also in such variants, intensive operation 92 may be performed by special purpose circuitry 3051 having an event-sequencing structure (including an arrangement of transistors and voltage levels in one or more semiconductor chips, e.g.) configured to generate a Boolean indication (implemented as a voltage level of a particular electrical node 3479, e.g.) whether or not the first patient and the medical device are in proximity. This can occur, for example, in a context in which the event-sequencing structure is configured to detect a location of the medical device or the first patient (or both) by virtue of being operably coupled with one or more sensors 3506, 4543 (via respective signal paths along which one or more digital signals 2564 may travel, e.g.) as described above. In a context in which the medical device is a stationary device 2015 (an exercise machine 2073 in a particular room of a nursing home 3802, e.g.), for example, the event-sequencing structure may be implemented as a global positioning system (in GPS module 3420, e.g.) adapted to generate the Boolean indication (at electrical node 3479, e.g.) whenever the special-purpose circuitry (of a portable primary unit 3405 carried or worn by patient 4550 that implements local event-sequencing logic 3005, e.g.) is in that particular room.

Also in such variants, extensive operation 58 may be performed by a special purpose configuration module 3704 implemented as or operably coupled with circuitry 3327 having an event-sequencing structure configured to enable the medical device selectively in response to a combination of two or more indications (electrical nodes 3478-3480 all having a voltage level representative of a "set" or "true" Boolean value, e.g.) as described above (and otherwise doing nothing, e.g.). This can occur, for example, in a context in which the medical device is initially disabled (so that it cannot function until operation 58, e.g.). Alternatively or additionally, configuration module 3704 may be configured to activate one or more disablement features 3365 of the medical device conditionally (responsive to one or more electrical nodes 3480 having a voltage level representative of a "reset" or "false" Boolean value, e.g.). Moreover a wall-mounted kiosk 4630 or other stationary device 3760 (in a room 4704 or hallway 3909 or other vicinity 4585 of the first patient, e.g.) implementing the medical device may, in some contexts, reside in network 4590.

Referring again to the flow variants of FIGS. 56 and 58-62 described above, intensive operation 83 may be performed by a special purpose response module 3664 comprising a selection module 3532 implemented as or operably coupled with circuitry 2971 having an event-sequencing structure (an arrangement of transistors and voltage levels in one or more semiconductor chips, e.g.) configured to select a playable prompt in response to input from or about a patient. This can occur, for example, in a context in which selection module 3532 associates each of many diagnostic prompts 2371-2375 with a corresponding trigger pattern 2361-2365; in which response module 3664 is configured so that each such trigger pattern spoken or entered by the first individual is recognized (via a touchscreen 4515 or speech recognition module 3427, e.g.) and triggers a corresponding playable prompt 2371-2375 to be transmitted to the first individual (via text-to-speech translation module 3428 and speaker 3509, e.g.).

In some variants, for example, a spoken or otherwise recognized pattern 2361 of "patient" (in a context in which no patient is currently selected, e.g.) may correspond to a playable prompt 2371 like "Please state the name of the patient." (A "patient" may generally be a mammal or other animal in scenarios described herein, unless the context of a particular scenario strongly suggests that the patient must be human.) Likewise a spoken or otherwise recognized pattern 2362 of "Richard Hyde" (in a context in which the first individual has just heard prompt 2371, e.g.) may correspond to a playable prompt 2372 like "What is the patient's date of birth?" Likewise a spoken or otherwise recognized pattern 2363 of a calendar date (in a context in which the first individual has just heard prompt 2372 and in which a local medical record 3194 is found for a Richard Hyde having that date of birth, e.g.) may correspond to a playable prompt 2373 like "Has Richard Hyde had medical care here before?" Likewise a spoken or otherwise recognized pattern 2364 of "yes" (in a context in which the first individual has just heard prompt 2373, e.g.) may correspond to a playable prompt 2374 like "Does Richard Hyde have any new symptoms today?" Likewise a spoken or otherwise recognized pattern 2365 of "yes" (in a context in which the first individual has just heard prompt 2374, e.g.) may correspond to a playable prompt 2375 like "Please describe the primary health issue for which Richard Hyde needs care today." Alternatively or additionally, one or more such prompts 2371-2379 may be displayed (via a touchscreen 4515 or display 4626 in a vicinity of the first individual, e.g.) and played (via speaker 3509, e.g.) simultaneously.

Also in such variants, intensive operation 95 may be performed by a special purpose detection module 3743 implemented as or operably coupled with circuitry 3115 having an event-sequencing structure (including an arrangement of transistors and voltage levels in one or more semiconductor chips comprising a video- or sound-clip capture module 3426 operably coupled to a special-purpose speech recognition module 3427, e.g.) configured to recognize a response after a prompt is played to an individual. This can occur, for example, in a context in which detection module 3743 recognizes one or more patterns 2362-2366 that may comprise the "second" data component. Alternatively or additionally, the second data component may include intake data 3507 comprising unrecognized content (a sound clip or other biometric data not recognized by detection module 3743, e.g.).

Also in such variants, extensive operation 54 may be performed by a special purpose configuration module 3702 implemented as or operably coupled with circuitry 3316 having an event-sequencing structure configured to cause a wearable article to indicate a data component as an automatic and conditional response (operably coupled with a sticker-printing dispenser 4633 or other machine at the "first" care facility that can configure a wrist band 1223, bandage 3852, sticker 4634, or other wearable article to include the "second" data component, e.g.). This can occur, for example, in a context in which the wearable article contains the second data component (as a video or audio clip in the form of an encrypted or other digital data file on a flash drive, e.g.) and in which data-handling device 3705 resides in one or more networks as described above.

Referring again to the flow variants of FIGS. 57 and 58-62 described above, intensive operation 91 may be performed jointly by two special purpose configuration modules 3701, 3703. This can occur, for example, in a context in which configuration module 3701 is implemented as circuitry 2972 having an event-sequencing structure (an arrangement of transistors and voltage levels in one or more semiconductor chips, e.g.) configured to associate patient 4250 or user 3780 with a regimen 2339 and in which configuration module 3703 is implemented as circuitry 3035 having an event-sequencing structure configured to associate one or more tasks 2444 of regimen 2339 with a particular time interval 2542 ("2 hours" or "from now until 7:30 pm," e.g.). In some contexts, for example, task 2444 may include conducting a counseling session (in person or via data-handling device 3705, e.g.) between patient 4250 and user 3780 (a nutritionist or other caregiver, e.g.).

Also in such variants, extensive operation 60 may be performed by a special purpose interface module 3515 implemented as or operably coupled with circuitry 3262 having an event-sequencing structure configured to cause a countdown timer 2310 to progress (until an associated task is complete or the deadline has passed, e.g.). This can occur, for example, in a context in which countdown timer 2310 is implemented in one or more wearable articles 4245 (in which the countdown timer 2310 is displayed in a portion 4231 of an image 4230, e.g.) or other data-handling devices 3705 (as a browser page or other remote real-time notification, e.g.); in which user 3780 has another such data-handling device 3705 (with a touchscreen 4115 or other display configured to implement countdown timer 2310, e.g.); and in which patient 4250 and user 3780 are required to begin their session (per a task definition component 4781 of record 4763, e.g.) by 7:30 pm (per a timing component 4782 of record 4763, e.g.). Moreover a computer 2670 or kiosk 4630 (having a stationary display 4626 or similar suitable medium 2305, e.g.) may, in some contexts, be configured to implement countdown timer 2310. Alternatively or additionally, in some variants, such devices can include an image 2576 that displays two or more instances of countdown timers 2310 so that two or more respective time intervals 2542-2543 (associated with respective healthcare-related tasks for which patient 4250 or his caregiver are responsible, e.g.) are visible simultaneously in the vicinity of the first individual.

In light of teachings herein, numerous existing techniques may be applied for configuring special-purpose circuitry or other structures effective for implementing a notification as described herein without undue experimentation. See, e.g., U.S. Pat. No. 8,060,562 ("Real time update notification"); U.S. Pat. No. 7,940,602 ("Real-time system and method of underwater depth discrepancy detection, recordation and alarm notification"); U.S. Pat. No. 7,924,149 ("System and method for providing alarming notification and real-time, critical emergency information to occupants in a building or emergency designed area and evacuation guidance system to and in the emergency exit route"); U.S. Pat. No. 7,899,739 ("Construction payment management system and method with real-time draw notification features"); U.S. Pat. No. 7,898,423 ("Real-time event notification"); U.S. Pat. No. 7,890,622 ("Real-time notification of device events"); U.S. Pat. No. 7,865,566 ("Method and apparatus for providing real-time notification for avatars"); U.S. Pat. No. 7,835,506 ("Method and system for real-time notification and disposition of voice services in a cable services network"); U.S. Pat. No. 7,813,481 ("Conversation recording with real-time notification for users of communication terminals"); U.S. Pat. No. 7,617,162 ("Real time push notification in an event driven network"); and U.S. Pat. No. 7,319,378 ("Anti-theft system for a vehicle with real-time notification feature").

Also in such variants, extensive operation 50 may be performed by a special purpose communication module 3682 implemented as or operably coupled with circuitry 3325 having an event-sequencing structure configured to transmit a Boolean indication 2557 whether or not the 7:30 pm deadline (specified by timing component 4782 of record 4763, e.g.) was met. This can occur, for example, in a context in which communication module 3682 is configured to transmit such data to records archive 820 or to some other recipient 2722 (a family member of patient 4250 or other subscriber, e.g.); in which the timely completion of such tasks would not otherwise get an appropriate degree of attention; and in which Boolean indication 2557 is implemented (as a voltage level, e.g.) on an electrical node 3489 (of a response unit 3605 operatively coupled with data-handling device 3705, e.g.). In some variants, for example, even a single such Boolean indication 2557 may be encoded (by a suitable code division multiple access protocol, e.g.) to be expressed across several nodes (signal transmission lines, e.g.).

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

CLAUSES 1. (Independent) A healthcare information management system comprising:
    one or more articles of manufacture including
    transistor-based circuitry having an event-sequencing structure configured for causing a first individual to receive a playable prompt that was automatically selected according to a first data component received from the first individual;
    transistor-based circuitry having an event-sequencing structure configured for receiving a second data component from the first individual after the first individual received the playable prompt that was automatically selected according to the first data component received from the first individual; and
    transistor-based circuitry having an event-sequencing structure configured for causing a wearable article at a first care facility to indicate the second data component received from the first individual after the first individual received the playable prompt that was automatically selected according to the first data component received from the first individual.

2. The healthcare information management system of any of the above SYSTEM CLAUSES, further comprising:
    a portable device associated with the first individual and including the transistor-based circuitry having the event-sequencing structure configured for causing the wearable article at the first care facility to indicate the second data component received from the first individual after the first individual received the playable prompt that was automatically selected according to the first data component received from the first individual.

3. The healthcare information management system of any of the above SYSTEM CLAUSES, further comprising:
    a data-handling medium bearing the first data component received from the first individual including a name of the first individual.

4. The healthcare information management system of any of the above SYSTEM CLAUSES, further comprising:

a data-handling medium bearing the first data component received from the first individual including a name of a second individual.

5. The healthcare information management system of any of the above SYSTEM CLAUSES, further comprising:
a microphone configured to receive audio data from the first individual; and
a data processing module configured to extract the first data component from the audio data from the first individual.

6. The healthcare information management system of any of the above SYSTEM CLAUSES, further comprising:
a camera configured to receive image data from the first individual; and
a data processing module configured to extract the first data component from the video data from the first individual.

7. The healthcare information management system of any of the above SYSTEM CLAUSES, further comprising:
a user interface including the transistor-based circuitry having the event-sequencing structure configured for causing the first individual to receive the playable prompt that was automatically selected according to the first data component received from the first individual, the user interface including a keyboard configured to receive the first data component from the first individual.

8. The healthcare information management system of any of the above SYSTEM CLAUSES, further comprising:
a storage medium containing the playable prompt, the playable prompt comprising a digital data sequence.

9. The healthcare information management system of any of the above SYSTEM CLAUSES, further comprising:
a selection module configured to select the playable prompt responsive to the first data component.

10. The healthcare information management system of any of the above SYSTEM CLAUSES, further comprising:
an invocation module configured to cause a remote entity to select the playable prompt at least partly based on the first data component; and
an output module configured to play the playable prompt in a vicinity of the first individual.

11. The healthcare information management system of any of the above SYSTEM CLAUSES, further comprising:
a user interface including the transistor-based circuitry having the event-sequencing structure configured for causing the first individual to receive the playable prompt that was automatically selected according to the first data component received from the first individual, the user interface including a speaker configured to play an audio component of the playable prompt.

12. The healthcare information management system of any of the above SYSTEM CLAUSES, further comprising:
a user interface including the transistor-based circuitry having the event-sequencing structure configured for causing the first individual to receive the playable prompt that was automatically selected according to the first data component received from the first individual, the user interface including a display configured to play a video component of the playable prompt.

13. The healthcare information management system of any of the above SYSTEM CLAUSES, further comprising:
the wearable article, comprising a data-handling medium configured to bear a Boolean indication of whether or not a task associated with the first individual and with a time interval was performed within the time interval.

14. The healthcare information management system of any of the above SYSTEM CLAUSES, further comprising:
the wearable article, comprising a wrist band configured to indicate the second data component received from the first individual after the first individual received the playable prompt that was automatically selected according to the first data component received from the first individual.

15. The healthcare information management system of any of the above SYSTEM CLAUSES, further comprising:
the wearable article, comprising a printed surface configured to indicate information about the first individual, the information comprising the second data component received from the first individual after the first individual received the playable prompt that was automatically selected according to the first data component received from the first individual.

16. The healthcare information management system of any of the above SYSTEM CLAUSES, further comprising:
the wearable article, comprising a barcode configured to indicate the second data component received from the first individual after the first individual received the playable prompt that was automatically selected according to the first data component received from the first individual.

17. The healthcare information management system of any of the above SYSTEM CLAUSES, further comprising:
the wearable article, comprising a data-handling medium configured to indicate a current health status, the current health status comprising the second data component received from the first individual after the first individual received the playable prompt that was automatically selected according to the first data component received from the first individual.

18. The healthcare information management system of any of the above SYSTEM CLAUSES, further comprising:
an application-specific integrated circuit, including the transistor-based circuitry having the event-sequencing structure configured for causing the wearable article at the first care facility to indicate the second data component received from the first individual after the first individual received the playable prompt that was automatically selected according to the first data component received from the first individual.

19. The healthcare information management system of any of the above SYSTEM CLAUSES, further comprising:
the transistor-based circuitry having the event-sequencing structure configured for causing the wearable article at the first care facility to indicate the second data component received from the first individual after the first individual received the playable prompt that was automatically selected according to the first data component received from the first individual including at least
transistor-based circuitry having an event-sequencing structure configured for looking up a communication delay as a function of a therapeutic protocol associated with a recipient of the therapeutic protocol, the recipient being or not being the first individual; and
transistor-based circuitry having an event-sequencing structure configured for transmitting a query as an automatic response to an expiration of the communication delay.

20. The healthcare information management system of any of the above SYSTEM CLAUSES, further comprising:
the transistor-based circuitry having the event-sequencing structure configured for causing the wearable article at the first care facility to indicate the second data component received from the first individual after the first individual received the playable prompt that was automatically selected according to the first data component received from the first individual including at least
transistor-based circuitry having an event-sequencing structure configured for looking up a communication delay as a function of a medical condition associated with a recipient of the wearable article, the recipient being or not being the first individual; and transistor-based circuitry having an event-sequencing structure configured for transmitting a query as an automatic response to an expiration of the communication delay.

21. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for causing an individual to be contacted by a fallback mode of communication as a conditional response to receiving no reply from the individual by a prior mode of communication, the prior mode of communication being telephonic, the individual being the first individual or a patient of the first individual.

22. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for contacting an individual by a fallback mode of communication as an automatic and conditional response to receiving no reply from the individual by a prior mode of communication, the fallback mode of communication being telephonic, the individual being the first individual or a patient of the first individual.

23. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for updating a locally-resident subscriber registry in response to the first individual entering a service zone.

24. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for obtaining an indication that a specific pathology in the first individual has been treated at a first hospital and an indication that the specific pathology in the first individual has been treated at a second hospital, the first care facility being the first hospital.

25. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for retrieving a medical treatment record of the first individual selectively in response to an explicit indication of a payment reduction that identifies the first individual.

26. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for retrieving a medical treatment record relating to a set of one or more pathologies selectively in response to an explicit indication of a payment reduction that identifies the set.

27. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for detecting a wireless device within an effective range of a stationary device, the wearable article being the wireless device.

28. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for obtaining an explicit indication whether a record of treating a medical condition in the first individual with a particular protocol contains any extrinsic evidence that treating the medical condition with the particular protocol has precedent.

29. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for initiating a telephone call between the first individual and another entity as an automatic response to the first individual not being compliant with a health regimen and to an indication that the other entity is available.

30. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for signaling a decision whether to transfer a resource to the first individual partly based on an indication that the first individual is not compliant with a health regimen and partly based on an indication that the first individual has accepted a telephone call.

31. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for causing a locally-resident subscriber registry to be updated with an indication of the first individual.

32. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for determining whether a medical device is in a vicinity of another device, the other device being the device associated with the first individual.

33. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for responding to an event with an audible notification, the event being the wearable article at the first care facility being configured to indicate the second data component received from the first individual after the first individual received the playable prompt that was automatically selected according to the first data.

34. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for responding to a payment-reduction event relating to a first medical treatment by causing a selective retrieval of one or more records that lack any prominence indication relating to the first medical treatment from an archive that includes at least one prominence indication relating to a second medical treatment.

35. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for detecting a passive wireless transponder within a vicinity of a vehicle, the wearable article including the passive wireless transponder.

36. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for obtaining the second data component, the second data component including an indication whether or not the first individual is compliant with a first health regimen.

37. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for triggering a search of a particular records archive by providing a selective search criterion, one that results in an exclusion of a first element in the particular records archive and an inclusion of a second element in the particular records archive, the second element referring to the first individual or to a patient of the first individual.

38. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for transmitting a real-time notification to another entity as an automatic response to an interface on or near the first individual detecting a particular event relating to the first individual.

39. The healthcare information management system of any of the above SYSTEM CLAUSES, further comprising:

the transistor-based circuitry having the event-sequencing structure configured for causing the wearable article at the first care facility to indicate the second data component received from the first individual after the first individual received the playable prompt that was automatically selected according to the first data component received from the first individual including at least transistor-based circuitry having an event-sequencing structure configured for implementing a failsafe preventing medical equipment from operating until an order that associates the medical equipment with the first individual is received and until an indication is received that the first individual is in a vicinity of the medical equipment.

40. (Independent) A healthcare information management method comprising: causing a first individual to receive a playable prompt that was automatically selected according to a first data component received from the first individual;

receiving a second data component from the first individual after the first individual received the playable prompt that was automatically selected according to the first data component received from the first individual; and invoking transistor-based circuitry having an event-sequencing structure configured for causing a wearable article at a first care facility to indicate the second data component received from the first individual after the first individual received the playable prompt that was automatically selected according to the first data component received from the first individual.

41. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least looking up a communication delay as a function of a therapeutic protocol associated with a recipient of the therapeutic protocol, the recipient being or not being the first individual; and transmitting a query as an automatic response to an expiration of the communication delay.

42. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least looking up a communication delay as a function of a medical condition associated with a recipient of the wearable article, the recipient being or not being the first individual; and transmitting a query as an automatic response to an expiration of the communication delay.

43. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least causing an individual to be contacted by a fallback mode of communication as a conditional response to receiving no reply from the individual by a prior mode of communication, the prior mode of communication being telephonic, the individual being the first individual or a patient of the first individual.

44. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least contacting an individual by a fallback mode of communication as an automatic and conditional response to receiving no reply from the individual by a prior mode of communication, the fallback mode of communication being telephonic, the individual being the first individual or a patient of the first individual.

45. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least updating a locally-resident subscriber registry in response to the first individual entering a service zone.

46. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least obtaining an indication that a specific pathology in the first individual has been treated at a first hospital and an indication that the specific pathology in the first individual has been treated at a second hospital, the first care facility being the first hospital.

47. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least retrieving a medical treatment record of the first individual selectively in response to an explicit indication of a payment reduction that identifies the first individual.

48. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least retrieving a medical treatment record relating to a set of one or more pathologies selectively in response to an explicit indication of a payment reduction that identifies the set.

49. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least detecting a wireless device within an effective range of a stationary device, the wearable article being the wireless device.

50. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least obtaining an explicit indication whether a record of treating a medical condition in the first individual with a particular protocol contains any extrinsic evidence that treating the medical condition with the particular protocol has precedent.

51. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least initiating a telephone call between the first individual and another entity as an automatic response to the first individual not being compliant with a health regimen and to an indication that the other entity is available.

52. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least signaling a decision whether to transfer a resource to the first individual partly based on an indication that the first individual is not compliant with a health regimen and partly based on an indication that the first individual has accepted a telephone call.

53. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least causing a locally-resident subscriber registry to be updated with an indication of the first individual.

54. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least determining whether a medical device is in a vicinity of another device, the other device being the device associated with the first individual.

55. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least responding to an event with an audible notification, the event being the wearable article at the first care facility being configured to indicate the second data component received from the first individual after the first individual received the playable prompt that was automatically selected according to the first data.

56. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least responding to a payment-reduction event relating to a first medical treatment by causing a selective retrieval of one or more records that lack any prominence indication relating to the first medical treatment from an archive that includes at least one prominence indication relating to a second medical treatment.

57. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least detecting a passive wireless transponder within a vicinity of a vehicle, the wearable article including the passive wireless transponder.

58. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least obtaining the second data component, the second data component including an indication whether or not the first individual is compliant with a first health regimen.

59. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least triggering a search of a particular records archive by providing a selective search criterion, one that results in an exclusion of a first element in the particular records archive and an inclusion of a second element in the particular records archive, the second element referring to the first individual or to a patient of the first individual.

60. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least transmitting a real-time notification to another entity as an automatic response to an interface on or near the first individual detecting a particular event relating to the first individual.

61. The healthcare information management system of any of the above METHOD CLAUSES, further comprising:

the invoking the transistor-based circuitry having the event-sequencing structure configured for causing the wearable article at the first care facility to indicate the second data component received from the first individual after the first individual received the playable prompt that was automatically selected according to the first data component received from the first individual including at least implementing a failsafe preventing medical equipment from operating until an order that associates the medical equipment with the first individual is received and until an indication is received that the first individual is in a vicinity of the medical equipment.

62. (Independent) A healthcare information management method comprising:

obtaining an association between data indicating a current health status of a first individual and a record designator; and causing a wearable article at a first care facility to include the data indicating the current health status of the first individual as an automatic and conditional response to local input at the first care facility matching the record designator.

63. The healthcare information management method of CLAUSE 62 further comprising:

performing the operation(s) of any one or more of the above METHOD CLAUSES that depend from METHOD CLAUSE 40.

64. (Independent) A healthcare information management method comprising:

obtaining an indication via a first device local to a first individual that the first individual is noncompliant with a first health regimen;

obtaining an indication via a second device that a second individual is available to participate in an electronic intercommunication; and signaling the electronic intercommunication as an automatic and conditional response to the indication via the first device local to the first individual that the first individual is noncompliant with the first health regimen and to the indication via the second device that the second individual is available to participate in the electronic intercommunication.

65. The healthcare information management method of CLAUSE 64 further comprising:

performing the operation(s) of any one or more of the above METHOD CLAUSES that depend from METHOD CLAUSE 40.

66. (Independent) A healthcare information management method comprising:

obtaining via a first device a scalar indication of how well a first health regimen has been followed by a first individual;

obtaining via a second device a scalar indication of how well a second health regimen has been followed by a second individual; and characterizing a performance of a third individual with a scalar evaluation obtained by mathematically combining the scalar indication of how well the first health regimen has been followed by the first individual with the scalar indication of how well the second health regimen has been followed by the second individual.

67. The healthcare information management method of CLAUSE 66 further comprising:

performing the operation(s) of any one or more of the above METHOD CLAUSES that depend from METHOD CLAUSE 40.

68. (Independent) A healthcare information management method comprising:

obtaining a field of view within which a specific portion of the field of view includes a view of a first patient;

obtaining user input selectively indicating the first patient by identifying the specific portion that depicts the first patient; and signaling medical data about the first patient as an automatic and conditional response to the user input selectively indicating the first patient by identifying the specific portion that depicts the first patient.

69. The healthcare information management method of CLAUSE 68 further comprising:

performing the operation(s) of any one or more of the above METHOD CLAUSES that depend from METHOD CLAUSE 40.

70. (Independent) A healthcare information management method comprising:

causing a first individual to receive a playable prompt that was automatically selected according to a first data component received from the first individual;

receiving a second data component from the first individual after the first individual received the playable prompt that was automatically selected according to the first data component received from the first individual; and causing a wearable article at a first care facility to indicate the second data component received from the first individual after the first individual received the playable prompt that was automatically selected according to the first data component received from the first individual.

71. The healthcare information management method of CLAUSE 70 further comprising:

performing the operation(s) of any one or more of the above METHOD CLAUSES that depend from METHOD CLAUSE 40.

72. (Independent) A healthcare information management method comprising:

obtaining a first indication whether or not a first patient has violated a first health regimen;

obtaining a second indication whether or not the first patient has violated the first health regimen;

signaling a decision whether or not to initiate an electronic communication between the first patient and a provider as an automatic and conditional response to the first indication whether or not the first patient has violated the first health regimen but not to the second indication whether or not the first patient has violated the first health regimen; and signaling a decision whether or not to route the provider to the first patient as a conditional response to the first indication whether or not the first patient has violated the first health regimen and to the second indication whether or not the first patient has violated the first health regimen.

73. The healthcare information management method of CLAUSE 72 further comprising:

performing the operation(s) of any one or more of the above METHOD CLAUSES that depend from METHOD CLAUSE 40.

74. (Independent) A healthcare information management method comprising:

assigning a component of an artificial incentive to a first patient partly based on an indication that the first patient has been admitted to a first institution in relation to a particular condition and partly based on an indication that the first patient has not undergone an institutional readmission; and transmitting to the first patient a result of assigning the component of the artificial incentive to the first patient partly based on the indication that the first patient has been admitted to the first institution in relation to the particular condition and partly based on the indication that the first patient has not undergone the institutional readmission.

75. The healthcare information management method of CLAUSE 74 further comprising:

performing the operation(s) of any one or more of the above METHOD CLAUSES that depend from METHOD CLAUSE 40.

76. (Independent) A healthcare information management method comprising:

obtaining an indication that an order associates a first patient with a medical device;

obtaining an indication that the medical device is in a vicinity of the first patient; and enabling the medical device conditionally, partly based on the indication that the order associates the first patient with the medical device and partly based on the indication that the medical device is in the vicinity of the first patient.

77. The healthcare information management method of CLAUSE 76 further comprising:

performing the operation(s) of any one or more of the above METHOD CLAUSES that depend from METHOD CLAUSE 40.

78. (Independent) A healthcare information management method comprising:

identifying a first health regimen associated with a first individual, the first health regimen including one or more healthcare-related tasks associated with a time interval;

causing a countdown timer to indicate a remaining portion of the time interval associated with the one or more healthcare-related tasks visibly in a vicinity of the first individual; and signaling a Boolean indication of whether or not any of the one or more healthcare-related tasks associated with the time interval were performed within the time interval after the countdown timer has indicated the remaining portion of the time interval associated with the one or more healthcare-related tasks visibly in the vicinity of the first individual.

79. The healthcare information management method of CLAUSE 78 further comprising:

performing the operation(s) of any one or more of the above METHOD CLAUSES that depend from METHOD CLAUSE 40.

80. (Independent) A healthcare information management method comprising:

causing an electronic record of a first protocol for a particular condition to be annotated with a scan of a document; and retrieving the electronic record of the first protocol after the electronic record of the first protocol is annotated with the scan of the document partly based on an indication of a first patient undergoing the first protocol and partly based on an indication of an institutional readmission.

81. The healthcare information management method of CLAUSE 80 further comprising:

performing the operation(s) of any one or more of the above METHOD CLAUSES that depend from METHOD CLAUSE 40.

82. (Independent) A healthcare information management method comprising:

obtaining an indication that a particular condition was treated in a first patient with a first protocol;

causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol.

83. The healthcare information management method of CLAUSE 82 further comprising:

performing the operation(s) of any one or more of the above METHOD CLAUSES that depend from METHOD CLAUSE 40.

84. (Independent) A healthcare information management method comprising:

obtaining an indication of a first protocol being employed in relation to a particular condition in a first patient;

requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol.

85. The healthcare information management method of CLAUSE 84 further comprising:
performing the operation(s) of any one or more of the above METHOD CLAUSES that depend from METHOD CLAUSE 40.

86. (Independent) A healthcare information management method comprising:
obtaining an association between a particular condition and a first protocol;
causing a comparison between a threshold and a prominence indication of treating the particular condition with the first protocol after the association between then particular condition and the first protocol is obtained; and
signaling a decision whether to caution a caregiver partly based on the association between the particular condition and the first protocol and partly based on the comparison between the threshold and the prominence indication of treating the particular condition with the first protocol.

87. The healthcare information management method of CLAUSE 86 further comprising:
performing the operation(s) of any one or more of the above METHOD CLAUSES that depend from METHOD CLAUSE 40.

88. (Independent) A healthcare information management method comprising:
obtaining an association between a care administration space and a first device;
obtaining via a second device a patient consent conditionally authorizing a release of a first medical record, the second device being a mobile device; and
causing the first device to receive the first medical record partly based on the second device entering the care administration space and partly based on the patient consent authorizing the release of the first medical record.

89. The healthcare information management method of CLAUSE 88 further comprising:
performing the operation(s) of any one or more of the above METHOD CLAUSES that depend from METHOD CLAUSE 40.

90. (Independent) A healthcare information management method comprising:
obtaining an indication of a first device associated with and wearable by a patient hospitalized for a particular condition;
obtaining an indication of a second device associated with and wearable by a caregiver;
causing a recordation of a timestamp as an automatic response to the first device associated with and wearable by the patient and the second device associated with and wearable by a caregiver both being in a single common location; and
describes causing a retrieval of the timestamp in response to an indication of an institutional readmission after the recordation of the timestamp indicating the first device associated with and wearable by the patient and the second device associated with and wearable by the caregiver both having been in the single common location.

91. The healthcare information management method of CLAUSE 90 further comprising:
performing the operation(s) of any one or more of the above METHOD CLAUSES that depend from METHOD CLAUSE 40.

92. (Independent) A system comprising:
means for performing the operation(s) of any one or more of the above METHOD CLAUSES.

93. (Independent) An article of manufacture comprising:
one or more physical media configured to bear a device-detectable implementation of a method including at least
causing a first individual to receive a playable prompt that was automatically selected according to a first data component received from the first individual;
receiving a second data component from the first individual after the first individual received the playable prompt that was automatically selected according to the first data component received from the first individual; and
causing a wearable article at a first care facility to indicate the second data component received from the first individual after the first individual received the playable prompt that was automatically selected according to the first data component received from the first individual.

94. The article of manufacture of CLAUSE 93 in which a portion of the one or more physical media comprises:
one or more signal-bearing media configured to transmit a binary sequence manifesting one or more device-executable instructions configured to perform the operation(s) of any one or more of the above METHOD CLAUSES.

95. (Independent) An article of manufacture comprising:
one or more physical media bearing a device-detectable output manifesting an occurrence of
causing a first individual to receive a playable prompt that was automatically selected according to a first data component received from the first individual;
receiving a second data component from the first individual after the first individual received the playable prompt that was automatically selected according to the first data component received from the first individual; and
causing a wearable article at a first care facility to indicate the second data component received from the first individual after the first individual received the playable prompt that was automatically selected according to the first data component received from the first individual.

96. The article of manufacture of CLAUSE 95 in which a portion of the one or more physical media comprises:
one or more signal-bearing media bearing at least one binary sequence from an event-sequencing structure configured to perform the operation(s) of any one or more of the above METHOD CLAUSES.

All of the patents and other publications referred to above are incorporated herein by reference generally—including those identified in relation to particular new applications of existing techniques—to the extent not inconsistent herewith (in each respective latest edition, where applicable). While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:
1. A system, comprising:
circuitry for receiving at least one input from at least one personal communication device associated with at least one device identifier, the at least one input indicative of the at least one personal communication device entering a service zone;
circuitry for associating the at least one personal communication device with a particular patient identifier based at least partly on the circuitry for receiving the at least one input from the at least one personal communication device associated with the at least one device identifier;

circuitry for selecting a playable prompt, the selected playable prompt including at least one of audio, image, or video content, based at least partly on the circuitry for associating the at least one personal communication device with the particular patient identifier;

circuitry for causing the selected playable prompt to be output in a manner perceivable by a particular patient associated with the particular patient identifier;

circuitry for obtaining medical intake data including at least one indication of at least one of speech or appearance of the particular patient subsequent to the causing the selected playable prompt to be output;

circuitry for detecting medically relevant data related to the particular patient from the at least one indication of the at least one of speech or appearance of the particular patient;

circuitry for causing the at least one personal communication device to display at least one detectable structure, the at least one detectable structure including at least one encoding associated with at least some of the obtained medical intake data; and circuitry for implementing a failsafe preventing medical equipment from operating until an indication is received from electronic detection that the at least one personal communication device associated with the at least one device identifier associated with the particular patient identifier is in a vicinity of the medical equipment and until the display of the at least one detectable structure is recognized by a detection device operably coupled with the medical equipment.

2. The system of claim 1, wherein the circuitry for causing the at least one personal communication device to display at least one detectable structure, the at least one detectable structure including at least one encoding associated with at least some of the obtained medical intake data received from the particular patient comprises:

circuitry for causing the at least one personal communication device to display a barcode configured to indicate the at least some of the obtained medical intake data.

3. The system of claim 1, further comprising:
circuitry for updating a locally-resident subscriber registry based at least partly on the at least one input indicative of the at least one personal communication device entering the service zone.

4. An article of manufacture, comprising:
at least one non-transitory computer-readable medium including at least:
one or more instructions for receiving at least one input from at least one personal communication device associated with at least one device identifier, the at least one input indicative of the at least one personal communication device entering a service zone;
one or more instructions for associating the at least one personal communication device with a particular patient identifier based at least partly on the one or more instructions for receiving the at least one input from the at least one personal communication device associated with the at least one device identifier;
one or more instructions for selecting a playable prompt, the selected playable prompt including at least one of audio, image, or video content, based at least partly on the one or more instructions for associating the at least one personal communication device with the particular patient identifier;

one or more instructions for causing the selected playable prompt to be output in a manner perceivable by a particular patient associated with the particular patient identifier;

one or more instructions for obtaining medical intake data including at least one indication of at least one of speech or appearance of the particular patient subsequent to the causing the selected playable prompt to be output;

one or more instructions for detecting medically relevant data related to the particular patient from the at least one indication of the at least one of speech or appearance of the particular patient;

one or more instructions for causing the at least one personal communication device to display at least one detectable structure, the at least one detectable structure including at least one encoding associated with at least some of the obtained medical intake data and one or more instructions for implementing a failsafe preventing medical equipment from operating until an indication is received from electronic detection that the at least one personal communication device associated with the at least one device identifier associated with the particular patient identifier is in a vicinity of the medical equipment and until the display of the at least one detectable structure is recognized by a detection device operably coupled with the medical equipment.

5. The system of claim 1, wherein the circuitry for receiving at least one input from at least one personal communication device associated with at least one device identifier, the at least one input indicative of the at least one personal communication device entering a service zone comprises:

circuitry for detecting that a smartphone associated with the at least one device identifier has established a wireless connection with a stationary device associated with the service zone; and wherein the circuitry for associating the at least one personal communication device with a particular patient identifier based at least partly on the circuitry for receiving the at least one input from the at least one personal communication device associated with the at least one device identifier includes at least:

circuitry for identifying the particular patient identifier based at least partly on the at least one device identifier.

6. The system of claim 1, further comprising:
circuitry for obtaining an explicit indication whether a record of treating the particular patient for a medical condition with a particular protocol contains any extrinsic evidence that treating the medical condition with the particular protocol has precedent.

7. The system of claim 1, further comprising:
circuitry for initiating a telephone call between the particular patient and another entity as an automatic response to the particular patient not being compliant with a health regimen based at least partly on the circuitry for obtaining medical intake data including at least one indication of at least one of speech or appearance of the particular patient.

8. The system of claim 1, further comprising:
circuitry for signaling a decision whether to transfer a resource to the particular patient based at least partly on an indication that the particular patient is not compliant with a health regimen and based at least partly on an indication that the particular patient has accepted a telephone call relating to a particular timed administration of a particular treatment specified by the health regimen.

9. The system of claim 1, wherein the circuitry for associating the at least one personal communication device with a particular patient identifier based at least partly on the circuitry for receiving the at least one input from the at least one personal communication device associated with the at least one device identifier comprises:
 circuitry for causing a locally-resident subscriber registry to be updated with an indication that the particular patient has entered a service zone based at least partly on an inference that the at least one personal communication device is possessed by the particular patient and based at least partly on an identification of the particular patient using the at particular patient identifier.

10. The system of claim 1, wherein the circuitry for receiving at least one input from at least one personal communication device associated with at least one device identifier, the at least one input indicative of the at least one personal communication device entering a service zone comprises:
 circuitry for detecting that the at least one personal communication device is within a particular vicinity of a medical device associated with the service zone.

11. The system of claim 1, further comprising:
 circuitry for providing an audible notification as a substantially real-time notification to a device at a care facility, the device at the care facility configured to alert upon detection of medically relevant data.

12. The system of claim 1, wherein the circuitry for obtaining medical intake data including at least one indication of at least one of speech or appearance of the particular patient subsequent to the causing the selected playable prompt to be output comprises:
 circuitry for causing one or more of at least one microphone or at least one image sensor of the at least one personal device to capture one or more of at least some audio data or at least some video data as the medical intake data; and
 circuitry for detecting the at least one indication of at least one of speech or appearance of the particular patient from within the one or more of at least some audio data or at least some video data.

13. The system of claim 1, further comprising:
 circuitry for transmitting a substantially real-time notification to at least one other entity as an automatic response to an interface on or near the particular patient detecting a particular event relating to the particular patient.

14. The system of claim 1, wherein the circuitry for implementing a failsafe preventing medical equipment from operating until an indication is received from electronic detection that the at least one personal communication device associated with the at least one device identifier associated with the particular patient identifier is in a vicinity of the medical equipment and until the display of the at least one detectable structure is recognized by a detection device operably coupled with the medical equipment comprises:
 circuitry for enabling the medical equipment to function only after receiving an indication of a barcode having been scanned, the barcode configured to indicate at least some of the obtained medical intake data.

15. The system of claim 1, further comprising:
 circuitry for transmitting a message causing an audible notification to be output as a substantially real-time notification.

16. The system of claim 1, wherein the circuitry for obtaining medical intake data including at least one indication of at least one of speech or appearance of the particular patient subsequent to the causing the selected playable prompt to be output comprises:
 circuitry for receiving at least one spoken word input from the particular patient via the at least one personal communication device.

17. The system of claim 1, wherein the circuitry for causing the selected playable prompt to be output in a manner perceivable by a particular patient associated with the particular patient identifier comprises:
 circuitry for playing at least one of an audio, image or video prompt that was automatically selected based at least partly on the circuitry for associating the at least one personal communication device with the particular patient identifier, the playable prompt configured to a particular condition associated with the particular patient associated with the particular patient identifier.

18. The system of claim 1, wherein the circuitry for obtaining medical intake data including at least one indication of at least one of speech or appearance of the particular patient subsequent to the causing the selected playable prompt to be output comprises:
 circuitry for capturing at least one of a spoken word input from the particular patient, an image input representing the particular patient, a video input representing the particular patient, or a touch input from the particular patient as the obtained medical intake data.

19. The system of claim 1, wherein the circuitry for causing the at least one personal communication device to display at least one detectable structure, the at least one detectable structure including at least one encoding associated with at least some of the obtained medical intake data comprises:
 circuitry for causing the at least one personal communication device to display a barcode configured to indicate the at least some of the obtained medical intake data.

20. The system of claim 1, wherein the circuitry for causing the at least one personal communication device to display at least one detectable structure, the at least one detectable structure including at least one encoding associated with at least some of the obtained medical intake data comprises:
 circuitry for encoding the at least some of the obtained medical intake data in at least one transponder of the at least one personal communication device.

21. The system of claim 1, wherein the circuitry for implementing a failsafe preventing medical equipment from operating until an order that associates the medical equipment with the particular patient is received and until an indication is received from electronic detection that the at least one personal communication device associated with the at least one device identifier associated with the particular patient identifier is in a vicinity of the medical equipment comprises:
 circuitry for enabling the medical equipment to function only after a detection module proximate to the medical equipment detects a presence of the at least one personal communication device associated with the at least one device identifier associated with the particular patient identifier.

22. A method, comprising:
receiving at least one input from at least one personal communication device associated with at least one device identifier, the at least one input indicative of the at least one personal communication device entering a service zone;
associating the at least one personal communication device with a particular patient identifier based at least partly on the receiving the at least one input from the at least one personal communication device associated with the at least one device identifier;
selecting a playable prompt, the selected playable prompt including at least one of audio, image, or video content, based at least partly on the associating the at least one personal communication device with the particular patient identifier;
causing the selected playable prompt to be output in a manner perceivable by a particular patient associated with the particular patient identifier;
obtaining medical intake data including at least one indication of at least one of speech or appearance of the particular patient subsequent to the causing the selected playable prompt to be output;
detecting medically relevant data related to the particular patient from the at least one indication of the at least one of speech or appearance of the particular patient;
causing the at least one personal communication device to display at least one detectable structure, the at least one detectable structure including at least one encoding associated with at least some of the obtained medical intake data; and
implementing a failsafe preventing medical equipment from operating until an indication is received from electronic detection that the at least one personal communication device associated with the at least one device identifier associated with the particular patient identifier is in a vicinity of the medical equipment and until the display of the at least one detectable structure is recognized by a detection device operably coupled with the medical equipment,
wherein the receiving, associating, selecting, causing, obtaining, detecting, and implementing are at least partly implemented using at least one processing device.

23. The system of claim 1, wherein the circuitry for associating the at least one personal communication device with a particular patient identifier based at least partly on the circuitry for receiving the at least one input from the at least one personal communication device associated with the at least one device identifier comprises:
circuitry for associating the at least one device identifier with at least one medical record, the at least one medical record associated with at least one identity of at least one particular patient.

24. The system of claim 1, wherein the circuitry for obtaining medical intake data including at least one indication of at least one of speech or appearance of the particular patient subsequent to the causing the selected playable prompt to be output comprises:
circuitry for identifying at least one medical condition previously associated with the at least one particular patient; and
circuitry for detecting at least one symptom associated with the identified at least one medical condition based at least partly on the at least one of speech or appearance of the particular patient.

25. The system of claim 24, wherein the circuitry for detecting at least one symptom associated with the identified at least one medical condition based at least partly on the at least one of speech or appearance of the particular patient comprises:
circuitry for detecting biometric data associated with the at least one symptom.

26. The system of claim 1, wherein the circuitry for causing the at least one personal communication device to display at least one detectable structure, the at least one detectable structure including at least one encoding associated with at least some of the obtained medical intake data comprises:
circuitry configured for generating a barcode based at least partly on the at least some of the obtained medical intake data; and
circuitry configured for transmitting the generated barcode to the at least one personal communication device, the transmitted barcode configured for display on the at least one personal communication device.

27. The system of claim 1, wherein the circuitry for receiving at least one input from at least one personal communication device associated with at least one device identifier, the at least one input indicative of the at least one personal communication device entering a service zone comprises:
circuitry configured for detecting that the at least one personal communication device is within an effective range of at least one wireless transceiver associated with the service zone.

28. The system of claim 1, wherein the circuitry for receiving at least one input from at least one personal communication device associated with at least one device identifier, the at least one input indicative of the at least one personal communication device entering a service zone comprises:
circuitry configured for detecting that at least one of a personal smartphone or a tablet computer as the at least one personal communication device has entered the service zone.

29. The system of claim 1, wherein the circuitry for associating the at least one personal communication device with a particular patient identifier based at least partly on the circuitry for receiving the at least one input from the at least one personal communication device associated with the at least one device identifier comprises:
circuitry for associating the particular patient identifier with the at least one personal communication device based at least partly on at least one application running on the at least one personal communication device.

30. The system of claim 1, wherein the circuitry for causing the at least one personal communication device to display at least one detectable structure, the at least one detectable structure including at least one encoding associated with at least some of the obtained medical intake data comprises:
circuitry for transmitting the at least one detectable structure to the at least one personal communication device in a device-readable format.

31. The system of claim 1, wherein the circuitry for causing the selected playable prompt to be output in a manner perceivable by a particular patient associated with the particular patient identifier comprises:

circuitry for transmitting the selected playable prompt to the at least one personal communication device in a device-playable format.

32. The system of claim 1, wherein the circuitry for obtaining medical intake data including at least one indication of at least one of speech or appearance of the particular patient subsequent to the causing the selected playable prompt to be output comprises:
  circuitry for presenting a user interface on the personal communication device, the user interface configured to receive user input responsive to a request for the medical intake data conveyed by the selected playable prompt.

33. The system of claim 1, wherein the circuitry for obtaining medical intake data including at least one indication of at least one of speech or appearance of the particular patient subsequent to the causing the selected playable prompt to be output comprises:
  circuitry for receiving a patient consent conveyed by an utterance of the particular patient included in the at least one indication of at least one of speech or appearance of the particular patient.

34. The system of claim 33, wherein the circuitry for receiving a patient consent conveyed by an utterance of the particular patient included in the at least one indication of at least one of speech or appearance of the particular patient comprises:
  circuitry for receiving a patient consent for at least one of performance of a medical procedure or release of a medical record conveyed by the utterance of the particular patient included in the at least one indication of at least one of speech or appearance of the particular patient.

35. The system of claim 1, wherein the circuitry for receiving at least one input from at least one personal communication device associated with at least one device identifier, the at least one input indicative of the at least one personal communication device entering a service zone comprises:
  circuitry for receiving at least some GPS data from the at least one personal communication device associated with at least one device identifier, the at least some GPS data one input indicative of a proximity of the at least one personal communication device to the service zone.

36. The system of claim 1, further comprising:
  circuitry for causing the at least one personal communication device to display an indication of an availability of an artificial incentive for receipt by the particular patient upon a manifestation of an improvement in a condition associated with the individual indicated by the detected medically relevant data.

37. The system of claim 1, wherein the circuitry for receiving at least one input from at least one personal communication device associated with at least one device identifier, the at least one input indicative of the at least one personal communication device entering a service zone comprises:
  circuitry for receiving at least one input from at least one device wearable by a patient hospitalized for a particular condition, the at least one input indicative of the at least one device wearable by the patient hospitalized for the particular condition entering a service zone;
  circuitry for receiving at least one input from at least one device wearable by a caregiver, the at least one input indicative of the at least one device wearable by the caregiver entering the service zone; and
  circuitry for initiating a timestamp as an automatic response to the both the at least one device wearable by the patient hospitalized for the particular condition and the at least one device wearable by the caregiver being in a single common location.

38. The system of claim 1, wherein the associating the at least one personal communication device with a particular patient identifier based at least partly on the circuitry for receiving the at least one input from the at least one personal communication device associated with the at least one device identifier comprises:
  circuitry for triggering a search of a particular records archive by providing the at least one device identifier as a selective search criterion, one that results in the particular patient identifier being returned by the search of the particular records archive.

* * * * *